(12) United States Patent
Oberboersch et al.

(10) Patent No.: US 8,124,624 B2
(45) Date of Patent: Feb. 28, 2012

(54) SUBSTITUTED SULFONAMIDE COMPOUNDS

(75) Inventors: Stefan Oberboersch, Aachen (DE); Melanie Reich, Aachen (DE); Stefan Schunk, Aachen (DE); Michael Engels, Turnhout (BE); Ruth Jostock, Stolberg (DE); Tieno Germann, Aachen (DE); Sabine Hees, Aachen (DE)

(73) Assignee: Gruenenthal GmbH, Aachen (DE)

( * ) Notice: Subject to any disclaimer, the term of this patent is extended or adjusted under 35 U.S.C. 154(b) by 336 days.

(21) Appl. No.: 12/420,447

(22) Filed: Apr. 8, 2009

(65) Prior Publication Data

US 2009/0264407 A1 Oct. 22, 2009

Related U.S. Application Data

(60) Provisional application No. 61/043,254, filed on Apr. 8, 2008.

(30) Foreign Application Priority Data

Apr. 8, 2008 (EP) .................................. 08006959

(51) Int. Cl.
*A61K 31/4545* (2006.01)
*A61K 31/454* (2006.01)
*C07D 401/14* (2006.01)
*C07D 401/06* (2006.01)
(52) U.S. Cl. ......... 514/316; 514/326; 546/187; 546/208
(58) Field of Classification Search ............. 514/211.09, 514/316, 326; 546/187, 208; 540/552
See application file for complete search history.

(56) References Cited

FOREIGN PATENT DOCUMENTS

| WO | WO 2004/087700 A1 | 10/2004 |
| WO | WO 2007/140383 A2 | 12/2007 |
| WO | WO 2008/024692 A1 | 2/2008 |

OTHER PUBLICATIONS

Giselle F. Passos et al., "Kinin $B_1$ Receptor Up-Regulation after Lipopolysaccharide Administration: Role of Proinflammatory Cytokines and Neutrophil Influx[1]", The Journal of Immunology, 2004, pp. 1839-1847, vol. 172, The American Association of Immunologists, Inc.
L.M. Fredrik Leeb-Lundberg et al., "International Union of Pharmacology. XLV. Classification of the Kinin Receptor Family: from Molecular Mechanisms to Pathophysiological Consequences", Pharmacological Reviews, 2005, pp. 27-77, vol. 57, No. 1, The American Society for Pharmacology and Experimental Therapeutics, USA.
R. Hayashi et al., "Bradykinin Stimulates IL-6 and IL-8 Production by Human Lung Fibroblasts Through ERK-and p38 MAPK-dependent Mechanisms", European Respiratory Journal, 2000, pp. 452-458, vol. 16, ISSN: 0903-1936.
Bichoy H. Gabra et al., "The Kinin System Mediates Hyperalgesia through the Inducible Bradykinin B1 Receptor Subtype: Evidence in Various Experimental Animal Models of Type 1 and Type 2 Diabetic Neuropathy", Biol. Chem., Feb. 2006, pp. 127-143, vol. 387.
Joao B. Calixto et al., "Kinin $B_1$ Receptors: Key G-protein-coupled Receptors and their Role in Inflammatory and Painful Processes", British Journal of Pharmacology, 2004, pp. 803-818, vol. 143, 2004 Nature Publishing Group.
Sara H. Bengtson et al., "Kinin Receptor Expression During Staphylococcus Aureus Infection", Blood, Sep. 15, 2006, pp. 2055-2063, vol. 108, No. 6, The American Society of Hematology.
Antoni Stadnicki et al., "Immunolocalization and Expression of Kinin $B_1R$ and $B_2R$ Receptors in Human Inflammatory Bowel Disease", Am. J. Physiol. Gastrointest. Liver Physiol, Mar. 31, 2005, pp. G361-G366, vol. 289, American Physiological Society.
Joao B. Pesquero et al., "Genetically Altered Animal Models in the Kallikrein-Kinin System", Biol. Chem., Feb. 2006, pp. 119-126, vol. 387.
Joao B. Pesquero et al., "Hypoalgesia and Altered Inflammatory Responses in Mice Lacking Kinin B1 Receptors", PNAS, Jul. 5, 2000, pp. 8140-8145, vol. 97, No. 14.
A. Prat et al., "Bradykinin $B_1$ Receptor Expression and Function on T Lymphocytes in Active Multiple Sclerosis", Neurology, Dec. 10, 1999, pp. 2087-2092, vol. 53, No. 9, 1999 American Academy of Neurology, ISSN: 0028-3878.
J. Fred Hess, et al., "Generation and characterization of a humanized bradykinin B1 receptor mouse", Biol. Chem., vol. 387, pp. 195-201, Feb. 2006.
International Search Report dated Feb. 11, 2010 (Three (3) pages).
European Search Report dated Oct. 13, 2008 (Seven (7) pages).
PCT/ISA/237 (Eight (8) pages), 2007.

*Primary Examiner* — Kamal Saeed
*Assistant Examiner* — Kristin Bianchi
(74) *Attorney, Agent, or Firm* — Crowell & Moring LLP

(57) ABSTRACT

Substituted sulfonamide compounds corresponding to formula I:

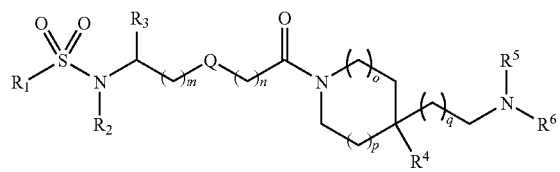

a process for their preparation, pharmaceutical compositions comprising such compounds, and the use of such substituted sulfonamide compounds in pharmaceutical compositions for the treatment of pain or other disorders or diseases that are mediated at least in part by B1R receptors.

20 Claims, No Drawings

SUBSTITUTED SULFONAMIDE COMPOUNDS

CROSS REFERENCE TO RELATED APPLICATIONS

This application claims priority from U.S. provisional patent application No. 61/043,254 and European patent application no. EP 08006959.4, both filed Apr. 8, 2008, the entire disclosures of which are incorporated herein by reference.

BACKGROUND OF THE INVENTION

The present invention relates to substituted sulfonamide compounds, to a process for their preparation, to pharmaceutical compositions comprising these compounds, and to the use of substituted sulfonamide compounds in the preparation of pharmaceutical compositions for the treatment of disorders or diseases that are mediated at least in part by B1R receptors.

Unlike the constitutive expression of the bradykinin 2 receptor (B2R), the bradykinin 1 receptor (B1R) is not expressed or is expressed only weakly in most tissues. However, the expression of B1R in various cells is inducible. For example, following inflammation reactions there is a rapid and pronounced induction of B1R in neuronal cells but also in various peripheral cells such as fibroblasts, endothelial cells, granulocytes, macrophages and lymphocytes. Accordingly, in the course of inflammation reactions there is a switch from B2R to B1R dominance in the cells that are involved. The cytokines interleukin-1 (IL-1) and tumour necrosis factor alpha (TNFα) play a substantial part in this B1R up-regulation (Passos et al., J. Immunol. 2004, 172, 1839-1847). Following activation with specific ligands, B1R-expressing cells are then themselves able to secrete inflammation-promoting cytokines such as IL-6 and IL-8 (Hayashi et al., Eur. Respir. J. 2000, 16, 452-458). This results in the immigration of further inflammatory cells, for example neutrophilic granulocytes (Pesquero et al., PNAS 2000, 97, 8140-8145). By way of these mechanisms, the bradykinin B1R system can contribute to the chronification of diseases. This is proved by a large number of animal experiments (overviews in Leeb-Lundberg et al., Pharmacol. Rev. 2005, 57, 27-77 and Pesquero et al., Biol. Chem. 2006, 387, 119-126). In humans too, enhanced expression of B1R is found, for example, in enterocytes and macrophages in the affected tissue of patients with inflammatory intestinal diseases (Stadnicki et al., Am. J. Physiol. Gastrointest. Liver Physiol. 2005, 289, G361-366) or on T-lymphocytes of patients with multiple sclerosis (Prat et al., Neurology, 1999; 53, 2087-2092), or activation of the bradykinin B2R-B1R system is found following infections with *Staphylococcus aureus* (Bengtson et al., Blood 2006, 108, 2055-2063). Infections with *Staphylococcus aureus* are responsible for symptoms such as superficial skin infections to septic shock.

Due to the described pathophysiological relationships there is a great therapeutic potential for the use of B1R antagonists in acute and, in particular, chronic inflammatory diseases. These include respiratory diseases (Asthma bronchiale, allergies, COPD/chronic-obstructive pulmonary disease, cystic fibrosis, etc.), inflammatory intestinal diseases (ulcerative colitis, CD/Crohn's disease, etc.), neurological diseases (multiple sclerosis, neurodegeneration, etc.), inflammations of the skin (atopic dermatitis, psoriasis, bacterial infections, etc.) and mucosa (Behcet's disease, pelvitis, prostatitis, etc.), rheumatic diseases (rheumatoid arthritis, osteoarthritis, etc.), septic shock and reperfusion syndrome (following heart attack, stroke).

In addition, the bradykinin (receptor) system is also involved in regulating angiogenesis (potential as an angiogenesis inhibitor in cancer and macular degeneration of the eye), and B1R knockout mice are protected against the induction of excess weight as a result of a particularly high-fat diet (Pesquero et al., Biol. Chem. 2006, 387, 119-126). B1R antagonists are therefore suitable also for the treatment of obesity.

B1R antagonists are suitable in particular for the treatment of pain, in particular inflammatory pain and neuropathic pain (Calixto et al., Br. J. Pharmacol. 2004, 1-16), in particular diabetic neuropathy (Gabra et al., Biol. Chem. 2006, 387, 127-143). They are also suitable for the treatment of migraine.

In the development of B1R modulators there is the problem, however, that the human and the rat B1R receptor differ so widely that many compounds which are good B1R modulators on the human receptor have only a poor or no affinity for the rat receptor. This makes animal pharmacology studies considerably more difficult, since many studies are usually conducted on the rat. However, if there is no activity on the rat receptor, neither action nor side-effect on the rat can be investigated on the rat. This has already meant that transgenic animals with human B1 receptors have been produced for animal pharmacology studies (Hess et al., Biol. Chem. 2006; 387(2):195-201). Working with transgenic animals is more expensive, however, than working with the unmodified animals. However, since in the development of pharmaceutical compositions precisely long-term toxicity studies on the rat belong to the standard investigations, but this does not make sense in the case of a lack of activity on the receptor, the development of such compounds lacks an important established instrument for checking safety. There is therefore a need for novel B1R modulators, B1R modulators that bind both to the rat receptor and to the human receptor offering particular advantages.

SUMMARY OF THE INVENTION

Accordingly, it was an object of the present invention to provide novel compounds which are suitable in particular as pharmacological active ingredients in pharmaceutical compositions, especially in pharmaceutical compositions for the treatment of disorders or diseases that are mediated at least in part by B1R receptors.

This and other objects are achieved by the substituted sulfonamide compounds according to the invention.

The invention thus provides substituted sulfonamide compounds of the general formula I

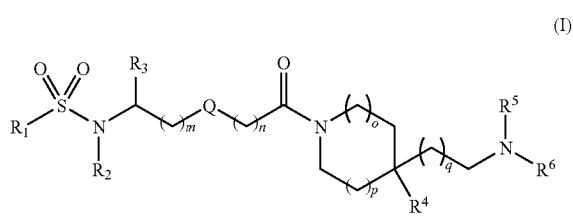

(I)

wherein
m represents 0, 1 or 2;
n represents 1 or 2;
o represents 0, 1 or 2;
p represents 0, 1 or 2;
q represents 0, 1, 2, 3 or 4;
Q represents a single bond, —O— or —CH$_2$—;

$R^1$ represents aryl or heteroaryl, or aryl or heteroaryl bonded via a $C_{1-3}$-alkylene group;

$R^2$ and $R^3$ are defined as described under (i) or (ii):

(i) $R^2$ represents H, $C_{1-6}$-alkyl, $C_{3-8}$-cycloalkyl, bicyclic 8- to 12-membered carbocyclyl, $CH(aryl)_2$, aryl or heteroaryl; or $C_{3-8}$-cycloalkyl, bicyclic 8- to 12-membered carbocyclyl, $CH(aryl)_2$, aryl or heteroaryl bonded via a $C_{1-6}$-alkylene group, $C_{2-6}$-alkenylene group or $C_{2-6}$-alkynylene group; and $R^3$ represents H, $C_{1-6}$-alkyl, aryl or heteroaryl; or aryl or heteroaryl bonded via a $C_{1-6}$-alkylene group, $C_{2-6}$-alkenylene group or $C_{2-6}$-alkynylene group; or (ii) $R^2$ and $R^3$, together with the group —N—(CH—)— joining them, form a heterocycle, which can be fused to an aryl or heteroaryl group, wherein the heterocycle is saturated or at least monounsaturated, but is not aromatic, is 4-, 5-, 6- or 7-membered and can contain, in addition to the N heteroatom to which $R^2$ is bonded, at least one further heteroatom or a heteroatom group selected from the group consisting of N, $NR^7$, O, S, S=O and $S(=O)_2$;

wherein $R^7$ represents H, $C_{1-6}$-alkyl, —C(=O)—$R^8$, $C_{3-8}$-cycloalkyl, aryl, heteroaryl, or $C_{3-8}$-cycloalkyl, aryl or heteroaryl bonded via a $C_{1-3}$-alkylene group, and $R^8$ denotes $C_{1-6}$-alkyl, $C_{3-8}$-cycloalkyl, aryl, heteroaryl, or $C_{3-8}$-cycloalkyl, aryl or heteroaryl bonded via a $C_{1-3}$-alkylene group;

$R^4$ denotes aryl, heteroaryl, or aryl or heteroaryl bonded via a $C_{1-6}$-alkylene group;

$R^5$ and $R^6$ each independently denote H, $C_{1-6}$-alkyl, $C_{3-8}$-cycloalkyl, or $C_{3-8}$-cycloalkyl bonded via a $C_{1-3}$-alkylene group, wherein $R^5$ and $R^6$ do not simultaneously represent H; or $R^5$ and $R^6$ together represent a substituted or unsubstituted 5- or 6-membered heteroaryl which can contain, in addition to the N atom to which $R^5$ and $R^6$ are bonded, also at least one further heteroatom from the group N, O and S, or $R^5$ and $R^6$ together represent a group selected from —$(CH_2)_d$— and —$(CH_2)_e$—X—$(CH_2)_f$—, wherein d denotes 2, 3, 4, 5 or 6 and e and f each independently denote 1, 2 or 3, with the proviso that e+f is not greater than 5; and X denotes $NR^{12}$, $CF_2$, O, S, S(=O) or $S(=O)_2$, and wherein $R^{12}$ denotes H, $C_{1-6}$-alkyl, $C_{3-8}$-cycloalkyl, aryl, heteroaryl, or $C_{3-8}$-cycloalkyl, aryl or heteroaryl bonded via a $C_{1-3}$-alkylene group; and wherein the above-mentioned groups $C_{1-6}$-alkyl, $C_{1-6}$-alkylene, $C_{2-6}$-alkenylene, $C_{2-6}$-alkynylene, $C_{3-8}$-cycloalkyl, $C_{3-8}$-heterocycloalkyl, bicyclic 8- to 12-membered carbocyclyl, aryl and heteroaryl can in each case be unsubstituted or mono- or poly-substituted by identical or different substituents, and the above-mentioned groups $C_{1-6}$-alkyl, $C_{1-6}$-alkylene, $C_{2-6}$-alkenylene and $C_{2-6}$-alkynylene can in each case be branched or unbranched;

in the form of an individual enantiomer or of an individual diastereoisomer, of the racemate, of the enantiomers, of the diastereoisomers, mixtures of the enantiomers and/or diastereoisomers, as well as in each case in the form of their bases and/or physiologically acceptable salts.

Within the scope of the present invention, the term "halogen" preferably denotes F, Cl, Br and I, particularly preferably F, Cl and Br.

Within the scope of this invention, the term "$C_{1-6}$-alkyl" includes acyclic saturated hydrocarbon groups having 1, 2, 3, 4, 5 or 6 carbon atoms, which can be branched- or straight-chained (unbranched) as well as unsubstituted or substituted one or more times, for example 2, 3, 4 or 5 times, by identical or different substituents. The alkyl groups can preferably be selected from the group consisting of methyl, ethyl, n-propyl, isopropyl, n-butyl, isobutyl, sec-butyl, tert-butyl, n-pentyl, isopentyl, neopentyl and hexyl. Particularly preferred alkyl groups can be selected from the group consisting of methyl, ethyl, n-propyl, isopropyl, n-butyl, sec-butyl, isobutyl and tert-butyl.

Within the scope of this invention, the term "$C_{2-6}$-alkenyl" includes acyclic unsaturated hydrocarbon groups having 2, 3, 4, 5 or 6 carbon atoms, which can be branched- or straight-chained (unbranched) as well as unsubstituted or substituted one or more times, for example 2, 3, 4 or 5 times, by identical or different substituents. Alkenyl groups contain at least one C=C double bond. Alkenyl groups can preferably be selected from the group consisting of vinyl, prop-1-enyl, allyl, 2-methylprop-1-enyl, but-1-enyl, but-2-enyl, but-3-enyl, but-1,3-dienyl, 2-methylprop-1-enyl, but-2-en-2-yl, but-1-en-2-yl, pentenyl and hexenyl. Particularly preferred alkenyl groups can be selected from the group consisting of vinyl, prop-1-enyl, allyl, 2-methylprop-1-enyl, but-1-enyl, but-2-enyl, but-3-enyl, but-1,3-dienyl, 2-methylprop-1-enyl, but-2-en-2-yl and but-1-en-2-yl.

Within the scope of this invention, the term "$C_{3-8}$-cycloalkyl" denotes cyclic saturated hydrocarbons having 3, 4, 5, 6, 7 or 8 carbon atoms, which can be unsubstituted or substituted on one or more ring members by one or more, for example by 2, 3, 4 or 5, identical or different substituents. $C_{3-8}$-Cycloalkyl can preferably be selected from the group consisting of cyclopropyl, cyclobutyl, cyclopentyl, cyclohexyl, cycloheptyl and cyclooctyl.

Within the scope of this invention, the term "aryl" denotes aromatic hydrocarbons, in particular phenyls and naphthyls. The aryl groups can also be fused with further saturated, (partially) unsaturated or aromatic ring systems. Each aryl group can be unsubstituted or substituted one or more times, for example 2, 3, 4 or 5 times, it being possible for the aryl substituents to be identical or different and to be located at any desired and possible position of the aryl. Aryl can advantageously be selected from the group consisting of phenyl, 1-naphthyl and 2-naphthyl, which can in each case be unsubstituted or substituted one or more times, for example by 2, 3, 4 or 5 groups.

Within the scope of the present invention, the term "heteroaryl" denotes a 5-, 6- or 7-membered cyclic aromatic group containing at least one, optionally also 2, 3, 4 or 5, heteroatom(s), it being possible for the heteroatoms to be identical or different and for the heteroaryl to be unsubstituted or substituted one or more times, for example 2, 3, 4 or 5 times, by identical or different substituents. The substituents can be bonded at any desired and possible position of the heteroaryl. The heterocycle can also be part of a bi- or polycyclic system, in particular a mono-, bi- or tri-cyclic system, which can then be more than 7-membered in total, preferably up to 14-membered. Preferred heteroatoms are selected from the group consisting of N, O and S. The heteroaryl group is preferably selected from the group consisting of pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, benzooxazolyl, benzoxadiazolyl, imidazothiazolyl, dibenzofuranyl, dibenzothienyl, phthalazinyl, pyrazolyl, imidazolyl, thiazolyl, oxadiazolyl, isoxazolyl, pyridinyl, pyridazinyl, pyrimidinyl, pyrazinyl, pyranyl, indazolyl, purinyl, indolizinyl, quinolinyl, isoquinolinyl, quinazolinyl, quinoxalinyl, carbazolyl, phenazinyl, phenothiazinyl and oxadiazolyl, it being possible for bonding to the compounds of the general structure I to take place via any desired and possible ring member of the heteroaryl group. The heteroaryl group can particularly preferably be selected from the group consisting of furyl, thienyl and pyridinyl.

Within the scope of the present invention, the expression "bicyclic 8- to 12-membered carbocyclyl" denotes cyclic hydrocarbon compounds consisting of two fused ring systems, the two ring systems together containing from 8 to 12 ring members and no heteroatoms. The two ring systems can have different ring sizes as well as different degrees of saturation. That is to say, each of the two ring systems independently can be either aromatic, saturated or partially unsaturated. Bicyclic 8- to 12-membered carbocycles are understood as being in particular compounds that consist of an aromatic ring system fused with a saturated ring system. Bonding to the general structure I can take place via any desired and possible ring member of the carbocyclyl group, but preferably via a ring member of an unsaturated ring. Particularly preferably, the bicyclic 8- to 12-membered carbocycle can be selected from the group consisting of 2,3-dihydro-1H-indenyl and 1,2,3,4-tetrahydronaphthyl.

Within the scope of the present invention, the term "$C_{1-6}$-alkylene group" includes acyclic saturated hydrocarbon groups having 1, 2, 3, 4, 5 or 6 carbon atoms, which can be branched- or straight-chained (unbranched) as well as unsubstituted or substituted one or more times, for example 2, 3, 4 or 5 times, by identical or different substituents and which link a corresponding group to the general structure of higher order. The alkylene groups can preferably be selected from the group consisting of —$CH_2$—, —$CH_2$—$CH_2$—, —CH($CH_3$)—, —$CH_2$—$CH_2$—$CH_2$—, —CH($CH_3$)—$CH_2$—, —CH($CH_2CH_3$)—, —$CH_2$—($CH_2$)$_2$—$CH_2$—, —CH($CH_3$)—$CH_2$—$CH_2$—, —$CH_2$—CH($CH_3$)—$CH_2$—, —CH($CH_3$)—CH($CH_3$)—, —CH($CH_2CH_3$)—$CH_2$—, —C($CH_3$)$_2$—$CH_2$—, —CH($CH_2CH_2CH_3$)—, —C($CH_3$)($CH_2CH_3$)—, —$CH_2$—($CH_2$)$_3$—$CH_2$—, —CH($CH_3$)—$CH_2$—$CH_2$—$CH_2$—, —$CH_2$—CH($CH_3$)—$CH_2$—$CH_2$—, —CH($CH_3$)—$CH_2$—CH($CH_3$)—, —CH($CH_3$)—CH($CH_3$)—$CH_2$—, —C($CH_3$)$_2$—$CH_2$—$CH_2$—, —$CH_2$—C($CH_3$)$_2$—$CH_2$—, —CH($CH_2CH_3$)—$CH_2$—$CH_2$—, —$CH_2$—CH($CH_2CH_3$)—$CH_2$—, —C($CH_3$)$_2$—CH($CH_3$)—, —CH($CH_2CH_3$)—CH($CH_3$)—, —C($CH_3$)($CH_2CH_3$)—$CH_2$—, —CH($CH_2CH_2CH_3$)—$CH_2$—, —C($CH_2CH_2CH_3$)—$CH_2$—, —CH($CH_2CH_2CH_2CH_3$)—, —C($CH_3$)($CH_2CH_2CH_3$)—, —C($CH_2CH_3$)$_2$— and —$CH_2$—($CH_2$)$_4$—$CH_2$—. Particularly preferably, the alkylene groups can be selected from the group consisting of —$CH_2$—, —$CH_2$—$CH_2$— and —$CH_2$—$CH_2$—$CH_2$—.

Within the scope of the present invention, the term "$C_{2-6}$-alkenylene group" includes acyclic, mono- or poly-unsaturated, for example di-, tri- or tetra-unsaturated, hydrocarbon groups having 2, 3, 4, 5 or 6 carbon atoms, which can be branched- or straight-chained (unbranched) as well as unsubstituted or substituted one or more times, for example 2, 3, 4 or 5 times, by identical or different substituents and which link a corresponding group to the general structure of higher order. The alkenylene groups contain at least one C═C double bond. The alkenylene groups can preferably be selected from the group consisting of —CH═CH—, —CH═CH—$CH_2$—, —C($CH_3$)═$CH_2$—, —CH═CH—$CH_2$—$CH_2$—, —$CH_2$—CH═CH—$CH_2$—, —CH═CH—CH═CH—, —C($CH_3$)═CH—$CH_2$—, —CH═C($CH_3$)—$CH_2$—, —C($CH_3$)═C($CH_3$)—, —C($CH_2CH_3$)═CH—, —CH═CH—$CH_2$—$CH_2$—$CH_2$—, —$CH_2$—CH═CH—$CH_2$—$CH_2$—, —$CH_2$—$CH_2$—CH═CH—$CH_2$—$CH_2$—, —CH═CH—CH═CH—$CH_2$—$CH_2$—, and —CH═CH—CH═CH—$CH_2$—.

Within the scope of the invention, the term "$C_{2-6}$-alkynylene group" includes acyclic, mono- or poly-unsaturated, for example di-, tri- or tetra-unsaturated, hydrocarbon groups having 2, 3, 4, 5 or 6 carbon atoms, which can be branched- or straight-chained (unbranched) as well as unsubstituted or substituted one or more times, for example 2, 3, 4 or 5 times, by identical or different substituents and which link a corresponding group to the general structure of higher order. The alkynylene groups contain at least one C≡C triple bond. The alkynylene groups can preferably be selected from the group consisting of —C≡C—, —C≡C—$CH_2$—, —C≡C—$CH_2$—$CH_2$—, —C≡C—CH($CH_3$)—, —$CH_2$—C≡C—$CH_2$—, —C≡C—C≡C—, —C≡C—C($CH_3$)$_2$—, —C≡C—$CH_2$—$CH_2$—$CH_2$—, —$CH_2$—C≡C—$CH_2$—$CH_2$—, —C≡C—C≡C—$CH_2$— and —C≡C—$CH_2$—C≡C—.

Within the scope of the present invention, the expression "aryl or heteroaryl bonded via a $C_{1-6}$-alkylene group, $C_{2-6}$-alkenylene group or $C_{2-6}$-alkynylene group" means that the $C_{1-6}$-alkylene groups, $C_{2-6}$-alkenylene groups, $C_{2-6}$-alkynylene groups as well as aryl or heteroaryl have the meanings defined above and the aryl or heteroaryl is bonded to the general structure of higher order via a $C_{1-6}$-alkylene group, $C_{2-6}$-alkenylene group or $C_{2-6}$-alkynylene group. Examples include benzyl, phenethyl and phenylpropyl.

Within the scope of the present invention, the expression "$C_{3-8}$-cycloalkyl and heterocyclyl bonded via a $C_{1-6}$-alkylene group, $C_{2-6}$-alkenylene group or $C_{2-6}$-alkynylene group" means that the $C_{1-6}$-alkylene group, $C_{2-6}$-alkenylene group, $C_{2-6}$-alkynylene group, $C_{3-8}$-cycloalkyl and heterocyclyl have the meanings defined above and $C_{3-8}$-cycloalkyl and heterocyclyl are bonded to the general structure of higher order via a $C_{1-6}$-alkylene group, $C_{2-6}$-alkenylene group or $C_{2-6}$-alkynylene group.

In connection with "alkyl", "alkenyl", "alkylene", "alkenylene", "alkynylene" and "cycloalkyl", the term "substituted" within the scope of this invention is understood as meaning the substitution of a hydrogen by F, Cl, Br, I, CN, $NH_2$, NH—$C_{1-6}$-alkyl, NH—$C_{1-6}$-alkylene-OH, $C_{1-6}$-alkyl, N($C_{1-6}$-alkyl)$_2$, N($C_{1-6}$-alkylene-OH)$_2$, $NO_2$, SH, S—$C_{1-6}$-alkyl, S-benzyl, O—$C_{1-6}$-alkyl, OH, O—$C_{1-6}$-alkylene-OH, ═O, O-benzyl, C(═O)$C_{1-6}$-alkyl, $CO_2H$, $CO_2$—$C_{1-6}$-alkyl or benzyl, wherein polysubstituted groups are to be understood as being groups which are polysubstituted, for example di- or tri-substituted, either on different atoms or on the same atom, for example trisubstituted on the same carbon atom, as in the case of $CF_3$ or $CH_2CF_3$, or at different positions, as in the case of CH(Cl)—CH═CH—$CHCl_2$. Polysubstitution can be carried out with the same or with different substituents, such as, for example, in the case of CH(OH)—CH═CH—$CHCl_2$.

In relation to "aryl" and "heteroaryl", "substituted" within the scope of this invention is understood as meaning the substitution of one or more hydrogen atoms of the corresponding ring system one or more times, for example 2, 3, 4 or 5 times, by F, Cl, Br, I, CN, $NH_2$, NH—$C_{1-6}$-alkyl, NH—$C_{1-6}$-alkylene-OH, N($C_{1-6}$-alkyl)$_2$, N($C_{1-6}$-alkylene-OH)$_2$, NH-aryl$^1$, N(aryl$^1$)$_2$, N($C_{1-6}$-alkyl)aryl$^1$, pyrrolinyl, piperazinyl, morpholinyl, $NO_2$, SH, S—$C_{1-6}$-alkyl, OH, O—$C_{1-6}$-alkyl, O—$C_{1-6}$-alkyl-OH, C(═O)$C_{1-6}$-alkyl, $NHSO_2C_{1-6}$-alkyl, $NHCOC_{1-6}$-alkyl, $CO_2H$, $CH_2SO_2$-phenyl, $CO_2$—$C_{1-6}$-alkyl, $OCF_3$, $CF_3$, —O—$CH_2$—O—, —O—$CH_2$—$CH_2$—O—, —O—C($CH_3$)$_2$—$CH_2$—, unsubstituted $C_{1-6}$-alkyl, pyrrolidinyl, imidazolyl, piperidinyl, benzyloxy, phenoxy, phenyl, naphthyl, pyridinyl, —$C_{1-3}$-alkylene-aryl$^1$, benzyl, thienyl, furyl, wherein aryl$^1$ represents phenyl, furyl, thienyl or pyridinyl, on one atom or on different atoms, wherein the above-mentioned substituents—unless indicated otherwise—can themselves optionally be substituted by the mentioned substituents. The polysubstitution of aryl and heteroaryl can be carried out with the same or with different substituents. Preferred substituents for aryl and heteroaryl can be selected from the group consisting of —O—$C_{1-3}$-alkyl, unsubstituted $C_{1-6}$-alkyl, F, Cl, Br, I, $CF_3$, $OCF_3$, OH, SH, phenyl, naphthyl, furyl, thienyl and pyridinyl, in particular from the group consisting of F, Cl, Br, $CF_3$, $CH_3$ and $OCH_3$.

In relation to "bicyclic 8- to 12-membered carbocyclyl", "substituted" within the scope of this invention is to be understood as meaning the mono- or poly-substitution of hydrogen atoms of the corresponding ring systems of the bicyclic carbocyclyl. The substituents that are bonded to a saturated or partially unsaturated ring system of the carbocyclyl are independently selected from the group of substituents defined above for cycloalkyl, that is to say from F, Cl, Br, I, CN, $NH_2$, NH—$C_{1-6}$-alkyl, NH—$C_{1-6}$-alkylene-OH, $C_{1-6}$-alkyl, N($C_{1-6}$-alkyl)$_2$, N($C_{1-6}$-alkylene-OH)$_2$, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$-alkyl, $CO_2H$, $CO_2$—$C_{1-6}$-alkyl and benzyl, wherein in a polysubstitution a plurality of hydrogen atoms of a ring member and/or one hydrogen atom on a plurality of ring members is/are substituted. Substituents that are bonded to an aromatic ring system of the carbocyclyl are independently selected from the group of substituents defined above for aryl or heteroaryl, that is to say from F, Cl, Br, I, CN, $NH_2$, NH—$C_{1-6}$-alkyl, NH—$C_{1-6}$-alkylene-OH, N($C_{1-6}$-alkyl)$_2$, N($C_{1-6}$-alkylene-OH)$_2$, NH-aryl$^1$, N(aryl$^1$)$_2$, N($C_{1-6}$-alkyl)aryl$^1$, pyrrolinyl, piperazinyl, morpholinyl, $NO_2$, SH, S—$C_{1-6}$-alkyl, OH, O—$C_{1-6}$-alkyl, O—$C_{1-6}$-alkyl-OH, C(=O)$C_{1-6}$-alkyl, $NHSO_2C_{1-6}$-alkyl, $NHCOC_{1-6}$-alkyl, $CO_2H$, $CH_2SO_2$-phenyl, $CO_2$—$C_{1-6}$-alkyl, $OCF_3$, $CF_3$, —O—$CH_2$—O—, —O—$CH_2$—$CH_2$—O—, —O—C($CH_3$)$_2$—$CH_2$—, unsubstituted $C_{1-6}$-alkyl, pyrrolidinyl, imidazolyl, piperidinyl, benzyloxy, phenoxy, phenyl, naphthyl, pyridinyl, —$C_{1-3}$-alkylene-aryl$^1$, benzyl, thienyl, furyl, wherein aryl$^1$ represents phenyl, furyl, thienyl or pyridinyl. Preferred substituents for aromatic ring members of bicyclic 8- to 12-membered carbocyclyl can be selected from the group consisting of —O—$C_{1-3}$-alkyl, unsubstituted $C_{1-6}$-alkyl, F, Cl, Br, I, $CF_3$, $OCF_3$, OH, SH, phenyl, naphthyl, furyl, thienyl and pyridinyl, in particular from the group consisting of F, Cl, Br, $CF_3$, $CH_3$ and $OCH_3$.

Within the scope of the present description, the symbol

used in formulas denotes the linking of a corresponding group to the particular general structure of higher order.

Within the scope of this invention, the term "physiologically acceptable salt" is understood as meaning preferably salts of the compounds according to the invention with inorganic or organic acids which are physiologically acceptable—in particular when used in humans and/or mammals. Examples of suitable acids are hydrochloric acid, hydrobromic acid, sulfuric acid, methanesulfonic acid, formic acid, acetic acid, oxalic acid, succinic acid, tartaric acid, mandelic acid, fumaric acid, maleic acid, lactic acid, citric acid, glutamic acid, 1,1-dioxo-1,2-dihydro-1$\lambda^6$-benzo[d]isothiazol-3-one (saccharinic acid), monomethylsebacic acid, 5-oxo-proline, hexane-1-sulfonic acid, nicotinic acid, 2-, 3- or 4-aminobenzoic acid, 2,4,6-trimethyl-benzoic acid, α-liponic acid, acetylglycine, hippuric acid, phosphoric acid and/or aspartic acid. The salts of hydrochloric acid (hydrochlorides) and of citric acid (citrates) are particularly preferred.

In a preferred embodiment of the present invention, $R^1$ in the substituted sulfonamide compounds according to the invention represents phenyl, naphthyl, indolyl, benzofuranyl, benzothiophenyl (benzothienyl); benzooxazolyl, benzo-oxadiazolyl, pyrrolyl, furanyl, thienyl, pyridinyl, pyridazinyl, pyrimidinyl, pyrazinyl, imidazothiazolyl, carbazolyl, dibenzofuranyl or dibenzothiophenyl (dibenzothienyl), benzyl or phenethyl, preferably phenyl, naphthyl, benzothiophenyl, benzoxadiazolyl, thiophenyl, pyridinyl, imidazothiazolyl or dibenzofuranyl, particularly preferably phenyl or naphthyl, in each case unsubstituted or mono- or poly-substituted by identical or different substituents, wherein the substituents are preferably selected from the group consisting of —O—$C_{1-3}$-alkyl, $C_{1-6}$-alkyl, F, Cl, Br, I, $CF_3$, $OCF_3$, OH, SH, phenyl, naphthyl, furyl, thienyl and pyridinyl.

In a further preferred embodiment of the present invention, $R^1$ in the substituted sulfonamide compounds according to the invention represents phenyl or naphthyl, wherein the phenyl or naphthyl is unsubstituted or mono- or poly-substituted, for example di-, tri-, tetra- or penta-substituted, by identical or different substituents selected from the group consisting of methyl, methoxy, $CF_3$, $OCF_3$, F, Cl and Br.

In a further preferred embodiment, $R^1$ in the sulfonamide compounds according to the invention is selected from the group consisting of 4-methoxy-2,3,6-trimethylphenyl, 4-methoxy-2,6-dimethylphenyl, 4-methoxy-2,3,5-trimethylphenyl, 2,4,6-trimethylphenyl, 2-chloro-6-methylphenyl, 2,4,6-trichlorophenyl, 2-chloro-6-(trifluoromethyl)phenyl, 2,6-dichloro-4-methoxyphenyl, 2-methylnaphthyl, 2-chloronaphthyl, 2-fluoronaphthyl, 2-chloro-4-(trifluoromethoxy)phenyl, 4-chloro-2,5-dimethylphenyl, 2,3-dichlorophenyl, 3,4-dichlorophenyl, 2,4-dichlorophenyl, 2-(trifluoromethyl)phenyl, 3-(trifluoromethyl)phenyl, 4-(trifluoromethyl)phenyl, 1-naphthyl and 2-naphthyl.

In a further preferred embodiment, p and o in the sulfonamide compounds according to the invention represent 1, or p represents 1 and o represents 0.

In a further preferred embodiment, in the sulfonamide compounds of formula I according to the invention, Q represents a single bond, m represents 0 or 1, and n represents 1 or 2; or Q represents —O—, m represents 1 or 2, and n represents 1.

In a further preferred embodiment, in the sulfonamide compounds according to the invention of the general formula I, Q represents a single bond, m represents 1 and n represents 2. In a specific embodiment of these compounds, $R^2$ and $R^3$, together with the group —N—(CH—)— joining them, form a heterocycle, which can be fused to an aryl or heteroaryl group, wherein the heterocycle is saturated or at least monounsaturated, but is not aromatic, is 4-, 5-, 6- or 7-membered and can contain, in addition to the N heteroatom to which $R^2$ is bonded, at least one further heteroatom or a heteroatom group selected from the group consisting of N, $NR^7$, O, S, S=O and S(=O)$_2$; wherein $R^7$ represents H, $C_{1-6}$-alkyl, —C(=O)—$R^8$, $C_{3-8}$-cycloalkyl, aryl, heteroaryl, or $C_{3-8}$-cycloalkyl, aryl or heteroaryl bonded via a $C_{1-3}$-alkylene group, and $R^8$ denotes $C_{1-6}$-alkyl, $C_{3-8}$-cycloalkyl, aryl, heteroaryl, or $C_{3-8}$-cycloalkyl, aryl or heteroaryl bonded via a $C_{1-3}$-alkylene group; especially $R^2$ and $R^3$ together with the group —N—(CH—)— joining them can form a piperidinyl group.

In a further preferred embodiment of the sulfonamide compounds according to the invention of the general formula I, $R^4$ denotes phenyl, phenyl bonded via a $C_{1-3}$-alkylene group; 2-, 3- or 4-pyridinyl, or 2-, 3- or 4-pyridinyl bonded via a $C_{1-3}$- alkylene group, wherein phenyl in each case can be mono- or poly-substituted by F, $C_1$ or $CF_3$. In particular, phenyl can be monosubstituted in the 3- or 4-position, in particular by F.

In a further preferred embodiment of the sulfonamide compounds according to the invention of the general formula I, q denotes 0, 1 or 2, in particular 1 or 2.

In a further preferred embodiment of the sulfonamide compounds according to the invention of the general formula I, $R^5$ and $R^6$ each independently represent unsubstituted or mono- or poly-substituted $C_{1-6}$-alkyl; or $R^5$ and $R^6$ together represent a group selected from —N═CH—CH═CH—, —CH═CH—N═CH—, —CH$_2$—CH$_2$—CH$_2$—; —CH$_2$—CH$_2$—CH$_2$—CH$_2$—, —CH$_2$—CH$_2$—CH$_2$—CH$_2$—CH$_2$— and —CH$_2$—CH$_2$—NR$^9$—CH$_2$—CH$_2$—, wherein $R^9$ represents H or $C_{1-6}$-alkyl. In particular, $R^5$ and $R^6$, including the N atom to which they are bonded, can form a group selected from

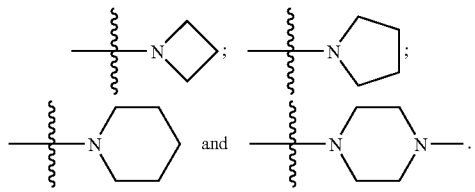

In a further preferred embodiment of the sulfonamide compounds according to the invention of the general formula I, $R^2$ represents H, $C_{1-6}$-alkyl, $C_{3-6}$-cycloalkyl, 8- to 10-membered benzo-fused cycloalkyl, CH(phenyl)$_2$, aryl or heteroaryl; or $R^2$ represents $C_{3-6}$-cycloalkyl, CH(phenyl)$_2$, aryl or heteroaryl bonded via a $C_{1-6}$-alkylene group, $C_{2-6}$-alkenylene group or $C_{2-6}$-alkynylene group, wherein the groups $C_{1-6}$-alkyl, $C_{3-6}$-cycloalkyl, $C_{2-6}$-alkylene, $C_{2-6}$-alkenylene, $C_{2-6}$-alkynylene, 8- to 10-membered benzo-fused cycloalkyl, aryl and heteroaryl can in each case be unsubstituted or substituted, aryl and heteroaryl can in particular be mono- or poly-substituted by identical or different substituents selected from the group consisting of $C_{1-6}$-alkyl, $C_{1-6}$-alkyl-O—, F, Cl, Br, I, $CF_3$, $OCF_3$, OH and SH.

In a further preferred embodiment of the substituted sulfonamide compounds according to the invention of the general formula I, $R^2$ represents H, substituted or unsubstituted $C_{1-6}$-alkyl, 2,3-dihydro-1H-indenyl or cyclopropyl; or $R^2$ represents CH(phenyl)$_2$, phenyl, pyridinyl, or phenyl or pyridinyl bonded via a $C_{1-6}$-alkylene group, wherein phenyl or pyridinyl is in each case unsubstituted or mono- or poly-substituted by identical or different substituents, wherein the groups are selected from the group consisting of methyl, ethyl, n-propyl, isopropyl, n-butyl, isobutyl, sec-butyl, tert-butyl, methoxy, F, Cl, Br, I, $CF_3$, $OCF_3$ and OH.

In a further variant of the compounds according to the invention of the general formula I, $R^3$ represents H, $C_{1-6}$-alkyl or aryl; or $R^3$ represents aryl bonded via a $C_{1-6}$-alkylene group, $C_{2-6}$-alkenylene group or $C_{2-6}$-alkynylene group, wherein the groups $C_{1-6}$-alkyl, $C_{3-6}$-cycloalkyl, $C_{2-6}$-alkylene, $C_{2-6}$-alkenylene, $C_{2-6}$-alkynylene or aryl can in each case be unsubstituted or substituted, aryl can in particular be mono- or poly-substituted by identical or different substituents selected from the group consisting of $C_{1-6}$-alkyl, $C_{1-6}$-alkyl-O—, F, Cl, Br, I, $CF_3$, $OCF_3$, OH and SH. In particular, $R^3$ can represent H or phenyl, wherein phenyl is itself in each case unsubstituted or mono- or poly-substituted by identical or different substituents, wherein the substituents are selected from the group consisting of methyl, ethyl, n-propyl, isopropyl, n-butyl, isobutyl, sec-butyl, tert-butyl, methoxy, F, Cl, Br, I, $CF_3$, $OCF_3$ and OH.

In a further preferred embodiment of the compounds according to the invention of the general formula I, the groups $R^2$ and $R^3$, together with the group —N—(CH—)— joining them, form a heterocycle of the general formula (II):

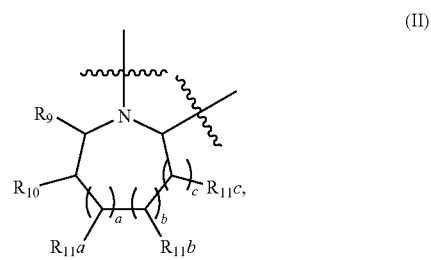

(II)

wherein
a, b and c each independently represent 0 or 1; and
$R^9$, $R^{10}$, $R^{11a}$, $R^{11b}$ and $R^{11c}$ each independently represent H, or two vicinal groups from $R^9$, $R^{10}$, $R^{11a}$, $R^{11b}$ and $R^{11c}$ form a 5- or 6-membered fused aryl or heteroaryl group, which can be unsubstituted or mono- or poly-substituted by identical or different substituents. In particular, the heterocycle (II) can be selected from

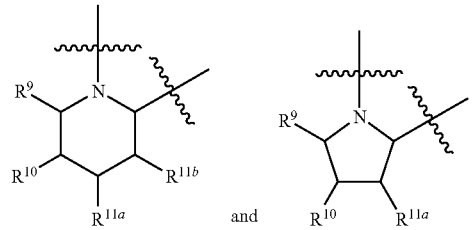

In particular, the groups $R^9$ and $R^{10}$ can together form a fused benzo group.

Persons skilled in the art will understand that the partial structure of the general formula (I) represented by the heterocycle (II)

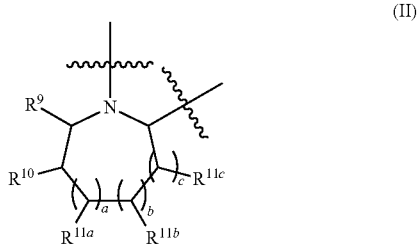

(II)

can assume the following forms for the particular values 0 and 1 of the indices a, b and c:

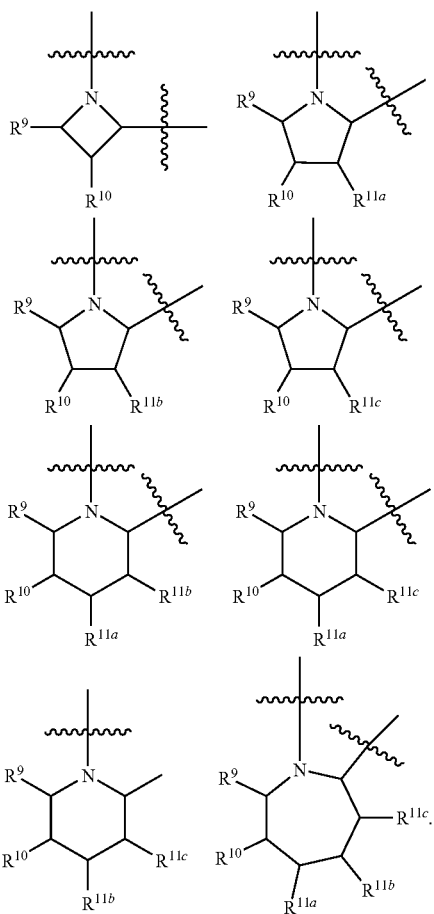

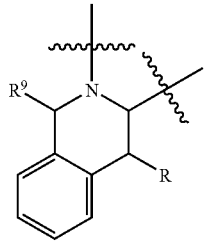

wherein R represents the corresponding group of $R^{11b}$ or $R^{11c}$; and for a heterocycle (II) in which one of the indices a, b or c=0 and the other two each =1 and two adjacent groups from $R^{11a}$, $R^{11b}$ or $R^{11c}$ form a fused benzene ring, the following form is obtained:

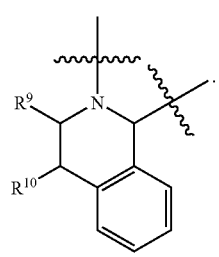

If the ring size of the heterocycles according to (II) described above permits it, that is to say for compounds in which a+b+c=2 or 3, it is also possible for two pairs of adjacent groups to form a fused ring, for example:

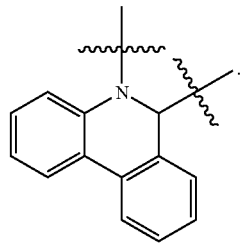

Persons skilled in the art will further understand that, where two vicinal (adjacent) groups from $R^9$, $R^{10}$, $R^{11a}$, $R^{11b}$ and $R^{11c}$ form a (fused) ring which is aromatic or is unsaturated on one or both of the carbon atoms that are linked to the vicinal groups, this/these carbon atom(s) cannot contain a further hydrogen.

For example, for a heterocycle according to (II) in which one of the indices a, b or c=0 and the other two each =1 and the adjacent groups $R^9$ and $R^{10}$ form a fused benzene ring, the following form is accordingly obtained:

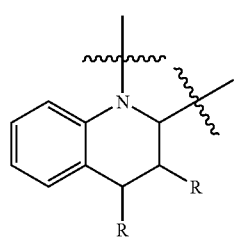

wherein R represents the corresponding group of $R^{11a}$, $R^{11b}$ or $R^{11c}$;

for a heterocycle according to (II) in which one of the indices a, b or c=0 and the other two each =1 and the adjacent groups $R^{10}$ and $R^{11a}$ or $R^{11b}$ form a fused benzene ring, the following form is accordingly obtained:

In a further preferred embodiment, the substituted sulfonamide compounds according to the invention are compounds of the general formula Ia

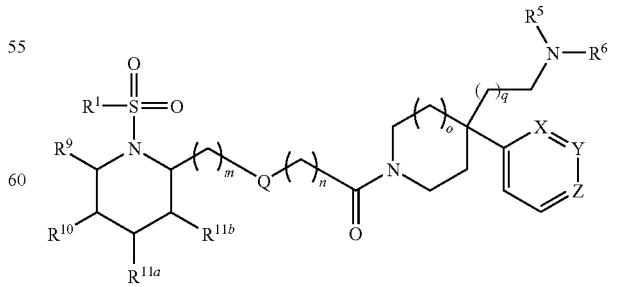

wherein X, Y or Z represent N, C—H; C—F, C—Cl or C—CF$_3$, with the proviso that only ever one of X, Y and Z is other than CH, wherein X, Y and Z preferably do not simultaneously represent C—H, and the groups Q, $R^1$, $R^5$ and $R^6$, $R^9$, $R^{10}$, $R^{11a}$ and $R^{11b}$ as well as the variables b, m, n, o and q can in each case have the meanings as in the embodiments according to the invention described hereinbefore.

In another preferred embodiment, the substituted sulfonamide compounds according to the invention are compounds of the general formula Ib

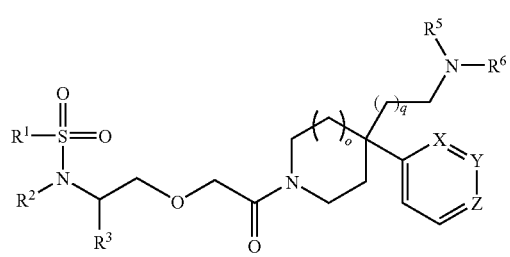

(Ib)

wherein X, Y or Z represent N, C—H; C—F, C—Cl or C—CF$_3$, with the proviso that only ever one of X, Y and Z is other than CH, wherein X, Y and Z preferably do not simultaneously represent C—H, and the groups Q, $R^1$, $R^5$ and $R^6$, $R^9$, $R^{10}$, $R^{11a}$ and $R^{11b}$ as well as the variables o and q can in each case have the meanings as in the embodiments according to the invention described hereinbefore.

In a further preferred embodiment, the substituted sulfonamide compounds according to the invention are compounds corresponding to the following formulas Ic, Id, Ie, If, and Ig:

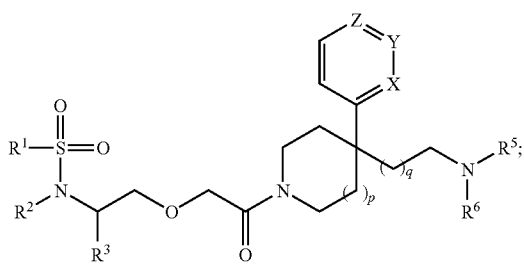

Ic

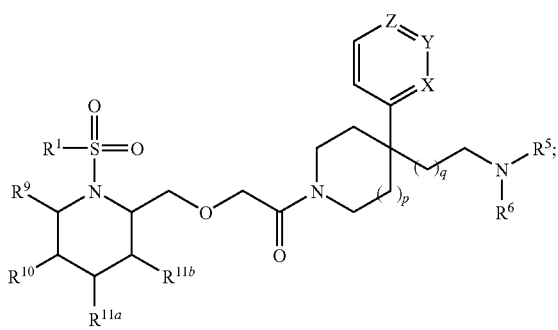

Id

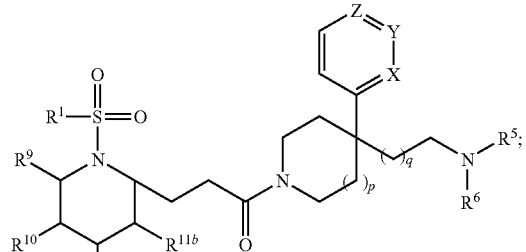

Ie

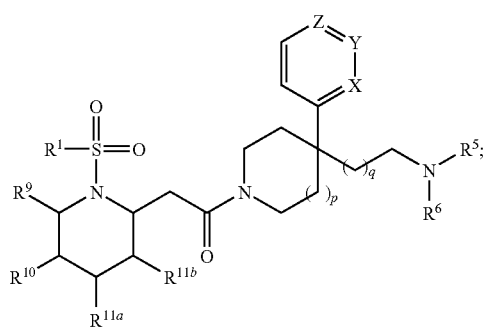

If

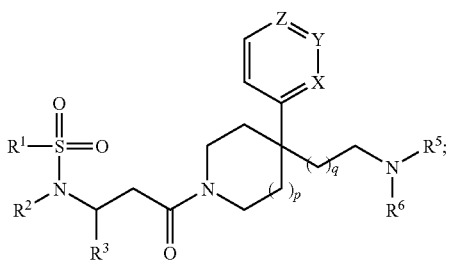

Ig wherein in the compounds of the general formulas Ic to Ig X, Y and Z are independently selected from the group consisting of CH, N, C—F, C—Cl and C—CF$_3$, with the proviso that only ever one of X, Y and Z is other than CH and X, Y and Z do not simultaneously represent C—H; and wherein the groups $R^1$, $R^2$, $R^3$, $R^5$, $R^6$, $R^9$, $R^{10}$, $R^{11a}$ and $R^{11b}$ as well as the variables p and q can in each case have the meanings described in the embodiments described hereinbefore. In the compounds of formulas Ic to Ig, p preferably represents 0 or 1, in particular 1, q preferably represents 1 or 2, X and Z preferably represent CH and Y represents N or C—F, preferably N. Furthermore, in the compounds of the general formulas Ic to Ig, $R^1$ preferably represents phenyl or naphthyl, wherein phenyl or naphthyl is unsubstituted or mono- or poly-substituted, for example di-, tri-, tetra- or penta-substituted, by identical or different substituents selected from the group consisting of methyl, methoxy, CF$_3$, OCF$_3$, F, Cl and Br; in particular, $R^1$ represents 4-methoxy-2,6-dimethylphenyl, 4-chloro-2,5-dimethylphenyl, 2,3-dichlorophenyl, 2,4-dichlorophenyl, 3,4-dichlorophenyl, 2-chloro-6-methylphenyl, 2-methyl-4-chlorophenyl, 2-(trifluoromethyl)phenyl, 3-(trifluoromethyl)phenyl, 1-naphthyl or 2-naphthyl. In the compounds of the general formulas Ic to Ig, $R^2$ is preferably selected from H, methyl, cyclopropyl, —CH(Ph)$_2$, (pyridin-3-yl)methyl and 2,3-dihydro-1H-inden-1-yl; the benzo group or the phenyl groups in $R^2$ can be unsubstituted or substituted, preferably by a substituent selected from methyl, methoxy, $CF_3$, F, Cl and Br. In the compounds of the general formulas Ic to Ig, $R^3$ is preferably selected from H and phenyl, wherein the phenyl group can be unsubstituted or substituted, preferably by a substituent selected from methyl, methoxy, $CF_3$, F, Cl and Br. In the compounds of the general formulas Ic to Ig, $R^5$ and $R^6$ independently of one another preferably represent unsubstituted or mono- or poly-substituted $C_{1-6}$-alkyl, in particular methyl, ethyl, n-propyl, isopropyl, n-butyl, isobutyl, sec-butyl or tert-butyl; or $R^5$ and $R^6$ together form a group selected from —N=CH—CH=CH—, —CH=CH—N=CH—, —CH$_2$—CH$_2$—CH$_2$—; —CH$_2$—CH$_2$—CH$_2$—CH$_2$—, —CH$_2$—CH$_2$—CH$_2$—CH$_2$—CH$_2$— and —CH$_2$—CH$_2$—NR$^9$—CH$_2$—CH$_2$—, wherein $R^9$ represents H or $C_{1-6}$-alkyl, in particular methyl, ethyl, n-propyl, isopropyl, n-butyl, isobutyl, sec-butyl or tert-butyl. In the compounds of the general formulas Ic to Ig, $R^9$, $R^{10}$, $R^{11a}$ and $R^{11b}$, each independently represent H, or two vicinal groups from $R^9$, $R^{10}$, $R^{11a}$ and $R^{11b}$, preferably $R^9$ and $R^{10}$, form a fused benzo group, which can be unsubstituted or mono- or poly-substituted by identical or different substituents, preferably by groups independently selected from the group consisting of methyl, methoxy, $CF_3$, F, Cl and Br.

In further preferred embodiments of the substituted sulfonamide compounds according to the invention, the partial structure A* from the general formula I

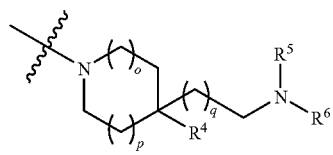

(A*)

represents a group selected from

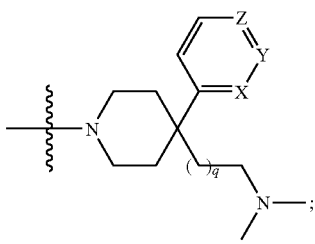

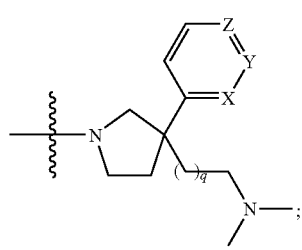

-continued

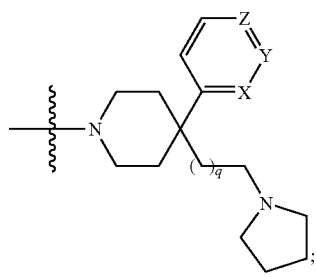

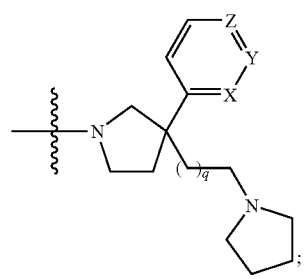

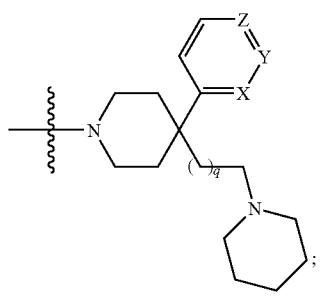

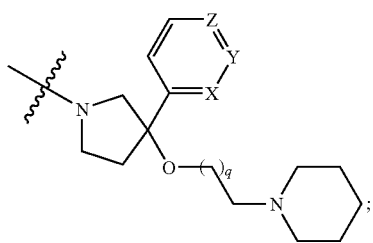

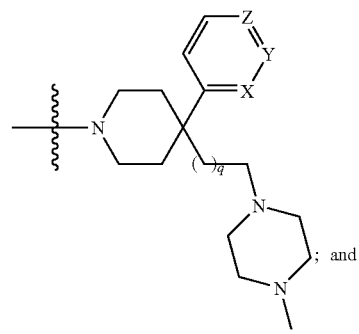

-continued

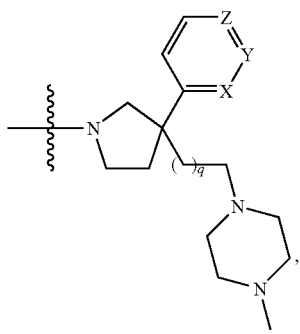

wherein q represents 0, 1 or 2, preferably 1 or 2, and X, Y and Z represent N, C—H; C—F, C—Cl or C—CF$_3$, with the proviso that only ever one of X, Y and Z is other than CH, wherein X, Y and Z preferably do not simultaneously represent C—H. It is particularly preferred for Y or Z, in particular Z, to represent N or CF. In a preferred embodiment, Y represents N and X and Z accordingly represent CH.

In further preferred embodiments of the substituted sulfonamide compounds according to the invention, the partial structure S* from the general formula I

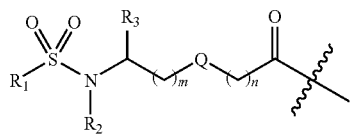

(S*)

is selected from the group consisting of

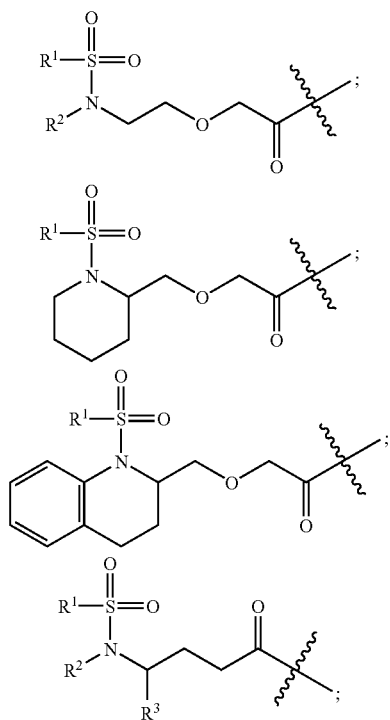

-continued

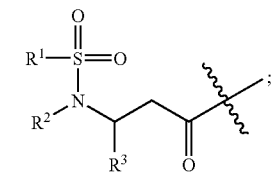

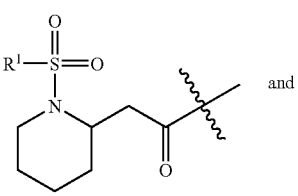

and

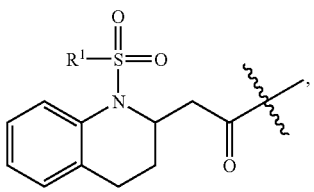

wherein the groups $R^1$, $R^2$ and $R^3$ have the meanings as in the embodiments according to the invention described hereinbefore.

In further preferred embodiments of the substituted sulfonamide compounds according to the invention, the above shown partial structure S* is selected from the group consisting of

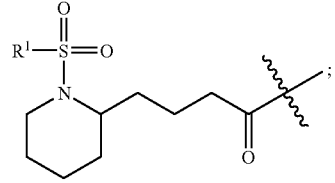

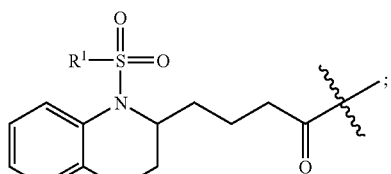

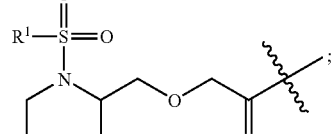

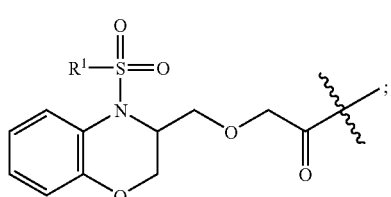

-continued

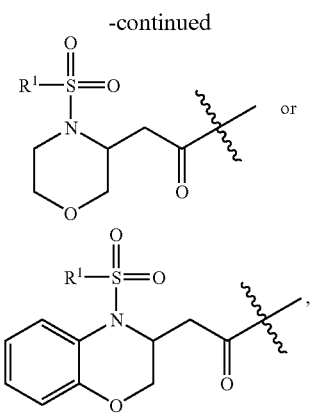

wherein R¹ has the meanings as in the embodiments according to the invention described hereinbefore and the fused benzen group can be substituted as described above with reference to the term "aryl".

In a further preferred embodiment of the present invention, the sulfonamide compounds according to the invention are selected from the group consisting of:

(1) N-(3-Oxo-1-phenyl-3-(4-(pyridin-3-yl)-4-(2-(pyrrolidin-1-yl)ethyl)piperidin-1-yl)propyl)naphthalene-2-sulfonamide;
(2) 2-((1-(4-Methoxy-2,6-dimethylphenylsulfonyl)piperidin-2-yl)methoxy)-1-(4-(pyridin-3-yl)-4-(2-(pyrrolidin-1-yl)ethyl)piperidin-1-yl)ethanone;
(3) 4-Methoxy-N,2,6-trimethyl-N-(2-(2-oxo-2-(4-(pyridin-3-yl)-4-(2-(pyrrolidin-1-yl)ethyl)piperidin-1-yl)ethoxy)ethyl)benzenesulfonamide;
(4) 1-(4-(Pyridin-3-yl)-4-(2-(pyrrolidin-1-yl)ethyl)piperidin-1-yl)-2-(1-(3-(trifluoromethyl)phenylsulfonyl)piperidin-2-yl)ethanone;
(5) 3-(1-(4-Chloro-2,5-dimethylphenylsulfonyl)piperidin-2-yl)-1-(4-(pyridin-3-yl)-4-(2-(pyrrolidin-1-yl)ethyl)piperidin-1-yl)propan-1-one;
(6) 2-((1-(3,4-Dichlorophenylsulfonyl)-1,2,3,4-tetrahydroquinolin-2-yl)methoxy)-1-(4-(pyridin-3-yl)-4-(2-(pyrrolidin-1-yl)ethyl)piperidin-1-yl)ethanone;
(7) N-(3-(4-(2-(Dimethylamino)ethyl)-4-(pyridin-3-yl)piperidin-1-yl)-3-oxo-1-phenylpropyl)naphthalene-2-sulfonamide;
(8) 1-(4-(2-(Dimethylamino)ethyl)-4-(pyridin-3-yl)piperidin-1-yl)-2-((1-(4-methoxy-2,6-dimethylphenylsulfonyl)piperidin-2-yl)methoxy)ethanone;
(9) N-(2-(2-(4-(2-(Dimethylamino)ethyl)-4-(pyridin-3-yl)piperidin-1-yl)-2-oxoethoxy)ethyl)-4-methoxy-N,2,6-trimethylbenzenesulfonamide;
(10) 1-(4-(2-(Dimethylamino)ethyl)-4-(pyridin-3-yl)piperidin-1-yl)-2-(1-(3-(trifluoromethyl)phenylsulfonyl)piperidin-2-yl)ethanone;
(11) 3-(1-(4-Chloro-2,5-dimethylphenylsulfonyl)piperidin-2-yl)-1-(4-(2-(dimethylamino)ethyl)-4-(pyridin-3-yl)piperidin-1-yl)propan-1-one;
(12) 2-((1-(3,4-Dichlorophenylsulfonyl)-1,2,3,4-tetrahydroquinolin-2-yl)methoxy)-1-(4-(2-(dimethylamino)ethyl)-4-(pyridin-3-yl)piperidin-1-yl)ethanone;
(13) 4-Methoxy-N,2,6-trimethyl-N-(2-(2-oxo-2-(4-(pyridin-3-yl)-4-(3-(pyrrolidin-1-yl)propyl)piperidin-1-yl)ethoxy)ethyl)benzenesulfonamide;
(14) 1-(4-(Pyridin-3-yl)-4-(3-(pyrrolidin-1-yl)propyl)piperidin-1-yl)-2-(1-(3-(trifluoromethyl)phenylsulfonyl)piperidin-2-yl)ethanone;
(15) 3-(1-(4-Chloro-2,5-dimethylphenylsulfonyl)piperidin-2-yl)-1-(4-(pyridin-3-yl)-4-(3-(pyrrolidin-1-yl)propyl)piperidin-1-yl)propan-1-one;
(16) 2-((1-(4-Methoxy-2,6-dimethylphenylsulfonyl)piperidin-2-yl)methoxy)-1-(4-(pyridin-3-yl)-4-(3-(pyrrolidin-1-yl)propyl)piperidin-1-yl)ethanone;
(17) N-(3-Oxo-1-phenyl-3-(4-(pyridin-3-yl)-4-(3-(pyrrolidin-1-yl)propyl)piperidin-1-yl)propyl)naphthalene-2-sulfonamide;
(18) 2-((1-(3,4-Dichlorophenylsulfonyl)-1,2,3,4-tetrahydroquinolin-2-yl)methoxy)-1-(4-(pyridin-3-yl)-4-(3-(pyrrolidin-1-yl)propyl)piperidin-1-yl)ethanone;
(19) 3-(1-(4-Chloro-2,5-dimethylphenylsulfonyl)piperidin-2-yl)-1-(4-(3-(dimethylamino)propyl)-4-(pyridin-3-yl)piperidin-1-yl)propan-1-one;
(20) N-(3-(4-(3-(Dimethylamino)propyl)-4-(pyridin-3-yl)piperidin-1-yl)-3-oxo-1-phenylpropyl)naphthalene-2-sulfonamide;
(21) 2-((1-(3,4-Dichlorophenylsulfonyl)-1,2,3,4-tetrahydroquinolin-2-yl)methoxy)-1-(4-(3-(dimethylamino)propyl)-4-(pyridin-3-yl)piperidin-1-yl)ethanone;
(22) 1-(4-(3-(Dimethylamino)propyl)-4-(pyridin-3-yl)piperidin-1-yl)-2-((1-(4-methoxy-2,6-dimethylphenylsulfonyl)piperidin-2-yl)methoxy)ethanone;
(23) N-(2-(2-(4-(3-(Dimethylamino)propyl)-4-(pyridin-3-yl)piperidin-1-yl)-2-oxoethoxy)ethyl)-4-methoxy-N,2,6-trimethylbenzenesulfonamide;
(24) 1-(4-(3-(Dimethylamino)propyl)-4-(pyridin-3-yl)piperidin-1-yl)-2-(1-(3-(trifluoromethyl)phenylsulfonyl)piperidin-2-yl)ethanone;
(25) (S)-2-((1-(4-Methoxy-2,6-dimethylphenylsulfonyl)piperidin-2-yl)methoxy)-1-(4-(pyridin-3-yl)-4-(pyrrolidin-1-ylmethyl)piperidin-1-yl)ethanone;
(26) 2-[[1-[(4-Methoxy-2,6-dimethyl-phenyl)sulfonyl]-piperidin-2-yl]-methoxy]-1-[4-pyridin-3-yl-4-(3-pyrrolidin-1-yl-propyl)-piperidin-1-yl]-ethanone;
(27) 2-[[1-[(4-Methoxy-2,6-dimethyl-phenyl)sulfonyl]-piperidin-2-yl]-methoxy]-1-[4-pyridin-3-yl-4-(3-pyrrolidin-1-yl-propyl)-piperidin-1-yl]-ethanone;
(28) 2-[[1-[(4-Methoxy-2,6-dimethyl-phenyl)sulfonyl]-piperidin-2-yl]-methoxy]-1-[4-pyridin-4-yl-4-(3-pyrrolidin-1-yl-propyl)-piperidin-1-yl]-ethanone;
(29) 4-Methoxy-N,2,6-trimethyl-N-[2-[2-oxo-2-[4-pyridin-3-yl-4-(3-pyrrolidin-1-yl-propyl)-piperidin-1-yl]-ethoxy]-ethyl]-benzenesulfonic acid amide;
(30) 4-Methoxy-N,2,6-trimethyl-N-[2-[2-oxo-2-[4-pyridin-4-yl-4-(3-pyrrolidin-1-yl-propyl)-piperidin-1-yl]-ethoxy]-ethyl]-benzenesulfonic acid amide;
(31) 4-Methoxy-N,2,3,6-tetramethyl-N-[2-[2-oxo-2-[4-pyridin-3-yl-4-(3-pyrrolidin-1-yl-propyl)-piperidin-1-yl]-ethoxy]-ethyl]-benzenesulfonic acid amide;
(32) 4-Methoxy-N,2,3,6-tetramethyl-N-[2-[2-oxo-2-[4-pyridin-4-yl-4-(3-pyrrolidin-1-yl-propyl)-piperidin-1-yl]-ethoxy]-ethyl]-benzenesulfonic acid amide;
(37) N-Benzyl-4-Methoxy-2,6-dimethyl-N-[2-[2-oxo-2-[4-pyridin-3-yl-4-(3-pyrrolidin-1-yl-propyl)-piperidin-1-yl]-ethoxy]-ethyl]-benzenesulfonic acid amide;
(38) N-Benzyl-4-Methoxy-2,6-dimethyl-N-[2-[2-oxo-2-[4-pyridin-3-yl-4-(3-pyrrolidin-1-yl-propyl)-piperidin-1-yl]-ethoxy]-ethyl]-benzenesulfonic acid amide;
(39) N-Benzyl-4-Methoxy-2,6-dimethyl-N-[2-[2-oxo-2-[4-pyridin-4-yl-4-(3-pyrrolidin-1-yl-propyl)-piperidin-1-yl]-ethoxy]-ethyl]-benzenesulfonic acid amide;
(40) N-Benzyl-4-Methoxy-2,6-dimethyl-N-[2-[2-oxo-2-[4-pyridin-4-yl-4-(3-pyrrolidin-1-yl-propyl)-piperidin-1-yl]-ethoxy]-ethyl]-benzenesulfonic acid amide;

(41) 1-[4-Pyridin-3-yl-4-(3-pyrrolidin-1-yl-propyl)-piperidin-1-yl]-2-[[1-[[2-(trifluoromethyl)-phenyl]sulfonyl]-piperidin-2-yl]-methoxy]-ethanone;
(42) 1-[4-Pyridin-3-yl-4-(3-pyrrolidin-1-yl-propyl)-piperidin-1-yl]-2-[[1-[[2-(trifluoromethyl)-phenyl]sulfonyl]-piperidin-2-yl]-methoxy]-ethanone;
(43) 1-[4-Pyridin-4-yl-4-(3-pyrrolidin-1-yl-propyl)-piperidin-1-yl]-2-[[1-[[2-(trifluoromethyl)-phenyl]sulfonyl]-piperidin-2-yl]-methoxy]-ethanone;
(44) 1-[4-Pyridin-4-yl-4-(3-pyrrolidin-1-yl-propyl)-piperidin-1-yl]-2-[[1-[[2-(trifluoromethyl)-phenyl]sulfonyl]-piperidin-2-yl]-methoxy]-ethanone;
(45) 2-[2-[1-[(4-Methoxy-2,6-dimethyl-phenyl)sulfonyl]-piperidin-2-yl]-ethoxy]-1-[4-pyridin-3-yl-4-(3-pyrrolidin-1-yl-propyl)-piperidin-1-yl]-ethanone;
(46) 2-[2-[1-[(4-Methoxy-2,6-dimethyl-phenyl)sulfonyl]-piperidin-2-yl]-ethoxy]-1-[4-pyridin-3-yl-4-(3-pyrrolidin-1-yl-propyl)-piperidin-1-yl]-ethanone;
(47) N-Methyl-N-[4-Oxo-4-[4-pyridin-3-yl-4-(3-pyrrolidin-1-yl-propyl)-piperidin-1-yl]-butyl]-3-(trifluoromethyl)-benzenesulfonic acid amide;
(48) 4-Methoxy-2,6-Dimethyl-N-[2-[2-oxo-2-[4-pyridin-3-yl-4-(3-pyrrolidin-1-yl-propyl)-piperidin-1-yl]-ethoxy]-ethyl]-N-phenyl-benzenesulfonic acid amide;
(49) 4-Methoxy-2,6-Dimethyl-N-[2-[2-oxo-2-[4-pyridin-3-yl-4-(3-pyrrolidin-1-yl-propyl)-piperidin-1-yl]-ethoxy]-ethyl]-N-phenyl-benzenesulfonic acid amide;
(50) 4-Methoxy-2,6-Dimethyl-N-[2-[2-oxo-2-[4-pyridin-4-yl-4-(3-pyrrolidin-1-yl-propyl)-piperidin-1-yl]-ethoxy]-ethyl]-N-phenyl-benzenesulfonic acid amide;
(51) 2-[[1-(Naphthalen-2-ylsulfonyl)-1,2,3,4-tetrahydro-quinolin-2-yl]-methoxy]-1-[4-pyridin-3-yl-4-(3-pyrrolidin-1-yl-propyl)-piperidin-1-yl]-ethanone;
(52) 2-[[1-(Naphthalen-2-ylsulfonyl)-1,2,3,4-tetrahydro-quinolin-2-yl]-methoxy]-1-[4-pyridin-3-yl-4-(3-pyrrolidin-1-yl-propyl)-piperidin-1-yl]-ethanone;
(53) 2-[[1-[(4-Methoxy-2,6-dimethyl-phenyl)sulfonyl]-1,2,3,4-tetrahydro-quinolin-2-yl]-methoxy]-1-[4-pyridin-3-yl-4-(3-pyrrolidin-1-yl-propyl)-piperidin-1-yl]-ethanone;
(54) 2-[[1-[(4-Methoxy-2,6-dimethyl-phenyl)sulfonyl]-1,2,3,4-tetrahydro-quinolin-2-yl]-methoxy]-1-[4-pyridin-3-yl-4-(3-pyrrolidin-1-yl-propyl)-piperidin-1-yl]-ethanone;
(55) 2-[[1-[(4-Methoxy-2,6-dimethyl-phenyl)sulfonyl]-1,2,3,4-tetrahydro-quinolin-2-yl]-methoxy]-1-[4-pyridin-4-yl-4-(3-pyrrolidin-1-yl-propyl)-piperidin-1-yl]-ethanone;
(56) 4-[1-[(2-Chloro-6-methyl-phenyl)sulfonyl]-piperidin-2-yl]-1-[4-pyridin-4-yl-4-(3-pyrrolidin-1-yl-propyl)-piperidin-1-yl]-butan-1-one;
(57) 1-[4-Pyridin-3-yl-4-(3-pyrrolidin-1-yl-propyl)-piperidin-1-yl]-4-[1-[[2-(trifluoromethyl)-phenyl]sulfonyl]-piperidin-2-yl]-butan-1-one;
(58) 1-[4-Pyridin-4-yl-4-(3-pyrrolidin-1-yl-propyl)-piperidin-1-yl]-4-[1-[[2-(trifluoromethyl)-phenyl]sulfonyl]-piperidin-2-yl]-butan-1-one;
(59) 1-[4-Pyridin-4-yl-4-(3-pyrrolidin-1-yl-propyl)-piperidin-1-yl]-4-[1-[[2-(trifluoromethyl)-phenyl]sulfonyl]-piperidin-2-yl]-butan-1-one;
(60) 4-[1-[(4-Methoxy-2,6-dimethyl-phenyl)sulfonyl]-piperidin-2-yl]-1-[4-pyridin-3-yl-4-(3-pyrrolidin-1-yl-propyl)-piperidin-1-yl]-butan-1-one;
(61) 4-[1-[(4-Methoxy-2,6-dimethyl-phenyl)sulfonyl]-piperidin-2-yl]-1-[4-pyridin-3-yl-4-(3-pyrrolidin-1-yl-propyl)-piperidin-1-yl]-butan-1-one;
(62) 4-[1-[(4-Methoxy-2,6-dimethyl-phenyl)sulfonyl]-piperidin-2-yl]-1-[4-pyridin-4-yl-4-(3-pyrrolidin-1-yl-propyl)-piperidin-1-yl]-butan-1-one;
(63) 4-[1-[(4-Methoxy-2,6-dimethyl-phenyl)sulfonyl]-piperidin-2-yl]-1-[4-pyridin-4-yl-4-(3-pyrrolidin-1-yl-propyl)-piperidin-1-yl]-butan-1-one;
(64) 4-[1-(Naphthalen-1-ylsulfonyl)-piperidin-2-yl]-1-[4-pyridin-4-yl-4-(3-pyrrolidin-1-yl-propyl)-piperidin-1-yl]-butan-1-one;
(65) N-Benzhydryl-N-[2-[2-oxo-2-[4-pyridin-4-yl-4-(3-pyrrolidin-1-yl-propyl)-piperidin-1-yl]-ethoxy]-ethyl]-methanesulfonic acid amide;
(66) N-Benzhydryl-N-[2-[2-oxo-2-[4-pyridin-4-yl-4-(3-pyrrolidin-1-yl-propyl)-piperidin-1-yl]-ethoxy]-ethyl]-methanesulfonic acid amide;
(67) 2-[[4-[(4-Methoxy-2,6-dimethyl-phenyl)sulfonyl]-3,4-dihydro-2H-[1,4]benzoxazin-3-yl]-methoxy]-1-[4-pyridin-3-yl-4-(3-pyrrolidin-1-yl-propyl)-piperidin-1-yl]-ethanone;
(68) 2-[[4-[(4-Methoxy-2,6-dimethyl-phenyl)sulfonyl]-3,4-dihydro-2H-[1,4]benzoxazin-3-yl]-methoxy]-1-[4-pyridin-3-yl-4-(3-pyrrolidin-1-yl-propyl)-piperidin-1-yl]-ethanone;
(69) 2-[[4-[(4-Methoxy-2,6-dimethyl-phenyl)sulfonyl]-3,4-dihydro-2H-[1,4]benzoxazin-3-yl]-methoxy]-1-[4-pyridin-4-yl-4-(3-pyrrolidin-1-yl-propyl)-piperidin-1-yl]-ethanone;
(70) 2-[[4-[(4-Methoxy-2,6-dimethyl-phenyl)sulfonyl]-3,4-dihydro-2H-[1,4]benzoxazin-3-yl]-methoxy]-1-[4-pyridin-4-yl-4-(3-pyrrolidin-1-yl-propyl)-piperidin-1-yl]-ethanone;
(71) 4-Methoxy-2,6-Dimethyl-N-[2-[2-oxo-2-[4-pyridin-3-yl-4-(3-pyrrolidin-1-yl-propyl)-piperidin-1-yl]-ethoxy]-ethyl]-N-(quinolin-3-yl-methyl)-benzenesulfonic acid amide;
(72) 2-[[4-[(2-chlor-6-methyl-phenyl)sulfonyl]-3,4-dihydro-2H-[1,4]benzoxazin-3-yl]-methoxy]-1-[4-pyridin-3-yl-4-(3-pyrrolidin-1-yl-propyl)-piperidin-1-yl]-ethanone;
(73) 1-[4-Pyridin-3-yl-4-(3-pyrrolidin-1-yl-propyl)-piperidin-1-yl]-2-[[4-[[2-(trifluoromethyl)-phenyl]sulfonyl]-3,4-dihydro-2H-[1,4]benzoxazin-3-yl]-methoxy]-ethanone;
(74) 1-[4-Pyridin-3-yl-4-(3-pyrrolidin-1-yl-propyl)-piperidin-1-yl]-2-[[4-[[2-(trifluoromethyl)-phenyl]sulfonyl]-3,4-dihydro-2H-[1,4]benzoxazin-3-yl]-methoxy]-ethanone;
(75) 1-[4-Pyridin-4-yl-4-(3-pyrrolidin-1-yl-propyl)-piperidin-1-yl]-2-[[4-[[2-(trifluoromethyl)-phenyl]sulfonyl]-3,4-dihydro-2H-[1,4]benzoxazin-3-yl]-methoxy]-ethanone;
(76) N-(4H-[1,3]Benzodioxin-7-yl-methyl)-4-methoxy-2,6-dimethyl-N-[2-[2-oxo-2-[4-pyridin-4-yl-4-(3-pyrrolidin-1-yl-propyl)-piperidin-1-yl]-ethoxy]-ethyl]-benzenesulfonic acid amide;
(77) 2-Chloro-N-[2-[2-[4-(3-chlorophenyl)-4-(3-pyrrolidin-1-yl-propyl)-piperidin-1-yl]-2-oxo-ethoxy]-ethyl]-N-cyclopropyl-6-methyl-benzenesulfonic acid amide;
(78) 2-Chloro-N-cyclopropyl-6-methyl-N-[2-[2-oxo-2-[4-(3-pyrrolidin-1-yl-propyl)-4-[3-(trifluoromethyl)phenyl]-piperidin-1-yl]-ethoxy]-ethyl]-benzenesulfonic acid amide;
(79) 2-Chloro-N-cyclopropyl-N-[2-[2-[4-(3-fluorophenyl)-4-(3-pyrrolidin-1-yl-propyl)-piperidin-1-yl]-2-oxo-ethoxy]-ethyl]-6-methyl-benzenesulfonic acid amide;
(80) 2-[[(2S)-1-[(4-Methoxy-2,6-dimethyl-phenyl)sulfonyl]-piperidin-2-yl]-methoxy]-1-[4-pyridin-3-yl-4-(2-pyrrolidin-1-yl-ethyl)-piperidin-1-yl]-ethanone hydrochloride; and
(81) 2-[[(2S)-1-[(4-Methoxy-2,6-dimethyl-phenyl)sulfonyl]-piperidin-2-yl]-methoxy]-1-[4-pyridin-3-yl-4-(3-pyrrolidin-1-yl-propyl)-piperidin-1-yl]-ethanone hydrochloride.

The numbering of the individual embodiments of the compounds according to the invention that is used above is retained in the explanations of the present invention that are given hereinbelow, in particular in the description of the examples.

The compounds according to the invention preferably exhibit an antagonistic action on the human B1R receptor or the B1R receptor of the rat. In a preferred embodiment of the invention, the compounds according to the invention exhibit an antagonistic action both on the human B1R receptor (hB1R) and on the B1R receptor of the rat (rB1R).

Particular preference is given to compounds that exhibit an inhibition of at least 15%, 25%, 50%, 70%, 80% or 90% on the human B1R receptor and/or on the B1R receptor of the rat in the FLIPR assay at a concentration of 10 µM. Most particular preference is given to compounds that exhibit an inhibition of at least 70%, in particular of at least 80% and particularly preferably of at least 90%, on the human B1R receptor and on the B1R receptor of the rat at a concentration of 10 µM.

The agonistic or antagonistic action of substances can be quantified on the bradykinin receptor 1 (B1R) of the species human and rat using ectopically expressing cell lines (CHO K1 cells) and with the aid of a $Ca^{2+}$-sensitive dye (Fluo-4) using a fluorescent imaging plate reader (FLIPR). The indication in % activation is based on the $Ca^{2+}$ signal after addition of Lys-Des-Arg$^9$-bradykinin (0.5 nM) or Des-Arg$^9$-bradykinin (100 nM). Antagonists lead to suppression of the $Ca^{2+}$ influx after the addition of the agonist. % Inhibition compared with the maximum achievable inhibition is indicated.

The substances according to the invention can act, for example, on B1R, which is relevant in connection with various diseases, so that they are suitable as a pharmaceutical active ingredient in pharmaceutical compositions. The invention accordingly further provides pharmaceutical compositions comprising at least one substituted sulfonamide compound according to the invention as well as, optionally, suitable additives and/or auxiliary substances and/or optionally further active ingredients.

The pharmaceutical compositions according to the invention optionally comprise, in addition to at least one substituted sulfonamide compound according to the invention, suitable additives and/or auxiliary substances, that is to say also carriers, fillers, solvents, diluents, colorings and/or binders, and can be administered as liquid pharmaceutical composition forms in the form of injection solutions, drops or juices, or as semi-solid pharmaceutical composition forms in the form of granules, tablets, pellets, patches, capsules, plasters/spray-on plasters or aerosols. The choice of the auxiliary substances etc. and the amounts thereof to be employed depend on whether the pharmaceutical composition is to be administered orally, perorally, parenterally, intravenously, intraperitoneally, intradermally, intramuscularly, intranasally, buccally, rectally or topically, for example to the skin, the mucous membranes or into the eyes. Preparations in the form of tablets, dragées, capsules, granules, drops, juices and syrups are suitable for oral administration, and solutions, suspensions, readily reconstitutable dry formulations and sprays are suitable for parenteral, topical and inhalatory administration. Sulfonamide compounds according to the invention in a depot, in dissolved form or in a plaster, optionally with the addition of agents which promote penetration through the skin, are suitable formulations for percutaneous administration. Forms of preparation which can be used orally or percutaneously can release the substituted sulfonamide compounds according to the invention in a delayed manner. The substituted sulfonamide compounds according to the invention can also be used in parenteral long-term depot forms, such as, for example, implants or implanted pumps. In principle, other further active ingredients known to the person skilled in the art can be added to the pharmaceutical compositions according to the invention.

The amount of active ingredient to be administered to the patient varies according to the weight of the patient, the type of administration, the indication and the severity of the disease. From 0.00005 to 50 mg/kg, preferably from 0.01 to 5 mg/kg, of at least one substituted sulfonamide compound according to the invention are conventionally administered.

In a preferred form of the pharmaceutical composition, a substituted sulfonamide compound according to the invention that is present is in the form of a pure diastereoisomer and/or enantiomer, in the form of the racemate or in the form of a non-equimolar or equimolar mixture of the diastereoisomers and/or enantiomers.

B1R is involved in particular in the occurrence of pain. Accordingly, the substituted sulfonamide compounds according to the invention can be used in the preparation of a pharmaceutical composition for the treatment of pain, in particular of acute, visceral, neuropathic or chronic pain.

Accordingly, the invention further provides the use of a substituted sulfonamide compound according to the invention for the treatment of and/or in the preparation of a pharmaceutical composition for the treatment of pain, in particular of acute, visceral, neuropathic or chronic pain.

In a further embodiment the use of a substituted sulfonamide according to the invention for the treatment and/or in the preparation of a pharmaceutical composition for the treatment of inflammatory pain is provided.

The invention further provides the use of a substituted sulfonamide compound according to the invention for the treatment and/or in the preparation of a pharmaceutical composition for the treatment of diabetes, respiratory diseases, for example Asthma bronchiale, allergies, COPD/chronic-obstructive pulmonary disease or cystic fibrosis; inflammatory intestinal diseases, for example ulcerative colitis or CD/Crohn's disease; neurological diseases, for example multiple sclerosis or neurodegeneration; inflammations of the skin, for example atopic dermatitis, psoriasis or bacterial infections; rheumatic diseases, for example rheumatoid arthritis or osteoarthritis; septic shock; reperfusion syndrome, for example following heart attack or stroke, obesity; and as an angiogenesis inhibitor.

It can be preferred in one of the above uses for a substituted sulfonamide compound that is used to be in the form of a pure diastereoisomer and/or enantiomer, in the form of the racemate or in the form of a non-equimolar or equimolar mixture of the diastereoisomers and/or enantiomers.

The invention further provides a method of treating, in particular in one of the above-mentioned indications, a non-human mammal or a human being requiring treatment of pain, in particular chronic pain, by administration of a therapeutically effective dose of a substituted sulfonamide compound according to the invention, or of a pharmaceutical composition according to the invention.

The invention further provides a process for the preparation of the substituted sulfonamide compounds according to the invention, as set out in the following description, examples and claims.

In an aspect of the present invention, the substituted sulfonamide compounds of the invention are prepared by the following process:

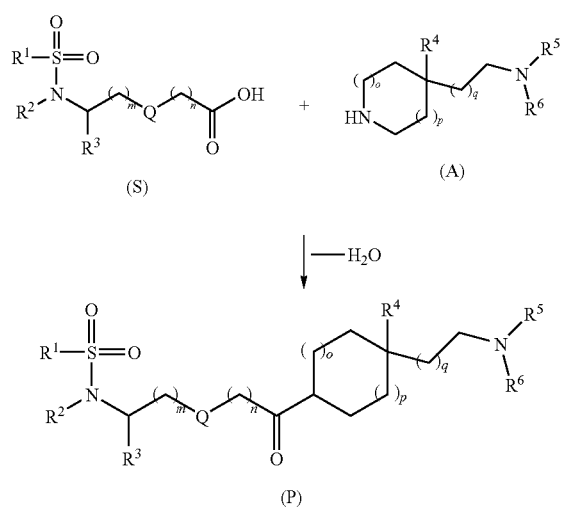

(S) + (A)

↓ −H₂O (P)

The free amines (A) and the carboxylic acids (S) are reacted in an amide formation in the presence at least of a water-removing agent and of an organic base, in an organic solvent, to give the compounds (P) according to the invention.

As water-removing agents there can be used, for example, sodium sulfate or magnesium sulfate, phosphorus oxide or reagents such as, for example, CDI, DCC (optionally polymer-bonded), TBTU, EDCI, PyBOP or PFPTFA, also in the presence of HOAt or HOBt. As organic bases there can be used, for example, triethylamine, DIPEA or pyridine, and as organic solvents there can be used THF, dichloromethane, diethyl ether, dioxane, DMF or acetonitrile. The temperature in the amide-formation step (1) is preferably from 0 to 50° C.

In a variant of the process, the PG-protected compounds (GP-A)

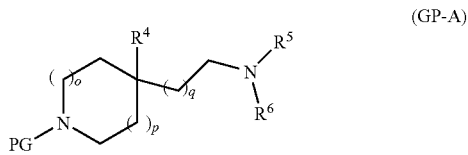

of the amine structural units (A) can be deprotected in a preceding step under conditions known to the person skilled in the art and added to the acid and then reacted as described above to give the end products (P).

General Synthesis Process for the Preparation of Acyclic Acid Structural Units

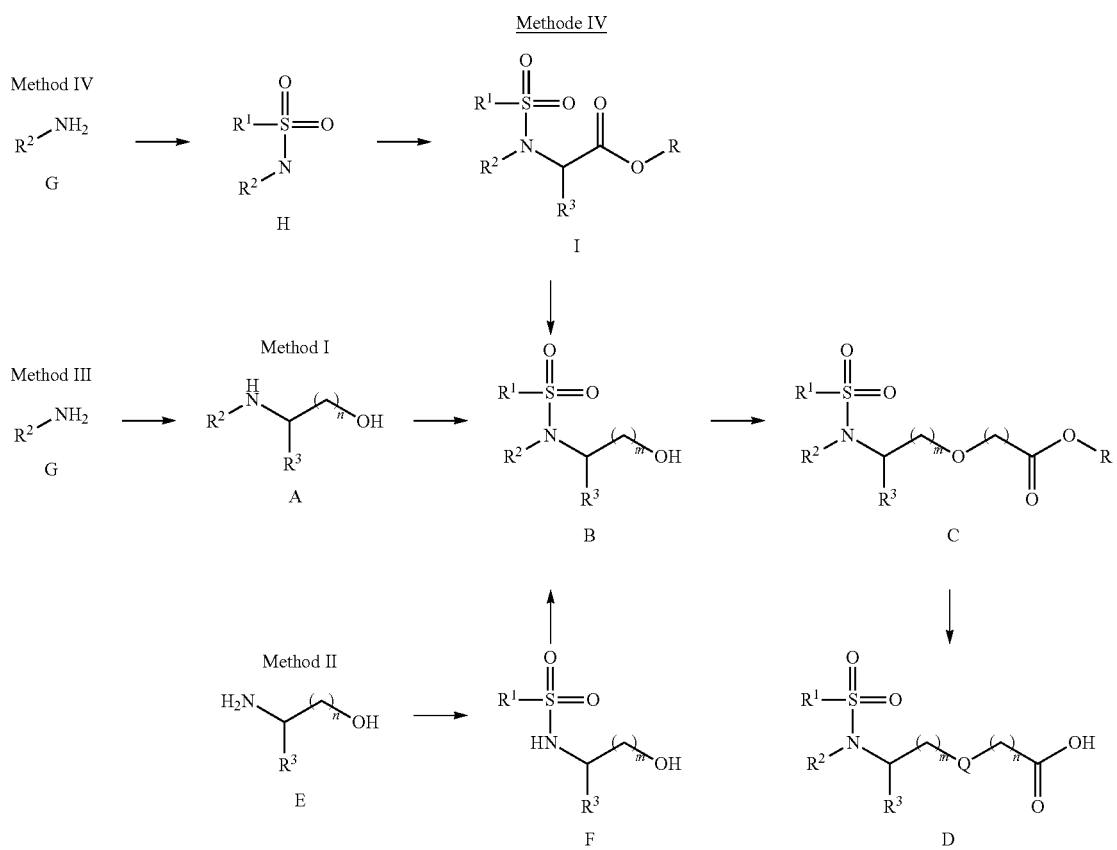

In Method I, the racemic (R and S configuration) or enantiomerically pure (R or S configuration) amino alcohols A are reacted in a sulfonylation with sulfonyl chlorides, bromides or pentafluorophenolate $R_3SO_2X$ (X=Cl, Br, OPFP), optionally in the presence of an organic or inorganic base, for example potassium carbonate, sodium carbonate, sodium hydrogen carbonate, diisopropylethylamine, triethylamine, pyridine, dimethylaminopyridine, diethylamine or DBU, preferably in an organic solvent, for example acetone, acetonitrile, dichloromethane or tetrahydrofuran, and at a temperature of from 0° C. to reflux temperature, to give the sulfonylated amino alcohols B.

The sulfonylated amino alcohols B are reacted in an alkylation reaction with halogenated ester compounds using tetrabutylammonium chloride or bromide or tetrabutylammonium hydrogen sulfate in a phase transfer reaction using an organic solvent, such as THF, toluene, benzene or xylene, and an inorganic base, such as potassium hydroxide, sodium hydroxide, sodium carbonate, sodium hydrogen carbonate, potassium carbonate, or in the presence of an organic or inorganic base, conventional inorganic bases are metal alcoholates such as sodium methanolate, sodium ethanolate, potassium tert-butylate, lithium or sodium bases such as lithium diisopropylamide, butyllithium, tert-butyllithium, sodium methylate, or metal hydrides such as potassium hydride, lithium hydride, sodium hydride, conventional organic bases are diisopropylethylamine, triethylamine, in an organic solvent, such as dichloromethane, THF or diethyl ether, at from 0° C. to reflux temperature, to give the products of the general structure C.

In Method II, the racemic (R and S configuration) or enantiomerically pure (R or S configuration) amino alcohols E are reacted in a sulfonylation with sulfonyl chlorides, bromides or pentafluorophenolate $R_3SO_2X$ (X=Cl, Br, OPFP), optionally in the presence of an organic or inorganic base, for example potassium carbonate, sodium hydrogen carbonate, diisopropylethylamine, triethylamine, pyridine, dimethylaminopyridine, diethylamine or DBU, preferably in an organic solvent, for example acetone, acetonitrile, dichloromethane or tetrahydrofuran, and at a temperature of from 0° C. to reflux temperature, to give the sulfonylated amino alcohols F. The sulfonylated amino alcohols F are then reacted in an alkylation reaction with alkyl halides (RX, X=I, Br, Cl), mesylates or alternative alkylating reagents, optionally in the presence of an organic or inorganic base, for example sodium hydride, potassium carbonate, cesium carbonate, DBU or DIPEA, preferably in an organic solvent, for example dimethylformamide, acetone, THF, acetonitrile, dioxane or these solvents as mixtures, at a temperature of from 0° C. to reflux temperature, to give the sulfonylated amino alcohols B.

In Methods I-III, the ester compounds C are reacted in an ester cleavage using organic acids, such as trifluoroacetic acid, or aqueous inorganic acids, such as hydrochloric acid, or using aqueous inorganic bases, such as lithium hydroxide, potassium hydroxide, sodium hydroxide, sodium carbonate, sodium hydrogen carbonate, potassium carbonate, in organic solvents, such as methanol, dioxane, dichloromethane, THF, diethyl ether or these solvents as mixtures, at from 0° C. to room temperature, to give the acid stages of the general formula D.

In Method III, commercial amines or amines obtainable by the person skilled in the art are alkylated with 2-bromoethanol or compounds in organic solvents, such as ethanol, methanol, ether, THF or dichloromethane, at a temperature of from 0° C. to reflux temperature, for up to 20 hours. The further process proceeds analogously to the other methods.

In Method IV, amines are reacted in a sulfonylation with sulfonyl chlorides, bromides or pentafluorophenolate $R_3SO_2X$ (X=Cl, Br, OPFP), optionally in the presence of an organic or inorganic base, for example potassium carbonate, sodium carbonate, sodium hydrogen carbonate, diisopropylethylamine, triethylamine, pyridine, dimethylaminopyridine, diethylamine or DBU, preferably in an organic solvent, for example acetone, acetonitrile, dichloromethane or tetrahydrofuran, and at a temperature of from 0° C. to reflux temperature, to give the sulfonylated compounds H.

The sulfonylated amines are then reacted in an alkylation reaction with methyl 2-bromoacetate or compounds H in an alkylation reaction, optionally in the presence of an organic or inorganic base, for example sodium hydride, potassium carbonate, caesium carbonate, DBU or DIPEA, preferably in an organic solvent, for example dimethylformamide, acetone, THF, acetonitrile, dioxane or these solvents as mixtures, to give the sulfonylated amino esters I.

The sulfonylated amino esters I are reacted in a reduction reaction to give a sulfonylated amino alcohol B using metal hydrides as reducing agents, such as, for example, $LiAlH_4$, $BH_3 \times DMS$ or $NaBH_4$, in an organic solvent, such as THF or diethyl ether. The further process of Method IV corresponds to the other methods.

General Synthesis Process for the Preparation of Cyclic Acid Structural Units

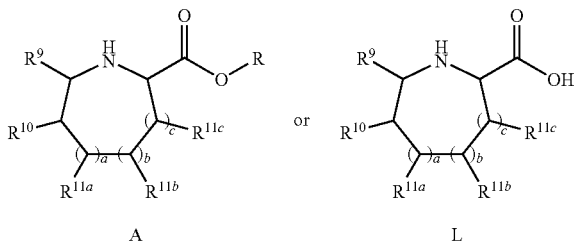

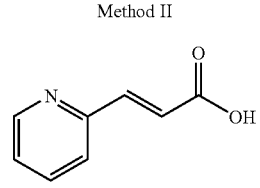

-continued

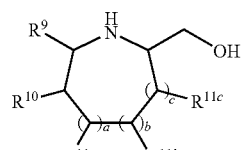

B

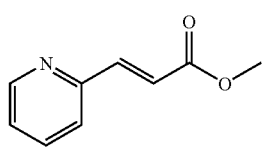

F

Method III

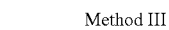

G

Method IV

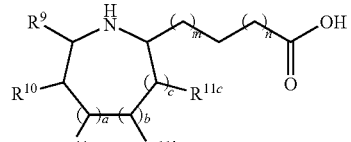

K

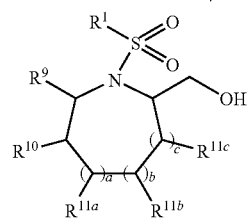

C

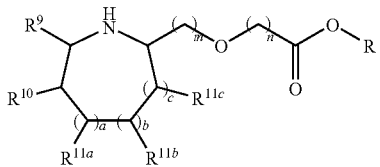

H

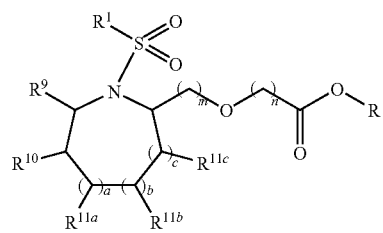

D

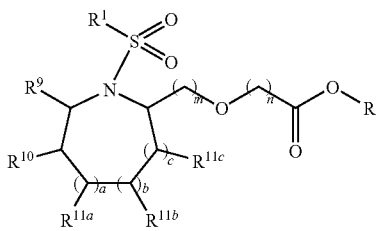

I

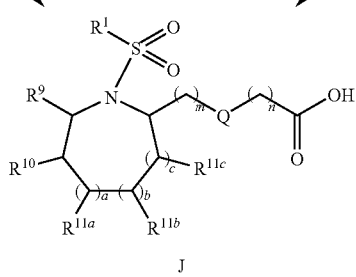

J

In Method I, the racemic (R and S configuration) or enantiomerically pure (R or S configuration) amino acid esters A or amino acids L are reacted by a reduction to give an amino alcohol B, using metal hydrides as reducing agents, such as, for example, LiAlH$_4$, BF$_3$ etherate, BH$_3$×DMS or NaBH$_4$, in an organic solvent, such as THF or diethyl ether, at temperatures of from 0° C. to reflux temperature. The amino alcohols B are reacted further in a sulfonylation with sulfonyl chlorides, bromides or pentafluorophenolate R$_3$SO$_2$X (X=Cl, Br, OPFP), optionally in the presence of an organic or inorganic base, for example potassium carbonate, sodium hydrogen carbonate, diisopropylethylamine, triethylamine, pyridine, dimethylaminopyridine, diethylamine or DBU, preferably in an organic solvent, for example acetone, acetonitrile, dichloromethane or tetrahydrofuran, and at a temperature of from 0° C. to reflux temperature, to give the sulfonylated amino alcohols C.

The sulfonylated amino alcohols C are reacted in an alkylation reaction with halogenated ester compounds using tetrabutylammonium chloride or bromide or tetrabutylammonium hydrogen sulfate in a phase transfer reaction using an organic solvent, such as THF, toluene, benzene or xylene, and an inorganic base, such as potassium hydroxide, sodium hydroxide, sodium carbonate, sodium hydrogen carbonate, potassium carbonate, or in the presence of an organic or inorganic base, conventional inorganic bases are metal alcoholates, such as sodium methanolate, sodium ethanolate, potassium tert-butylate, lithium or sodium bases, such as lithium diisopropylamide, butyllithium, tert-butyllithium, sodium methylate, or metal hydrides, such as potassium hydride, lithium hydride, sodium hydride, conventional organic bases are diisopropylethylamine, triethylamine, in an organic solvent, such as dichloromethane, THF or diethyl ether, at from 0° C. to reflux temperature, to give the products of the general structure D.

In Method II, 3-(pyridin-2-yl)acrylic acid E is esterified using water-removing reagents, for example inorganic acids such as $H_2SO_4$ or phosphorus oxides or organic reagents such as thionyl chloride, in organic solvents, such as THF, diethyl ether, methanol, ethanol or dichloromethane, to give the stage F, at temperatures of from room temperature to reflux temperature.

In Methods II and III, the ester stages F and G are hydrogenated in a hydrogenation under conditions known to the person skilled in the art in organic solvents, such as THF, chloroform, and in the presence of catalysts such as platinum oxides, with hydrogen under normal pressure or excess pressure, to give the intermediates H.

In Methods II-III, stage H is reacted further in a sulfonylation with sulfonyl chlorides, bromides or pentafluorophenolate $R_3SO_2X$ (X=Cl, Br, OPFP), optionally in the presence of an organic or inorganic base, for example potassium carbonate, sodium hydrogen carbonate, diisopropylethylamine, triethylamine, pyridine, diethylamine or DBU, preferably in an organic solvent, for example acetonitrile, dichloromethane or tetrahydrofuran, at from 0° C. to reflux temperature, to give the sulfonylated amino esters I.

In Methods I-III, the ester compounds D and I are reacted in an ester cleavage using organic acids, such as trifluoroacetic acid, or aqueous inorganic acids, such as hydrochloric acid, or using aqueous inorganic bases, such as lithium hydroxide, potassium hydroxide, sodium hydroxide, sodium carbonate, sodium hydrogen carbonate, potassium carbonate, in organic solvents, such as methanol, dioxane, dichloromethane, THF, diethyl ether or these solvents as mixtures, at from 0° C. to room temperature, to give the acid stages of the general formula J.

In Method IV, the racemic (R and S configuration) or enantiomerically pure (R or S configuration) amino acids K are esterified using water-removing reagents, for example inorganic acids such as $H_2SO_4$ or phosphorus oxides or organic reagents such as thionyl chloride, in organic solvents, such as THF, diethyl ether, methanol, ethanol or dichloromethane, to give the amino esters H. The further procedure of the general process corresponds to Methods II-III.

General Synthesis of the Amine Structural Units

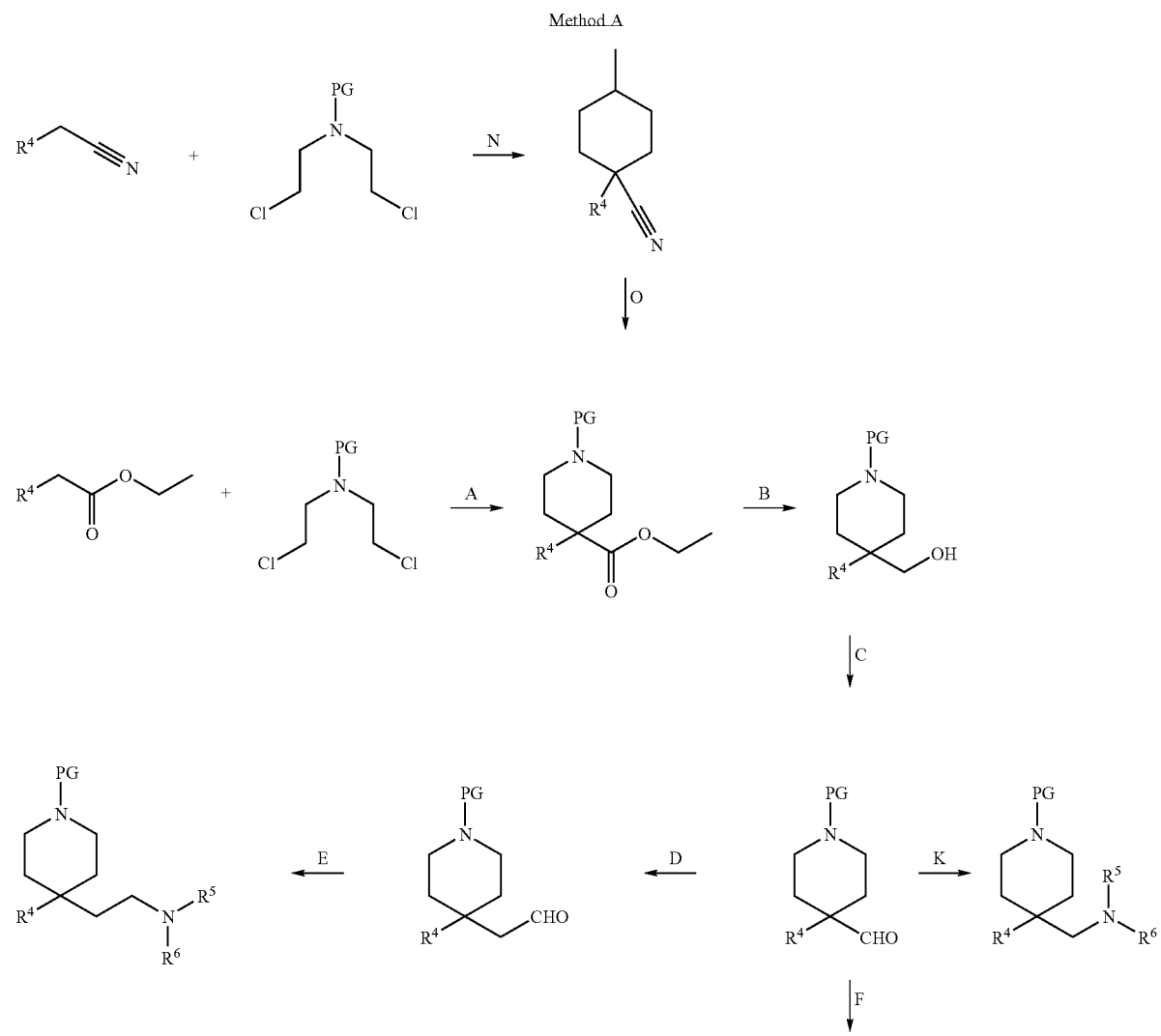

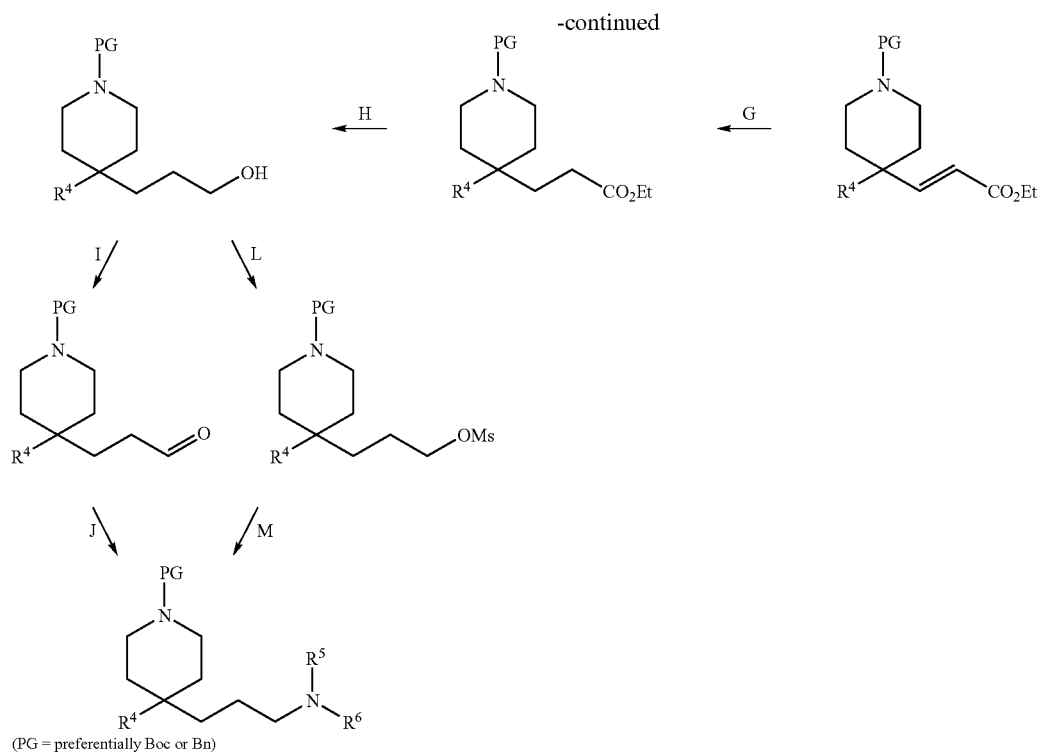

(PG = preferentially Boc or Bn)

As part of the preparation of the amine structural units a switch of protecting group may be necessary at some stage during the synthesis. Suitable protecting groups are known to the person skilled in the art, for example, Boc (tert-butoxycarbonyl) and Bn (benzyl), and can be introduced and removed according to known literature procedures.

1. Philip J. Kocienski, Protecting Groups, 3rd Edition, Georg Thieme Verlag, 2005 (ISBN 3-13-135603-0), in particular pages 505-511, 570-585, 606-609, 614-617, 625
2. Peter G. M. Wuts, Theodora W. Greene, Greene's Protective Groups in Organic Synthesis, 4th Edition, Wiley-Interscience, 2007 (ISBN-13: 978-0-471-69754-1) in particular pages 696-932

A/N: The initial substitution reaction of a CH-acidic compound, such as, for example, pyridyl ethyl acetate, with an alkyl halide to give the piperidine compound can be carried out in solvents such as, for example, methanol, ethanol, i-propanol, t-butanol, acetone, acetonitrile, DMF, DME, DMSO, toluene, benzene, tetrahydrofuran or liquid $NH_3$ with the addition of bases, such as, for example, potassium hydroxide, sodium hydride, sodium or potassium methanolate, ethanolate, i-propylate, t-butylate, lithium or sodium amide, lithium diisopropylamide, potassium carbonate, pyridine or elemental sodium, and optionally with the addition of sodium or potassium iodide, HMPA, 18-Crown-6 or 1-butyl-3-methylimidazolinium hexafluorophosphate.

B/H: The reduction of the ester function to the alcohol can be carried out with the aid of various reducing agents. There are suitable, for example, $LiBH_4$ or $NaBH_4$ in solvents such as, for example, diethyl ether, toluene, THF, water, methanol, ethanol or mixtures of these solvents, optionally with the addition of auxiliary reagents such as, for example, boric acid esters. It is, however, possible to use, as a further boron hydride, also $Zn(BH_4)_2$ in, for example, DME. However, the reduction can also be carried out with $BH_3\text{-}Me_2S$ complex in solvents such as, for example, THF or DCM. In addition to the boron compounds, the complex aluminium hydrides such as, for example, DIBAH or LAH in solvents such as, for example, diethyl ether, benzene, toluene, THF, DCM, DME, hexane or mixtures of these solvents, are also suitable for the reduction of the ester function to the alcohol.

C/I: As is known to the person skilled in the art, various methods are available for the oxidation of the alcohol to the aldehyde, for example the Jones, Corey-Kim, Sarett or Swern oxidation.

In the Jones oxidation, $Cr_2O_3$ in $H_2SO_4$ in solvents such as, for example, diethyl ether is used as oxidizing agent.

In the Corey-Kim oxidation, N-chlorosuccinimide and dimethyl sulfide in, for example, toluene is used as oxidising agent, while in the Sarett oxidation the Collins reagent ($CrO_3*2$ pyridine) is used.

In the Swern oxidation there is used, as is known to the person skilled in the art, a mixture of oxalyl chloride and DMSO with the addition of a base, such as, for example, triethylamine or pyridine.

However, the oxidation can also be carried out with a mixture of TEMPO and p-(diacetoxyiodo)toluene in solvents such as, for example, chloroform or cyclohexane or with the aid of the Corey reagent (pyridinium chlorochromate) in solvents such as, for example, DCM with the addition of a base, such as, for example, sodium acetate or sodium hydrogen carbonate, or by oxidation with $MnO_2$ in, for example, DCM.

D: The aldehyde is obtained under conditions known to the person skilled in the art in a Wittig reaction using a corresponding phosphonium compound, for example (methoxymethyl)triphenyl-phosphonium chloride, and a strong base, for example potassium tert-butylate, n-butyllithium, s-butyllithium, phenyllithium, lithium diisopropylamide or lithium hexamethyldisilazide, in organic solvents, such as THF, diethyl ether, cyclohexane, toluene or a mixture of the solvents, at a temperature of from −78° C. to +30° C., after acidic working up of the reaction mixture.

E/J/K: The subsequent reductive amination can be carried out, as is known to the person skilled in the art, by reaction with amines and subsequent reduction with reducing agents such as, for example, NaBH(OAc)$_3$, NaBH$_4$, LiBH$_3$CN, NaBH$_3$CN, borane-pyridine complex or α-picoline-borane complex, in solvents such as, for example, ethanol, methanol, DCM, DCE, THF, DMF, benzene, toluene or mixtures of these solvents, optionally with the addition of acids, such as, for example, HCl or acetic acid. Alternatively, the aldehyde can be reacted with a corresponding amine to give the imine, optionally with the addition of water-removing agents, and then converted into the amine by catalytic hydrogenation. Suitable as catalysts are, for example, Pt$_2$O, Pd on carbon or Raney nickel in solvents such as, for example, ethanol or methanol.

F: As is known to the person skilled in the art, the unsaturated ester can be prepared in a Wittig-Horner reaction from the aldehyde and ethyl 2-(dimethoxy-phosphoryl)acetate or methyl or ethyl 2-(diethylphosphino)acetate using bases, such as, for example, NaH, K$_2$CO$_3$, sodium ethanolate, potassium tert-butylate, lithium diisopropylamide or n-butyllithium, in solvents such as, for example, water, THF, diethyl ether, diisopropyl ether, hexane, benzene, toluene, 1,2-dimethoxyethane, DMF or DMSO. Reagents, such as, for example, MgBr$_2$, triethylamine or HMPT, are optionally added.

G: As is known to the person skilled in the art, the double bond of the unsaturated ester can be reduced by hydrogenolysis with homogeneous or heterogeneous catalysts or by reaction with reducing agents. There is suitable as homogeneous catalyst, for example, tris(triphenylphosphane) rhodium chloride in solvents such as, for example, benzene or toluene. As heterogeneous catalysts there can be used, for example, Pt on carbon, palladium on carbon, Raney nickel or Pt$_2$O in solvents such as, for example, acetic acid, methanol, ethanol, ethyl acetate, hexane, chloroform or mixtures of these solvents. Acids, such as, for example, sulfuric acid or hydrochloric acid, can optionally be added. There is suitable as reducing agent, for example, L-selectride in, for example, THF.

L: As is known to the person skilled in the art, the methyl sulfonate compounds can be obtained by reacting the alcohol in at least one solvent, preferably chosen from the group consisting of dichloromethane, dioxane, diethyl ether, tetrahydrofuran, acetonitrile and DMF, with methylsulfonyl chloride, in the presence of a suitable base, preferably chosen from the group consisting of caesium carbonate, calcium carbonate, potassium carbonate, triethylamine, diisopropylethylamine and pyridine.

M: As is known to a person skilled in the art, the methyl sulfonate compounds can be reacted with a suitable amine in at least one solvent, preferably chosen from the group consisting of dichloromethane, dioxane, diethyl ether, tetrahydrofuran, acetonitrile, toluene and DMF, in the presence of an excess of a base, preferably chosen from the group consisting of caesium carbonate, calcium carbonate, potassium carbonate, potassium bicarbonate, sodium bicarbonate, triethylamine, diisopropylethylamine and pyridine.

O: As is known to the person skilled in the art, the nitriles can be hydrolysed to the corresponding carboxylic acids the presence of a suitable acid, for example sulfuric or hydrochloric acid, preferably at elevated temperatures. The acids formed can be converted to the corresponding carboxylic esters (for example methyl or ethyl esters) in the presence of the corresponding alcohols in the same or a separate step. Alternatively, the nitriles may be converted to the corresponding esters in the presence of, for example, HCl, HBr, p-toluenesulfonic acid or trimethylsilyl chloride, in a suitable alcohol, for example methanol or ethanol. Depending on the amine protecting group employed and the reaction conditions chosen for the conversion of the nitrile to the ester it may be necessary to re-introduce the protecting group.

Finally the preferred BOC protecting group can be removed to give the free amine, for example, by reaction with HCl in organic solvents, such as dioxane, methanol, ethanol, acetonitrile or ethyl acetate, or by reaction with trifluoroacetic acid or methanesulfonic acid in methylene chloride or tetrahydrofuran.

Chain lengths q (see Formula I) can be adjusted by repeating step D as desired, also in combination with step F.

Method B

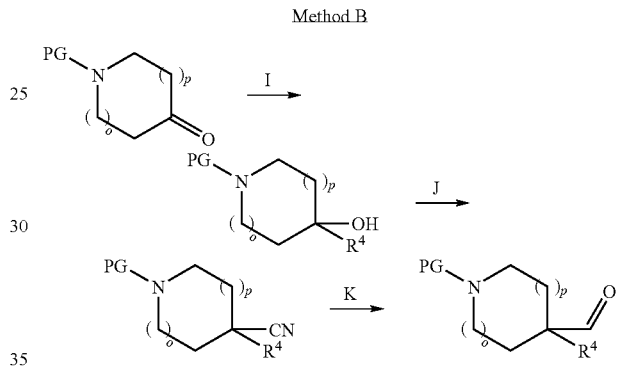

I: In order to produce the bond lengths o, p, the commercial carbonyl compound is reacted in the first step with metal organyls, typically Li or Mg organyls (Grignard), in solvents such as, for example, toluene, benzene, hexane, pentane, THF or diethyl ether, optionally with the addition of, for example, CeCl$_3$ to give the tertiary alcohol.

J: In step J, the alcohols are reacted using trimethylchlorosilane/sodium iodide, trimethylsilyl cyanide/BF$_3$ etherate, DMF in organic solvents, such as THF, ether, DCM, chloroform, acetonitrile, at from −78° C. to reflux temperature for from 1 to 10 hours, to give the nitriles.

K: The reduction to the aldehydes is carried out in step K using reducing agents such as diisobutylaluminum hydride in organic solvents such as THF, ether, toluene or benzene, at temperatures of from −78° C. to reflux temperature for from 1 to 10 hours.

The further general process is carried out analogously to method A.

EXAMPLES

The invention will be explained in further detail hereinafter with reference to the following illustrative examples, without limiting the general inventive idea.

The chemicals and solvents used were obtained commercially from the conventional suppliers (e.g. Acros, Avocado, Aldrich, Bachem, Fluka, Lancaster, Maybridge, Merck, Sigma, TCI, etc.) or were synthesised by the methods known to the person skilled in the art. Commercially available materials, for example Al$_2$O$_3$ or silica gel [for example from E. Merck, Darmstadt, Germany], were used as the stationary phase for column chromatography. Thin-layer chromatography investigations were carried out with commercially available HPTLC pre-coated plates (for example silica gel 60 F 254 from E. Merck, Darmstadt). The mixing ratios of solvents, eluants or for chromatographic investigations are always given in volume/volume unless indicated otherwise. Unless indicated otherwise, analysis was carried out by mass spectroscopy (ESI-MS).

Abbreviations
eq. equivalent(s)
DCM dichloromethane
min minute(s)
RT room temperature
TFA trifluoroacetic acid
KOtBu potassium tert-butylate
sat. saturated
LAH lithium aluminium hydride
EDCI N-(3-dimethylaminopropyl)-N'-ethyl-carbodiimide
HOBt 1-hydroxy-1H-benzotriazole
DIPEA diisopropylethylamine
OPFP O-pentafluorophenyl
THF tetrahydrofuran
DMS dimethyl sulfide
DMAP dimethylaminopyridine
MsCl—methanesulfonyl chloride
DMF—N,N-dimethylformamide
DMSO—dimethyl sulfoxide
TFA—trifluoroacetic acid
aq.—aqueous
h—hour(s)
(In the following description, the terms "structural units" and "building blocks" are used synonymously.)

Synthesis of the Acid Structural Units for Parallel Synthesis

The acid structural units S1-S28 used in the parallel synthesis described below were prepared as follows:

| No. | Product | Name |
|-----|---------|------|
| S1 | | 2-(1-(3-(Trifluoromethyl)phenylsulfonyl)piperidin-2-yl)acetic acid |
| S2 | | 3-(1-(4-Chloro-2,5-dimethylphenylsulfonyl)piperidin-2-yl)propionic acid |
| S3 | | 2-((1-(4-Methoxy-2,6-dimethylphenylsulfonyl)piperidin-2-yl)methoxy)-acetic acid |

-continued

| No. | Product | Name |
|---|---|---|
| S4 | | 2-((1-(3,4-Dichlorophenylsulfonyl)-1,2,3,4-tetrahydroquinolin-2-yl)-methoxy)acetic acid |
| S5 | | 2-(2-(4-Methoxy-N,2,6-trimethyl-phenylsulfonamido)ethoxy)acetic acid |
| S6 | | 3-(Naphthalene-2-sulfonamido)-3-phenylpropionic acid |
| S-07 | | 2-[2-[[(4-Methoxy-2,3,6-trimethyl-phenyl)sulfonyl]-methyl-amino]-ethoxy]-acetic acid (S-07) |
| S-09 | | 2-[2-[Benzyl-[(4-methoxy-2,6-dimethyl-phenyl)sulfonyl]-amino]-ethoxy]-acetic acid (S-09) |
| S-10 | | 2-[[1-[[2-(Trifluoromethyl)-phenyl]sulfonyl]-piperidin-2-yl]-methoxy]-acetic acid (S-10) |

-continued

| No. | Product | Name |
|---|---|---|
| S-12 | 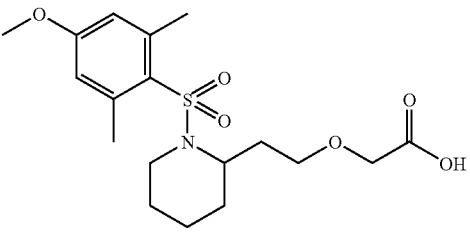 | 2-[2-[1-[(4-Methoxy-2,6-dimethyl-phenyl)sulfonyl]-piperidin-2-yl]-ethoxy]-acetic acid (S-12) |
| S-13 | 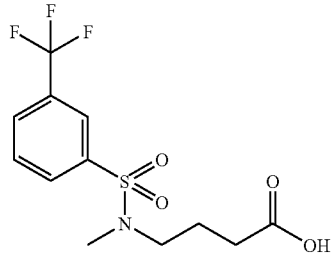 | 4-[Methyl-[[3-(trifluoromethyl)phenyl]sulfonyl]-amino]-butyric acid (S-13) |
| S-15 | 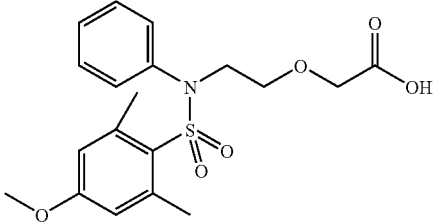 | 2-[2-(N-[(4-Methoxy-2,6-dimethyl-phenyl)sulfonyl]-anilino)-ethoxy]-acetic acid (S-15) |
| S-16 | 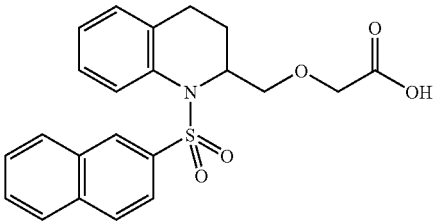 | 2-[[1-(Naphthalen-2-ylsulfonyl)-1,2,3,4-tetrahydro-quinolin-2-yl]-methoxy]-acetic acid (S-16) |
| S-17 | 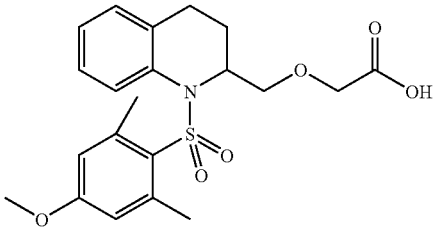 | 2-[[1-[(4-Methoxy-2,6-dimethyl-phenyl)sulfonyl]-1,2,3,4-tetrahydro-quinolin-2-yl]-methoxy]-acetic acid (S-17) |
| S-18 | 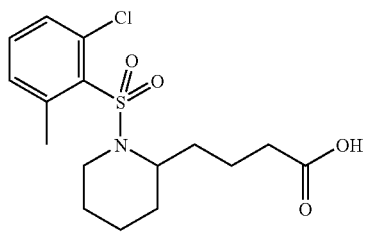 | 4-[1-[(2-Chloro-6-methyl-phenyl)sulfonyl]-piperidin-2-yl]-butyric acid (S-18) |

| No. | Product | Name |
|---|---|---|
| S-19 | 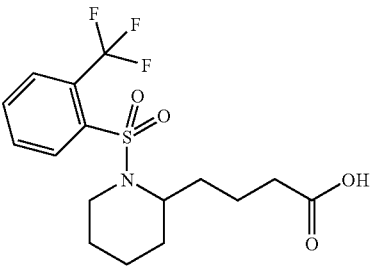 | 4-[1-[[2-(Trifluoromethyl)-phenyl]sulfonyl]-piperidin-2-yl]-butyric acid (S-19) |
| S-20 | 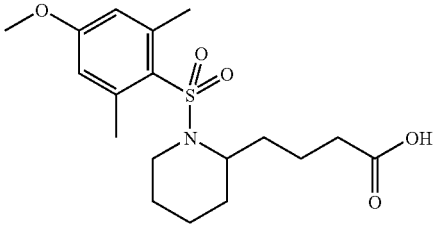 | 4-[1-[(4-Methoxy-2,6-dimethyl-phenyl)sulfonyl]-piperidin-2-yl]-butyric acid (S-20) |
| S-21 | 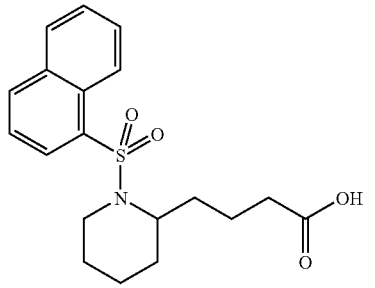 | 4-[1-(Naphthalen-1-ylsulfonyl)-piperidin-2-yl]-butyric acid (S-21) |
| S-23 | 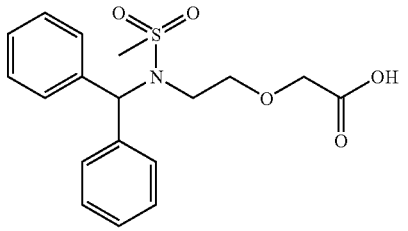 | 2-[2-(Benzhydryl-methylsulfonyl-amino)-ethoxy]-acetic acid (S-23) |
| S-24 | 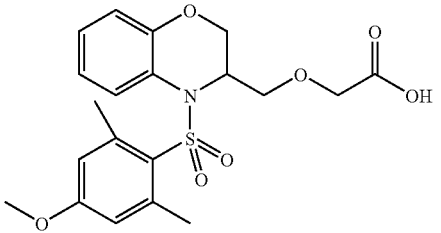 | 2-[[4-[(4-Methoxy-2,6-dimethyl-phenyl)sulfonyl]-3,4-dihydro-2H-[1,4]benzoxazin-3-yl]-methoxy]-acetic acid (S-24) |

-continued

| No. | Product | Name |
|---|---|---|
| S-25 | | 2-[2-[[(4-Methoxy-2,6-dimethyl-phenyl)sulfonyl]-(quinolin-3-yl-methyl)-amino]-ethoxy]-acetic acid (S-25) |
| S-26 | | 2-[[4-[(2-Chloro-6-methyl-phenyl)sulfonyl]-3,4-dihydro-2H-[1,4]benzoxazin-3-yl]-methoxy]-acetic acid (S-26) |
| S-27 | | 2-[[4-[[2-(Trifluoromethyl)-phenyl]sulfonyl]-3,4-dihydro-2H-[1,4]benzoxazin-3-yl]-methoxy]-acetic acid (S-27) |
| S-28 | | 2-[2-[4H-[1,3]Benzodioxin-7-yl-methyl-[(4-methoxy-2,6-dimethyl-phenyl)sulfonyl]-amino]-ethoxy]-acetic acid (S-28) |

4-Methoxy-2,6-dimethylbenzene-1-sulfonyl chloride

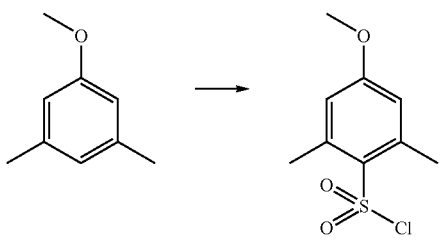

A solution of 3,5-dimethylanisole (102.5 g, 753 mmol) in DCM (1000 ml) was cooled to 0° C. A solution of chlorosulfonic acid (251 ml, 3763 mmol) in DCM (250 ml) was added dropwise to this solution. After a reaction time of 10 min, the reaction solution was added to an ice bath (1000 ml), and the phases were separated and extracted again with DCM (250 ml). The combined organic phases were washed with water (1000 ml) and saturated sodium chloride solution (1000 ml), dried over $Na_2SO_4$ and concentrated. The product was purified by column chromatography on silica gel (heptane/DCM 5:1). Yield: 63.5 g, 36%

Synthesis of the Amino Alcohols

(1,2,3,4-Tetrahydroquinolin-2-yl)methanol

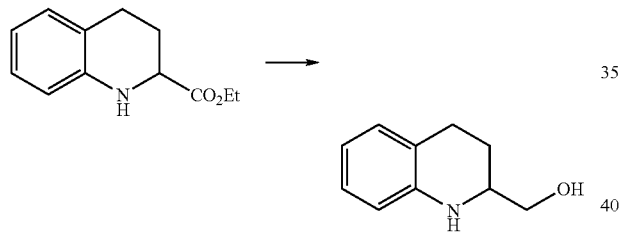

1,2,3,4-Tetrahydroquinoline-2-carboxylic acid ethyl ester (4.75 g, 25 mmol) in THF (5 ml/mmol) was added dropwise at 0° C. to a suspension of LAH (2 eq.) in THF (50 ml). The reaction mixture was stirred for 1 h at RT and then heated for 4 h under reflux. After addition of saturated aqueous $Na_2SO_4$ solution, filtration was carried out and the organic solvent was removed in vacuo. The product was purified by column chromatography (silica gel, ethyl acetate/hexane 3:7).
Yield: 50%

Synthesis of the Amino Acid Esters

Ethyl 2-(piperidin-2-yl)acetate hydrochloride

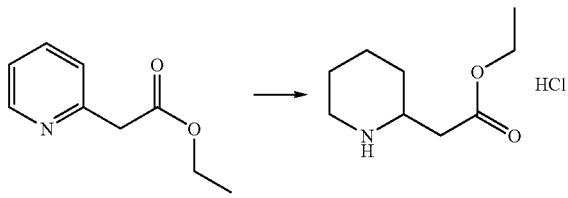

Ethyl 2-(pyridin-2-yl)acetate (24.51 g, 148.4 mmol) was dissolved in ethanol (130 ml), and $PtO_2$ (3.37 g, 14.84 mmol, 0.1 eq.) and chloroform (20 ml) were added. The suspension was stirred overnight under a $H_2$ atmosphere (8 bar) at 40° C. According to TLC monitoring (silica gel, DCM/methanol 95:5), the reaction was incomplete, so that further chloroform (15 ml) was added and stirring was carried out for a further 2 d under a $H_2$ atmosphere (8 bar) at 40° C. (TLC monitoring). After cooling, the catalyst was first removed by filtration over filtering earth and the filtrate was concentrated to dryness in vacuo. The ethyl 2-(piperidin-2-yl)acetate hydrochloride was used in the next stage without being purified further. Yield: 31.51 g, >100%

Methyl 3-(piperidin-2-yl)propionate hydrochloride

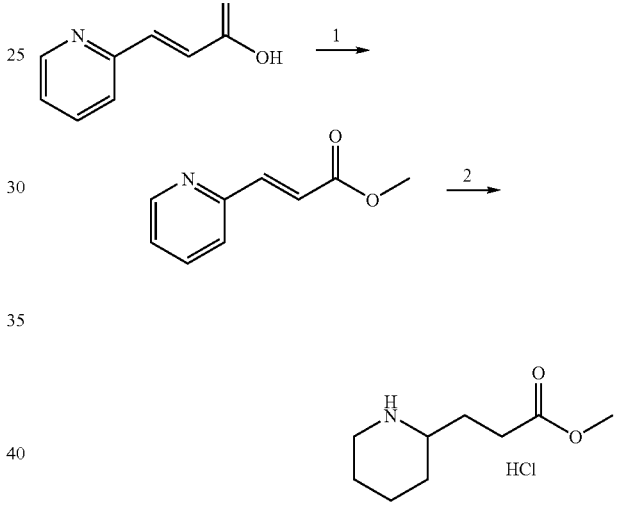

Stage 1. $H_2SO_4$ (12.8 ml, 240 mmol) was added to a solution of 3-(2-pyridyl)-acrylic acid (23.88 g, 160 mmol) in methanol (750 ml). The reaction mixture was heated overnight under reflux and, after cooling to RT, was poured into saturated aqueous $NaHCO_3$ solution (1000 ml). The methanol was removed using a rotary evaporator and the aqueous phase was extracted twice with ethyl acetate (400 ml). The organic phase was washed with saturated NaCl solution (500 ml), dried over $Na_2SO_4$ and concentrated. The crude product of methyl 3-(pyridin-2-yl)acrylate was used in the next stage without being purified further. Yield: 22.19 g, 85%

Stage 2. Methyl 3-(pyridin-2-yl)acrylate (22.15 g, 136 mmol) was dissolved in THF (300 ml) and chloroform (10.9 ml), and $PtO_2$ (3.08 g, 13.6 mmol, 0.1 eq.) was added under a nitrogen atmosphere. The solution was first rinsed with nitrogen for 10 min and was then stirred overnight under a $H_2$ atmosphere (8 bar). After cooling, rinsing with nitrogen was first carried out again, the catalyst was removed by filtering over filtering earth and then rinsed with DCM, and the filtrate was concentrated to dryness in vacuo. The methyl 3-(piperidin-2-yl)propionate hydrochloride was used in the next stage without being purified further.

Yield: 27.95 g, 99%

Methyl 3-amino-3-phenylpropionate

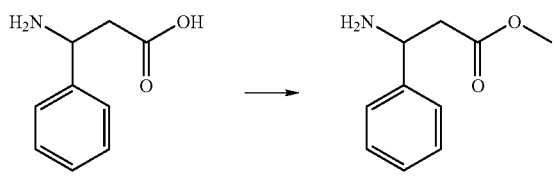

Thionyl chloride (19.1 g, 162 mmol) was added dropwise to a solution, cooled to 0° C., of 3-amino-3-phenylpropionic acid (8.9 g, 54 mmol) in methanol (150 ml). The reaction mixture was then stirred for 12 h under reflux (TLC control). The solvent was removed completely and the residue was dried in vacuo. The crude product was used in the next stage without being purified further.

Sulfonylation of the Amino Alcohols or Amino Acid Esters

Method A

The corresponding amino alcohol or amino acid ester (1.1 eq.) was dissolved in DCM (4 ml/mmol), and triethylamine (2.2 eq.) was added. The solution was cooled to 0° C.; a solution of the corresponding sulfonic acid chloride (1 eq.) dissolved in DCM (2.3 ml/mmol) was added dropwise, and stirring was carried out for 1.5 h at RT. When the reaction was complete, HCl (0.5 M, 2.3 ml/mmol) was added, and the phases were separated, washed with water, dried over $Na_2SO_4$ and concentrated. The crude product was purified by column chromatography.

Method B

Pyridine (5 eq.), DMAP (0.5 eq.) and 3,4-dichlorobenzenesulfonyl chloride (1.2 eq.) dissolved in DCM (2.6 ml/mmol sulfonic acid chloride) were added to a suspension, cooled to 0° C., of the alcohol (1 eq.) in DCM (5 ml/mmol). After stirring for 5 h at 0° C., DCM was added and washing with aqueous copper sulfate solution, water and saturated NaCl solution was carried out. After drying over $Na_2SO_4$ and filtration, the solvent was removed in vacuo. The crude product was purified by column chromatography.

| Sulfonic acid chloride | Amino alcohol/ amino acid ester | Method | Product | Purification |
| --- | --- | --- | --- | --- |
| 3-Trifluoro-methyl-benzene-sulfonyl chloride | Ethyl 2-(piperidin-2-yl)acetate hydrochloride | A | Ethyl 2-(1-(3-(trifluoromethyl)-phenylsulfonyl)-piperidin-2-yl)acetate | silica gel, DCM |
| 4-Chloro-2,5-dimethyl-benzene-sulfonyl chloride | Methyl 3-(piperidin-2-yl)-propionate hydrochloride | A | Methyl 3-(1-(4-chloro-2,5-dimethyl-phenylsulfonyl)-piperidin-2-yl)-propionate | silica gel, heptane/ethyl acetate, 6:1 → 3:1 |

-continued

| Sulfonic acid chloride | Amino alcohol/ amino acid ester | Method | Product | Purification |
|---|---|---|---|---|
| 4-Methoxy-2,6-dimethyl-benzene-1-sulfonyl chloride | 2-Piperidine-methanol | A | 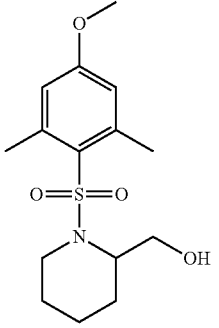<br>(1-(4-Methoxy-2,6-dimethylphenylsulfonyl)-piperidin-2-yl)methanol | — |
| 3,4-Dichloro-benzene-sulfonyl chloride | (1,2,3,4-tetrahydroquinolin-2-yl)methanol | B | 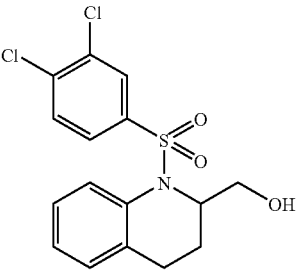<br>(1-(3,4-dichloro-phenyl-sulfonyl)-1,2,3,4-tetrahydro-quinolin-2-yl)-methanol | silica gel, DCM/ methanol, 95:5 |
| 4-Methoxy-2,6-dimethyl-benzene-1-sulfonyl chloride | 2-(Methylamino)-ethanol | A | 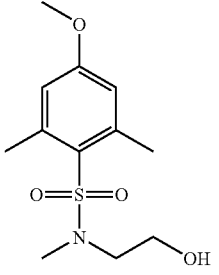<br>N-(2-hydroxyethyl)-4-methoxy-N,2,6-trimethylbenzene-sulfonamide | — |

| Sulfonic acid chloride | Amino alcohol/ amino acid ester | Method | Product | Purification |
|---|---|---|---|---|
| Naphthalene-2-sulfonyl chloride | Methyl 3-amino-3-phenylpropionate | A | 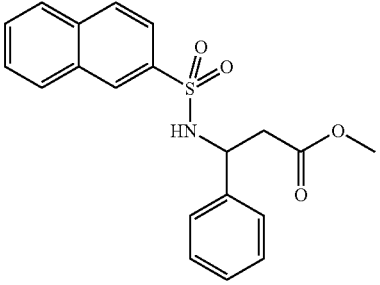  Methyl 3-(naphthalene-2-sulfonamido)-3-phenylpropionate | silica gel, ethyl acetate/hexane, 3:7 |

Synthesis of the tert-butyl methoxyacetates

Method A n-Bu$_4$NCl (0.33 eq.) was added to a solution of the corresponding sulfonylated amino alcohol (1 eq.) in toluene (6 ml/mmol). The reaction solution was cooled to 0° C., and NaOH solution (35%, 6 ml/mmol amino alcohol) was added. Tert-butyl bromoacetate (1.5 eq.) was added dropwise to this solution, and then stirring was carried out for 3 h at RT. The organic phase was separated off and washed three times with water (7 ml/mmol), dried over Na$_2$SO$_4$ and concentrated. The crude product was purified by column chromatography.

Method B

A solution of the sulfonamide (1 eq.) dissolved in THF (6.3 ml/mmol) was added dropwise, with stirring, to a suspension, cooled to 0° C., of NaH (2 eq.) in THF (10 ml/mmol). After stirring for 45 min at that temperature, a solution of tert-butyl bromoacetate (1.5 eq.) in THF (2 ml/mmol) was added. The reaction mixture was heated for 20 h at 50° C. It was then cooled to 0° C., ice was added, and extraction with ethyl acetate was carried out. The organic phase was washed with saturated aqueous NaCl solution and dried over Na$_2$SO$_4$. After filtration, the solvent was removed in vacuo. The crude product was purified by column chromatography.

| Sulfonylated amino alcohol | Method | Product | Purification |
|---|---|---|---|
| 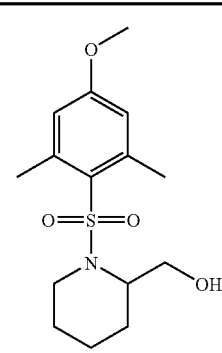  (1-(4-Methoxy-2,6-dimethyl-phenylsulfonyl)-piperidin-2-yl)methanol | A | 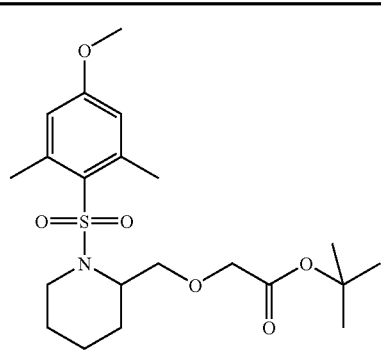  tert-Butyl 2-((1-(4-methoxy-2,6-dimethylphenylsulfonyl)-piperidin-2-yl)methoxy)-acetate | silica gel, heptane/ethyl acetate, 3:1 |

| Sulfonylated amino alcohol | Method | Product | Purification |
|---|---|---|---|
| 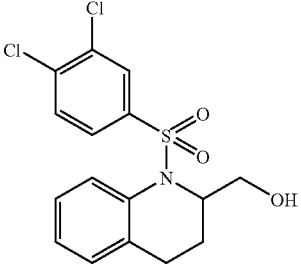<br>(1-(3,4-Dichlorophenyl-sulfonyl)-1,2,3,4-tetrahydro-quinolin-2-yl)methanol | B | 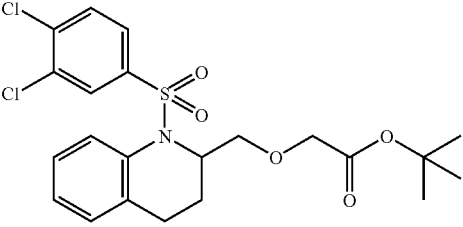<br>tert-Butyl 2-((1-(3,4-dichlorophenylsulfonyl)-1,2,3,4-tetrahydroquinolin-2-yl)methoxy)acetate | silica gel, hexane/ethyl acetate, 9:1 |
| 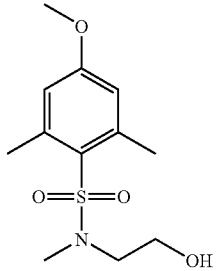<br>N-(2-Hydroxyethyl)-4-methoxy-N,2,6-trimethyl-benzenesulfonamide | A | 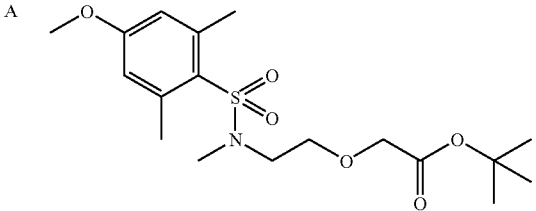<br>tert-Butyl 2-(2-(4-methoxy-N,2,6-trimethylphenyl-sulfonamido)ethoxy)acetate | |

Saponification of the Esters

Method A

The corresponding tert-butyl-methoxy acetate was stirred for 2 h at RT in a solution of TFA (0.7 ml/mmol) and DCM (4.7 ml/mmol). When the reaction was complete, the solvent was removed using a rotary evaporator, and the residue was taken up in toluene and concentrated again.

Method B

The corresponding ester (1 eq.) was dissolved in a mixture of methanol (5.5 ml/mmol), dioxane (1.5 ml/mmol) and aqueous NaOH solution (4 M, 6 eq.) and stirred overnight. When the reaction was complete (TLC monitoring), the solution was concentrated. The crude product was taken up in ethyl acetate (22 ml/mmol) and with $KHSO_4$ solution (0.5 M, 22 ml/mmol). The aqueous phase was extracted again with ethyl acetate, and the combined organic phases were washed with saturated NaCl solution (500 ml), dried over $Na_2SO_4$ and concentrated.

Method C

Aqueous NaOH solution (6 M, 3 ml/mmol) was added to a solution of the corresponding ester (1 eq.) in THF (3 ml/mmol). After a reaction time of 1 h, the solvent was removed using a rotary evaporator and cooled to 0° C. HCl (6 M, 3 ml/mmol) was added, and extraction with ethyl acetate was carried out. The organic phase was dried over $Na_2SO_4$ and concentrated.

Method D

First triethylsilane (1.55 eq.) and then TFA (0.8 ml/mmol) were added to a solution of the acetic acid tert-butyl ester compound (1 eq.) in DCM (8 ml/mmol), and stirring was carried out for 5 h at RT. The mixture was then concentrated in vacuo, and the residue was taken up repeatedly in toluene and concentrated again each time. The crude product was dissolved in ethyl acetate and extracted with 5% $NaHCO_3$ solution. The combined aqueous phases were adjusted to pH 1 with conc. hydrochloric acid and extracted with ethyl acetate again. The combined organic phases were dried over $Na_2SO_4$ and concentrated in vacuo.

Method E $LiOH*H_2O$ (2 eq.) was added at a reaction temperature of 0° C. to a solution of the ester (1 eq.) in a methanol/water mixture (3:1, 10 ml/mmol). The reaction mixture was stirred for 16 h at RT. The solvent was removed under reduced pressure, and the residue was taken up in water and washed with DCM. The aqueous phase was then carefully acidified with HCl (1 N) and extracted with ethyl acetate. The organic phase was washed with water and sat. NaCl solution and dried over $Na_2SO_4$. After removal of the solvent, the product was obtained in adequate purity.

| Ester | Method | Product |
|---|---|---|
| 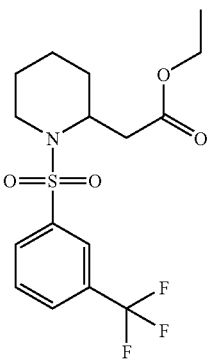<br>Ethyl 2-(1-(3-(trifluoromethyl)-phenyl-sulfonyl)-piperidin-2-yl)acetate | B | 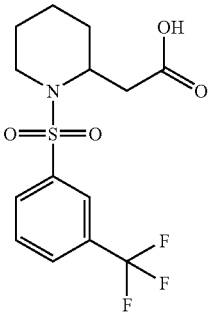<br>2-(1-(3-(Trifluoromethyl)phenyl-sulfonyl)piperidin-2-yl)acetic acid (S-01) |
| 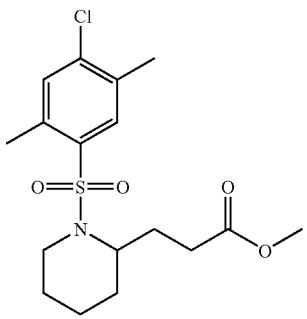<br>Methyl 3-(1-(4-chloro-2,5-dimethylphenylsulfonyl)piperidin-2-yl)propionate | C | 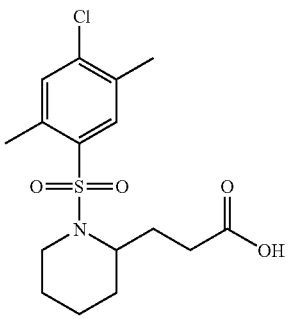<br>3-(1-(4-Chloro-2,5-dimethyl-phenylsulfonyl)piperidin-2-yl)propionic acid (S-02) |
| 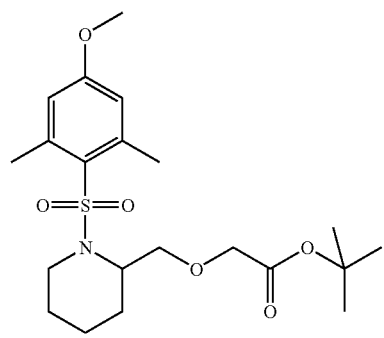<br>tert-Butyl 2-((1-(4-methoxy-2,6-dimethylphenylsulfonyl)piperidin-2-yl)methoxy)acetate | A | 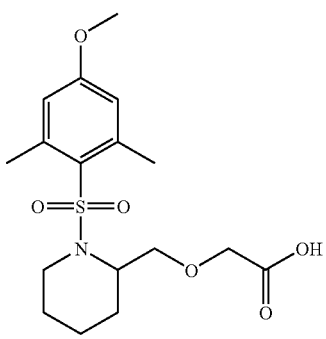<br>2-((1-(4-Methoxy-2,6-dimethylphenylsulfonyl)piperidin-2-yl)methoxy)-acetic acid (S-03) |
| 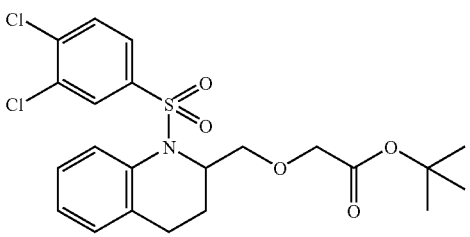<br>tert-Butyl 2-((1-(3,4-dichlorophenyl-sulfonyl)-1,2,3,4-tetrahydroquinolin-2-yl)methoxy)-acetate | A | 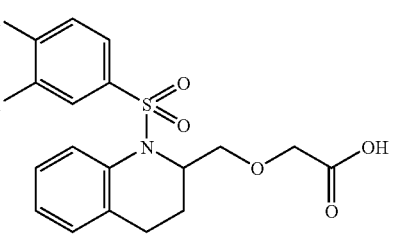<br>2-((1-(3,4-Dichlorophenyl-sulfonyl)-1,2,3,4-tetrahydro-quinolin-2-yl)methoxy)acetic acid (S-04) |

| Ester | Method | Product |
|---|---|---|
| 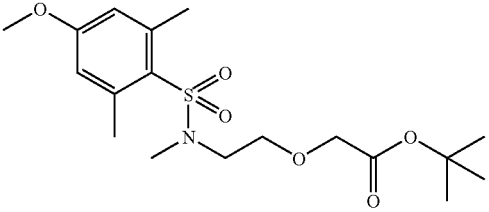<br>tert-Butyl 2-(2-(4-methoxy-N,2,6-trimethylphenyl-sulfonamido)-ethoxy)acetate | D | 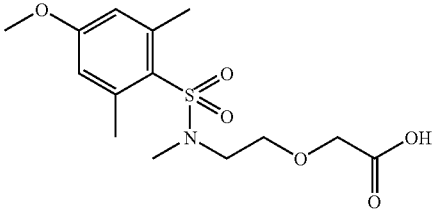<br>2-(2-(4-Methoxy-N,2,6-trimethyl-phenylsulfonamido)ethoxy)acetic acid (S-05) |
| 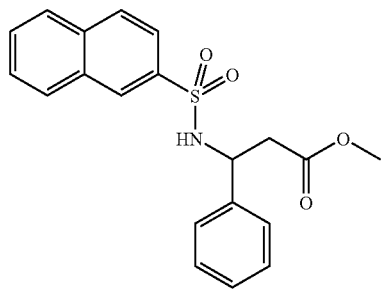<br>Methyl 3-(naphthalene-2-sulfonamido)-3-phenylpropionate | E | 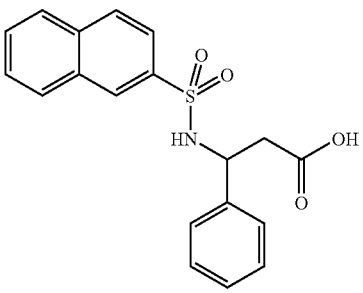<br>3-(Naphthalene-2-sulfonamido)-3-phenylpropionic acid (S-06) |

Synthesis of Acid Building Block S-07: 2-[2-[[(4-Methoxy-2,3,6-trimethylphenyl)sulfonyl]-methyl-amino]-ethoxy]-acetic acid (S-07)

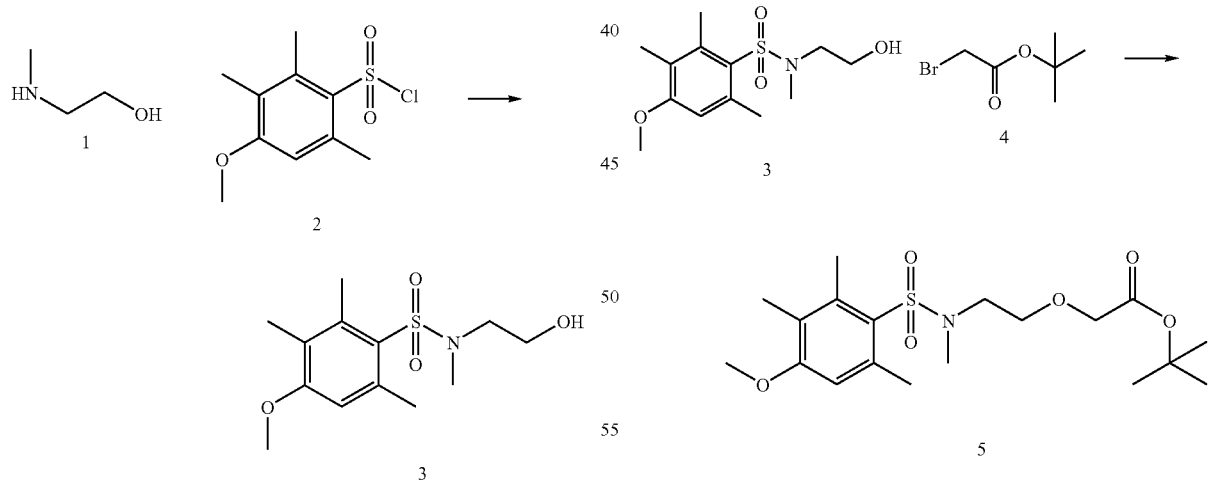

Step-1: To a solution of 2-Methylaminoethanol 1 (1 eq., 79.9 mmol) in 500 ml Dichlormethane was added triethylamine (1.2 eq., 95.9 mmol) and a solution of sulfonylchloride 2 (1.2 eq., 95.9 mmol) in 60 ml dichloromethane. The reaction mixture was stirred for 4 h at room temperature (TLC control). H₂O (100 ml) and sat. NaHCO₃-solution (100 ml) were added. After separation of the two phases, the aqueous phase was extracted 3× with Dichloromethane (250 ml). The combined organic phases were dried over Na₂SO₄, filtered and concentrated. The residue was purified by column chromatography (Silica, Diethyl ether/Hexane 8:2% 9:1), to afford the alcohol 3 (66.3 mmol, 83% yield).

Step-2: A mixture of alcohol 3 (1 eq., 74.8 mmol), tert.-butylbromacetate (2.1 eq., 157 mmol), tetrabutylammonium-hydrogensulfate (0.1 eq., 7.48 mmol), 50% NaOH-solution and toluene was stirred vigorously for 3.5 h at room temperature. After separation of the two phases, the aqueous phase was extracted 2× with diethyl ether (450 ml). The combined organic phases were dried over Na₂SO₄ and concentrated. Product 5 (67.3 mmol, 90%) was obtained and it was used in the next step without further purification.

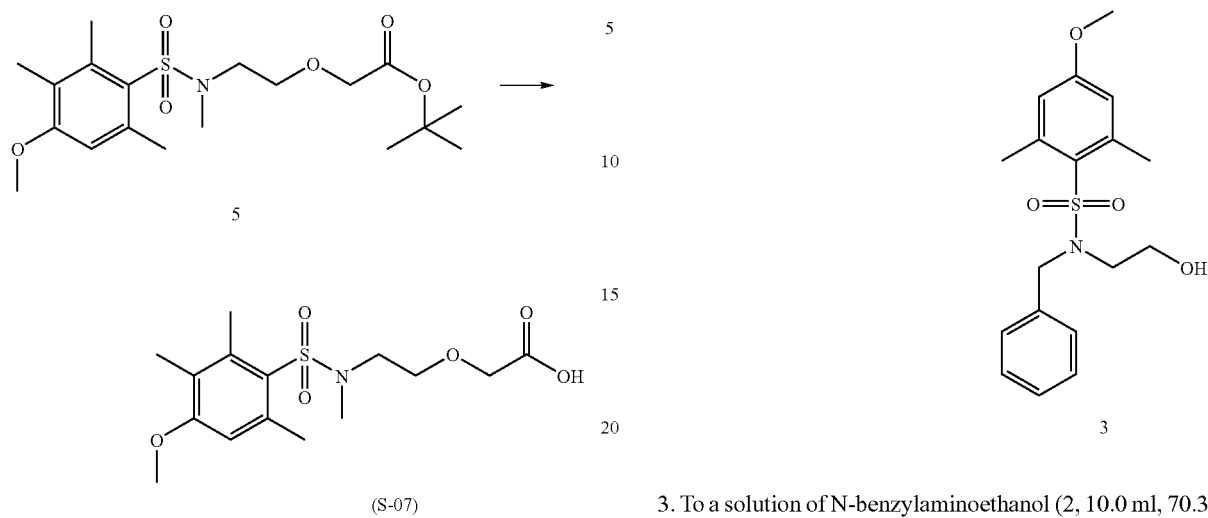

Step-3: Product 5 (1 eq., 67.3 mmol) was dissolved in dichlormethane and TFA (20 eq., 1345 mmol) was added. The reaction mixture was stirred for 4 h at room temperature (TLC controlled). The reaction mixture was dried over MgSO$_4$, filtered and completely evaporated. The residue was co-evaporated 2× with toluene (300 ml). The residue was then washed 3× with diisopropylether, whereas diisopropylether was decanted from the residue. The residue was suspended in Dichloromethane and was evaporated to dryness, to afford product S-07 (101.9 mmol, '151%').

3. To a solution of N-benzylaminoethanol (2, 10.0 ml, 70.3 mmol) in CH$_2$Cl$_2$ (200 ml) was added Et$_3$N (22.5 ml, 160 mmol). The mixture was cooled to 0° C. after which a solution of compound 1 (15.0 g, 63.9 mmol) in CH$_2$Cl$_2$ (100 ml) was added dropwise. The mixture was stirred for 3 h at room temperature. Aqueous 1 M HCl (150 ml) was added. After phase separation the organic layer was washed with water (100 ml), dried (Na$_2$SO$_4$) and evaporated under reduced pressure. Purification by column chromatography (silica, heptane/EtOAc, 2:1) afforded sulfonamide 3 (14.93 g, 67%).

Synthesis of Acid Building Block S-09: 2-[2-[Benzyl-[(4-methoxy-2,6-dimethylphenyl)sulfonyl]-amino]-ethoxy]-acetic acid (S-09)

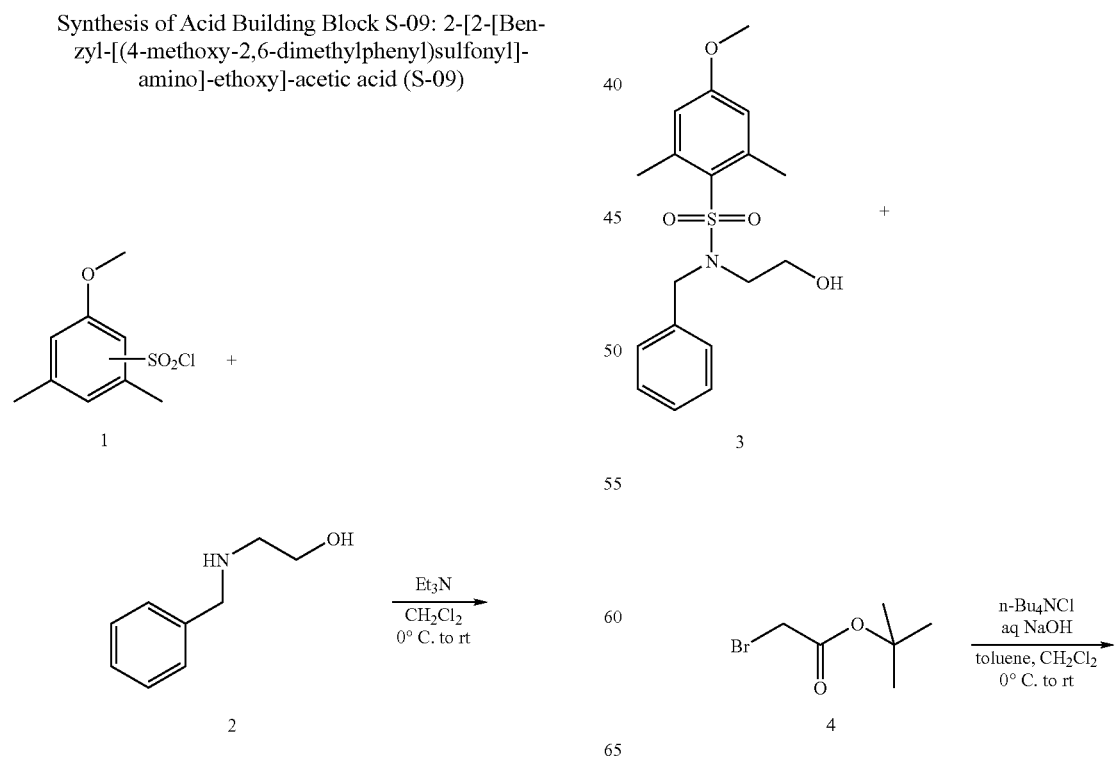

-continued

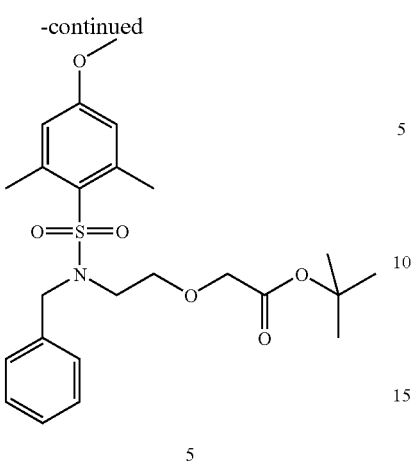

5

5. To a solution of compound 3 (14.9 g, 42.6 mmol) in toluene (100 ml) and $CH_2Cl_2$ (100 ml) was added n-$Bu_4NCl$ (3.95 g, 14.2 mmol). After cooling to 0° C., an aqueous 35% NaOH solution (175 ml) was added, followed by a dropwise addition of tert-butyl bromoacetate (4, 9.32 ml, 64 mmol). The reaction mixture was stirred at room temperature for 3 h. The organic layer was separated and washed with $H_2O$ (3×300 ml), dried ($Na_2SO_4$) and evaporated to dryness. Purification by column chromatography (silica, heptane/EtOAc, 3:1) afforded compound 5 (19.40 g, 98%).

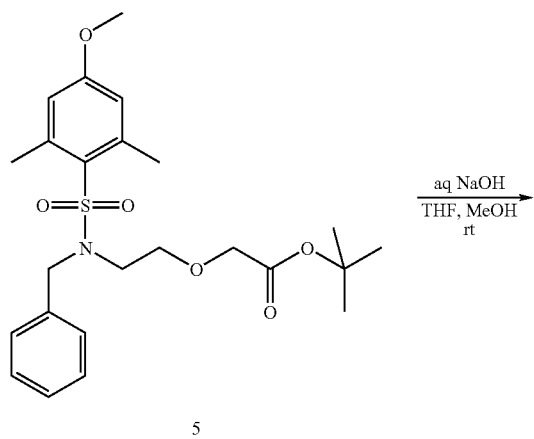

(S-09)

To a solution of compound 5 (19.4 g, 41.8 mmol) in THF (165 ml) and MeOH (150 ml) was added aqueous 6 M NaOH (150 ml, 900 mmol). The reaction mixture was stirred at room temperature. After 1 h the organic solvents were evaporated and aqueous 6 M HCl (155 ml) was added at 0° C. The aqueous layer was extracted with EtOAc (2×150 ml). The organic layers were combined, dried ($Na_2SO_4$) and evaporated to dryness. The product was co-evaporated with $Et_2O$ and i-$Pr_2O$ (2×) to yield compound S-09 (17.05 g, 100%).

Synthesis of Acid Building Block S-10: 2-[[1-[[2-(Trifluoromethyl)-phenyl]sulfonyl]-piperidin-2-yl]-methoxy]-acetic acid (S-10)

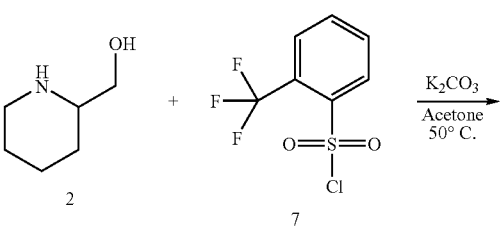

8. Alcohol 2 (4.3 g, 37.2 mmol) was suspended in acetone (150 ml). $K_2CO_3$ (10.27 g, 74.3 mmol) and 2-(trifluoromethyl)benzenesulfonyl chloride (7.10 g, 40.9 mmol) were subsequently added. The mixture was stirred overnight at 50° C. The reaction mixture was filtered after cooling to RT and the filtrate was evaporated to dryness under reduced pressure. The crude product was purified by column chromatography (silica, heptane/EtOAc 2:1) to afford 8.95 g (75%) of alcohol 8.

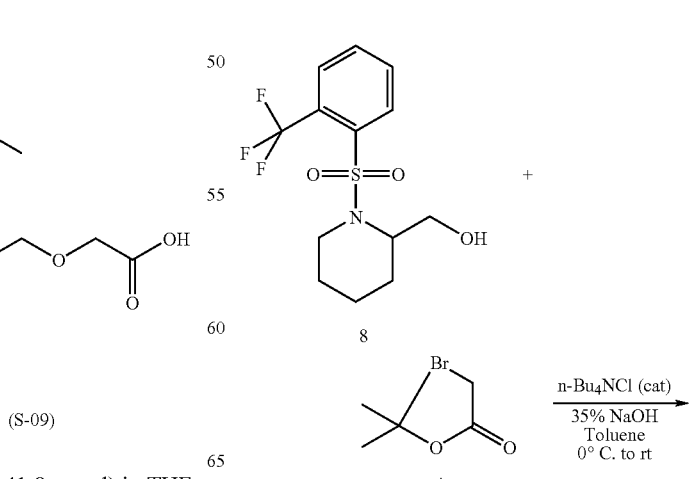

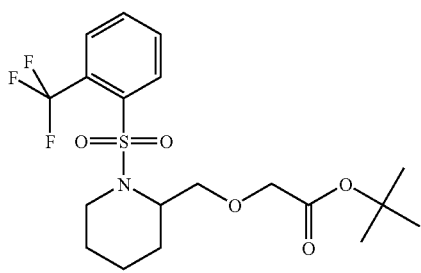

9

9. To a solution of alcohol 8 (8.95 g, 27.7 mmol) in toluene (100 ml) was added n-Bu₄NCl (2.54 g, 9.1 mmol). The reaction mixture was cooled to 0° C. after which aqueous 35% NaOH (100 ml) was added, followed by the addition of tert-butyl bromoacetate (4, 6.05 ml, 41.5 mmol). After stirring for 3 h at room temperature no more starting material was seen on TLC (silica, heptane/EtOAc, 2:1). The organic layer was separated and washed with H₂O (4×200 ml) and brine (200 ml) until neutral, dried (Na₂SO₄) and concentrated under reduced pressure. Purification by column chromatography (silica, heptane/EtOAc 4:1) afforded 11.57 g (96%) of ester 9.

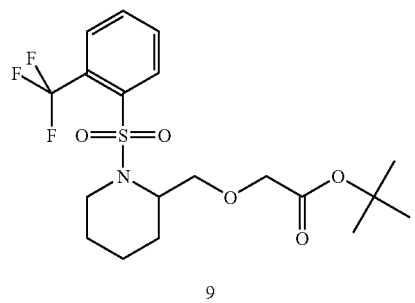

9

$$\xrightarrow{\text{NaOH (aq)}}_{\text{MeOH/THF rt}}$$

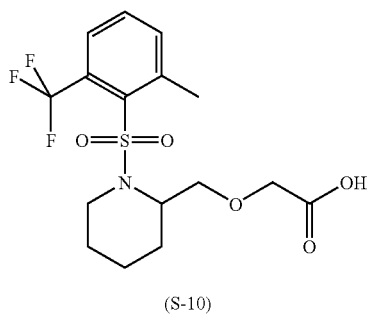

(S-10)

A mixture of ester 9 (11.57 g, 26.4 mmol), aqueous 6 M NaOH (88 ml, 528 mmol), MeOH (85 ml) and THF (85 ml) was stirred at room temperature for 30 min. The reaction was complete according to TLC (silica, heptane/EtOAc 2:1). The solution was then concentrated under reduced pressure to remove MeOH. The resulting suspension was acidified with aqueous 6 M HCl (120 ml) at 0° C. CH₂Cl₂ (300 ml) was added and after separation of the layers, the aqueous layer was extracted with CH₂Cl₂ (100 ml). The combined organic layers were dried (Na₂SO₄) and evaporated to dryness under reduced pressure affording 9.89 g (98%) of carboxylic acid S-10.

Synthesis of Acid Building Block S-12: 2-[2-[1-[(4-Methoxy-2,6-dimethylphenyl)sulfonyl]-piperidin-2-yl]-ethoxy]-acetic acid (S-12)

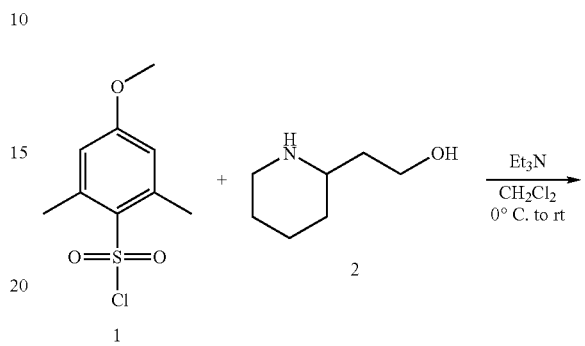

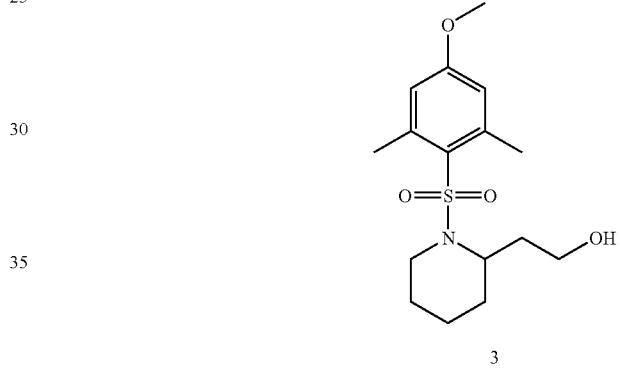

3

3. To a solution of 2-piperidineethanol (2, 5.63 g, 43.6 mmol) in CH₂Cl₂ (200 ml) was added Et₃N (14.1 ml, 109 mmol). At 0° C. was added 4-methoxy-2,6-dimethylbenzenesulfonyl chloride (1, 10.23 g, 43.6 mmol). The reaction mixture was stirred for 1 h at 0° C. and overnight at room temperature. Aqueous 1 M HCl (150 ml) was added and after separation of the layers the organic layer was washed with brine (150 ml), dried (Na₂SO₄) and evaporated to dryness to afford compound 3 (14.85 g, '104%').

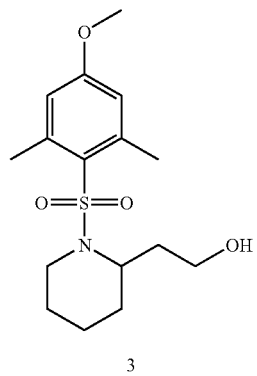

3

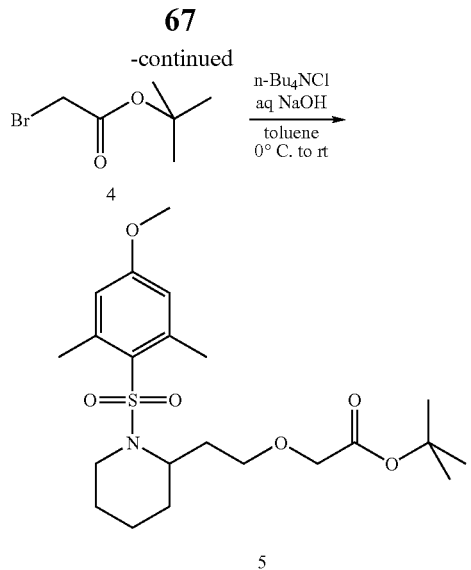

5. To a solution of alcohol 3 (14.8 g, max. 43.6 mmol) in toluene (200 ml) was added n-Bu₄NCl (4.04 g, 14.5 mmol). After cooling to 0° C., an aqueous 35% NaOH solution (200 ml) was added, followed by a dropwise addition of tert-butyl bromoacetate (4, 9.53 ml, 65.4 mmol). The reaction mixture was stirred at room temperature for 3 h. The organic layer was separated and washed with $H_2O$ (3×200 ml), dried ($Na_2SO_4$) and evaporated to dryness. Purification by column chromatography (silica, heptane/EtOAc, 4:1) yielded compound 5 (12.90 g, 67%, 2 steps).

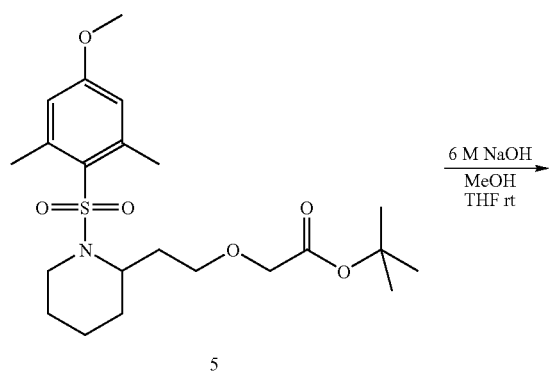

To a solution of ester 5 (12.90 g, 29.2 mmol) in THF (95 ml) and MeOH (95 ml) was added aqueous 6 M NaOH (95 ml). After 1 h organic solvents were evaporated and aqueous 6 M HCl (95 ml) was added at 0° C. The mixture was extracted with EtOAc (500 ml), dried ($Na_2SO_4$) and co-evaporated with $Et_2O$ (2×) to afford compound S-12 (11.07 g, 98%).

Synthesis of Acid Building Block S-13: 4-[Methyl-[[3-(trifluoromethyl)phenyl]sulfonyl]-amino]-butyric acid (S-13)

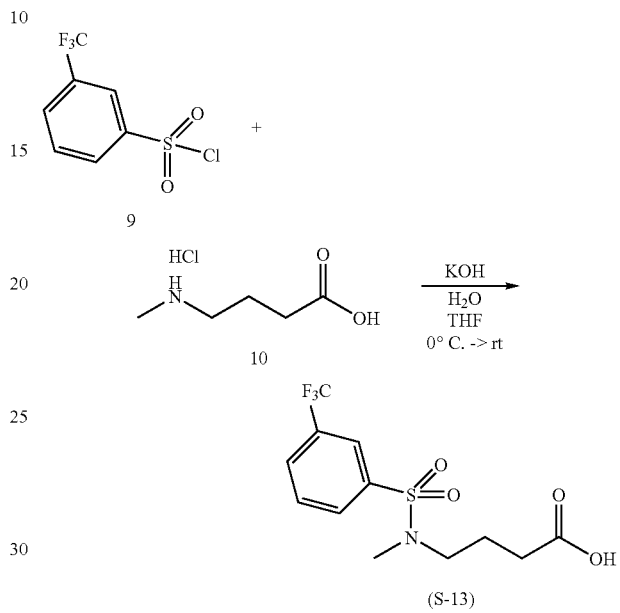

To a solution of KOH (16.5 g, 294 mmol) in $H_2O$ (75 ml) was added 4-(methylamino)butyric acid hydrochloride (10, 15.1 g, 98.1 mmol) and the reaction mixture was cooled with an icebath. A solution of 3-(trifluoromethyl)benzene-sulfonyl chloride (9, 12.0 g, 49.1 mmol) in THF (75 ml) was dropwise added to the reaction mixture and stirring was continued at room temperature overnight. Aqueous 6 M HCl (75 ml) was added to the reaction mixture while cooling with an icebath, after which $CH_2Cl_2$ was added. The organic layer was separated, washed with brine, dried ($Na_2SO_4$), concentrated and co-evaporated with a minimal amount of $Et_2O$. Crystallization of the residue out of EtOAc/heptane resulted in S-13 (11.32 g, 71%).

Synthesis of Acid Building Block S-15: 2-[2-(N-[(4-Methoxy-2,6-dimethylphenyl)sulfonyl]-anilino)-ethoxy]-acetic acid (S-15)

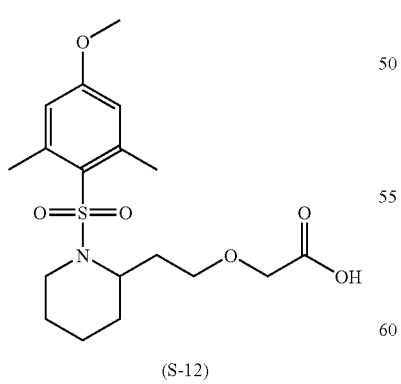
+
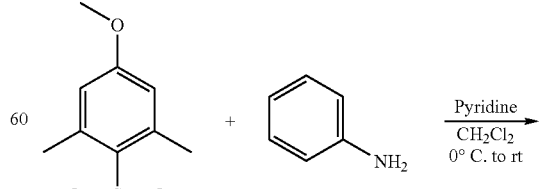

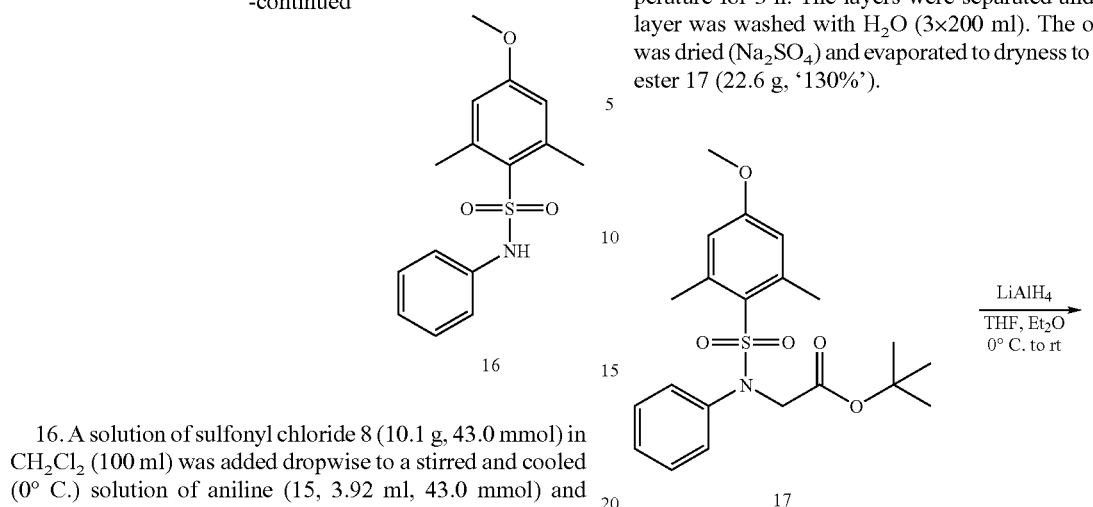

16. A solution of sulfonyl chloride 8 (10.1 g, 43.0 mmol) in CH$_2$Cl$_2$ (100 ml) was added dropwise to a stirred and cooled (0° C.) solution of aniline (15, 3.92 ml, 43.0 mmol) and pyridine (10.4 ml, 129 mmol) in CH$_2$Cl$_2$ (250 ml) and the reaction mixture was stirred at room temperature for 3 h. The mixture was washed with aqueous 0.5 M KHSO$_4$ (100 ml) and saturated aqueous NaHCO$_3$ (100 ml), dried (Na$_2$SO$_4$) and evaporated to dryness to afford crude sulfonamide 16 (14.87 g, '119%').

perature for 3 h. The layers were separated and the organic layer was washed with H$_2$O (3×200 ml). The organic layer was dried (Na$_2$SO$_4$) and evaporated to dryness to afford crude ester 17 (22.6 g, '130%').

18. A solution of 4 M LiAlH$_4$ in Et$_2$O (20.9 ml, 84.0 mmol) was added dropwise to a stirred and cooled (0° C.) solution of ester 17 (22.6 g, max. 43.0 mmol) in THF (225 ml). The reaction mixture was stirred for 15 min at 0° C. after complete addition and Na$_2$SO$_4$·10H$_2$O was added until gas evolution stopped and was stirred at room temperature overnight. The mixture was filtered over a small pad of Na$_2$SO$_4$ and the filtrate was evaporated to dryness. The crude product was purified by column chromatography (silica, heptane/EtOAc, 2:1) to afford alcohol 18 (11.25 g, 78% over 3 steps).

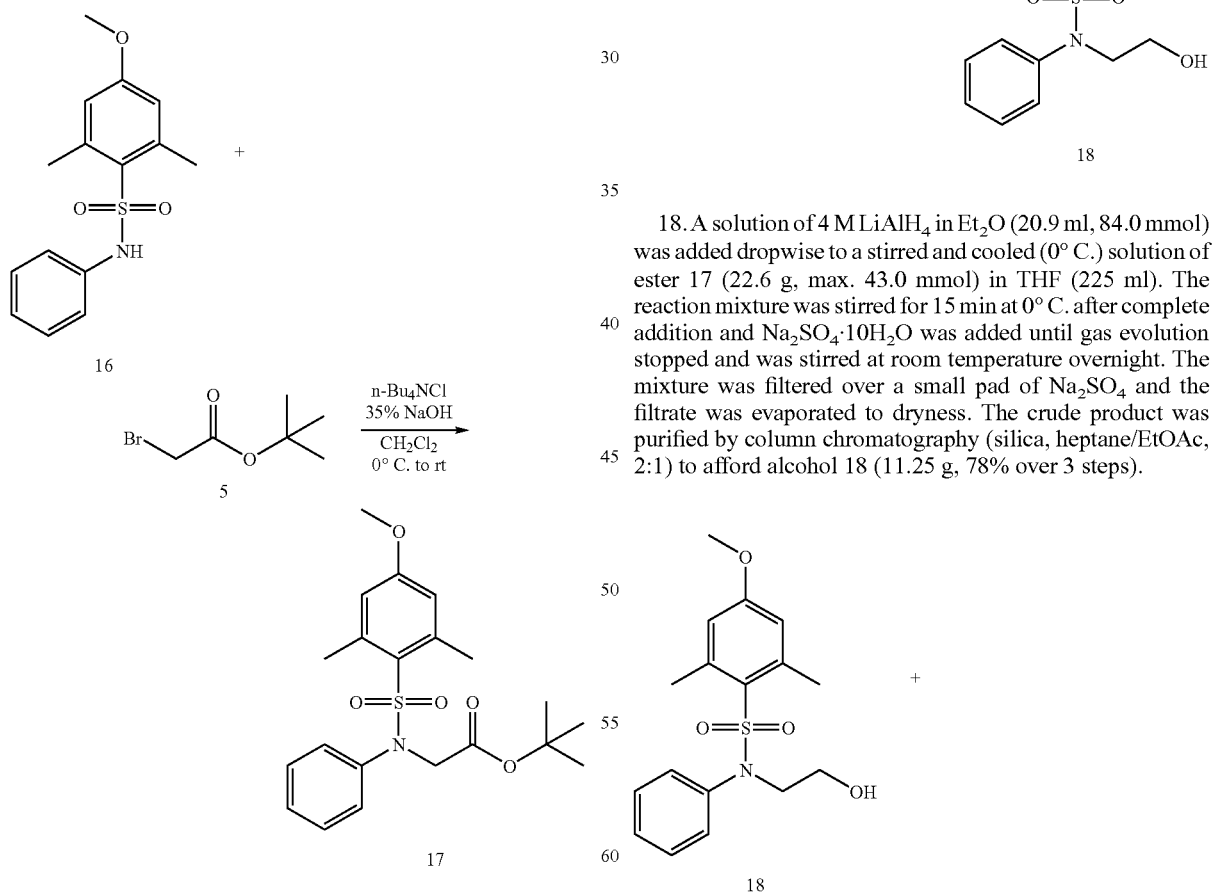

17. A solution of sulfonamide 16 (14.72 g, max. 43.0 mmol) and n-Bu$_4$NCl (1.50 g, 5.40 mmol) in CH$_2$Cl$_2$ (150 ml) was cooled to 0° C. and aqueous 35% NaOH (150 ml) was added. After 10 min tert-butyl bromoacetate (5, 11.2 ml, 76.0 mmol) was added and the mixture was stirred at room tem-

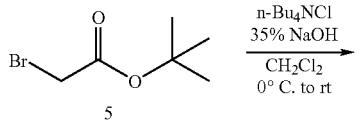

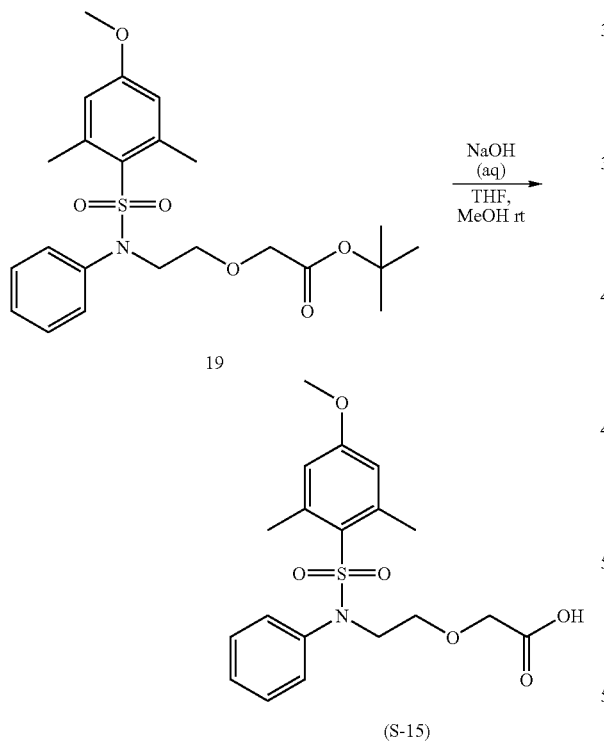

19. To a solution of alcohol 18 (11.24 g, 33.5 mmol) and n-Bu₄NCl (992 mg, 3.57 mmol) in CH₂Cl₂ (120 ml) was added aqueous 35% NaOH (120 ml) at 0° C. followed by tert-butyl bromoacetate (5, 7.43 ml, 50.3 mmol) and the reaction mixture was then stirred at room temperature. After 3 h the layers were separated and the organic phase was washed with H₂O (3×250 ml). The organic layer was dried (Na₂SO₄) and evaporated to dryness. Purification by column chromatography (silica, heptane/EtOAc, 3:1) afforded ester 19 (12.00 g, 80%) as a yellow oil.

To a solution of ester 19 (12.00 g, 26.70 mmol) in MeOH (200 ml) and THF (200 ml) was added aqueous 4 M NaOH (200 ml, 800 mmol) and the reaction mixture was stirred at room temperature. After 3 h the organic solvents were evaporated and the aqueous layer was acidified with aqueous 6 M HCl (250 ml). The aqueous layer was extracted with CH₂Cl₂ (200 ml) and the combined organic layers were dried (Na₂SO₄) and evaporated to dryness to afford building block S-15 (11.27 g, '107%').

Synthesis of Acid Building Block S-16: 2-[[1-(Naphthalen-2-ylsulfonyl)-1,2,3,4-tetrahydro-quinolin-2-yl]-methoxy]-acetic acid (S-16)

Synthesis of acid building block S-16 was performed in analogy to the synthesis of building block (S-17) with naphthalene-2-sulfonyl chloride instead of 4-methoxy-2,6-dimethylbenzene-1-sulfonyl chloride.

Synthesis of Acid Building Block S-17: 2-[[1-[(4-Methoxy-2,6-dimethylphenyl)sulfonyl]-1,2,3,4-tetrahydro-quinolin-2-yl]-methoxy]-acetic acid (S-17)

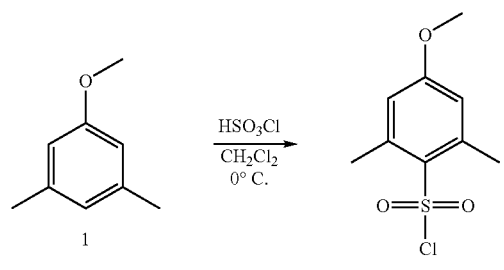

2. A solution of chlorosulfonic acid (247 ml, 3687 mmol) in CH₂Cl₂ (250 ml) was added dropwise to a solution of 3,5-dimethylanisole (1, 100.44 g, 737 mmol) in CH₂Cl₂ (1 L) at 0° C. After 15 min, the reaction mixture was poured into ice-water (1.5 L) and extracted with CH₂Cl₂ (250 ml). The organic layer was quickly washed with ice-cold H₂O (1 L), ice-cold aqueous saturated NaHCO₃ (1 L), dried (Na₂SO₄) and concentrated under reduced pressure. Purification by column chromatography (silica, heptane/CH₂Cl₂, 5:1) afforded sulfonyl chloride 2 (79.64 g, 46%) as a yellow oil which crystallised at −20° C. in the freezer overnight. The product was stored under argon in a freezer due to instability issues.

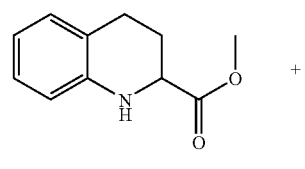

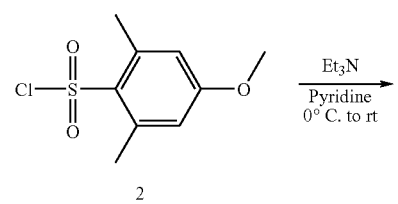

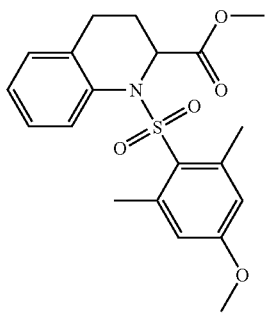

4

4. To a mixture of ester 3 (8.24 g, 43.1 mmol) in dry pyridine (10.5 ml, 129 mmol) was added sulfonyl chloride 2 (20.23 g, 86 mmol) and the mixture was stirred overnight at 40° C. CH$_2$Cl$_2$ (100 ml) was added and the reaction mixture was washed with aqueous 1 M HCl (100 ml), dried (Na$_2$SO$_4$) and evaporated to dryness under reduced pressure. Purification by column chromatography (silica, toluene/EtOAc, 24:1) afforded sulfonamide 4 (14.39 g, 86%).

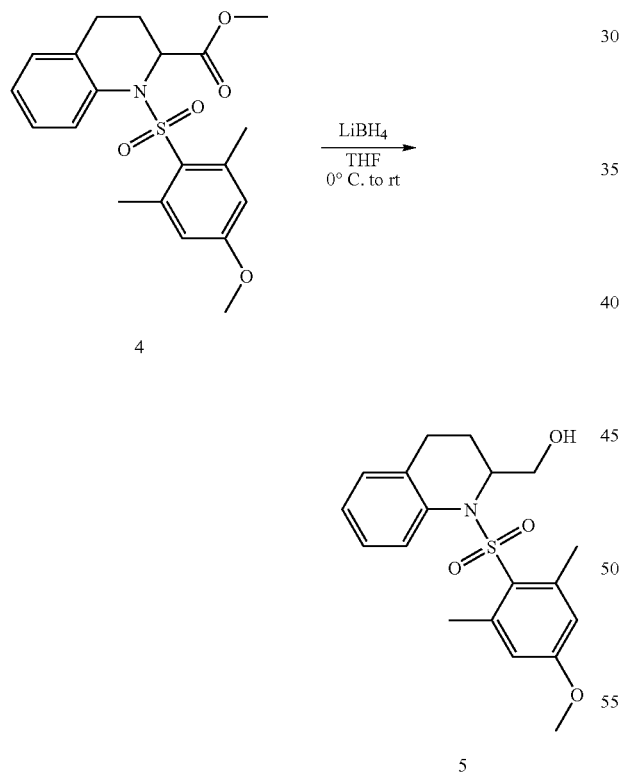

5. Sulfonamide 4 (14.29 g, 36.7 mmol) was dissolved in dry THF (100 ml). After cooling to 0° C. a solution of 2 M LiBH$_4$ in THF (33.0 ml, 66.0 mmol) was added dropwise slowly and the reaction mixture was stirred at room temperature overnight. The reaction was not complete according to TLC (silica, heptane/EtOAc, 1:1), additional 2 M LiBH$_4$ in THF (18.35 ml, 36.7 mmol) was added and the reaction mixture was stirred at room temperature overnight. The reaction was complete according to TLC. The reaction mixture was quenched by adding Na$_2$SO$_4$·10H$_2$O and H$_2$O, additional Na$_2$SO$_4$ was added to remove any residual H$_2$O, filtered, dried (Na$_2$SO$_4$) and evaporated to dryness under reduced pressure. The residue was dissolved in CH$_2$Cl$_2$ (100 ml), washed with H$_2$O (100 ml) and evaporated to dryness under reduced pressure to afford alcohol 5 (14.01 g, '106'%).

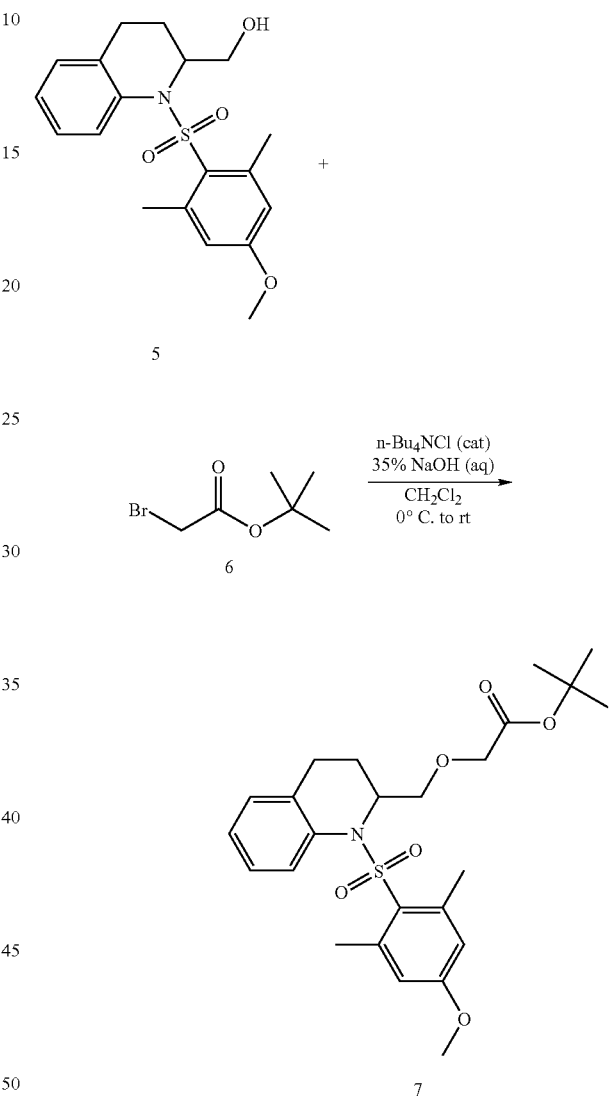

7. To a solution of alcohol 5 (13.23 g, max 34.7 mmol) in CH$_2$Cl$_2$ (80 ml) was added n-Bu$_4$NCl (3.36 g, 12.1 mmol). The reaction mixture was cooled to 0° C. after which aqueous 35% NaOH (84 ml) was added, followed by the addition of tert-butyl 2-bromoacetate (6, 6.40 ml, 43.9 mmol). After stirring for 4 h at room temperature no more starting material was observed on TLC (silica, heptane/EtOAc, 1:1). The organic layer was separated, washed with H$_2$O (3×150 ml) and brine (150 ml) until neutral, dried (Na$_2$SO$_4$) and concentrated under reduced pressure. Purification was carried out by subjecting the crude compound twice to column chromatography (silica, heptane/EtOAc, 4:1) and afforded ester 7 (14.90 g, 90% over 2 steps).

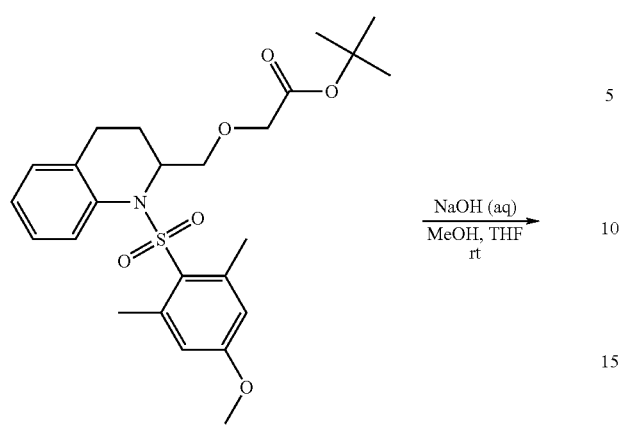

7 complete according to TLC (silica, heptane/EtOAc 2:1). The solution was then concentrated under reduced pressure to remove the organic solvents. The resulting suspension was acidified with aqueous 6 M HCl (120 ml) while cooling at 0° C. $CH_2Cl_2$ (250 ml) was added and after separation of the layers, the organic layer was dried ($Na_2SO_4$) and evaporated to dryness under reduced pressure affording carboxylic acid S-17 (12.64 g, 97%).

Synthesis of Acid Building Blocks S-18, S-19, S-20: 4-[1-[(2-Chloro-6-methylphenyl)sulfonyl]-piperidin-2-yl]-butyric acid (S-18), 4-[1-[[2-(Trifluoromethyl)-phenyl]sulfonyl]-piperidin-2-yl]-butyric acid (S-19), and 4-[1-[(4-Methoxy-2,6-dimethyl-phenyl)sulfonyl]-piperidin-2-yl]-butyric acid (S-20)

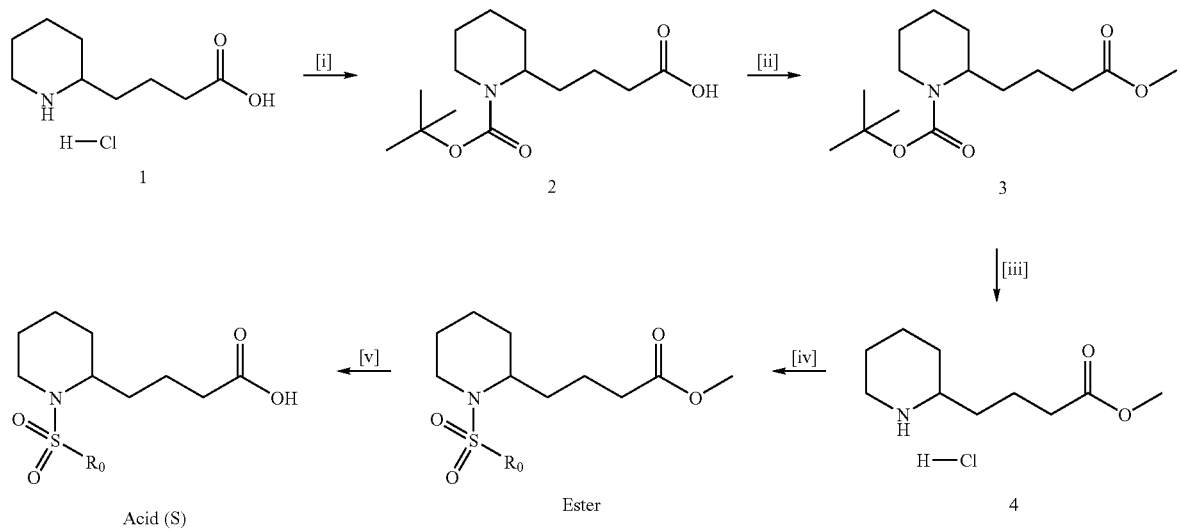

-continued

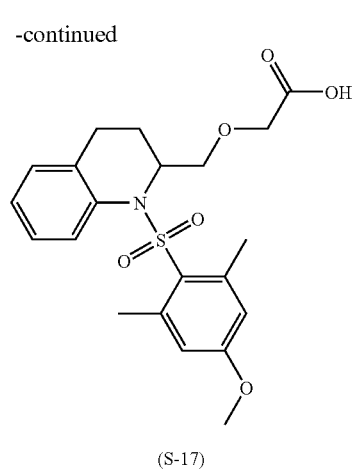

(S-17)

A mixture of ester 7 (14.82 g, 31.2 mmol), MeOH (110 ml), THF (110 ml) and aqueous 4 M NaOH (117 ml, 467 mmol) was stirred at room temperature for 2 h. The reaction was Step (i): 4-(1-tert-Butoxycarbonyl)piperidin-2-yl)butanoic acid (2)

4-Piperidin-2-ylbutanoic acid Hydrochloride (10.0 g, 48.3 mmol), and $K_2CO_3$ (26.6 g, 193.1 mmol) was dissolved in dest. water (70 ml) and Dioxane (124 ml). The reaction mixture was cooled to 0° C. and at this temperature Di-tert-butyldicarbonate (11.4 g, 53.1 mmol) was added slowly. The reaction mixture was stirred for 24 h at room temperature. After completion of the reaction water and Ethylacetate were added, the two phases were separated. The aqueous Phase was extracted once with Ethylacetate. Afterwards the aqueous Phase was triturated with 2 M HCL (aqueous) to reach pH=2. At this pH the aqueous phase was extracted 4× with Dichloromethane. The combined organic layers were dried over Magnesium sulfate, filtered out and evaporated to complete dryness to give (2) (13.13 g, 100%).

Step (ii): tert-Butyl-2-(4-methoxy-4-oxobutyl)piperidine-1-carboxylate (3)

To a solution of 4-(1-tert-Butoxycarbonyl)piperidin-2-yl) butanoic acid (2) (26 g, 95.8 mmol) in Dichloromethane1,1'-carbonyldiimidazole (23.3 g, 143.7 mmol) was added. The reaction mixture was stirred for 1 h at room temperature.

Subsequently Methanol (19.4 ml, 479 mmol) was added and the reaction mixture was stirred over night. The completion of the reaction was controlled via Thin-layer chromatography. After completion the reaction mixture was washed 3× with saturated solution NH$_4$CL (aqueous) and 2× with brine. The organic layer was dried over Magnesium sulfate, filtered out and evaporated in vacuum to afford tert-Butyl-2-(4-methoxy-4-oxobutyl)piperidine-1-carboxylate (3) (25.67 g, 94%).

Step (iii): Methyl 4-(piperidin-2-yl)butanoate hydrochloride (4)

To a solution of tert-Butyl-2-(4-methoxy-4-oxobutyl)piperidine-1-carboxylate (3) (25.67 g, 89.9 mmol) in Methanol was added dropwise acetyl chloride. The reaction mixture was stirred for 5 h at room temperature. The completion of the reaction was controlled via Thin-layer chromatography. After completion the reaction mixture was evaporated in vacuum to give Methyl 4-(piperidin-2-yl)butanoate hydrochloride (4) (20.14 g, 100%)

General Procedure GP I—Sulfonylation (Ester 30-34)

Step (iv): To a solution of methyl 4-(piperidin-2-yl)butanoate hydrochloride (4) (1 Equiv.) in Dichloromethane the sulfonyl chloride (3 Equiv.) was added. Subsequently N-Ethyl-diisopropylamine (3 Equiv.) was added dropwise. The reaction mixture was stirred overnight at room temperature. The completion of the reaction was controlled via Thin-layer chromatography. After completion the reaction mixture was made acidic with 1 M HCl (aqueous) and the aqueous phase was saturated with brine and then extracted 3× with Dichloromethane. The combined organics layers were dried over Magnesium sulfate, filtered and evaporated in vacuum. Purification by column chromatography (Aluminium oxide; Hexane/Ethylacetate) gave us the desired product.

TABLE 1

Synthesis of the sulfonylated amino acid ester

| Ester No. | Structure | Name | Aminoacid ester (4) |
|---|---|---|---|
| Ester 20 | 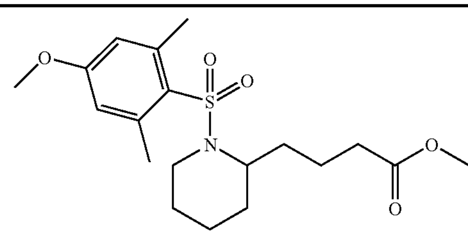 | Methyl 4-(1-(4-methoxy-2,6-dimethylphenylsulfonyl)piperidin-2-yl)butanoate (Ester 20) | Methyl 4-(piperidin-2-yl)butanoate hydrochloride (4) |
| Ester 18 | 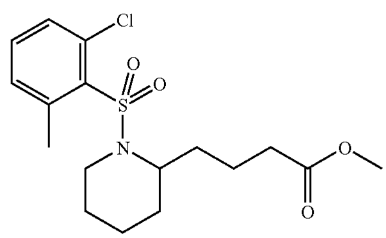 | Methyl 4-(1-(2-chloro-6-methylphenylsulfonyl)piperidin-2-yl)butanoate (Ester 18) | Methyl 4-(piperidin-2-yl)butanoate hydrochloride (4) |
| Ester 19 | 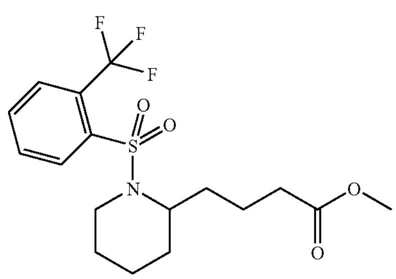 | Methyl 4-(1-(2-(trifluoromethyl)phenylsulfonyl)piperidin-2-yl)butanoate (Ester 19) | Methyl 4-(piperidin-2-yl)butanoate hydrochloride (4) |

| Ester No. | Sulfonylchloride | Synthesis according to | Yield | Comment |
|---|---|---|---|---|
| Ester 20 | 4-Methoxy-2,6-dimethylphenyl-1-sulfonyl chlorid | GP I | 63% (14.3 mmol) | Columnchromatography: Aluminiumoxid; Hexane/Ethylacetate 98.2 → 8:2 |
| Ester 18 | 2-Chloro-6-methylbenzene-1-sulfonylchloride | GP I | 93% (10.4 mmol) | Columnchromatography: Aluminiumoxid; Hexane/Ethylacetate 98.2 → 8:2 |
| Ester 19 | 2-(trifluoromethyl-)benzene-1-sulfonylchloride | GP I | 61% (11.5 mmol) | Columnchromatography: Aluminiumoxid; Hexane/Ethylacetatee 95:5 → 8:2 |

General Procedure GP II—Saponification (S18-20):
Step (v)

To a solution of (Ester 18-20) (1 Equiv.) in Methanol/Water Lithium hydroxide was added and the reaction mixture was stirred over night at room temperature. The completion of the reaction was controlled via Thin-layer chromatography. After completion the Methanol was evaporated in vacuum, and the residue was triturated with Ethylacetate. The mixture was made acidic with diluted HCl. The aqueous layer was extracted 2× with Ethylacetate, the combined organic layers were dried over sodium sulfate and were evaporated in vacuum to give the desired Product (S18-S20).

TABLE 2

Synthesis of Sulfonamide acids

| Acid No. | Structure | Name | Sulfonamidester(Ester) | Synthesis | Yield | Comments |
|---|---|---|---|---|---|---|
| S-20 | 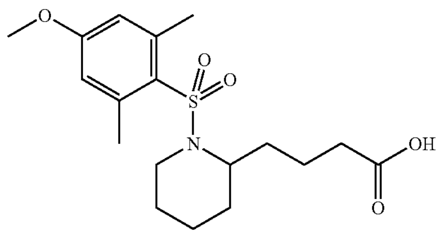 | 4-(1-(4-methoxy-2,6-dimethylphenyl-sulfonyl)piperidin-2-yl)butanoic acid | Methyl 4-(1-(4-methoxy-2,6-dimethylphenyl-sulfonyl)piperidin-2-yl)butanoate (Ester 20) | GP II | 90% (14.6 mmol) | |
| S-18 | 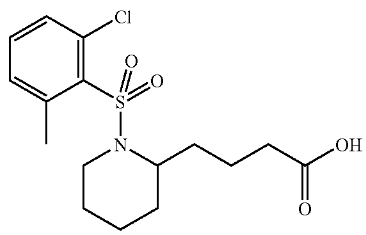 | 4-(1-(2-chloro-6-methylphenyl-piperidin-2-yl)butanoic acid | Methyl 4-(1-(2-chloro-6-methylphenyl-sulfonyl)piperidin-2-yl)butanoate (Ester 18) | GP II | 112% (8.22 mmol) | |
| S-19 | 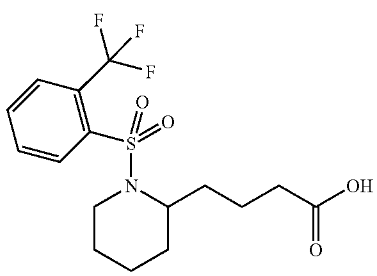 | 4-(1-(2-(trifluormethyl)phenylsulfonyl)piperidin-2-yl)butanoic acid | Methyl 4-(1-(2-(trifluoromethyl)phenylsulfonyl)piperidin-2-yl)butanoate (Ester 19) | GP II | 125% (11.1 mmol) | |

Synthesis of Acid Building Block S-21: 4-[1-(Naphthalen-1-ylsulfonyl)-piperidin-2-yl]-butyric acid (S-21)

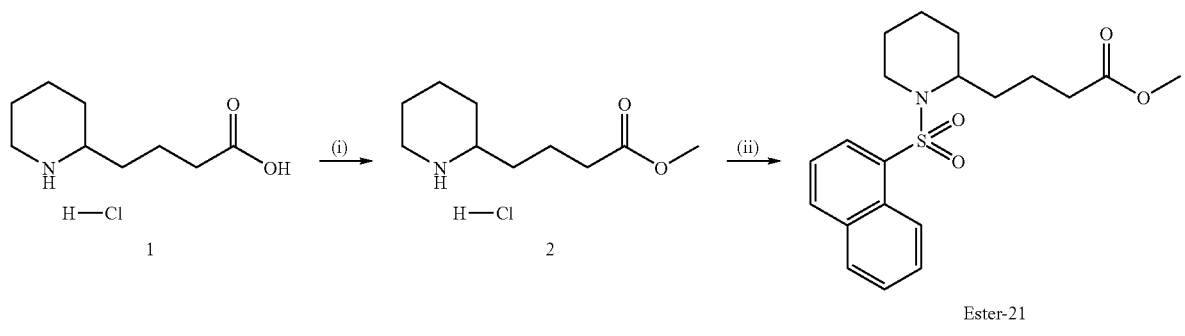

Ester-21

↓(iii)

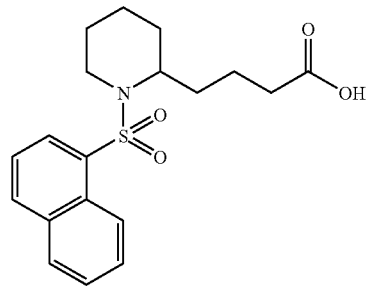

S-21

Step (i): Methyl 4-(piperidin-2-yl)butanoate hydrochloride (2)

A solution of 4-(2-piperidinyl)butanoic acid hydrochloride (5.95 g, 34.8 mmol) in Methanol (104 ml) is cooled to 0° C. At this temperature thionylchloride (7.54 ml, 104.3 mmol) is added slowly. The reaction mixture is heated to reflux for 12 h. The solvent is evaporated in vacuum. The residue is suspended in Ethylacetate and is heated to reflux. The suspension is filtered while it is still hot. In the filtrate a white solid dropped out, which was filtered out and dried in vacuum to give Methyl 4-(piperidin-2-yl)butanoate hydrochloride (2) (3.49 g, 45%)

Step (ii): Methyl 4-(1-(naphthalene-1-ylsulfonyl)piperidin-2-yl)butanoate (Ester-21)

To a solution of Methyl 4-(piperidin-2-yl)butanoate hydrochloride (2) (3.74 g, 20.2 mmol) in Dichloromethane (143 ml) Naphthalene-1-sulfonylchloride (13.7 g, 60.55 mmol) was added. Subsequently N-Ethyl-diisopropylamine (10.2 ml, 60 55 mmol.) was added dropwise. The reaction mixture was stirred overnight at room temperature. The completion of the reaction was controlled via Thin-layer chromatography. After completion the reaction mixture was made acidic with 1 M HCl (aqueous) and the aqueous phase was saturated with brine and then extracted 4× with Dichloromethane. The combined organics layers were dried over Magnesium sulfate, filtered and evaporated in vacuum. Purification by column chromatography (Aluminium oxide; Hexane/Ethylacetate 97:3-9:1) gave us the desired Product Methyl 4-(1-(naphthalene-1-ylsulfonyl)piperidin-2-yl)butanoate (Ester 21) (4.95 g, 65%)

Step (iii): 4-(1-(Naphthalen-1-ylsulfonyl)piperidin-2-yl)butanoic acid (S-21)

To a solution of Methyl 4-(1-(naphthalene-1-ylsulfonyl) piperidin-2-yl)butanoate (Ester-21) (4.95 g, 13.18 mmol.) in Methanol/Water (54 ml/36 ml) Lithium hydroxide (1.58 g, 65.9 mmol) was added and the reaction mixture was stirred over night at room temperature. The completion of the reaction was controlled via Thin-layer chromatography. After completion the Methanol was evaporated in vacuum, and the residue was triturated with Ethylacetate. The mixture was made acidic with diluted HCl. The aqueous layer was extracted 2× with Ethylacetate, the combined organic layers were dried over Sodium sulfate and were evaporated in vacuum to give the desired Product 4-(1-(Naphthalen-1-yl-sulfonyl)piperidin-2-yl)butanoic acid (S-21) (4.38 g, 91%).

Synthesis of Acid Building Block S-23: 2-[2-(Benzhydryl-methylsulfonyl-amino)-ethoxy]-acetic acid (S-23)

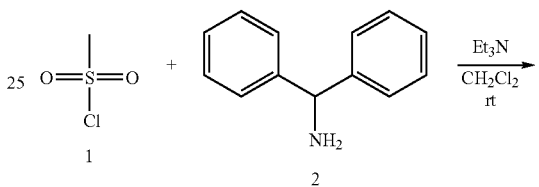

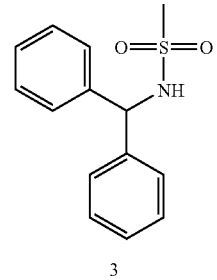

3

3. Sulfonyl chloride 1 (9.76 g, 85.2 mmol) and Et$_3$N (11.8 ml, 85.2 mmol) were dissolved in CH$_2$Cl$_2$ (100 ml) and a solution of diphenylmethanimine (2, 15.61 g, 85.2 mmol) in CH$_2$Cl$_2$ (40 ml) was added dropwise over 10 min. The reaction mixture was stirred at room temperature for 18 h. The reaction mixture was washed with aqueous 0.5 M KHSO$_4$ (2×200 ml), brine (100 ml), dried over Na$_2$SO$_4$ and evaporated to dryness. Crystallisation from CH$_2$Cl$_2$ at 0-5° C. afforded 17.63 g (79%) of sulfonamide 3.

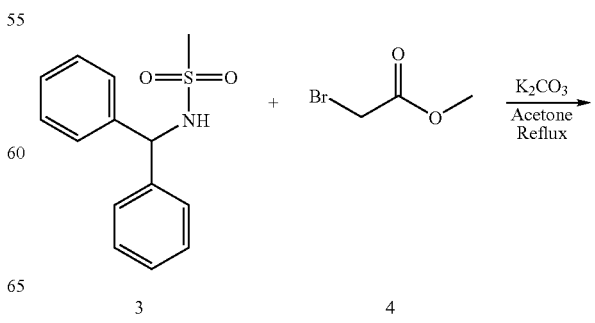

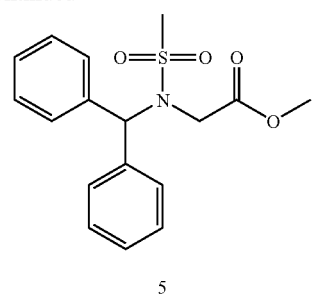

5

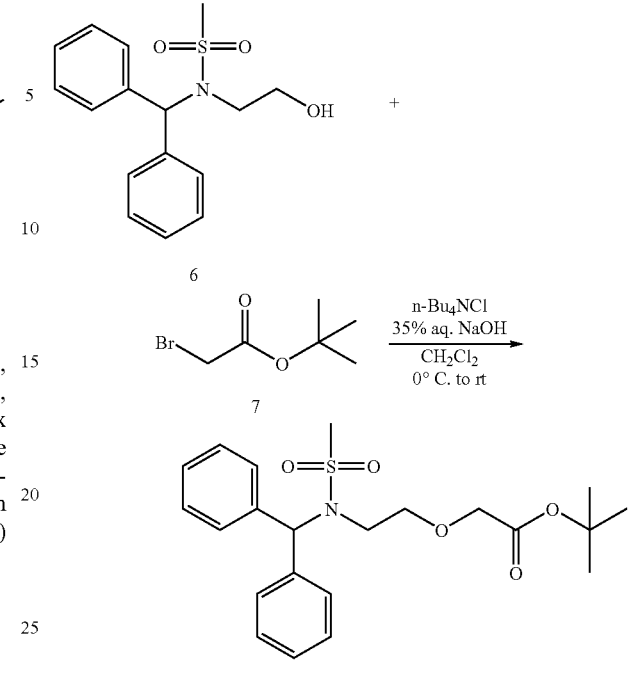

5. A suspension of sulfonamide 3 (17.50 g, 66.96 mmol), K₂CO₃ (18.51 g, 133.9 mmol) and methyl bromoacetate (4, 31.8 ml, 355 mmol) in acetone (500 ml) was stirred at reflux for 4 h. According to TLC (silica, heptane/EtOAc, 2:1) the conversion was complete and the reaction mixture was filtered and the filtrate was evaporated to dryness. Purification by column chromatography (silica, toluene/THF, 14:1) afforded 11.95 g (54%) of methyl ester 5.

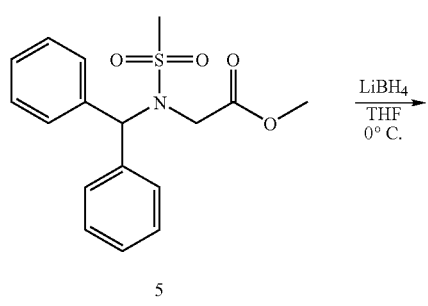

5

8. To a solution of alcohol 6 (7.80 g, 25.5 mmol) and n-Bu₄NCl (710 mg, 2.55 mmol) in CH₂Cl₂ (100 ml) was added aqueous 35% NaOH (100 ml) at 0° C. followed by tert-butyl bromoacetate (7, 11.3 ml, 76.6 mmol) and the reaction mixture was then stirred at room temperature. After 3 h the layers were separated and the organic phase was washed with H₂O (3×150 ml). The organic layer was dried (Na₂SO₄) and evaporated to dryness. Purification by column chromatography (silica, heptane/EtOAc, 3:1) afforded ester 8 (9.06 g, 85%).

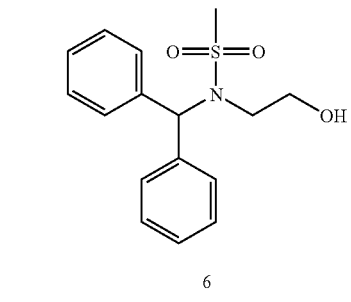

6

6. A solution of 2 M LiBH₄ in THF (26.6 ml, 53.2 mmol) was added dropwise to a stirred and cooled (0° C.) solution of ester 5 (11.83 g, 35.48 mmol) in THF (100 ml). The reaction mixture was stirred at room temperature for 5 h. According to TLC (silica, heptane/EtOAc, 1:1) conversion was incomplete and another amount of 2 M LiBH₄ in THF (26.6 ml, 53.2 mmol) was added. After stirring at room temperature overnight the reaction was complete according to TLC (silica, heptane/EtOAc, 1:1). Na₂SO₄.10H₂O was added until gas evolution ceased and subsequently H₂O was added followed by Na₂SO₄. The mixture was filtered over a small pad of Na₂SO₄ and the filtrate was evaporated to dryness. The product was dissolved in CH₂Cl₂ and dried again with Na₂SO₄. The product was purified by column chromatography (silica, heptane/EtOAc, 1:1) to afford alcohol 6 (7.87 g, 73%).

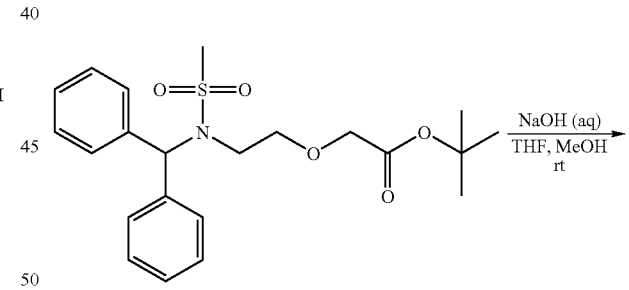

8

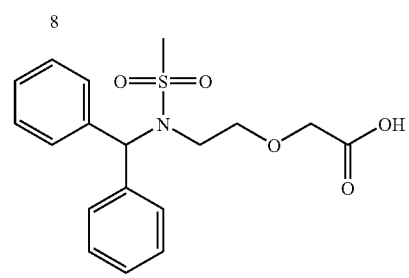

(S-23)

To a solution of ester 8 (9.05 g, 21.6 mmol) in MeOH (160 ml) and THF (160 ml) was added aqueous 4 M NaOH (162 ml, 647 mmol) and the reaction mixture was stirred at room Synthesis of Acid Building Block S-24: 2-[[4-[(4-Methoxy-2,6-dimethyl-phenyl)-sulfonyl]-3,4-dihydro-2H-[1,4]benzoxazin-3-yl]-methoxy]-acetic acid (S-24)

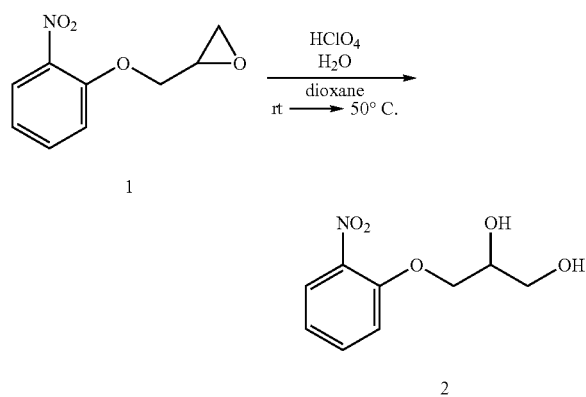

2. Perchloric acid (3.30 ml, 38.2 mmol) was added to a solution of 1 (37.3 g, 191 mmol) in dioxane (746 ml) and H$_2$O (568 ml) and the reaction mixture was stirred at 50° C. overnight. The reaction mixture was concentrated to half its volume and aqueous saturated NaHCO$_3$ was added. The H$_2$O layer was extracted with CH$_2$Cl$_2$ (2×) and the combined organic layer was washed with brine, dried (Na$_2$SO$_4$) and concentrated. Purification by column chromatography (silica, heptane/EtOAc, 2:3) yielded 2 (30.6 g, 75%).

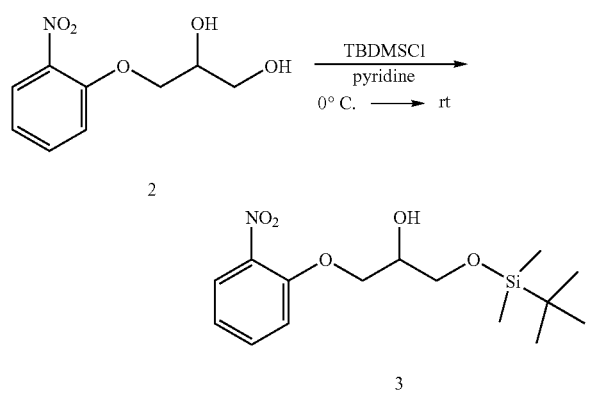

3. To a solution of 2 (30.6 g, 143 mmol) in pyridine (75 ml) was added tert-butyldimethylsilyl chloride (23.8 g, 158 mmol) while cooling with an icebath. The reaction mixture was stirred at room temperature for 2 h and afterwards concentrated and co-evaporated with toluene. The residue was dissolved in EtOAc, washed with H$_2$O, brine, dried (Na$_2$SO$_4$) and concentrated to give 3 (46.7 g, 99%).

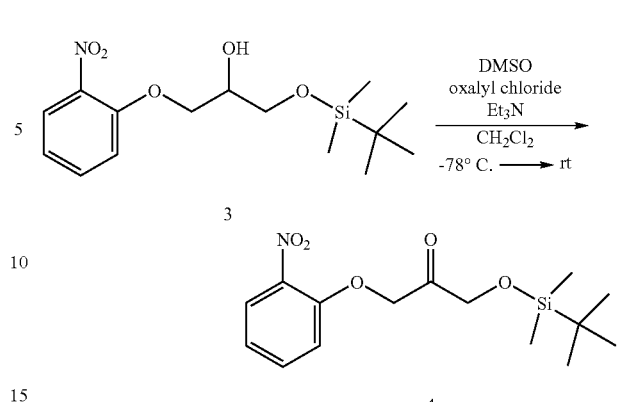

4. A solution of DMSO (21.24 ml, 299 mmol) in CH$_2$Cl$_2$ (600 ml) was dropwise added to a solution of oxalyl chloride (15.0 ml, 171 mmol) in CH$_2$Cl$_2$ (300 ml) in 30 min while maintaining the internal temperature below −65° C. A solution of 3 (46.7 g, 142 mmol) in CH$_2$Cl$_2$ (300 ml) was added dropwise in 15 min. while maintaining the temperature below −65° C. The reaction mixture was stirred an additional 45 minutes at −78° C., after which Et$_3$N (99.0 ml, 712 mmol) was added. After the reaction mixture was stirred at −78° C. for 45 min, the reaction mixture was allowed to warm to room temperature and stirring was continued for an additional hour. The reaction mixture was washed with H$_2$O and brine, dried (Na$_2$SO$_4$) and concentrated. The residue was dissolved in Et$_2$O, filtered and the filtrate was concentrated and crystallized (Et$_2$O/heptane) to result in 4 (30.9 g, 67%). The mother liquor was concentrated and crystallized (Et$_2$O/heptane) and gave extra 4 (2.27 g, 5%).

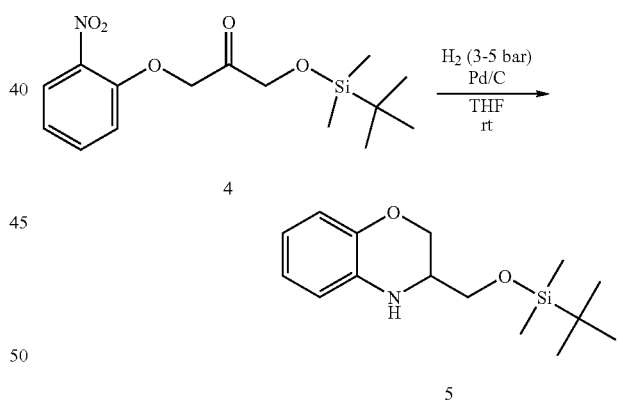

5. A mixture of 4 (18 g, 55.3 mmol) and 10% Pd/C (1.8 g, 1.7 mmol) in dry THF (150 ml) was stirred under an hydrogen atmosphere of ~3 bar for 2 days and then under an hydrogen atmosphere of 5 bar for 1 d. The reaction mixture was filtered over Celite and eluted with THF. The filtrate was concentrated and 10% Pd/C (1.8 g, 1.7 mmol) was added to the residue in dry THF (150 ml) and the resulting reaction mixture was stirred under an hydrogen atmosphere of ~5 bar for 1 d. The reaction mixture was filtered over Celite and eluted with THF. The filtrate was concentrated and purified by column chromatography (silica, heptane/Et$_2$O, 9:1) to yield 5 (7.11 g, 46%).

Another batch of 4 (15.06 g, 46.3 mmol) and Pd/C 10% Pd/C (1.5 g, 1.4 mmol) in dry THF (150 ml) was stirred under an hydrogen atmosphere (~5 bar) for 2 days. The reaction mixture was filtered over Celite and eluted with THF. The filtrate was concentrated and purified by column chromatography (silica, heptane/Et$_2$O, 9:1) to yield extra 5 (3.20 g, 25%).

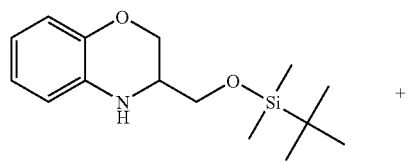

5

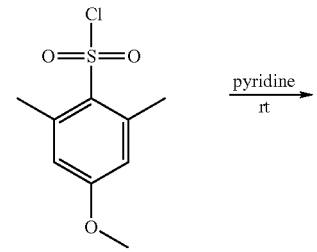

6

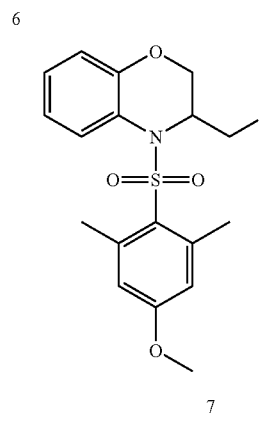

7

7. Sulfonyl chloride 6 (8.96 g, 38.2 mmol) was added to a solution of 5 (9.70 g, 34.7 mmol) in pyridine (8.42 ml) and the reaction mixture was stirred at room temperature for 2 d. The reaction mixture was concentrated, dissolved in CH$_2$Cl$_2$ and washed with H$_2$O, brine, dried (Na$_2$SO$_4$) and concentrated to give crude 7, which was directly used in the next step.

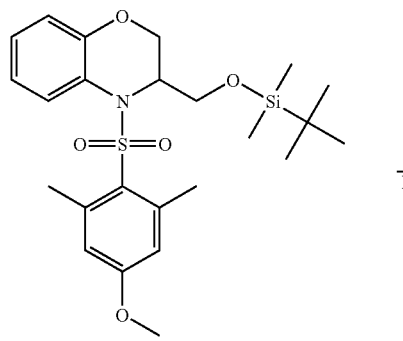

7

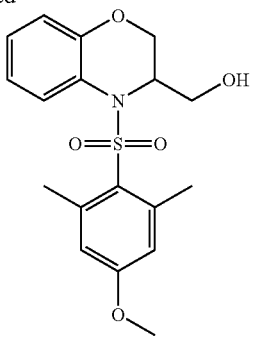

8

8. Crude 7 was dissolved in EtOH (~100 ml) and H$_2$O (~100 ml) with heating and was left standing overnight. The reaction mixture was concentrated, dissolved in CH$_2$Cl$_2$, washed with aqueous saturated NaHCO$_3$, brine, dried (Na$_2$SO$_4$) and concentrated. The residue was solidified with EtOAc/heptane (2:1) and some CH$_2$Cl$_2$. The resulting precipitate was washed with EtOAc/heptane (2:1) and dried on filter to yield 8 (9.68 g, 77% over 2 steps).

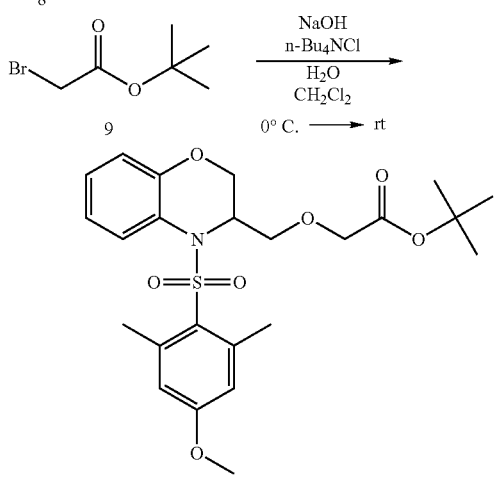

10

10. To an ice-cooled solution of 8 (9.68 g, 26.6 mmol) and n-Bu$_4$NCl (2.44 g, 8.79 mmol) in CH$_2$Cl$_2$ (130 ml) was sequentially added aqueous 35% NaOH solution (130 ml) and tert-butyl bromoacetate (9, 11.6 ml, 80.0 mmol). The reaction mixture was stirred at room temperature for 4.5 h, after which H₂O was added. The organic layer was separated, washed with H₂O (2×), dried (Na₂SO₄) and concentrated. The residue was purified by column chromatography (silica, heptane/EtOAc, 4:1->3:1) to provide 10 (11.9 g, 94%).

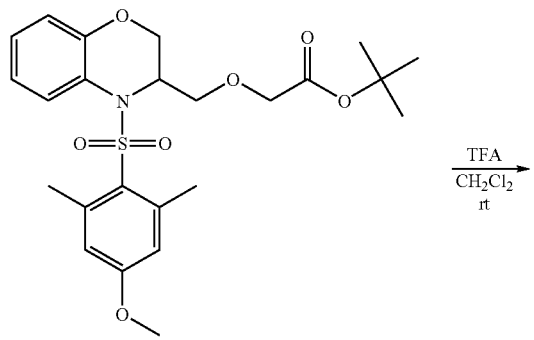

10

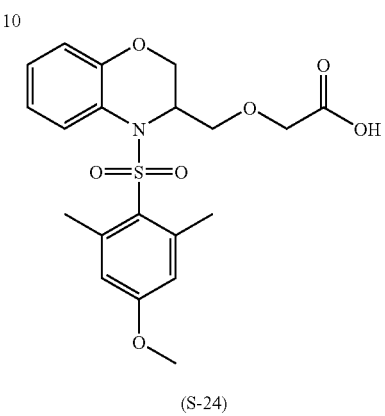

(S-24)

A solution of 10 (11.80 g, 24.7 mmol) and TFA (25 ml, 324 mmol) in CH₂Cl₂ (125 ml) was stirred at room temperature for 2.5 h. The reaction mixture was concentrated, co-evaporated with toluene (2×) and CH₂Cl₂ (2×). The residue was dried under vacuum for 1 day to furnish S-24 (10.26 g, 99%).

Synthesis of Acid Building Block S-25: 2-[2-[[(4-Methoxy-2,6-dimethylphenyl)sulfonyl]-(quinolin-3-yl-methyl)-amino]-ethoxy]-acetic acid (S-25)

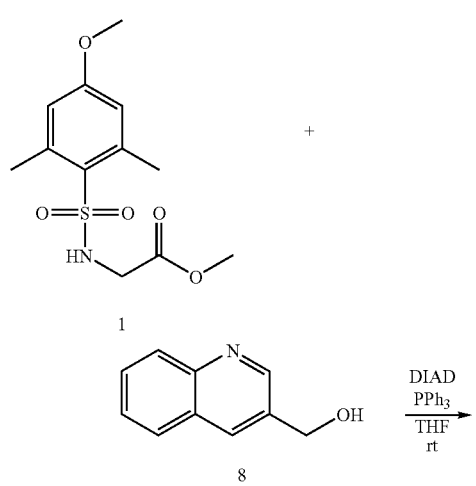

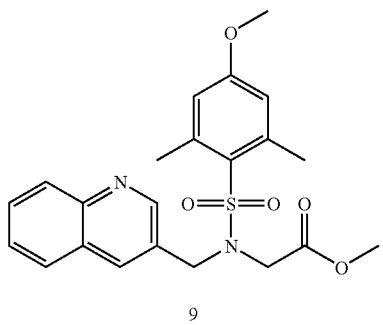

9

9. To a solution of compound 1 (7.52 g, 26.2 mmol), quinolin-3-ylmethanol (8, 5.00 g, 31.4 mmol) and PPh₃ (8.24 g, 31.4 mmol) in dry THF (150 ml) was added DIAD (6.11 ml, 31.4 mmol) and the reaction mixture was stirred at room temperature overnight and was then evaporated to dryness. Purification by column chromatography (silica, heptane/EtOAc, 2:1 to 1:1) afforded ester 9 (12.07 g, '108%').

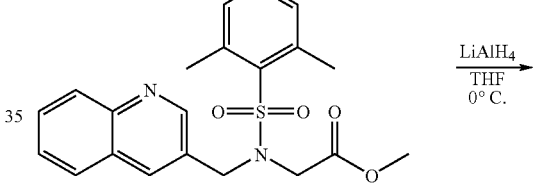

9

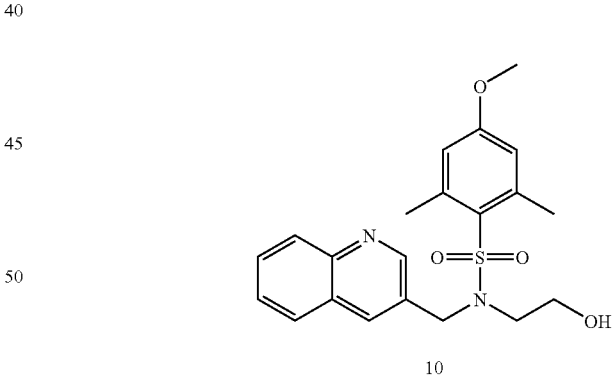

10

10. To a stirred and cooled (0° C.) solution of LiAlH₄ (2.4 M in THF, 35.2 ml, 85 mmol) in dry THF (100 ml), a solution of ester 9 (12.07 g, max. 26.2 mmol) in dry THF (100 ml) was added dropwise. After 1 h a mixture of THF/H₂O (1:1, ~26 ml) was added dropwise. The mixture was dried (Na₂SO₄) and filtered over a small pad of Na₂SO₄ and the residue was extensively rinsed with THF (2×250 ml). The filtrate was evaporated to dryness and purified by column chromatography (silica, CH₂Cl₂/(7 M NH₃ in MeOH), 98:2) to afford alcohol 10 (4.09 g, 36%, 2 steps).

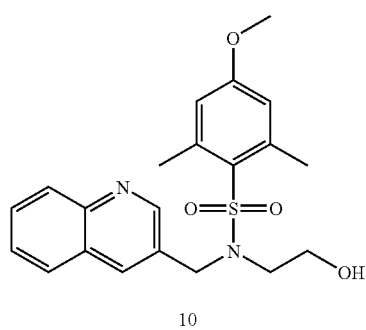

10

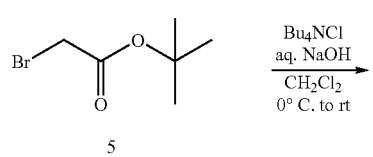

5

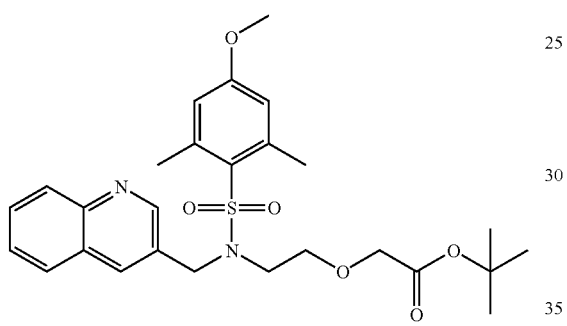

11

11. To a solution of alcohol 10 (7.45 g, 18.6 mmol) and Bu₄NCl (1.71 g, 6.14 mmol) in CH₂Cl₂ (100 ml) was added aqueous 35% NaOH (42.5 ml) at 0° C., followed by tert-butyl bromoacetate (5, 4.07 ml, 27.9 mmol). After 1 h more tert-butyl bromoacetate (5, 1.36 ml, 9.30 mmol) was added. After 30 min the organic layer was washed with H₂O (150 ml). The organic layer was concentrated partially and was then subjected directly to column chromatography (silica, heptane/EtOAc, 3:1 to 1:1) to afford ester 11 (7.36 g, 77%).

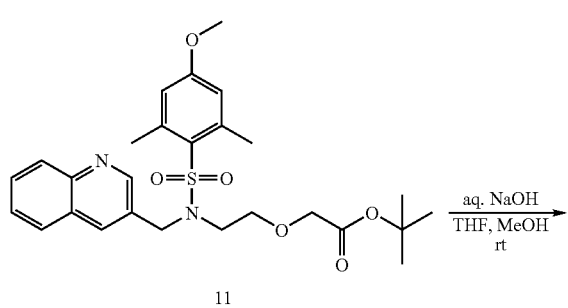

11

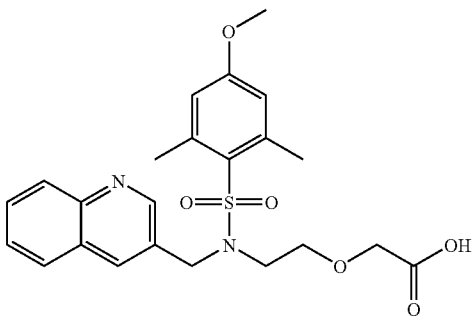

S-25

To a solution of ester 11 (7.36 g, 14.3 mmol) in THF (50 ml) and MeOH (50 ml) was added aqueous 6 M NaOH (47.7 ml, 286 mmol) and the mixture was stirred at room temperature. After 1 h the organic layers were evaporated and the remainder was acidified with aqueous 6 M HCl (55 ml) at 0° C. The mixture was extracted with CH₂Cl₂ (2×150 ml) and the combined organic layers were dried (Na₂SO₄) and evaporated to dryness to afford carboxylic acid S-25 (6.50 g, 99%).

Synthesis of Acid Building Block S-26: 2-[[4-[(2-Chloro-6-methyl-phenyl)-sulfonyl]-3,4-dihydro-2H-[1,4]benzoxazin-3-yl]-methoxy]-acetic acid (S-26)

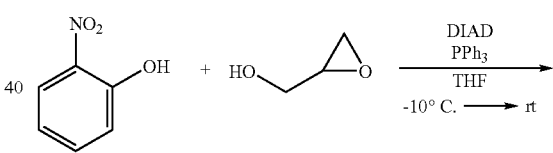

3

3. A solution of DIAD (149 ml, 719 mmol) in dry THF (200 ml) was added in 30 min to a solution of 2-nitrophenol (1, 100 g, 719 mmol), glycidol (2, 50.0 ml, 719 mmol) and PPh₃ (189 g, 719 mmol) in dry THF (800 ml) while keeping the temperature between −10° C. and −5° C. The reaction mixture was stirred for 1 h at this temperature range, after which stirring was continued at room temperature overnight. The reaction mixture was concentrated and the residue was stirred up in toluene, filtered and concentrated. Purification by column chromatography (silica, toluene/acetone, 95:5) afforded 3 (114.25 g, 81%).

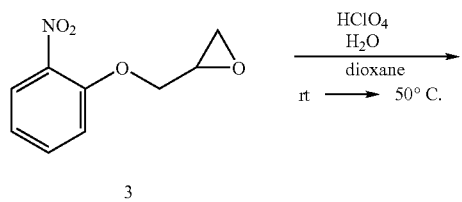

3

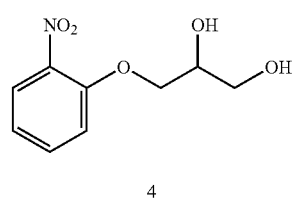

4

4. Perchloric acid (4.96 ml, 57.4 mmol) was added to a solution of 3 (56.02 g, 287 mmol) in dioxane (1124 ml) and H₂O (856 ml) and the reaction mixture was stirred at 50° C. overnight. The reaction mixture was concentrated to half its volume and aqueous saturated NaHCO₃ was added. The H₂O layer was extracted with CH₂Cl₂ (2x) and the combined organic layer was washed with brine, dried (Na₂SO₄) and concentrated. Purification by column chromatography (silica, heptane/EtOAc, 2:3->1:2) yielded 4 (47.45 g, 78%).

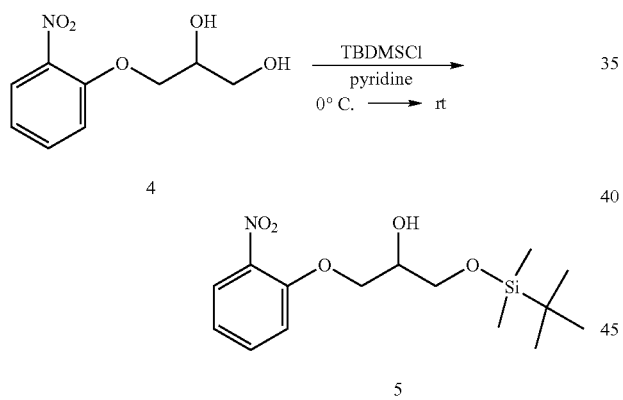

5. To a solution of 4 (47.45 g, 223 mmol) in pyridine (117 ml) was added tert-butyldimethylsilyl chloride (36.9 g, 245 mmol) while cooling with an icebath. The reaction mixture was stirred at room temperature for 2 h and afterwards concentrated and co-evaporated with toluene. The residue was dissolved in EtOAc, washed with H₂O, brine, dried (Na₂SO₄) and concentrated to give 5 (77.94 g, 100%).

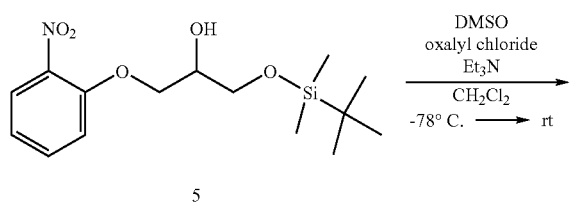

5

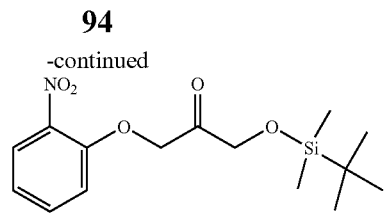

6

6. A solution of DMSO (35.0 ml, 500 mmol) in CH₂Cl₂ (1 L) was dropwise added to a solution of oxalyl chloride (25.0 ml, 286 mmol) in CH₂Cl₂ (500 ml) in 1 h while maintaining the internal temperature below −65° C. A solution of 5 (77.94 g, 221 mmol) in CH₂Cl₂ (500 ml) was added dropwise in 30 min. while maintaining the temperature below −65° C. The reaction mixture was stirred an additional 45 minutes at −78° C., after which Et₃N (166 ml, 1.190 mol) was added. After the reaction mixture was stirred at −78° C. for 45 min, the reaction mixture was allowed to warm to room temperature and stirring was continued for an additional hour. The reaction mixture was washed with H₂O and brine, dried (Na₂SO₄) and concentrated. The residue was dissolved in Et₂O, filtered and the filtrate was concentrated. The residue was filtered over a small layer of silica (heptane/EtOAc, 4:1) and crystallized (i-Pr₂O/heptane) to result in 6 (23.15 g, 32.1%). The mother liquor was concentrated and crystallized (heptane) to give extra 6 (3.20 g, 4%). The mother liquor was concentrated and purified by column chromatography (silica, heptane/EtOAc, 4:1->3:1), followed by crystallization (Et₂O/heptane) to yield extra 6 (4.16 g, 6%). All crystals were combined to give 6 (30.51 g, 42%).

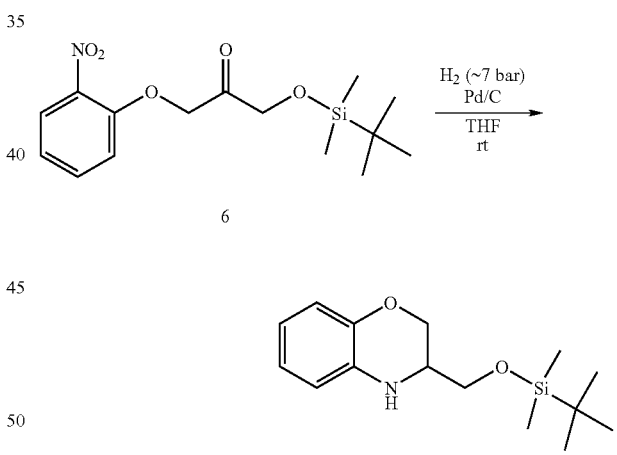

7

7. A mixture of 6 (24.36 g, 74.9 mmol) and 10% Pd/C (2.4 g, 23 mmol) in EtOH (350 ml) in a 1 L autoclave was stirred at 60° C. under a nitrogen atmosphere. After pressurizing the reaction vessel with hydrogen to ~7 bar, the pressure dropped rapidly while stirring vigorously. The pressurizing the reaction vessel with hydrogen to ~7 bar was repeated until the pressure remained almost constant for 10 min. The reaction mixture was then stirred at 60° C. and 4 bar overnight. The reaction mixture was filtered over Celite and eluted with EtOH. The filtrate was concentrated, co-evaporated with heptane and purified by column chromatography (silica, heptane/i-Pr₂O, 9:1->4:1) to yield 7 (14.75 g, 71%).

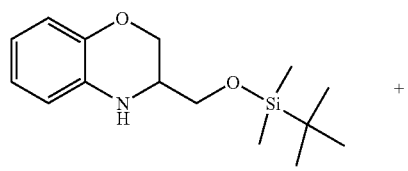

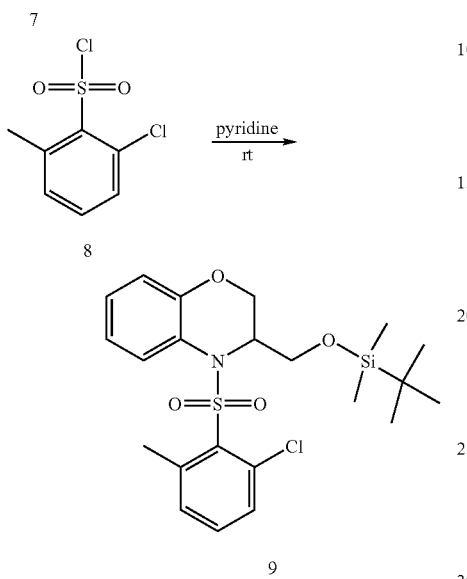

7. 2-chloro-6-methylbenzenesulfonyl chloride (8, 7.82 g, 34.8 mmol) was added to a solution of 7 (8.83 g, 31.6 mmol) in pyridine (7.67 ml, 95.0 mmol) and the reaction mixture was stirred at room temperature overnight. CH$_2$Cl$_2$ and H$_2$O were added to the reaction mixture and the organic layer was separated, washed with H$_2$O, brine, dried (Na$_2$SO$_4$) and concentrated to give crude 9, which was directly used as such in the next step.

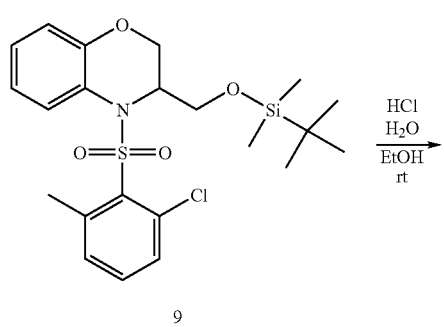

10. Aqueous 1 M HCl (50 ml, 50 mmol) was added to crude 9 in EtOH (200 ml) and the reaction mixture was stirred at room temperature overnight. The reaction mixture was concentrated, dissolved in CH$_2$Cl$_2$, washed with aqueous saturated NaHCO$_3$, dried (Na$_2$SO$_4$) and concentrated. The residue was purified by column chromatography (silica, heptane/EtOAc: 2:1) to yield 10 (7.75 g, 69%, 2 steps).

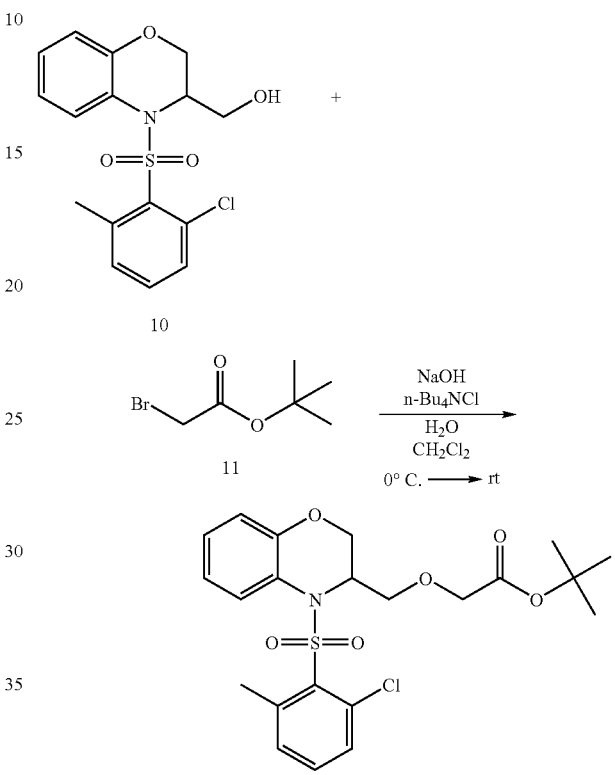

12. To an ice-cooled solution of 10 (7.75 g, 21.9 mmol) and n-Bu$_4$NCl (2.00 g, 7.23 mmol) in CH$_2$Cl$_2$ (110 ml) was sequentially added aqueous 35% NaOH solution (110 ml) and tert-butyl bromoacetate (11, 9.57 ml, 65.7 mmol). The reaction mixture was stirred at room temperature for 4 h, after which H$_2$O was added. The organic layer was separated, washed with H$_2$O and brine, dried (Na$_2$SO$_4$) and concentrated. The residue was purified by column chromatography (silica, heptane/EtOAc, 4:1) to provide 12 (9.98 g, 92%).

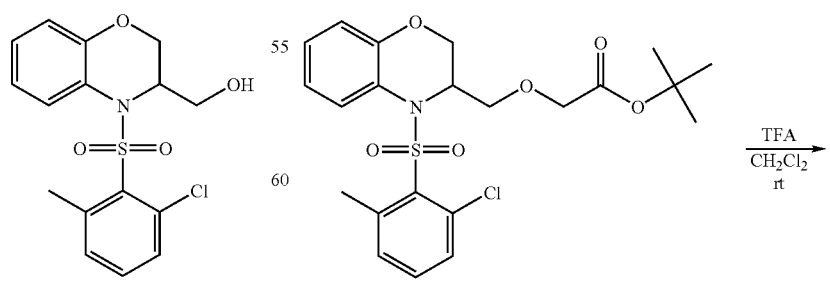

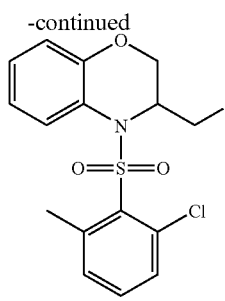

(S-26)

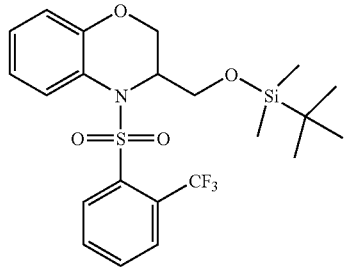

15

A solution of 12 (9.88 g, 20.1 mmol) and TFA (20 ml, 260 mmol) in $CH_2Cl_2$ (100 ml) was stirred at room temperature for 2 h. The reaction mixture was concentrated, co-evaporated with toluene (2×) and $CH_2Cl_2$ (2×). The residue was transferred to a jar with $CH_2Cl_2$, concentrated and dried under vacuum overnight to furnish S-26 (8.50 g, '103'%).

Synthesis of Acid Building Block S-27: 2-[[4-[[2-(Trifluoromethyl)-phenyl]-sulfonyl]-3,4-dihydro-2H-[1,4]benzoxazin-3-yl]-methoxy]-acetic acid (S-27)

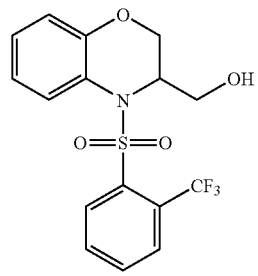

16

16. Aqueous 1 M HCl (50 ml, 50 mmol) was added to crude 15 in EtOH (200 ml) and the reaction mixture was stirred at room temperature overnight. The reaction mixture was concentrated, dissolved in $CH_2Cl_2$, washed with aqueous saturated $NaHCO_3$, dried ($Na_2SO_4$) and concentrated. The residue was purified by column chromatography (silica, heptane/EtOAc: 2:1) to yield 16 (10.29 g, 78%, 2 steps).

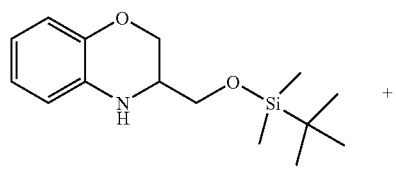

7

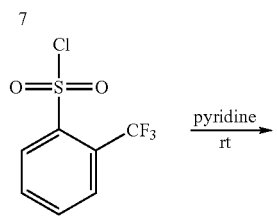

14

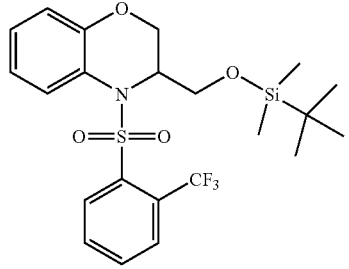

15

15. 2-(trifluoromethyl)benzenesulfonyl chloride (14, 8.50 g, 34.8 mmol) was added to a solution of 7 (8.83 g, 31.6 mmol) in pyridine (7.67 ml, 95.0 mmol) and the reaction mixture was stirred at room temperature overnight. $CH_2Cl_2$ and $H_2O$ were added to the reaction mixture and the organic layer was separated, washed with brine and concentrated to give crude 15, which was directly used as such in the next step.

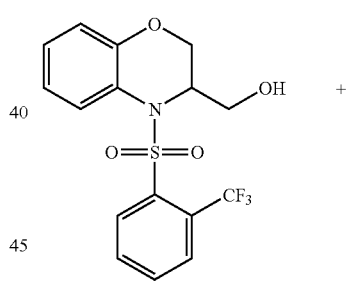

16

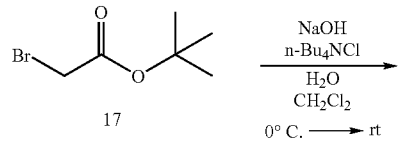

17

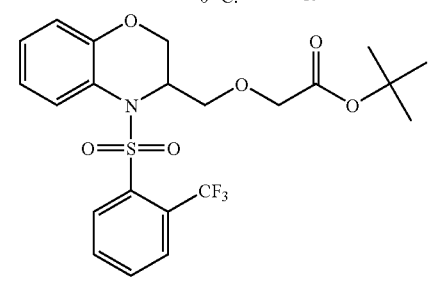

18

18. To an ice-cooled solution of 16 (10.29 g, 24.81 mmol) and n-Bu₄NCl (2.28 g, 8.19 mmol) in CH₂Cl₂ (125 ml) was sequentially added aqueous 35% NaOH solution (125 ml) and tert-butyl bromoacetate (17, 10.83 ml, 74.4 mmol). The reaction mixture was stirred at room temperature for 4 h, after which H₂O was added. The organic layer was separated, washed with H₂O and brine, dried (Na₂SO₄) and concentrated. The residue was purified by column chromatography (silica, heptane/EtOAc, 4:1) to provide 18 (11.65 g, 93%).

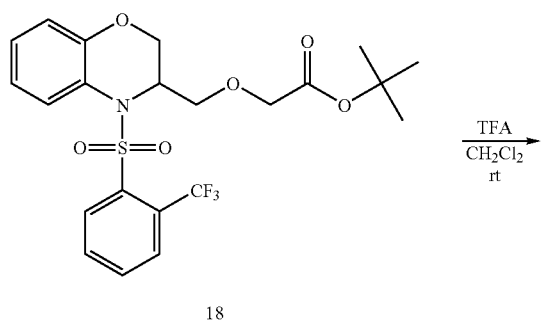

A solution of 18 (11.55 g, 22.98 mmol) and TFA (20 ml, 260 mmol) in CH₂Cl₂ (100 ml) was stirred at room temperature for 2 h. The reaction mixture was concentrated, co-evaporated with toluene (2×) and CH₂Cl₂ (2×). The residue was transferred to a jar with CH₂Cl₂, concentrated and dried under vacuum overnight to furnish S-27 (10.18 g, '103'%).

Synthesis of Acid Building Block S-28: 2-[2-[4H-[1,3]Benzodioxin-7-yl-methyl-[(4-methoxy-2,6-dimethyl-phenyl)sulfonyl]-amino]-ethoxy]-acetic acid (S-28)

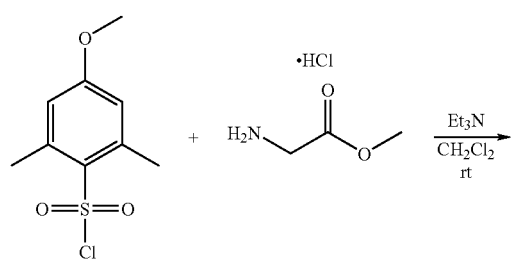

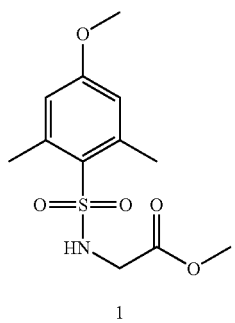

3. A solution of sulfonyl chloride 1 (15.0 g, 63.9 mmol) in CH₂Cl₂ (100 ml) was added dropwise to a stirred solution of methyl 2-aminoacetate hydrochloride (2, 8.83 g, 70.3 mmol) and Et₃N (31.2 ml, 224 mmol) in CH₂Cl₂ (200 ml). The reaction mixture was stirred at room temperature for 2 h and washed with aqueous 1 M HCl (100 ml). The organic layer was dried (Na₂SO₄) and evaporated to dryness to afford compound 3 (19.3 g, '105%').

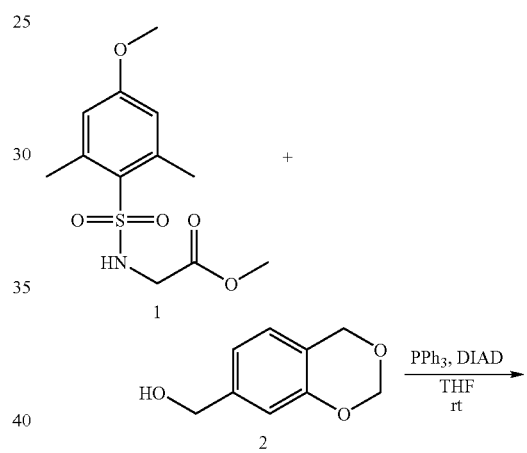

3. To a solution of compound 1 (9.08 g, max. 30.1 mmol), (4H-benzo[d][1,3]dioxin-7-yl)methanol (2, 5.25 g, 31.6 mmol) and PPh₃ (9.95 g, 37.9 mmol) in dry THF (200 ml) was added DIAD (7.37 ml, 37.9 mmol) and the mixture was stirred at room temperature overnight. The mixture was filtered and the filtrate was evaporated to dryness. Purification by column chromatography twice (silica, heptane/EtOAc, 3:1 and silica, toluene/EtOAc, 23:2) afforded sulfonamide 3 (5.29 g, 40%, 2 steps).

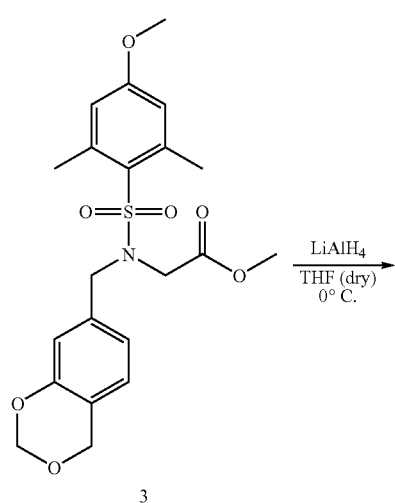

3

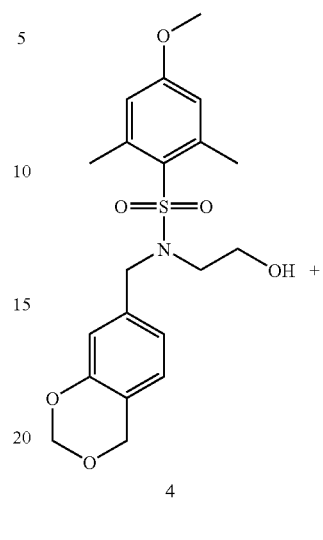

4

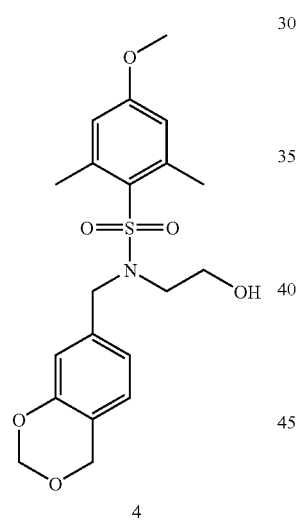

4

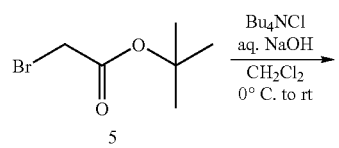

5

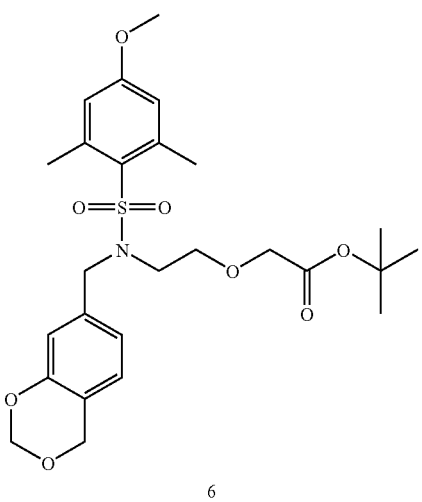

6

4. To a cooled (0° C.) and stirred solution of LiAlH$_4$ (2.4 M in THF, 15.2 ml, 36.4 mmol) in dry THF (50 ml), a solution of sulfonamide 3 (5.29 g, 12.2 mmol) in dry THF (100 ml) was added dropwise. After 5 min the reaction mixture was quenched with a mixture of THF/H$_2$O (1:1, 16 ml). The mixture was filtered over a small pad of Na$_2$SO$_4$ and rinsed with THF. The filtrate was evaporated to dryness to afford alcohol 4 (5.03 g, '102%').

6. To a cooled (0° C.) solution of alcohol 4 (5.03 g, max 12.2 mmol) and Bu₄NCl (1.10 g, 3.97 mmol) in CH₂Cl₂ (50 ml) was added aqueous 35% NaOH (27.5 ml) followed by tert-butyl bromoacetate (5, 2.63 ml, 18.04 mmol). The reaction mixture was then stirred at room temperature. After 2 h more tert-butyl bromoacetate (5, 438 µL, 3.01 mmol) was added. After 2 h the layers were separated and the organic layer was washed with H₂O (3×100 ml). The organic layer was dried (Na₂SO₄) and evaporated to dryness. Purification by column chromatography (silica, toluene/EtOAc, 23:2) afforded ester 6 (6.29 g, 99%, 2 steps).

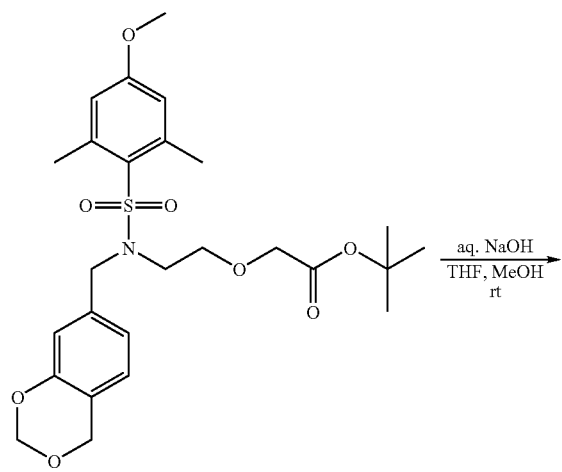

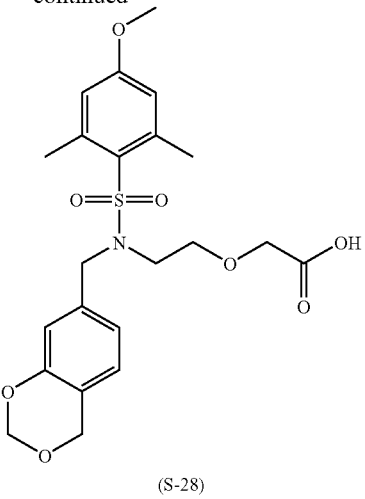

To a solution of ester 6 (6.25 g, 12.0 mmol) in THF (45 ml) and MeOH (45 ml) was added aqueous 6 M NaOH (39.9 ml, 240 mmol) and the reaction mixture was stirred at room temperature. After 1 h the organic solvents were evaporated. The residue was acidified with aqueous 6 M HCl (45 ml) and the mixture was extracted with CH₂Cl₂ (2×100 ml). The combined organic layers were dried (Na₂SO₄) and evaporated to dryness. Purification by column chromatography (silica, CH₂Cl₂/MeOH, 98:2+1% AcOH) afforded building block S-28 (4.40 g, 79%).

Synthesis of the Amine Structural Units for Parallel Synthesis

The following amine structural units were used within the scope of the parallel synthesis described below:

| | Structure | Name |
|---|---|---|
| A1 | 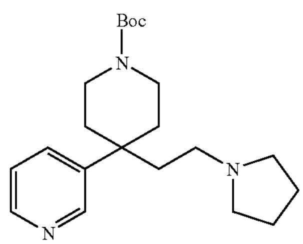 | tert-Butyl 4-(pyridin-3-yl)-4-(2-(pyrrolidin-1-yl)ethyl)piperidine-1-carboxylate |
| A2 | 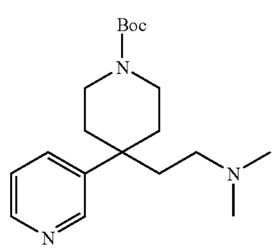 | tert-Butyl 4-(2-(dimethylamino)ethyl)-4-(pyridin-3-yl)piperidine-1-carboxylate |

-continued
| | Structure | Name |
|---|---|---|
| A3 | 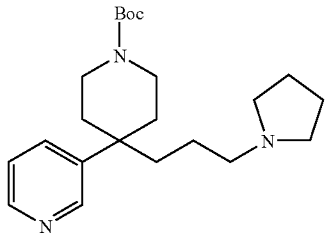 | tert-Butyl 4-(pyridin-3-yl)-4-(3-(pyrrolidin-1-yl)propyl)piperidine-1-carboxylate |
| A4 | 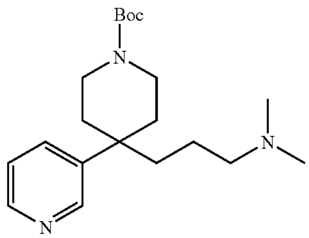 | tert-Butyl 4-(3-(dimethylamino)propyl)-4-(pyridin-3-yl)piperidine-1-carboxylate |
| A-05 | 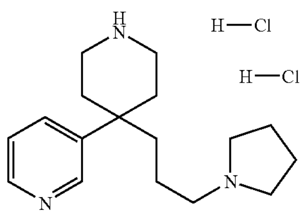 | 3-[4-(3-Pyrrolidin-1-yl-propyl)-piperidin-4-yl]-pyridine dihydrochloride (A-05) |
| A-06 | 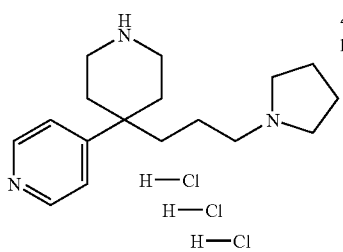 | 4-[4-(3-Pyrrolidin-1-yl-propyl)-piperidin-4-yl]-pyridine trihydrochloride (A-06) |
Synthesis of Amine Structural Units A1 and A2
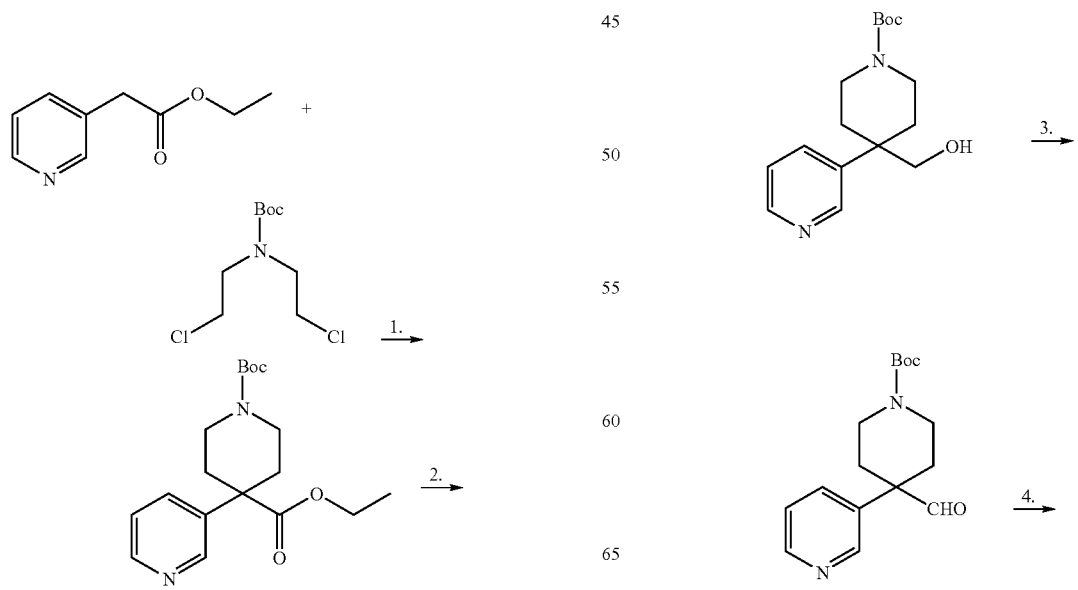

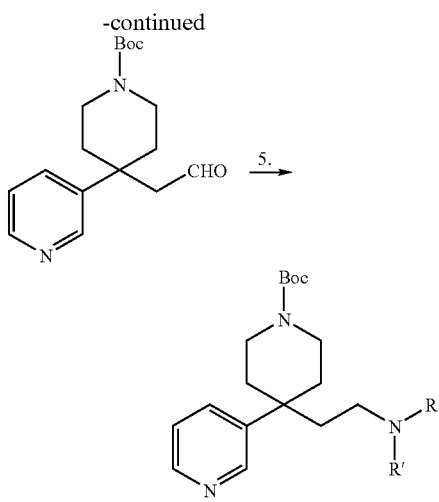

Stage 1. Pyridyl ethyl acetate (30.3 mmol) was added at 0° C. to a suspension of KOtBu (121.4 mmol) in DMF (30 ml). The reaction mixture was then stirred for 45 min at 25° C. The reaction mixture was cooled to 0° C. again, and bis-(2-chloroethyl)-carbamoyl tert-butyl ester (30.3 mmol) in DMF (45 ml) was added slowly. When the addition was complete, the mixture was heated to 25° C. and stirred for 16 h at that temperature (TLC monitoring). When the reaction was complete, the mixture was diluted with ethyl acetate and the organic phase was washed in succession with water and sat. sodium chloride solution and finally dried over Na$_2$SO$_4$. The solvent was removed using a rotary evaporator and the crude product was purified by column chromatography (silica gel, hexane/acetone, 9:1).

Stage 2. A solution of the ester obtained in stage 1 (1 eq.) in THF (2 ml/mmol) was added dropwise, under an argon atmosphere, to a suspension, cooled to 0° C., of LAH (1.2 eq.) in THF (3 ml/mmol). Stirring was then carried out for 2 h at 0° C. When the reaction was complete (TLC monitoring), the mixture was hydrolysed carefully with saturated aqueous sodium sulfate solution and filtered over filtering earth. The filtering earth was then washed with ethyl acetate. The phases were separated, and the organic phase was dried over Na$_2$SO$_4$ and concentrated. The resulting crude product was used further without being purified.

Stage 3. DMSO (2 eq.) was added at −78° C., under an argon atmosphere, to a solution of oxalyl chloride (1.1 eq.) in DCM (3 ml/mmol), and stirring was carried out for 15 min at that temperature. The alcohol from stage 2 (1 eq.), dissolved in DCM (3 ml/mmol), was added dropwise to the reaction mixture, and stirring was carried out for 1 h at that temperature. Triethylamine (5 eq.) was then added, and the mixture was heated slowly to RT and stirred for 1 h at RT. The reaction mixture was diluted with DCM, and the organic phase was washed in succession with saturated aqueous ammonium chloride solution, water and saturated NaCl solution. Drying over Na$_2$SO$_4$ and concentration were then carried out. The resulting crude product was used further without being purified.

Stage 4. A suspension of (methoxymethyl)triphenylphosphonium chloride (10 mmol) in dry THF (20 ml) was added dropwise at 0° C., under an argon atmosphere, to a solution of KOt-Bu (10 mmol) in dry THF (10 ml), and stirring was carried out for 15 min at that temperature. A solution of the aldehyde from stage 3 (6 mmol), dissolved in dry THF (30 ml), was added dropwise at 25° C., and stirring was then carried out for 16 h. The reaction mixture was cooled to 0° C. and acidified with aqueous HCl solution (6 N). Stirring was then carried out for a further 30 min at 0° C., followed by extraction with ethyl acetate. The aqueous phase was then rendered basic (pH 11) with NaOH solution (5 N) and extracted with DCM. The organic phase was dried over Na$_2$SO$_4$ and concentrated. The resulting crude product was used further without being purified.

Stage 5. The corresponding amine (0.7 eq.) and glacial acetic acid (2.5 eq.) were added to a solution of the aldehyde from stage 4 (1 eq.) in DCM (10 ml/mmol), and stirring was then carried out for 30 min. Triacetoxy borohydride (3 eq.) was then added, and stirring was carried out for 16 h at RT. When the reaction was complete (LCMS monitoring), the mixture was diluted with DCM, washed with saturated aqueous sodium hydrogen carbonate solution and dried over Na$_2$SO$_4$. The solvent was removed using a rotary evaporator and the resulting crude product was purified by column chromatography (silica gel, DCM/methanol, 9:1).

| | Structure | Name |
|---|---|---|
| A1 | 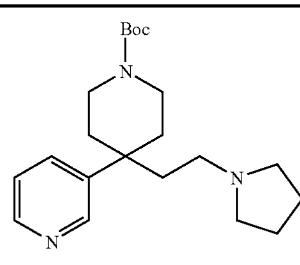 | tert-Butyl-4-(pyridin-3-yl)-4-(2-pyrrolidin-1-yl)ethyl)piperidine-1-carboxylate |
| A2 | 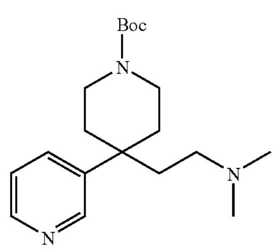 | tert-Butyl 4-(2-(dimethylamino)ethyl)-4-(pyridin-3-yl)piperidine-1-carboxylate |

Synthesis of Amine Structural Units A3 and A4

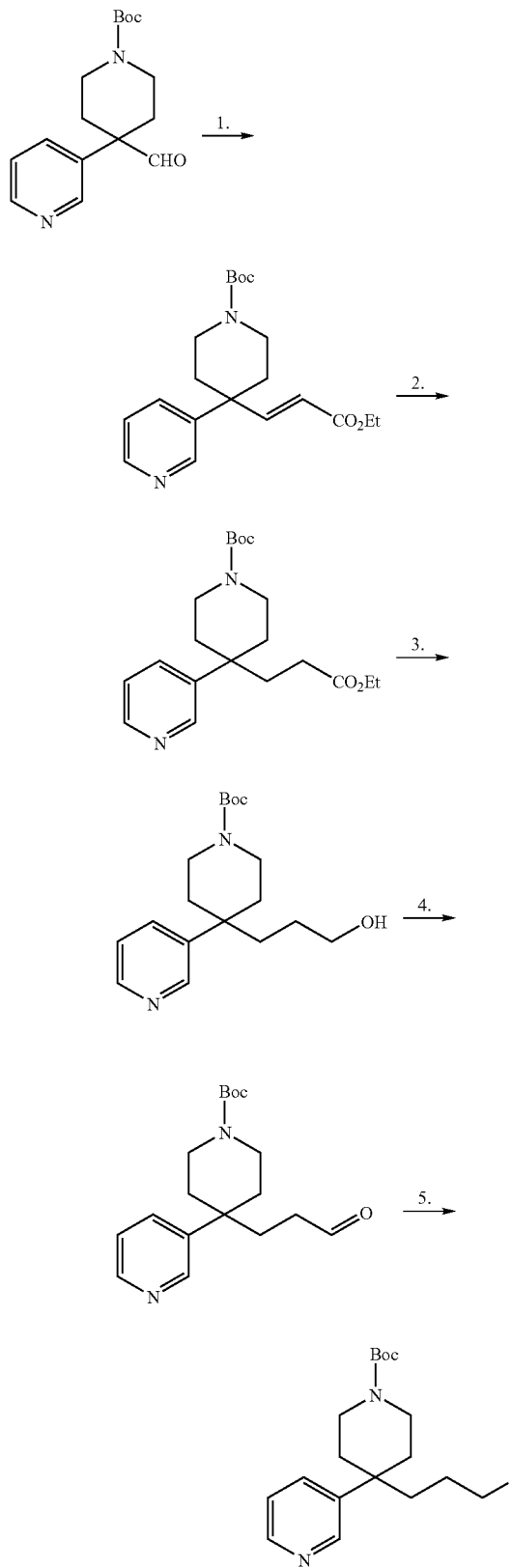

Stage 1. A solution of triethyl phosphonoacetate (1.1 eq.) in dry THF (5 ml/mmol) was added slowly to a suspension, cooled to 0° C., of NaH (60%, 1.1 eq.) in dry THF (5 ml/mmol), and stirring was carried out for 30 min at 25° C. The mixture was cooled to 0° C. again, and a solution of the aldehyde (1 eq.) in dry THF (5 ml/mmol) was added dropwise in such a manner that the temperature did not rise. When the addition was complete, stirring was carried out for 16 h at 25° C. Hydrolysis with ice and saturated NaCl solution was carried out. The aqueous phase was extracted with ethyl acetate, washed first with water and then with saturated NaCl solution and dried over $Na_2SO_4$. The solvent was removed using a rotary evaporator and the resulting crude product was purified by column chromatography (silica gel, ethyl acetate/hexane, 1:1).

Stage 2. To a solution of the ester from stage 1 (1 eq.) in methanol (5 ml/mmol), deoxygenation was carried out for 15 min with argon, and then 10% Pd/C (50 wt. %) was added. The mixture was hydrogenolysed for 1 h under atmospheric pressure (LCMS monitoring). Filtration over filtering earth was carried out, followed by washing with methanol. The solvent was removed and the resulting crude product was used further without being purified further.

Stage 3. A solution of the ester obtained in stage 2 (1 eq.) in THF (2 ml/mmol) was added dropwise, under an argon atmosphere, to a suspension, cooled to 0° C., of LAH (1.2 eq.) in THF (3 ml/mmol). Stirring was then carried out for 2 h at 0° C. When the reaction was complete (TLC monitoring), hydrolysis was carried out carefully with saturated aqueous sodium sulfate solution, followed by filtering over filtering earth. The filtering earth was then washed with ethyl acetate. The phases were separated, and the organic phase was dried over $Na_2SO_4$ and concentrated. The resulting crude product was used further without being purified.

Stage 4. DMSO (2 eq.) was added at −78° C., under an argon atmosphere, to a solution of oxalyl chloride (1.1 eq.) in DCM (3 ml/mmol), and stirring was carried out for 15 min at that temperature. The alcohol from stage 3 (1 eq.), dissolved in DCM (3 ml/mmol), was added dropwise to the reaction mixture, and stirring was carried out for 1 h at that temperature. Triethylamine (5 eq.) was then added, and the mixture was heated slowly to RT and stirred for 1 h at RT. The reaction mixture was diluted with DCM, and the organic phase was washed in succession with saturated aqueous ammonium chloride solution, water and saturated NaCl solution. It was then dried over $Na_2SO_4$ and concentrated. The resulting crude product was used further without being purified.

Stage 5. The corresponding amine (0.7 eq.) and glacial acetic acid (2.5 eq.) were added to a solution of the aldehyde from stage 4 (1 eq.) in DCM (10 ml/mmol), and stirring was then carried out for 30 min. Triacetoxy borohydride (3 eq.) was then added, and stirring was carried out for 16 h at RT. When the reaction was complete (LCMS monitoring), the mixture was diluted with DCM, washed with saturated aqueous sodium hydrogen carbonate solution and dried over $Na_2SO_4$. The solvent was removed using a rotary evaporator, and the resulting crude product was purified by column chromatography (silica gel, DCM/methanol, 9:1).

| | Structure | Name |
|---|---|---|
| A3 | 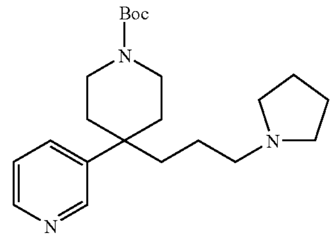 | tert-Butyl 4-(pyridin-3-yl)-4-(3-(pyrrolidin-1-yl)propyl)piperidine-1-carboxylate |
| A4 | 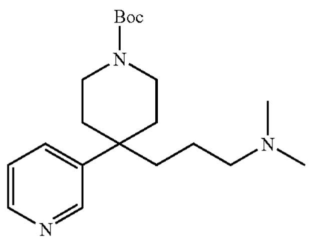 | tert-Butyl 4-(3-(dimethylamino)propyl)-4-(pyridin-3-yl)piperidine-1-carboxylate |

Synthesis of Amine Building Block A-05: 3-[4-(3-Pyrrolidin-1-yl-propyl)-piperidin-4-yl]-pyridine dihydrochloride (A-05)

Amine building block A-05 was prepared via boc-deprotection of A-03. The boc-protected amine A-03 (1 eq., 26.7 mmol) was dissolved in methanol, acetyl chloride (5 eq. 133.9 mmol) was added. The reaction mixture was stirred over night at room temperature. After the completion of the reaction (TLC-control), the solvent was evaporated under reduced pressure, to afford the desired product A-05 (30.3 mmol, '113%') as HCl-salt.

Synthesis of Amine Building Block A-06: 4-[4-(3-Pyrrolidin-1-yl-propyl)-piperidin-4-yl]-pyridine tri-hydrochloride (A-06)

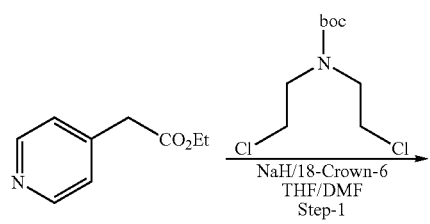

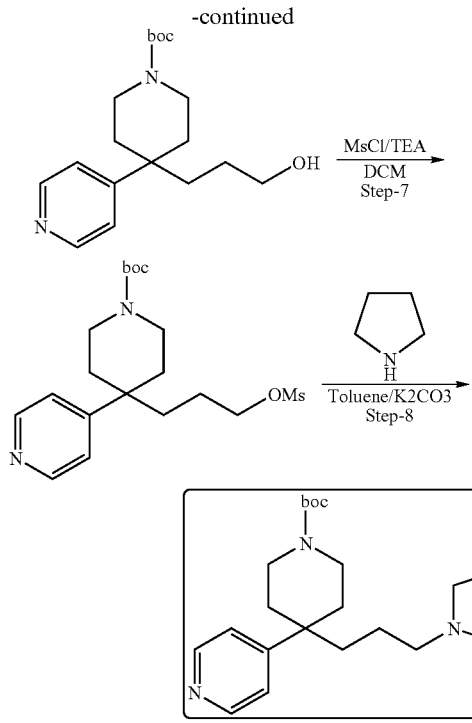

Step-1: To a THF solution (72 ml) of 4-pyridyl acetate (4 g) was added bis-(2-chloro-ethyl)-carbamic acid tert-butyl ester (3 eqv), NaH (3 eqv), 18-crown-6 (0.4 eqv) and DMF (10 ml) at 25° C. and the resulting reaction mixture was allowed to stir at same temperature for 4 hrs (monitored by TLC). Reaction was cooled to 0° C., quenched with crushed ice and diluted with ethyl acetate. Organic layer was washed successively with water and brine and finally dried over sodium sulfate. Evaporation of organic layer under reduced pressure gave the crude product which was purified by column chromatography. Yield: 67%

Step-2: To a cold (0° C.) suspension of LAH (1.2 eqv) in THF (3 ml/mmol) under argon atmosphere was added dropwise a solution of the ester (1 eqv) obtained from step-1 in THF (2 ml/mmol). After complete addition, reaction mixture was allowed to stir at this temperature for 2 hrs by which time starting material was completely consumed (monitored by TLC). Reaction was carefully quenched with a saturated aqueous solution of sodium sulfate and filtered over a celite bed. Residue was washed with ethyl acetate, combined organic layer was dried over sodium sulfate and evaporated under reduced pressure to get the crude alcohol which was used directly in the next step without any further purification. Yield: 90%

Step-3: To a DCM solution (3 ml/mmol) of oxalyl chloride (1.1 eqv) was added DMSO (2 eqv) at −78° C. under argon atmosphere and the resulting reaction mixture was stirred at this temperature for 15 minutes. To this cold reaction mixture was added the alcohol (1 eqv) obtained from step-2 in DCM (3 ml/mmol) dropwise and it was allowed to stir at this temperature for further 1 hr. Triethyl amine (5 eqv) was added to the reaction, it was slowly brought to ambient temperature and was allowed to stir for 1 hr. Reaction mixture was diluted with DCM, organic layer was washed successively with saturated aqueous ammonium chloride, water, brine and finally dried over sodium sulfate. Evaporation of organic layer under reduced pressure gave the crude product which was used directly in the next step without any further purification. Yield: Quantitative (crude)

Step-4: To a cold (0° C.) suspension of 60% NaH (1.1 eqv) in dry THF (5 ml/mmol) was added slowly a solution of triethyl phosphonoacetate (1.1 eqv) in THF (5 ml/mmol) and the resulting reaction mixture was allowed to stir at 25° C. for 30 minutes. It was then cooled to 0° C. and the aldehyde obtained from step-3 (1 eqv) in dry THF (5 ml/mmol) was added dropwise maintaining the same temperature and the reaction mixture was allowed to stir at 25° C. for 16 hrs by which time starting material was completely consumed. It was quenched with ice and brine solution, aqueous layer was extracted with ethyl acetate and the organic layer was washed successively with water and brine. It was dried over sodium sulfate and evaporated under reduced pressure to get the crude product which was purified by column chromatography (50% ethyl acetate in hexane). Yield: 80%

Step-5: A solution of the ester (1 eqv) obtained from step-4 in MeOH (5 ml/mmol) was deoxygenated with argon for 15 minutes followed by the addition of 10% Pd/C (50% by weight) and the resulting reaction mixture was hydrogenated under atmospheric pressure for 1 hr (monitored by LCMS). It was filtered through celite bed, residue washed with methanol and the combined organic layer was evaporated completely to get the crude product which was used directly in the next step without any further purification. Yield: 95% (crude)

Step-6: To a cold (0° C.) suspension of LAH (1.2 eqv) in THF (3 ml/mmol) under argon atmosphere was added dropwise a solution of the ester (1 eqv) obtained from step-5 in THF (2 ml/mmol). After complete addition, reaction mixture was allowed to stir at this temperature for 2 hrs by which time starting material was completely consumed (monitored by TLC). Reaction was carefully quenched with a saturated aqueous solution of sodium sulfate and filtered over a celite bed. Residue was washed with ethyl acetate, combined organic layer was dried over sodium sulfate and evaporated under reduced pressure to get the crude alcohol which was used directly in the next step without any further purification. Yield: 95%

Step-7: To a dichloromethane solution (22 ml) of the alcohol obtained from step-6 (5.3 mmol) was added TEA (21.2 mmol) and methane sulfonyl chloride (7.95 mmol) at 0° C. and the resulting reaction mixture was allowed to stir at same temperature for 2 hrs (monitored by TLC). Reaction was diluted with dichloromethane, washed successively with water and brine and finally dried over sodium sulfate. Evaporation of the organic layer under reduced pressure gave the crude product which was used directly in the next step. Yield: quantitative Step-8: To a toluene solution (30 ml) of the mesyl compound obtained from step-7 (5.3 mmol) was added potassium carbonate (26.5 mmol) and pyrrolidine (6.36 mmol) and the resulting reaction mixture was refluxed for 16 hrs. It was cooled to 25° C., diluted with ethyl acetate and the organic layer was washed successively with water and brine. After drying over sodium sulfate, organic layer was evaporated under reduced pressure to get the crude product which was purified by column chromatography (5% methanol in dichloromethane). Yield: 60%

Step-9: The boc-protected amine (1 eq., 26.7 mmol) was dissolved in methanol and cooled to 0° C. At this temperature acetyl chloride (5 eq. 133.9 mmol) was added. As a yellow solid dropped out, the volume of methanol was doubled to ensure better stirring. The reaction mixture was stirred over night at room temperature. After the completion of the reaction (TLC-control), the solvent was evaporated under reduced pressure, to afford the desired product (26.4 mmol, 99%) as HCl-salt.

Parallel Synthesis

I. Compounds 1 to 24

Methode A

Stage 1. TFA (20% in DCM, 5 ml/mmol) was added at 0° C. to the Boc-protected amine structural unit (1 eq.), and stirring was then carried out for 3 h at 25° C. (TLC monitoring). When the reaction was complete, the solvent was removed carefully and the product was used further directly without being purified further.

Stage 2. EDCI (1.0 eq.), HOBt (0.7 eq.) and DIPEA (2 eq.) were added to a solution of the corresponding acid structural unit (0.7 eq.) in DCM (3 ml/mmol), and the reaction mixture was stirred for 15 min at 25° C.

In another reaction vessel, the Boc-deprotected amine structural unit (1.0 eq.) was dissolved in DCM (2 ml/mmol) and cooled in an ice-bath, and DIPEA (2.5 eq.) was added. This mixture was added to the mixture of the acid structural unit. The reaction mixture was stirred for 16 h at 25° C. and then diluted with DCM. The organic phase was washed in succession with ammonium chloride solution, sodium hydrogen carbonate solution and sodium chloride solution and finally dried over $Na_2SO_4$. Purification was carried out using a purification system from Biotage working in parallel.

The example compounds listed in the following table, which were prepared by the above-described parallel syntheses, were analyzed inter a/ia on the basis of their molecular weight. The method used for the synthesis in each case, as well as the molecular weights measured by ESI-MS, are summarized in the following table.

| Example | Method | Name | Mass (ESI-MS) |
|---|---|---|---|
| 1 | A | N-(3-Oxo-1-phenyl-3-(4-(pyridin-3-yl)-4-(2-(pyrrolidin-1-yl)ethyl)piperidin-1-yl)propyl)naphthalene-2-sulfonamide | 596.3 |
| 2 | A | 2-((1-(4-Methoxy-2,6-dimethylphenylsulfonyl)piperidin-2-yl)methoxy)-1-(4-(pyridin-3-yl)-4-(2-(pyrrolidin-1-yl)ethyl)piperidin-1-yl)ethanone | 612.3 |
| 3 | A | 4-Methoxy-N,2,6-trimethyl-N-(2-(2-oxo-2-(4-(pyridin-3-yl)-4-(2-(pyrrolidin-1-yl)ethyl)piperidin-1-yl)ethoxy)ethyl)benzenesulfonamide | 572.3 |
| 4 | A | 1-(4-(Pyridin-3-yl)-4-(2-(pyrrolidin-1-yl)ethyl)piperidin-1-yl)-2-(1-(3-(trifluoromethyl)phenylsulfonyl)piperidin-2-yl)ethanone | 592.3 |
| 5 | A | 3-(1-(4-Chloro-2,5-dimethylphenylsulfonyl)piperidin-2-yl)-1-(4-(pyridin-3-yl)-4-(2-(pyrrolidin-1-yl)ethyl)piperidin-1-yl)propan-1-one | 600.3 |
| 6 | A | 2-((1-(3,4-Dichlorophenylsulfonyl)-1,2,3,4-tetrahydroquinolin-2-yl)methoxy)-1-(4-(pyridin-3-yl)-4-(2-(pyrrolidin-1-yl)ethyl)piperidin-1-yl)ethanone | 670.2 |
| 7 | A | N-(3-(4-(2-(Dimethylamino)ethyl)-4-(pyridin-3-yl)piperidin-1-yl)-3-oxo-1-phenylpropyl)naphthalene-2-sulfonamide | 570.3 |
| 8 | A | 1-(4-(2-(Dimethylamino)ethyl)-4-(pyridin-3-yl)piperidin-1-yl)-2-((1-(4-methoxy-2,6-dimethylphenylsulfonyl)-piperidin-2-yl)methoxy)ethanone | 586.3 |
| 9 | A | N-(2-(2-(4-(2-(Dimethylamino)ethyl)-4-(pyridin-3-yl)piperidin-1-yl)-2-oxoethoxy)ethyl)-4-methoxy-N,2,6-trimethylbenzenesulfonamide | 546.3 |
| 10 | A | 1-(4-(2-(Dimethylamino)ethyl)-4-(pyridin-3-yl)piperidin-1-yl)-2-(1-(3-(trifluoromethyl)phenylsulfonyl)piperidin-2-yl)ethanone | 566.3 |
| 11 | A | 3-(1-(4-Chloro-2,5-dimethylphenylsulfonyl)piperidin-2-yl)-1-(4-(2-(dimethylamino)ethyl)-4-(pyridin-3-yl)piperidin-1-yl)propan-1-one | 574.3 |
| 12 | A | 2-((1-(3,4-Dichlorophenylsulfonyl)-1,2,3,4-tetrahydroquinolin-2-yl)methoxy)-1-(4-(2-(dimethylamino)ethyl)-4-(pyridin-3-yl)piperidin-1-yl)ethanone | 644.2 |
| 13 | A | 4-Methoxy-N,2,6-trimethyl-N-(2-(2-oxo-2-(4-(pyridin-3-yl)-4-(3-(pyrrolidin-1-yl)propyl)piperidin-1-yl)ethoxy)ethyl)benzenesulfonamide | 586.3 |
| 14 | A | 1-(4-(Pyridin-3-yl)-4-(3-(pyrrolidin-1-yl)propyl)piperidin-1-yl)-2-(1-(3-(trifluoromethyl)phenylsulfonyl)piperidin-2-yl)ethanone | 606.3 |
| 15 | A | 3-(1-(4-Chloro-2,5-dimethylphenylsulfonyl)piperidin-2-yl)-1-(4-(pyridin-3-yl)-4-(3-(pyrrolidin-1-yl)propyl)piperidin-1-yl)propan-1-one | 614.3 |
| 16 | A | 2-((1-(4-Methoxy-2,6-dimethylphenylsulfonyl)piperidin-2-yl)methoxy)-1-(4-(pyridin-3-yl)-4-(3-(pyrrolidin-1-yl)propyl)piperidin-1-yl)ethanone | 626.4 |
| 17 | A | N-(3-Oxo-1-phenyl-3-(4-(pyridin-3-yl)-4-(3-(pyrrolidin-1-yl)propyl)piperidin-1-yl)propyl)naphthalene-2-sulfonamide | 610.3 |
| 18 | A | 2-((1-(3,4-Dichlorophenylsulfonyl)-1,2,3,4-tetrahydroquinolin-2-yl)methoxy)-1-(4-(pyridin-3-yl)-4-(3-(pyrrolidin-1-yl)propyl)piperidin-1-yl)ethanone | 684.2 |

-continued

| Example | Method | Name | Mass (ESI-MS) |
|---|---|---|---|
| 19 | A | 3-(1-(4-Chloro-2,5-dimethylphenylsulfonyl)piperidin-2-yl)-1-(4-(3-(dimethylamino)propyl)-4-(pyridin-3-yl)piperidin-1-yl)propan-1-one | 588.3 |
| 20 | A | N-(3-(4-(3-(Dimethylamino)propyl)-4-(pyridin-3-yl)piperidin-1-yl)-3-oxo-1-phenylpropyl)naphthalene-2-sulfonamide | 584.3 |
| 21 | A | 2-((1-(3,4-Dichlorophenylsulfonyl)-1,2,3,4-tetrahydroquinolin-2-yl)methoxy)-1-(4-(3-(dimethylamino)propyl)-4-(pyridin-3-yl)piperidin-1-yl)ethanone | 658.2 |
| 22 | A | 1-(4-(3-(Dimethylamino)propyl)-4-(pyridin-3-yl)piperidin-1-yl)-2-((1-(4-methoxy-2,6-dimethylphenylsulfonyl)-piperidin-2-yl)methoxy)ethanone | 600.3 |
| 23 | A | N-(2-(2-(4-(3-(Dimethylamino)propyl)-4-(pyridin-3-yl)piperidin-1-yl)-2-oxoethoxy)ethyl)-4-methoxy-N,2,6-trimethylbenzenesulfonamide | 560.3 |
| 24 | A | 1-(4-(3-(Dimethylamino)propyl)-4-(pyridin-3-yl)piperidin-1-yl)-2-(1-(3-(trifluoromethyl)phenylsulfonyl)piperidin-2-yl)ethanone | 580.3 |

II. Compounds 26 to 76

Parallel Synthesis Method for the Preparation of Examples 26 to 76

Although, in the following slightly different reaction conditions and reagents compared to compounds 1 to 25 are described for use in the parallel synthesis, it is clear that the above described Method A (especially stage 2) used for compounds 1 to 25 could also be utilized analogously as an alternative procedure to synthesize compounds 26 to 76.

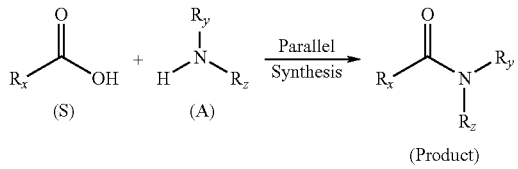

Acid building blocks S were converted with amines A to the product amide compounds in parallel fashion. The correlation between product and reagent, building block and method can be taken from the synthesis matrix shown below. The crude products from the parallel synthesis were analyzed by HPLC_MS and afterwards purified via reverse phase HPLC-MS. The identification of the products was demonstrated by analytical HPLC-MS measurements.

Equipment and Methods for HPLC-MS Analytics:
Parallel synthesis Method: HPLC: Waters Alliance 2795 with PDA Waters 2996;
MS: ZQ 2000 MassLynx Single Quadrupol MS Detector;
Column: Atlantis dC18 30×2.1 mm, 3 μm; Col. temp.: 40° C., EluentA: purified water+0.1% formic acid; Eluent B: methanol (gradient grade)+0.1% formic acid; Gradient: 0% B to 100% B in 2.3 min, 100% B for 0.4 min, 100% B to 0% B in 0.01 min, 0% B for 0.8 min; Flow: 1.0 ml/min; Ionisation: ES+, 25V; make up: 100 μL/min 70% methanol+0.2% formic acid; UV: 200-400 nm.

Equipment and Methods for HPLC-MS Purification:
Prep Pump Waters 2525; Make Up Pump: Waters 515; Auxillary Detector: Waters DAD 2487; MS Detector: Waters Micromass ZQ; Injector/Fraction Collector: Waters Sample Manager 2767; Gradient: Initial: 60% Water 40% Methanol-> 12-14.5 min: 0% Water 100% Methanol->14.5-15 min: 60% Water 40% Methanol; Flow: 35 ml/min Column: Macherey-Nagel, C18 Gravity, 100×21 mm, 5μ. Compounds were also be purified by a slight modification of the above method.

Synthesis of Compounds 26 to 76

To a solution of acid S (100 μmol) in 1 ml dichlormethane a solution of 1,1'-carbonyldiimidazole (150 μmol) in 1 ml dichlormethane was added and the reaction mixture was stirred at room temperature for 1.5 h. Afterwards a solution of amine A (150 μmol) and Hünigs base (500 μmol) in 1 ml dichlormethane was added. The mixture was stirred for 18 h at room temperature. The solvent was evaporated under reduced pressure in a vacuum centrifuge (brand: GeneVac). The final purification resulted from HPLC-MS. The final analytics resulted from LC-MS.

Synthesis Matrix for Compounds 26 to 76

| Example No. | Name | S | A | [M+] found | R.t. [min] |
|---|---|---|---|---|---|
| 26 | 2-[[1-[(4-Methoxy-2,6-dimethyl-phenyl)sulfonyl]-piperidin-2-yl]-methoxy]-1-[4-pyridin-3-yl-4-(3-pyrrolidin-1-yl-propyl)-piperidin-1-yl]-ethanone (26) | S-03 | A-05 | 627.4 | 1.29 |
| 27 | 2-[[1-[(4-Methoxy-2,6-dimethyl-phenyl)sulfonyl]-piperidin-2-yl]-methoxy]-1-[4-pyridin-3-yl-4-(3-pyrrolidin-1-yl-propyl)-piperidin-1-yl]-ethanone (27) | S-03 | A-05 | 627.4 | 1.31 |

-continued

| Example No. | Name | S | A | [M+] found | R.t. [min] |
|---|---|---|---|---|---|
| 28 | 2-[[1-[(4-Methoxy-2,6-dimethyl-phenyl)sulfonyl]-piperidin-2-yl]-methoxy]-1-[4-pyridin-4-yl-4-(3-pyrrolidin-1-yl-propyl)-piperidin-1-yl]-ethanone (28) | S-03 | A-06 | 627.3 | 1.52 |
| 29 | 4-Methoxy-N,2,6-trimethyl-N-[2-[2-oxo-2-[4-pyridin-3-yl-4-(3-pyrrolidin-1-yl-propyl)-piperidin-1-yl]-ethoxy]-ethyl]-benzenesulfonic acid amide (29) | S-05 | A-05 | 587.4 | 1.21 |
| 30 | 4-Methoxy-N,2,6-trimethyl-N-[2-[2-oxo-2-[4-pyridin-4-yl-4-(3-pyrrolidin-1-yl-propyl)-piperidin-1-yl]-ethoxy]-ethyl]-benzenesulfonic acid amide (30) | S-05 | A-06 | 587.3 | 1.32 |
| 31 | 4-Methoxy-N,2,3,6-tetramethyl-N-[2-[2-oxo-2-[4-pyridin-3-yl-4-(3-pyrrolidin-1-yl-propyl)-piperidin-1-yl]-ethoxy]-ethyl]-benzenesulfonic acid amide (31) | S-07 | A-05 | 601.4 | 1.29 |
| 32 | 4-Methoxy-N,2,3,6-tetramethyl-N-[2-[2-oxo-2-[4-pyridin-4-yl-4-(3-pyrrolidin-1-yl-propyl)-piperidin-1-yl]-ethoxy]-ethyl]-benzenesulfonic acid amide (32) | S-07 | A-06 | 601.3 | 1.41 |
| 37 | N-Benzyl-4-Methoxy-2,6-dimethyl-N-[2-[2-oxo-2-[4-pyridin-3-yl-4-(3-pyrrolidin-1-yl-propyl)-piperidin-1-yl]-ethoxy]-ethyl]-benzenesulfonic acid amide (37) | S-09 | A-05 | 663.5 | 1.39 |
| 38 | N-Benzyl-4-Methoxy-2,6-dimethyl-N-[2-[2-oxo-2-[4-pyridin-3-yl-4-(3-pyrrolidin-1-yl-propyl)-piperidin-1-yl]-ethoxy]-ethyl]-benzenesulfonic acid amide (38) | S-09 | A-05 | 663.5 | 1.4 |
| 39 | N-Benzyl-4-Methoxy-2,6-dimethyl-N-[2-[2-oxo-2-[4-pyridin-4-yl-4-(3-pyrrolidin-1-yl-propyl)-piperidin-1-yl]-ethoxy]-ethyl]-benzenesulfonic acid amide (39) | S-09 | A-06 | 663.4 | 1.61 |
| 40 | N-Benzyl-4-Methoxy-2,6-dimethyl-N-[2-[2-oxo-2-[4-pyridin-4-yl-4-(3-pyrrolidin-1-yl-propyl)-piperidin-1-yl]-ethoxy]-ethyl]-benzenesulfonic acid amide (40) | S-09 | A-06 | 663.4 | 1.62 |
| 41 | 1-[4-Pyridin-3-yl-4-(3-pyrrolidin-1-yl-propyl)-piperidin-1-yl]-2-[[1-[[2-(trifluoromethyl)-phenyl]sulfonyl]-piperidin-2-yl]-methoxy]-ethanone (41) | S-10 | A-05 | 637.4 | 1.26 |
| 42 | 1-[4-Pyridin-3-yl-4-(3-pyrrolidin-1-yl-propyl)-piperidin-1-yl]-2-[[1-[[2-(trifluoromethyl)-phenyl]sulfonyl]-piperidin-2-yl]-methoxy]-ethanone (42) | S-10 | A-05 | 637.4 | 1.3 |
| 43 | 1-[4-Pyridin-4-yl-4-(3-pyrrolidin-1-yl-propyl)-piperidin-1-yl]-2-[[1-[[2-(trifluoromethyl)-phenyl]sulfonyl]-piperidin-2-yl]-methoxy]-ethanone (43) | S-10 | A-06 | 637.3 | 1.4 |
| 44 | 1-[4-Pyridin-4-yl-4-(3-pyrrolidin-1-yl-propyl)-piperidin-1-yl]-2-[[1-[[2-(trifluoromethyl)-phenyl]sulfonyl]-piperidin-2-yl]-methoxy]-ethanone (44) | S-10 | A-06 | 637.3 | 1.37 |
| 45 | 2-[2-[1-[(4-Methoxy-2,6-dimethyl-phenyl)sulfonyl]-piperidin-2-yl]-ethoxy]-1-[4-pyridin-3-yl-4-(3-pyrrolidin-1-yl-propyl)-piperidin-1-yl]-ethanone (45) | S-12 | A-05 | 641.4 | 1.28 |
| 46 | 2-[2-[1-[(4-Methoxy-2,6-dimethyl-phenyl)sulfonyl]-piperidin-2-yl]-ethoxy]-1-[4-pyridin-3-yl-4-(3-pyrrolidin-1-yl-propyl)-piperidin-1-yl]-ethanone (46) | S-12 | A-05 | 641.4 | 1.3 |
| 47 | N-Methyl-N-[4-Oxo-4-[4-pyridin-3-yl-4-(3-pyrrolidin-1-yl-propyl)-piperidin-1-yl]-butyl]-3-(trifluoromethyl)-benzenesulfonic acid amide (47) | S-13 | A-05 | 581.3 | 1.24 |
| 48 | 4-Methoxy-2,6-Dimethyl-N-[2-[2-oxo-2-[4-pyridin-3-yl-4-(3-pyrrolidin-1-yl-propyl)-piperidin-1-yl]-ethoxy]-ethyl]-N-phenyl-benzenesulfonic acid amide (48) | S-15 | A-05 | 649.4 | 1.34 |
| 49 | 4-Methoxy-2,6-Dimethyl-N-[2-[2-oxo-2-[4-pyridin-3-yl-4-(3-pyrrolidin-1-yl-propyl)-piperidin-1-yl]-ethoxy]-ethyl]-N-phenyl-benzenesulfonic acid amide (49) | S-15 | A-05 | 649.4 | 1.34 |
| 50 | 4-Methoxy-2,6-Dimethyl-N-[2-[2-oxo-2-[4-pyridin-4-yl-4-(3-pyrrolidin-1-yl-propyl)-piperidin-1-yl]-ethoxy]-ethyl]-N- | S-15 | A-06 | 649.3 | 1.53 |

-continued

| Example No. | Name | S | A | [M+] found | R.t. [min] |
|---|---|---|---|---|---|
| | phenyl-benzenesulfonic acid amide (50) | | | | |
| 51 | 2-[[1-(Naphthalen-2-ylsulfonyl)-1,2,3,4-tetrahydro-quinolin-2-yl]-methoxy]-1-[4-pyridin-3-yl-4-(3-pyrrolidin-1-yl-propyl)-piperidin-1-yl]-ethanone (51) | S-16 | A-05 | 667.3 | 1.4 |
| 52 | 2-[[1-(Naphthalen-2-ylsulfonyl)-1,2,3,4-tetrahydro-quinolin-2-yl]-methoxy]-1-[4-pyridin-3-yl-4-(3-pyrrolidin-1-yl-propyl)-piperidin-1-yl]-ethanone (52) | S-16 | A-05 | 667.3 | 1.41 |
| 53 | 2-[[1-[(4-Methoxy-2,6-dimethyl-phenyl)sulfonyl]-1,2,3,4-tetrahydro-quinolin-2-yl]-methoxy]-1-[4-pyridin-3-yl-4-(3-pyrrolidin-1-yl-propyl)-piperidin-1-yl]-ethanone (53) | S-17 | A-05 | 675.5 | 1.41 |
| 54 | 2-[[1-[(4-Methoxy-2,6-dimethyl-phenyl)sulfonyl]-1,2,3,4-tetrahydro-quinolin-2-yl]-methoxy]-1-[4-pyridin-3-yl-4-(3-pyrrolidin-1-yl-propyl)-piperidin-1-yl]-ethanone (54) | S-17 | A-05 | 675.5 | 1.43 |
| 55 | 2-[[1-[(4-Methoxy-2,6-dimethyl-phenyl)sulfonyl]-1,2,3,4-tetrahydro-quinolin-2-yl]-methoxy]-1-[4-pyridin-4-yl-4-(3-pyrrolidin-1-yl-propyl)-piperidin-1-yl]-ethanone (55) | S-17 | A-06 | 675.4 | 1.61 |
| 56 | 4-[1-[(2-Chloro-6-methyl-phenyl)sulfonyl]-piperidin-2-yl]-1-[4-pyridin-4-yl-4-(3-pyrrolidin-1-yl-propyl)-piperidin-1-yl]-butan-1-one (56) | S-18 | A-06 | 615.3 | 1.54 |
| 57 | 1-[4-Pyridin-3-yl-4-(3-pyrrolidin-1-yl-propyl)-piperidin-1-yl]-4-[1-[[2-(trifluoromethyl)-phenyl]sulfonyl]-piperidin-2-yl]-butan-1-one (57) | S-19 | A-05 | 635.4 | 1.34 |
| 58 | 1-[4-Pyridin-4-yl-4-(3-pyrrolidin-1-yl-propyl)-piperidin-1-yl]-4-[1-[[2-(trifluoromethyl)-phenyl]sulfonyl]-piperidin-2-yl]-butan-1-one (58) | S-19 | A-06 | 635.3 | 1.51 |
| 59 | 1-[4-Pyridin-4-yl-4-(3-pyrrolidin-1-yl-propyl)-piperidin-1-yl]-4-[1-[[2-(trifluoromethyl)-phenyl]sulfonyl]-piperidin-2-yl]-butan-1-one (59) | S-19 | A-06 | 635.3 | 1.5 |
| 60 | 4-[1-[(4-Methoxy-2,6-dimethyl-phenyl)sulfonyl]-piperidin-2-yl]-1-[4-pyridin-3-yl-4-(3-pyrrolidin-1-yl-propyl)-piperidin-1-yl]-butan-1-one (60) | S-20 | A-05 | 625.5 | 1.35 |
| 61 | 4-[1-[(4-Methoxy-2,6-dimethyl-phenyl)sulfonyl]-piperidin-2-yl]-1-[4-pyridin-3-yl-4-(3-pyrrolidin-1-yl-propyl)-piperidin-1-yl]-butan-1-one (61) | S-20 | A-05 | 625.5 | 1.37 |
| 62 | 4-[1-[(4-Methoxy-2,6-dimethyl-phenyl)sulfonyl]-piperidin-2-yl]-1-[4-pyridin-4-yl-4-(3-pyrrolidin-1-yl-propyl)-piperidin-1-yl]-butan-1-one (62) | S-20 | A-06 | 625.4 | 1.59 |
| 63 | 4-[1-[(4-Methoxy-2,6-dimethyl-phenyl)sulfonyl]-piperidin-2-yl]-1-[4-pyridin-4-yl-4-(3-pyrrolidin-1-yl-propyl)-piperidin-1-yl]-butan-1-one (63) | S-20 | A-06 | 625.4 | 1.57 |
| 64 | 4-[1-(Naphthalen-1-ylsulfonyl)-piperidin-2-yl]-1-[4-pyridin-4-yl-4-(3-pyrrolidin-1-yl-propyl)-piperidin-1-yl]-butan-1-one (64) | S-21 | A-06 | 617.3 | 1.56 |
| 65 | N-Benzhydryl-N-[2-[2-oxo-2-[4-pyridin-4-yl-4-(3-pyrrolidin-1-yl-propyl)-piperidin-1-yl]-ethoxy]-ethyl]-methanesulfonic acid amide (65) | S-23 | A-06 | 619.3 | 1.45 |
| 66 | N-Benzhydryl-N-[2-[2-oxo-2-[4-pyridin-4-yl-4-(3-pyrrolidin-1-yl-propyl)-piperidin-1-yl]-ethoxy]-ethyl]-methanesulfonic acid amide (66) | S-23 | A-06 | 619.3 | 1.43 |
| 67 | 2-[[4-[(4-Methoxy-2,6-dimethyl-phenyl)sulfonyl]-3,4-dihydro-2H-[1,4]benzoxazin-3-yl]-methoxy]-1-[4-pyridin-3-yl-4-(3-pyrrolidin-1-yl-propyl)-piperidin-1-yl]-ethanone (67) | S-24 | A-05 | 677.5 | 1.4 |
| 68 | 2-[[4-[(4-Methoxy-2,6-dimethyl-phenyl)sulfonyl]-3,4-dihydro-2H-[1,4]benzoxazin-3-yl]-methoxy]-1-[4- | S-24 | A-05 | 677.5 | 1.41 |

-continued

| Example No. | Name | S | A | [M+] found | R.t. [min] |
|---|---|---|---|---|---|
| | pyridin-3-yl-4-(3-pyrrolidin-1-yl-propyl)-piperidin-1-yl]-ethanone (68) | | | | |
| 69 | 2-[[4-[(4-Methoxy-2,6-dimethyl-phenyl)sulfonyl]-3,4-dihydro-2H-[1,4]benzoxazin-3-yl]-methoxy]-1-[4-pyridin-4-yl-4-(3-pyrrolidin-1-yl-propyl)-piperidin-1-yl]-ethanone (69) | S-24 | A-06 | 677.4 | 1.62 |
| 70 | 2-[[4-[(4-Methoxy-2,6-dimethyl-phenyl)sulfonyl]-3,4-dihydro-2H-[1,4]benzoxazin-3-yl]-methoxy]-1-[4-pyridin-4-yl-4-(3-pyrrolidin-1-yl-propyl)-piperidin-1-yl]-ethanone (70) | S-24 | A-06 | 677.4 | 1.6 |
| 71 | 4-Methoxy-2,6-Dimethyl-N-[2-[2-oxo-2-[4-pyridin-3-yl-4-(3-pyrrolidin-1-yl-propyl)-piperidin-1-yl]-ethoxy]-ethyl]-N-(quinolin-3-yl-methyl)-benzenesulfonic acid amide (71) | S-25 | A-05 | 714.5 | 1.29 |
| 72 | 2-[[4-[(2-Chloro-6-methyl-phenyl)sulfonyl]-3,4-dihydro-2H-[1,4]benzoxazin-3-yl]-methoxy]-1-[4-pyridin-3-yl-4-(3-pyrrolidin-1-yl-propyl)-piperidin-1-yl]-ethanone (72) | S-26 | A-05 | 667.4 | 1.39 |
| 73 | 1-[4-Pyridin-3-yl-4-(3-pyrrolidin-1-yl-propyl)-piperidin-1-yl]-2-[[4-[[2-(trifluoromethyl)-phenyl]sulfonyl]-3,4-dihydro-2H-[1,4]benzoxazin-3-yl]-methoxy]-ethanone (73) | S-27 | A-05 | 687.4 | 1.37 |
| 74 | 1-[4-Pyridin-3-yl-4-(3-pyrrolidin-1-yl-propyl)-piperidin-1-yl]-2-[[4-[[2-(trifluoromethyl)-phenyl]sulfonyl]-3,4-dihydro-2H-[1,4]benzoxazin-3-yl]-methoxy]-ethanone (74) | S-27 | A-05 | 687.4 | 1.39 |
| 75 | 1-[4-Pyridin-4-yl-4-(3-pyrrolidin-1-yl-propyl)-piperidin-1-yl]-2-[[4-[[2-(trifluoromethyl)-phenyl]sulfonyl]-3,4-dihydro-2H-[1,4]benzoxazin-3-yl]-methoxy]-ethanone (75) | S-27 | A-06 | 687.3 | 1.51 |
| 76 | N-(4H-[1,3]Benzodioxin-7-yl-methyl)-4-methoxy-2,6-dimethyl-N-[2-[2-oxo-2-[4-pyridin-4-yl-4-(3-pyrrolidin-1-yl-propyl)-piperidin-1-yl]-ethoxy]-ethyl]-benzenesulfonic acid amide (76) | S-28 | A-06 | 721.4 | 1.57 |

(A = amine building block or amine structural unit; S = acid building block or amine structural unit)

Individual Substances

The person skilled in the art will understand that the acid and amine structural units used in the syntheses of individual substances described below can also be used analogously in the parallel synthesis described above.

Analytical Method for Individual Compounds:

The analytical studies were also carried out by mass spectroscopy. Equipment and Methods for HPLC-MS Analytics. HPLC: Waters Alliance 2795 with PDA Waters 2998; MS: Micromass Quattro Micro™ API; Column: Waters Atlantis® T3, 3 μm, 100 Å, 2.1×30 mm; temp.: 40° C., Eluent A: water+0.1% formic acid; Eluent B: acetonitrile+0.1% formic acid; Gradient: 0% B to 100% B in 8.8 min, 100% B for 0.4 min, 100% B to 0% B in 0.01 min, 0% B for 0.8 min; Flow: 1.0 mL/min; Ionisation: ES+, 25 V; Make up: 100 μL/min 70% methanol+0.2% formic acid; UV: 200-400 nm Example 25

(S)-2-((1-(4-Methoxy-2,6-dimethylphenylsulfonyl)piperidin-2-yl)methoxy)-1-(4-(pyridin-3-yl)-4-(pyrrolidin-1-ylmethyl)piperidin-1-yl)ethanone

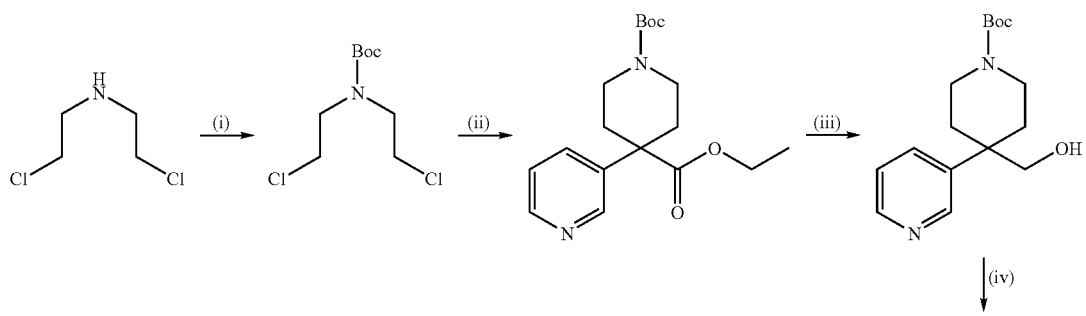

-continued

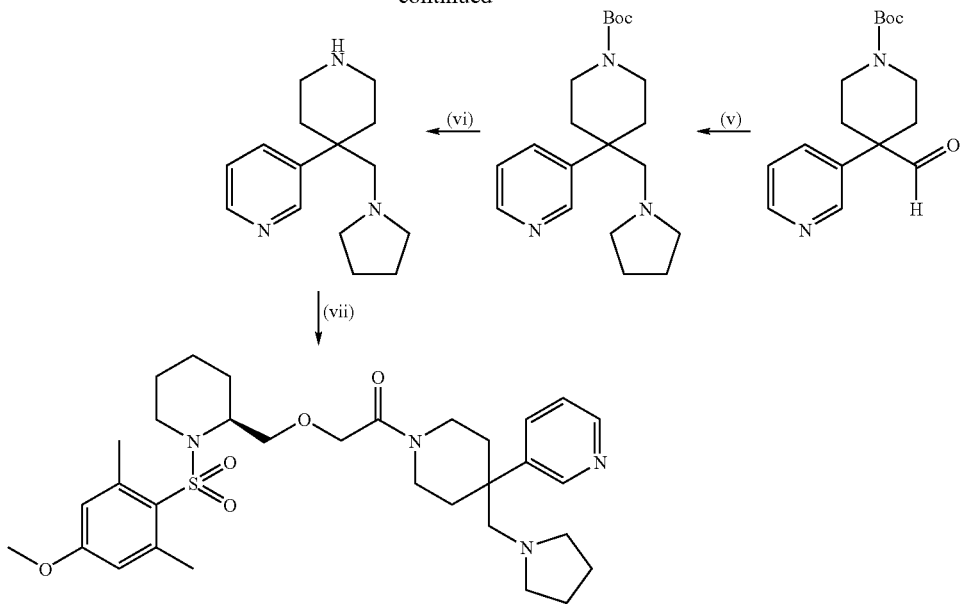

(i): Bis-(2-chloroethyl)amine (16.34 g, 91.5 mmol) was dissolved in dichloromethane (150 ml) and triethylamine (40 ml, 293 mmol) and cooled; Boc anhydride (20 ml, 218 mmol) was added dropwise at 0° C. The reaction mixture warmed to room temperature and was stirred for 16 h. Hydrolysis with ice and extraction with dichloromethane (500 ml) were carried out. The organic phase was washed with water and saturated sodium chloride solution, dried over sodium sulfate, filtered and concentrated in vacuo. The crude product was purified by column chromatography (silica gel) with 20% ethyl acetate in hexane. Yield: 49% (ii): A solution of pyridin-3-ylacetic acid ethyl ester (5 g, 30 mmol) in dry N,N-dimethylformamide (20 ml) was added dropwise at 0° C., under argon, to a suspension of potassium tert-butylate (7.54 g, 66.6 mmol) in dry N,N-dimethyl-formamide (30 ml). The reaction mixture was stirred for 45 min at room temperature and then cooled to 0° C. again; tert-butyl bis(2-chloroethyl)carbamate (7.23 g, 30 mmol), dissolved in N,N-dimethylformamide (20 ml), was added dropwise. The ice bath was removed and stirring was carried out for 16 h at room temperature. The reaction mixture was extracted with ethyl acetate (300 ml). The organic phase was washed with water and saturated sodium chloride solution, dried over sodium sulfate, filtered and concentrated in vacuo. The crude product was purified by column chromatography (neutral alumina) with 5% ethyl acetate in hexane.

Yield: 24%

(iii): A solution of 1-tert-butyl 4-ethyl-4-(pyridin-3-yl)piperidine-1,4-dicarboxylate (2.45 g, 7.3 mmol) in dry tetrahydrofuran (30 ml) was added in two portions at 0° C., under argon, to a suspension of lithium aluminium hydride (335 mg, 8.8 mmol) in dry tetrahydrofuran (25 ml). Stirring was carried out for 1 h at the same temperature, and then the mixture was hydrolysed with saturated sodium sulfate solution and stirred for 30 min at room temperature. The reaction mixture was filtered over Celite and washed with ethyl acetate (3×50 ml), and the filtrate was concentrated in vacuo. The crude product was used in the next synthesis step without being purified further. Yield: quantitative (iv): Dimethyl sulfoxide (2.2 eq.) in anhydrous dichloromethane (1.5 ml/mmol) was added dropwise at −78° C., under argon, to a solution of freshly distilled oxalyl chloride (1.1 eq.) in anhydrous dichloromethane (3 ml/mmol). Stirring was carried out for 10 min under unchanged conditions, and then a solution of tert-butyl 4-(hydroxymethyl)-4-(pyridin-3-yl)piperidine-1-carboxylate (1 eq.) in anhydrous dichloromethane (3 mol/mmol) was added dropwise at −78° C. The reaction mixture was stirred for 1 h, triethylamine (5 eq.) was added dropwise, and the cooling bath was removed. Stirring was carried out for 1 h at 25° C., and then the mixture was diluted with dichloromethane and washed with saturated ammonium chloride solution and saturated sodium chloride solution. The organic phase was dried over sodium sulfate, filtered and concentrated in vacuo. The crude product was used in the next stage without being purified. Yield: 90%

(v): To a solution of tert-butyl 4-formyl-4-(pyridin-3-yl) piperidine-1-carboxylate (0.4 g, 1.38 mmol) and pyrrolidine (0.135 ml, 1.66 mmol) in dichloromethane (30 ml) there was added at room temperature, under nitrogen, a catalytic amount of acetic acid (0.25 ml), followed by sodium triacetoxyborohydride (1.17 g, 5.52 mmol). The reaction mixture was stirred for 16 h and then hydrolyzed with ice, extracted with dichloromethane (150 ml) and washed with saturated sodium carbonate solution and saturated sodium chloride solution. The organic phase was dried over sodium sulfate and concentrated in vacuo. The crude product was purified by column chromatography (neutral alumina) with 2% methanol in dichloromethane, and the desired compound tert-butyl 4-(pyridin-3-yl)-4-(pyrrolidin-1-ylmethyl)piperidine-1-carboxylate was obtained in pure form. Yield: 16%

(vi): Trifluoroacetic acid (13 eq.) was added at 0° C. to a solution of tert-butyl 4-(pyridin-3-yl)-4-(pyrrolidin-1-ylmethyl)piperidine-1-carboxylate in dichloromethane (10 ml/mmol, 1 eq.). Stirring was carried out for 2 h at room temperature, and then the solvent was removed in vacuo and the residue was dried in vacuo. The crude product was used in the next stage without being purified further. Yield: quantitative (vii): Diisopropylethylamine (2.5 eq.), HOBT (1 eq.) and EDCI (1.5 eq.) were added at 0° C. to a solution of (S)-2-((1-

(4-methoxy-2,6-dimethylphenylsulfonyl)piperidin-2-yl) methoxy)acetic acid [carboxylic acid 1] (1 eq.) in dichloromethane (5 ml/mmol). This solution was stirred for 15 min at room temperature and then cooled to 0° C. again, and 3-(4-(pyrrolidin-1-ylmethyl)piperidin-4-yl)pyridine (1.2 eq.) was added. The reaction mixture was stirred for 16 h at 25° C., diluted with dichloromethane (30 ml) and washed with saturated ammonium chloride solution, saturated sodium chloride solution, saturated sodium carbonate solution and again with saturated sodium chloride solution. The organic phase was dried over sodium sulfate and concentrated in vacuo. The crude product was purified by column chromatography (2% methanol in dichloromethane). Yield: 25%

MS, $R_t$=2.8 min, m/z 599.3 (MH$^+$)

Example 77

2-Chloro-N-[2-[2-[4-(3-chlorophenyl)-4-(3-pyrrolidin-1-yl-propyl)-piperidin-1-yl]-2-oxo-ethoxy]-ethyl]-N-cyclopropyl-6-methyl-benzenesulfonic acid amide

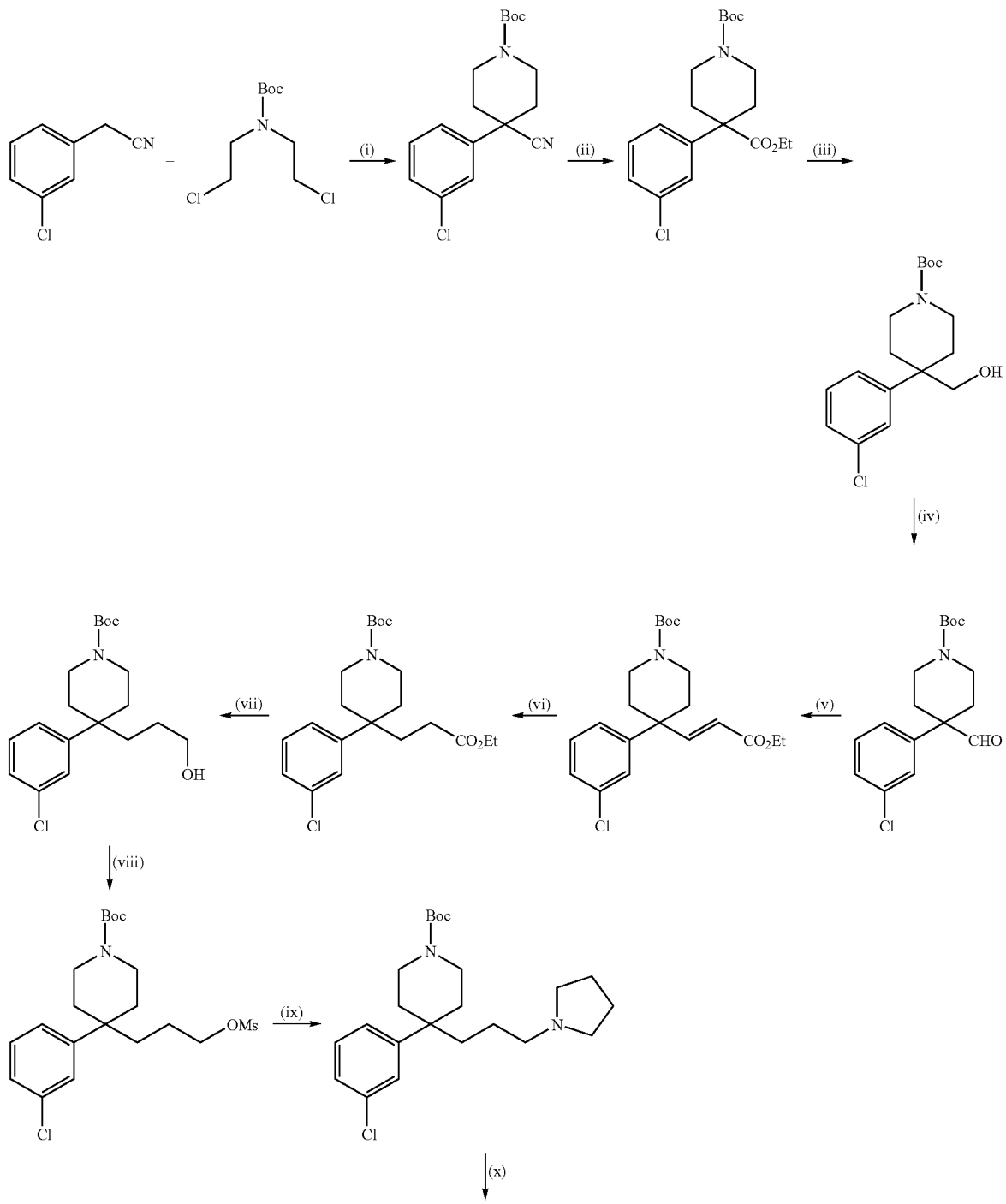

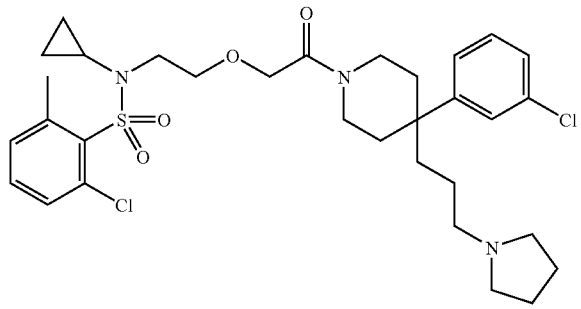

(i) A suspension of 2-(3-chlorophenyl)acetonitrile (0.5 g, 3.3 mmol), tert-butyl bis(2-chloroethyl)carbamate (3 eq.), KOH (4 eq.) and 18-Crown-6 (cat.) in toluene were refluxed for 12 h. After cooling, water was added to the reaction mixture and it was extracted with ethyl acetate. The organic layer was washed with water and brine, dried over sodium sulfate and concentrated in vacuo. The crude product was purified by column chromatography (silica). Yield: 70%

(ii) tert-Butyl 4-(3-chlorophenyl)-4-cyanopiperidine-1-carboxylate (1 g, 3 mmol) was heated in a solution of $H_2SO_4$/$H_2O$ (1:1) for 3 h. The reaction mixture was cooled and azeotropically distilled with ethanol (5×). It was then refluxed with ethanol for 16 h. The reaction mixture was concentrated in vacuo, redissolved in ethyl acetate and extracted with aq. Sodium hydrogen carbonate. The solvent was again removed in vacuo and the crude mixture was redissolved in dichloromethane. Triethylamin (4 eq.) and Boc anhydride (1.2 eq.) were added to the reaction mixture and it was stirred for 16 h at room temperature. After solvent removal in vacuo crude mixture was purified by column chromatography (silica). Yield: 45%

(iii) A solution of 1-tert-butyl 4-ethyl 4-(3-chlorophenyl) piperidine-1,4-dicarboxylate (0.5 g, 1.36 mmol) in tetrahydrofuran (5 ml) was added dropwise to a suspension of LAH (1.2 eq.) in tetrahydrofuran (5 ml) at 0° C. The resulting mixture was stirred at the same temperature for 1 h. Sat. aq. sodium sulfate solution was added to the reaction mixture and it was passed through a short bed of celite. The filtrate was concentrated in vacuo and the crude product was taken through to the next step without further purification.

(iv) Using standard Swern oxidation conditions (see step (v)/Example 80 or step (iii)/Example 81) tert-butyl 4-(3-chlorophenyl)-4-(hydroxymethyl)piperidine-1-carboxylate (0.5 g, 1.5 mmol) was oxidized to yield tert-butyl 4-(3-chlorophenyl)-4-formylpiperidine-1-carboxylate, which was directly taken through to the next step without further purification.

(v) Ethyl 2-(diethoxyphosphoryl)acetate (1.3 eq.) was added dropwise to a suspension of NaH (1.3 eq.) in tetrahydrofuran (5 ml) at 0° C. and the mixture was stirred for 30 min. tert-Butyl 4-(3-chlorophenyl)-4-formylpiperidine-1-carboxylate (0.45 g, 1.4 mmol) in tetrahydrofuran was added at 0° C. and the reaction mixture stirred overnight at room temperature. After quenching with water the reaction mixture was extracted with ethyl acetate and the organics were dried over sodium sulfate. After concentrating the organics in vacuo the crude product obtained was employed in the next step without further purification.

(vi) Using standard hydrogenation conditions (see step (v)/Example 81) (E)-tert-butyl 4-(3-chlorophenyl)-4-(3-ethoxy-3-oxoprop-1-enyl)piperidine-1-carboxylate (0.5 g, 1.3 mmol) was reduced to yield tert-butyl 4-(3-chlorophenyl)-4-(3-ethoxy-3-oxopropyl)piperidine-1-carboxylate using Pd/C as a catalyst.

(vii) A solution of tert-butyl 4-(3-chlorophenyl)-4-(3-ethoxy-3-oxopropyl)piperidine-1-carboxylate (1 g, 2.53 mmol) in tetrahydrofuran (6 ml) was added dropwise to a suspension of LAH (1.2 eq.) in tetrahydrofuran at 0° C. and the resulting mixture stirred at the same temperature for 1 h. The reaction mixture was quenched with aq. sat. sodium sulfate and then passed through a short celite pad. After solvent removal the crude product was employed in the next step without further purification.

(viii) MsCl (1.5 eq.) was added dropwise to a solution of tert-butyl 4-(3-chlorophenyl)-4-(3-hydroxypropyl)piperidine-1-carboxylate (0.9 g, 2.55 mmol) and triethylamine (4 eq.) in dichloromethane (5 ml) at 0° C. and the reaction mixture was stirred for 3 h at room temperature. The mixture was diluted with dichloromethane and washed with water and brine respectively. The organic layer was dried over sodium sulfate. After solvent removal the crude product obtained was employed in the next step without further purification.

(ix) A suspension containing tert-butyl 4-(3-chlorophenyl)-4-(3-(methylsulfonyloxy)propyl)piperidine-1-carboxylate (0.8 g, 1.86 mmol), pyrrolidine (2 eq.) and $K_2CO_3$ (5 eq.) in toluene was refluxed for 12 h. After cooling, the reaction mixture was washed with water and brine respectively and the crude product was by column chromatography (silica). Yield: 65%

(x) A solution of tert-butyl 4-(3-chlorophenyl)-4-(3-(pyrrolidin-1-yl)propyl)piperidine-1-carboxylate (0.15 g, 0.37 mmol) in dichloromethane (3 ml) was Boc-deprotected using standard reaction conditions (see step (vi)/example 25; TFA (3-13 eq.)) and added dropwise to a solution containing 2-(2-(2-chloro-N-cyclopropyl-6-methylphenylsulfonamido) ethoxy)acetic acid [carboxylic acid 2] (1 eq.), EDCI (1.5 eq.), HOBt (1 eq.) and DIPEA (6 eq.) in dichloromethane (5 ml) at 0° C. The resulting mixture was then stirred at room temperature for 16 h. The reaction mixture was diluted with dichloromethane and washed with aq. ammonium chloride, aq. sodium hydrogen carbonate and water respectively. The organic layer was dried over sodium sulfate, concentrated in vacuo and the crude product purified by chromatography (silica). Yield: 25%

MS, $R_t$=3.9 min, m/z=636.4 $[MH]^+$

Example 78
2-Chloro-N-cyclopropyl-6-methyl-N-[2-[2-oxo-2-[4-(3-pyrrolidin-1-yl-propyl)-4-[3-(trifluoromethyl)phenyl]-piperidin-1-yl]-ethoxy]-ethyl]-benzene-sulfonic acid amide
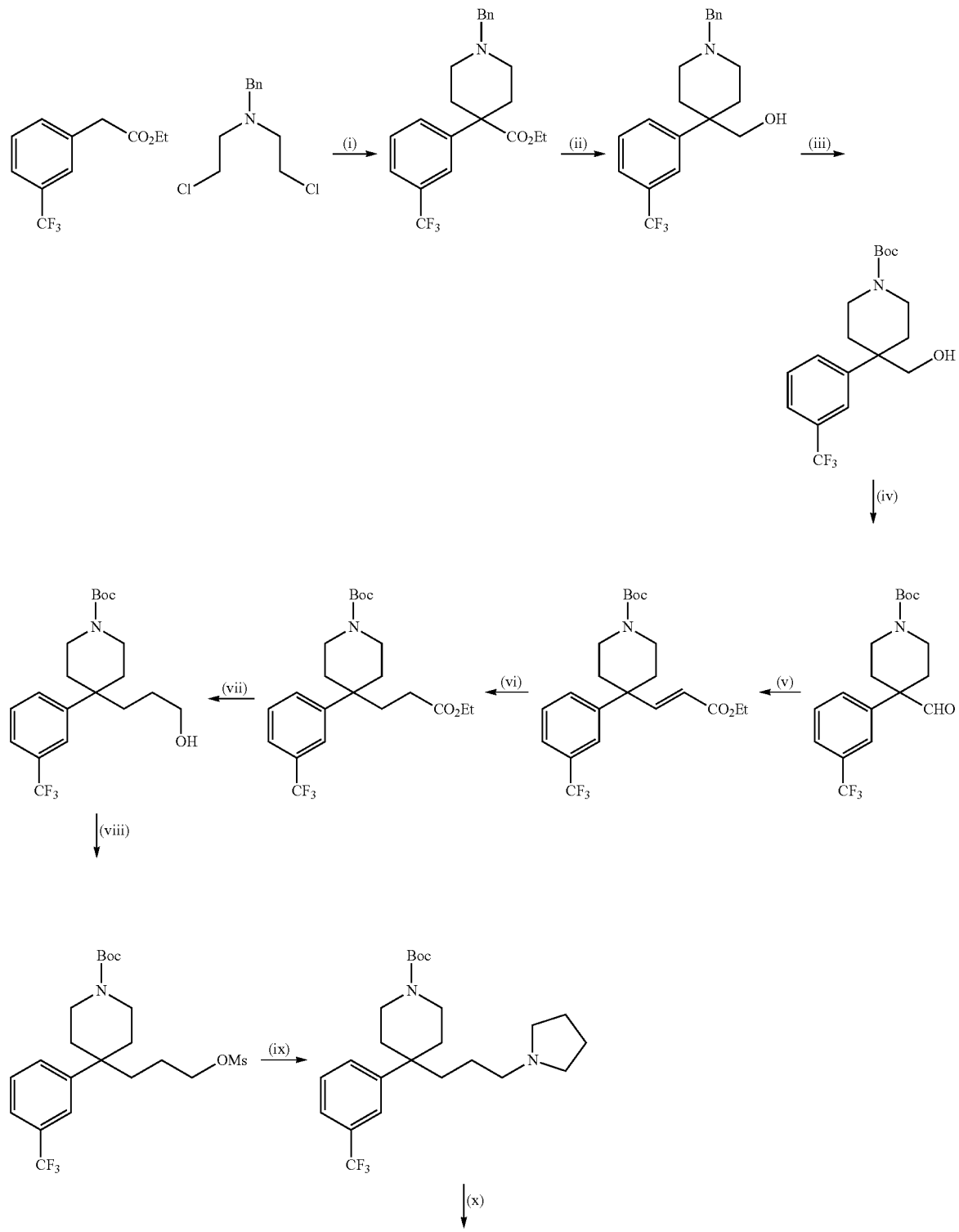

-continued

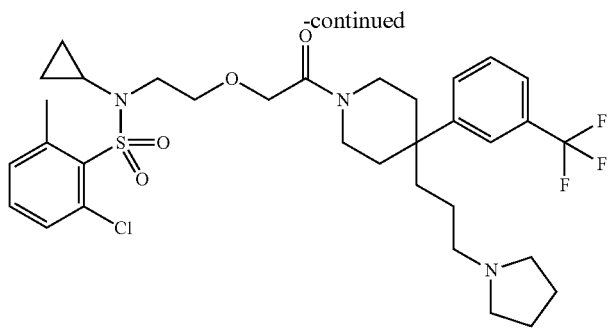

(i) A solution of ethyl 2-(3-(trifluoromethyl)phenyl)acetate (4.58 mmol, 1 g) in tetrahydrofuran (10 ml) was added to a suspension of NaH (3 eq.) and 18-Crown-6 (cat.) in tetrahydrofuran (20 ml) at 0° C. and the mixture was stirred for 30 min. N-Benzyl-2-chloro-N-(2-chloroethyl)ethanamine (1.2 eq.) in tetrahydrofuran (10 ml) was added at 0° C. and the reaction mixture was warmed to room temperature and stirred for 24 h. The crude reaction mixture was concentrated in vacuo, dissolved in ethyl acetate, washed with water and brine and dried over sodium sulfate. The crude product was purified by column chromatography (silica).

Yield: 26%

(ii) To a suspension of LAH (2 eq.) in tetrahydrofuran (10 ml) at 0° C. was added dropwise a solution of ethyl 1-benzyl-4-(3-(trifluoromethyl)phenyl)piperidine-4-carboxylate (1 mmol, 0.4 g) in tetrahydrofuran (10 ml) and the reaction mixture was stirred at room temperature for 2 h. The reaction mixture was quenched with aq. sat. sodium sulfate and the crude reaction mixture was passed through a short pad of celite and washed with excess ethyl acetate. After concentration the crude reaction mixture was taken through to the next step without further purification.

(iii) A solution containing (1-benzyl-4-(3-(trifluoromethyl)phenyl)piperidin-4-yl)methanol (1 mmol, 0.36 g) and Boc-anhydride (1 eq.) in methanol (15 ml) was hydrogenated using Pd/C as a catalyst for 16 h. The reaction mixture was passed through a bed of celite, concentrated and used in the next step without further purification.

(iv) Using standard Swern oxidation reaction conditions (see step (v)/Example 80 or step (iii)/Example 81), tert-butyl 4-(hydroxymethyl)-4-(3-(trifluoromethyl)phenyl)piperidine-1-carboxylate (1.2 mmol, 0.43 g) was oxidized to give 1-benzyl-4-(3-(trifluoromethyl)phenyl)piperidine-4-carbaldehyde which was used in the next step without further purification.

(v) A solution of ethyl 2-(diethoxyphosphoryl)acetate (1.3 eq.) in tetrahydrofuran (3 ml) was added dropwise to a suspension of NaH (1.3 eq.) in tetrahydrofuran (15 ml) at 0° C. and the resulting mixture was stirred for 30 min. 1-Benzyl-4-(3-(trifluoromethyl)phenyl)piperidine-4-carbaldehyde (1.12 mmol, 0.4 g in 20 ml tetrahydrofuran) was added dropwise to the reaction mixture at 0° C. The mixture was warmed to room temperature and stirred for 16 h. The reaction mixture was concentrated, re-dissolved in ethyl acetate and extracted with water and brine respectively. The organic layer was dried over sodium sulfate and after concentration the crude product was taken through to the next step without further purification.

(vi) Using standard hydrogenation conditions (see step (v)/Example 81) (E)-ethyl 3-(1-benzyl-4-(3-(trifluoromethyl)phenyl)piperidin-4-yl)acrylate (1.64 mmol, 0.7 g) was hydrogenated using Pd/C as a catalyst. The product was employed in the next step without further purification.

(vii) A solution of tert-butyl 4-(3-ethoxy-3-oxopropyl)-4-(3-(trifluoromethyl)phenyl)piperidine-1-carboxylate (1.3 mmol, 0.56 g) in tetrahydrofuran (5 ml) was added dropwise to a suspension of LAH (1.1 eq.) in tetrahydrofuran (15 ml) at 0° C. and the mixture was stirred at 0° C. for 2 h and then at room temperature for 3 h. The reaction mixture was quenched with sat. aq. sodium sulfate and passed through a short celite pad and concentrated. The crude product was employed in the next step without further purification.

(viii) Triethylamine (4 eq.) followed by MsCl (1.5 eq.) were added to a solution of tert-butyl 4-(3-hydroxypropyl)-4-(3-(trifluoromethyl)phenyl)piperidine-1-carboxylate (1.2 mmol, 0.46 g) in dichloromethane at 0° C. and the reaction mixture was warmed to room temperature and stirred for 3 h. The crude reaction mixture was concentrated, re-dissolved in dichloromethane and washed with water and brine respectively. The organic layer was dried over sodium sulfate. After concentration the crude product was used in the next step without further purification.

(ix) $K_2CO_3$ (5 eq.) and pyrrolidine (2 eq.) were added to solution of tert-butyl 4-(3-(methylsulfonyloxy)propyl)-4-(3-(trifluoromethyl)phenyl)piperidine-1-carboxylate (1.2 mmol, 0.54 g) in toluene (15 ml) and the reaction mixture was refluxed for 12 h. After cooling, the reaction mixture was extracted with water and brine respectively. The organic layer was concentrated under reduced pressure and the crude product thus obtained was taken through to the next step without further purification.

(x) tert-Butyl 4-(3-(pyrrolidin-1-yl)propyl)-4-(3-(trifluoromethyl)phenyl)piperidine-1-carboxylate (0.45 mmol, 0.2 g) was Boc-deprotected (see step (vi)/example 25; TFA (3-13 eq.)) and the resulting free amine was re-dissolved in dichloromethane and cooled to 0° C. To the reaction mixture were added DIPEA (6 eq.), EDCI (2 eq.) and HOBt (2 eq.) at 0° C. and the mixture was stirred at room temperature for 16 h. The reaction mixture was diluted with dichloromethane and washed with aq. ammonium chloride and aq. sodium hydrogen carbonate respectively. After water and brine washes the organic layer was dried over sodium sulfate, concentrated and purified by column chromatography (silica). Yield: 24%

MS, $R_t$=3.8 min, m/z=670.3 [MH]$^+$

Example 79
2-Chloro-N-cyclopropyl-N-[2-[2-[4-(3-fluorophenyl)-4-(3-pyrrolidin-1-yl-propyl)-piperidin-1-yl]-2-oxo-ethoxy]-ethyl]-6-methyl-benzenesulfonic acid amide
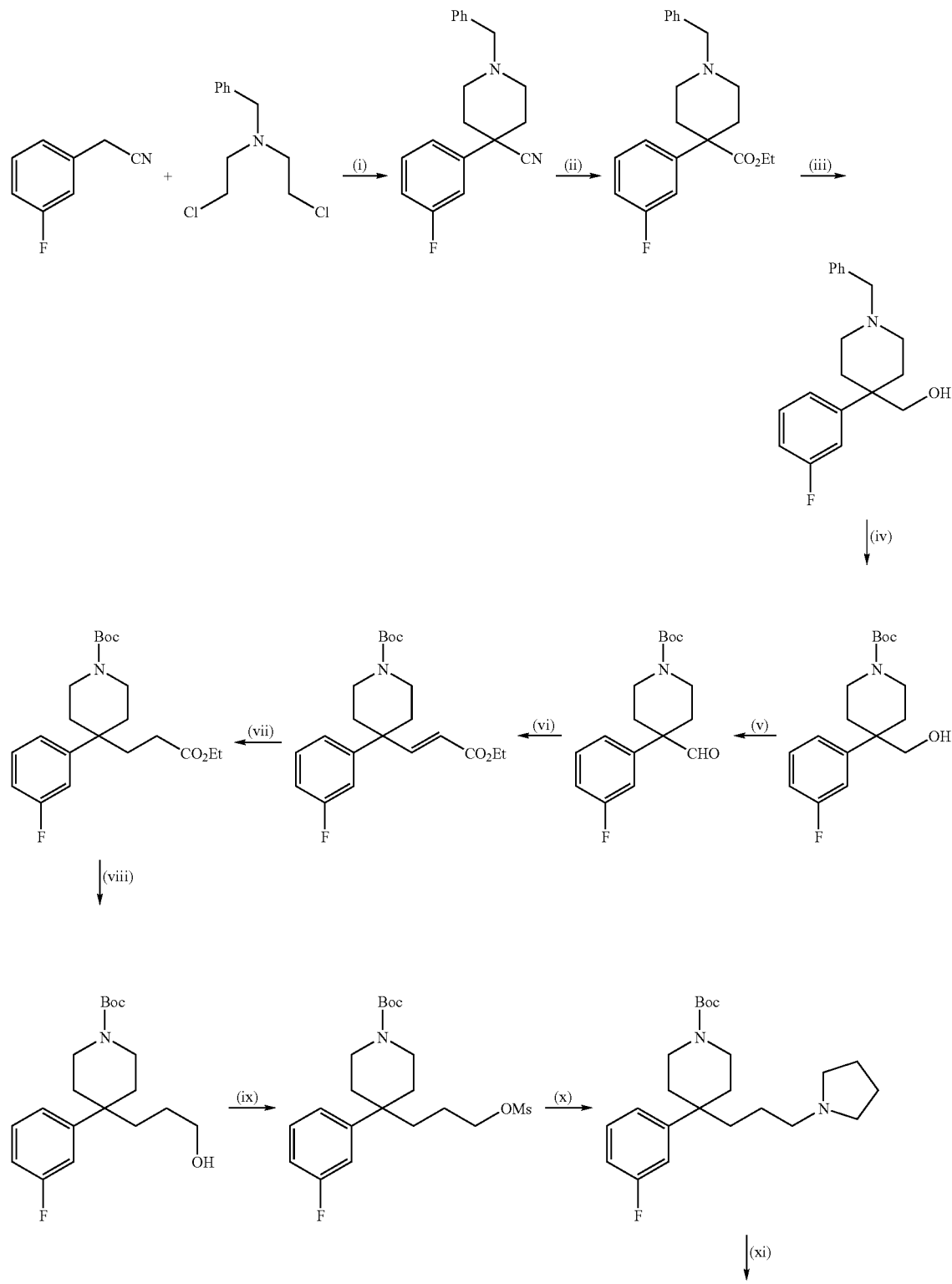

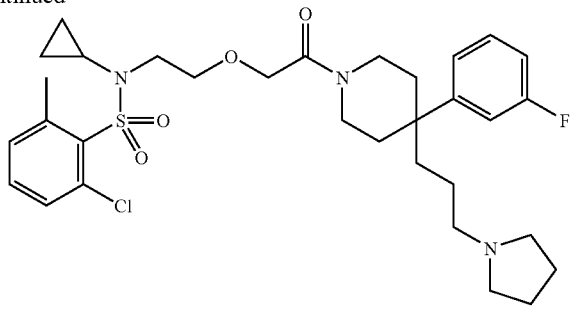

(i) To a cooled (0° C.) suspension of NaH (3.0 eq.) in tetrahydrofuran/DMF (2:1, 45 ml) was added 18-Crown-6 (cat.) and a solution of 2-(3-fluorophenyl)acetonitrile (1.5 g, 11.09 mmol, 1.0 eq.) in tetrahydrofuran (10 ml). The resulting mixture was stirred for 15 min. A solution of N-benzyl-bis-(2-chloroethyl)amine (13.30 mmol, 1.2 eq.) in tetrahydrofuran (15 ml) was added to the reaction mixture at 0° C. in a dropwise fashion and the reaction mixture was stirred at room temperature for 12 h. The reaction was quenched by addition of water and the mixture was extracted with ethyl acetate. The organic layer was washed with water, dried over sodium sulfate, concentrated in vacuo and purified by column chromatography (silica). Yield: 80%

(ii) 1-Benzyl-4-(3-fluorophenyl)piperidine-4-carbonitrile (3.2 g, 10.88 mmol) was heated to reflux in a solution of $H_2SO_4/H_2O$ (1:1, 32 ml) for 4 h. The reaction mixture was cooled, azeotropically distilled with ethanol (5×) and then refluxed with ethanol (150 ml) for 16 h. The mixture was concentrated in vacuo and water was added. The pH was adjusted to pH=10 by addition of 1N NaOH solution and the mixture extracted with ethyl acetate. The organic layer was dried over anhydrous sodium sulfate, concentrated in vacuo to yield the crude product which was used in the next step without further purification. Yield: 80%

(iii) A solution of ethyl 1-benzyl-4-(3-fluorophenyl)piperidine-4-carboxylate (1.0 g, 2.93 mmol) in tetrahydrofuran (20 ml) was added dropwise to a suspension of LAH (2.0 eq.) in tetrahydrofuran (40 ml) at 0° C. and the resulting mixture was stirred at the same temperature for 2 h. Saturated aq. sodium sulfate solution was added to the reaction mixture and it was then passed through a short bed of celite. The filtrate was concentrated in vacuo. The crude product was used in the next step with out further purification. Yield: quantitative (iv) To a solution of (1-benzyl-4-(3-fluorophenyl)piperidin-4-yl)methanol (0.50 g, 1.67 mmol) in methanol (10 ml) was added Boc-anhydride and Pd/C (0.50 g). The reaction mixture was stirred at room temperature for 16 h under an atmosphere of hydrogen using a hydrogen balloon. The mixture was filtered through a bed of celite and the filtrate was concentrated in vacuo to yield the crude product which was purified by column chromatography (silica). Yield: 25%

(v) Using standard Swern oxidation reaction conditions (see step (v)/Example 80 or step (iii)/Example 81), tert-butyl 4-(3-fluorophenyl)-4-(hydroxymethyl)piperidine-1-carboxylate (0.5 g, 1.61 mmol) was oxidized to yield tert-butyl 4-(3-fluorophenyl)-4-formylpiperidine-1-carboxylate which was directly taken through to the next step without further purification.

(vi) Ethyl 2-(diethoxyphosphoryl)acetate (1.3 eq.) was added dropwise to a suspension of NaH (1.3 eq.) in tetrahydrofuran (5 ml) at 0° C. and the resulting mixture stirred for 30 min. tert-Butyl 4-(3-fluorophenyl)-4-formylpiperidine-1-carboxylate (0.200 g, 0.651 mmol) in tetrahydrofuran was added to the mixture at 0° C. and the reaction was stirred overnight at room temperature. The reaction mixture was extracted with ethylacetate after quenching with water. The organic layer was dried over sodium sulfate and concentrated in vacuo. The crude product was used in the next step without further purification.

(vii) Using standard hydrogenation conditions (see step (v)/Example 81) (E)-tert-butyl 4-(3-ethoxy-3-oxoprop-1-enyl)-4-(3-fluorophenyl)piperidine-1-carboxylate (0.270 g, 0.716 mmol) was reduced to tert-butyl 4-(3-ethoxy-3-oxopropyl)-4-(3-fluorophenyl)piperidine-1-carboxylate using Pd/C as a catalyst.

(viii) A solution of tert-butyl 4-(3-ethoxy-3-oxopropyl)-4-(3-fluorophenyl)piperidine-1-carboxylate (0.237 g, 0.625 mmol) in tetrahydrofuran (5 ml) was added dropwise to a suspension of LAH (1.1 eq.) in tetrahydrofuran (5 ml) at 0° C. and the mixture was stirred at the same temperature for 2.5 h. The reaction mixture was quenched by addition of aq.sat. sodium sulfate solution and it was then passed through a short celite pad. After solvent removal in vacuo the crude product was used in the next step without further purification. Yield: 75%

(ix) MsCl (1.5 eq.) was added dropwise at 0° C. to a solution of tert-butyl 4-(3-fluorophenyl)-4-(3-hydroxypropyl)piperidine-1-carboxylate (0.170 g, 0.504 mmol, 1.0 eq.) and triethylamine (4.0 eq) in dichloromethane (5 ml) and the mixture was stirred for 3 h at room temperature. The reaction mixture was diluted with dichloromethane and washed with water and brine respectively. The organic layer was dried over sodium sulfate. After solvent removal in vacuo the crude product was employed in the next step without further purification.

(x) A suspension containing tert-butyl 4-(3-fluorophenyl)-4-(3-(methylsulfonyloxy)propyl)piperidine-1-carboxylate (0.200 g, 0.482 mmol), pyrrolidine (2.0 eq.) and $K_2CO_3$ (5.0 eq.) in toluene (10 ml) was refluxed for 12 h. After cooling, the reaction mixture was diluted with toluene and extracted with water and brine respectively. The crude product was purified by column chromatography (silica). Yield: 65%

(xi) A solution of tert-butyl 4-(3-fluorophenyl)-4-(3-(pyrrolidin-1-yl)propyl)piperidine-1-carboxylate (0.2379 mmol, 1.0 eq.) in dichloromethane (3 ml) was Boc-deprotected using standard reaction conditions (see step (vi)/example 25; TFA (3-13 eq.)) and added dropwise to a solution containing 2-(2-(2-chloro-N-cyclopropyl-6-methylphenylsulfonamido)ethoxy)acetic acid [carboxylic acid 2] (1 eq.), EDCI (1.5 eq), HOBt (1.0 eq.) and DIPEA (6.0 eq.) in dichloromethane (5 ml) at 0° C. The mixture was then stirred at room temperature for 16 hrs. The reaction mixture was diluted with dichloromethane and extracted with aq. ammonium chloride, aq. sodium hydrogen carbonate and water respectively. The organic layer was dried over sodium sulfate, concentrated in vacuo and the crude product purified by column chromatography (silica). Yield: 30%
MS, $R_t$=3.8 min, m/z=620.3 [MH]$^+$
Example 80
2-[[(2S)-1-[(4-Methoxy-2,6-dimethyl-phenyl)sulfonyl]-piperidin-2-yl]-methoxy]-1-[4-pyridin-3-yl-4-(2-pyrrolidin-1-yl-ethyl)-piperidin-1-yl]-ethanone hydrochloride
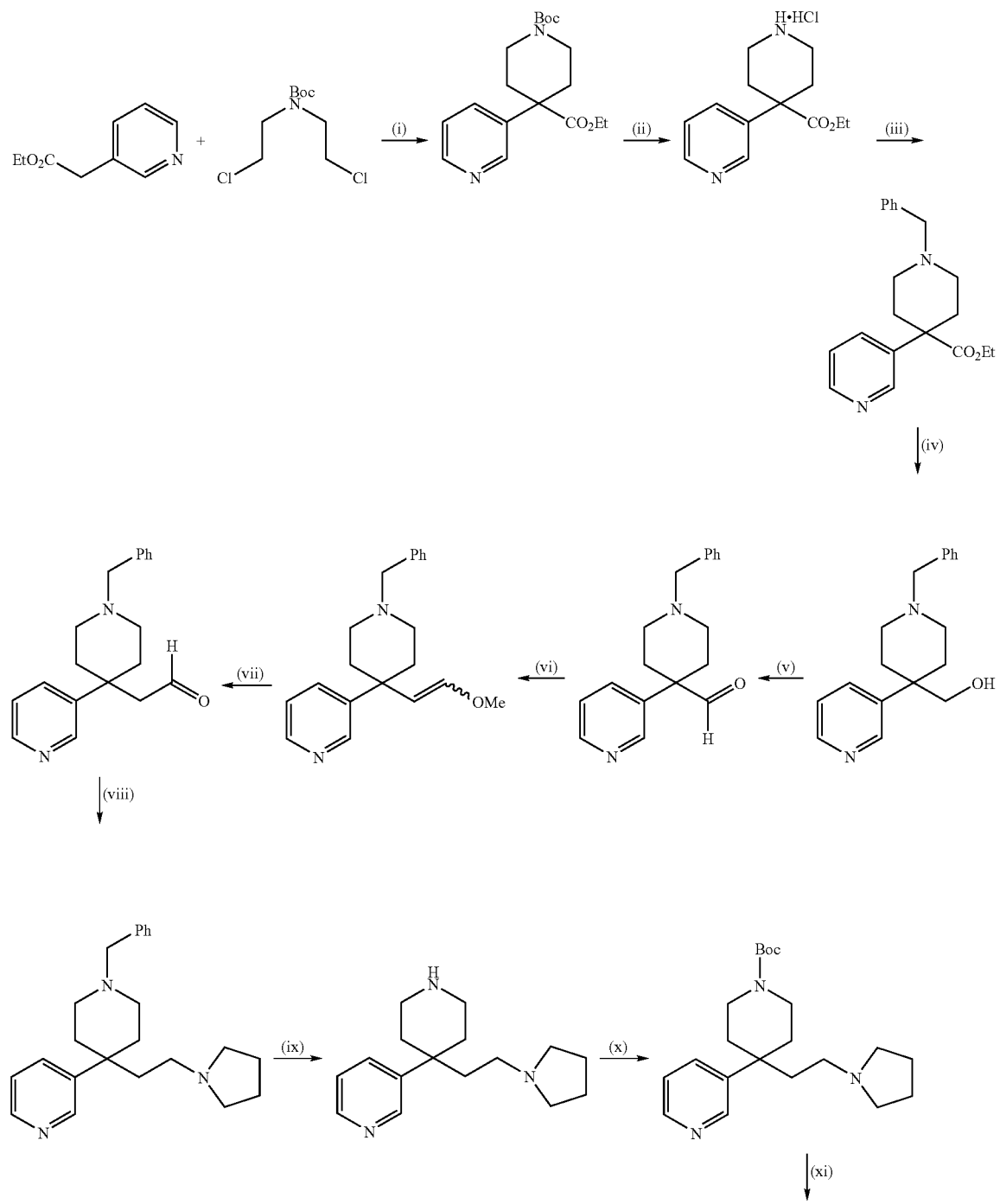

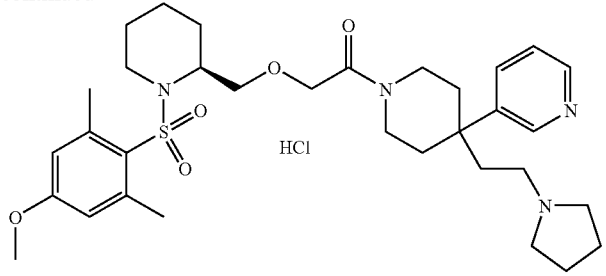

(i) To a tetrahydrofuran (36 ml) solution of ethyl 2-(pyridin-3-yl)acetate (2 g) was added tert-butyl bis(2-chloroethyl)carbamate (1.5 eq.), NaH (3 eq.), 18-crown-6 (0.2 eq.) and DMF (2 ml) at 25° C. and the resulting reaction mixture was allowed to stir at same temperature for 4 h (monitored by TLC). The reaction mixture was cooled to 0° C., quenched with crushed ice and diluted with ethyl acetate. The organic layer was washed with water and brine and finally dried over sodium sulfate. Evaporation of organic layer under reduced pressure gave the crude product which was purified by column chromatography. Yield: 25%

(ii) & (iii) To a solution of 1-tert-butyl 4-ethyl 4-(pyridin-3-yl)piperidine-1,4-dicarboxylate (2.2 g) in dioxane (5 ml) was added dioxane saturated with HCl (20 ml) at 0° C. and the resulting mixture was stirred for 2 h. The reaction mixture was concentrated in vacuo. To a solution of the crude intermediatete (ethyl 4-(pyridin-3-yl)piperidine-4-carboxylate hydrochloride) in dichloromethane (30 ml) was added benzaldehyde (1.2 eq.) and acetic acid (2 ml) and the mixture was stirred at room temperature for 30 min. Then triacetoxy sodium borohydride (2 eq.) was added and it was stirred for overnight. The reaction mixture was diluted with dichloromethane and washed with sodium bicarbonate, water and brine. The organic layer was dried over sodium sulfate. Evaporation of organic layer under reduced pressure gave the crude product which was purified by column chromatography. Yield: 60% (over two steps)

(iv) To a cold (0° C.) suspension of LAH (2 eq.) in tetrahydrofuran (3 ml/mmol) was added a solution of ethyl 1-benzyl-4-(pyridin-3-yl)piperidine-4-carboxylate (5 mmol) in tetrahydrofuran (2 ml/mmol) dropwise under an argon atmosphere. After addition was complete, the reaction mixture was allowed to stir at this temperature for 2 h by which time the starting material had been completely consumed (monitored by TLC). The reaction mixture was carefully quenched with a saturated aqueous sodium sulfate solution and filtered through a bed of celite. The residue was washed with ethyl acetate and the combined organic layers were dried over sodium sulfate. The organics were evaporated under reduced pressure to yield the crude product which was used directly in the next step without further purification. Yield: 91%

(v) To a dichloromethane (3 ml/mmol) solution of oxalyl chloride (1.1 eq.) was added DMSO (2 eq.) at −78° C. under argon atmosphere and the resulting mixture was stirred at this temperature for 15 min. To this cold mixture was added (1-benzyl-4-(pyridin-3-yl)piperidin-4-yl)methanol (2.7 mmol) in dichloromethane (3 ml/mmol) in a dropwise fashion. The resulting mixture was allowed to stir at this temperature for 1 h. Triethylamine (5 eq.) was added to the reaction mixture and it was allowed to slowly warm to ambient temperature and stir at this temperature for 1 h. The reaction mixture was diluted with dichloromethane and the organic layer was washed successively with saturated aqueous ammonium chloride, water and brine and finally dried over sodium sulfate. Evaporation of organic layer under reduced pressure gave the crude product which was used directly in the next step without further purification. Yield: 80%

(vi) & (vii) A solution of potassium tert-butoxide (15 mmol) in anhydrous tetrahydro-furan (10 ml) was added dropwise to a suspension of (methoxymethyl)triphenyl-phosphonium chloride (21 mmol) in anhydrous tetrahydrofuran (20 ml) at 0° C. under an argon atmosphere. The resulting mixture was stirred for 15 min at 0° C. (change of color to deep orange). A solution of 1-benzyl-4-(pyridin-3-yl)piperidine-4-carbaldehyde (3 mmol) in anhydrous tetrahydrofuran (30 ml) was added dropwise to the reaction mixture at 25° C. and it was stirred at that temperature for 16 h. The reaction mixture was cooled to 0° C. and acidified with 6N aq. HCl. After stirring for 1 h at room temperature, the reaction mixture was extracted with ethyl acetate and the aqueous layer was treated with 5N aq. NaOH solution until pH 11. The basified aqueous layer was extracted with dichloromethane. After drying over sodium sulfate and filtration, the solvent was removed in vacuo to yield the desired product which was used immediately in the next step. Yield: 55% (over two steps)

(viii) To a solution of 2-(1-benzyl-4-(pyridin-3-yl)piperidin-4-yl)acetaldehyde (1.22 mmol) in dichloromethane (30 ml) were added pyrrolidine (1.2 eq.) and acetic acid (2 ml) and the mixture was stirred at room temperature for 30 min. Triacetoxy sodium borohydride (4 eq.) was added and it was stirred overnight. The reaction mixture was diluted with dichloromethane and washed with sodium bicarbonate, water and brine, and the organic layer was dried over sodium sulfate. Evaporation of organic layer under reduced pressure gave the crude product which was purified by column chromatography. Yield: 58%

(ix) A solution of 3-(1-benzyl-4-(2-(pyrrolidin-1-yl)ethyl)piperidin-4-yl)pyridine (400 mg) in methanol (10 ml) was deoxygenated with argon. To it was added 10% $Pd(OH)_2$ (200 mg) and acetic acid (0.01 ml). The resulting reaction mixture was hydrogenated under atmospheric pressure for 16 h (monitored by TLC and LCMS). The reaction mixture was filtered through a bed of celite and the residue was washed with methanol. The combined organic layers were evaporated to dryness to give the crude product which was used directly in the next step without further purification. Yield: 55%

(x) To a dichloromethane solution (5 ml) of 3-(4-(2-(pyrrolidin-1-yl)ethyl)piperidin-4-yl)pyridine (1.2 mmol) was added DIPEA (1.5 eq.) and Boc-anhydride (1.2 eq.) at 0° C. The resulting reaction mixture was stirred at ambient temperature for 3 h. It was diluted with dichloromethane and the organic layer was washed successively with water and brine and then dried over sodium sulfate. Evaporation of the organic layer under reduced pressure gave the crude product which was purified by column chromatography (10% methanol in dichloromethane). Yield: 53%

(xi) To a solution of 2-(2-(4-methoxy-2,6-dimethylphenylsulfonyl)benzyloxy)acetic acid [carboxylic acid 1] (0.5 mmol) in dichloromethane (5 ml) were added DIPEA (4 eq.), EDCI. HCl (1.2 eq) and HOBt (1 eq.). Then a mixture of Boc-deprotected tert-butyl 4-(pyridin-3-yl)-4-(2-(pyrrolidin-1-yl)ethyl)piperidine-1-carboxylate (0.62 mmol) [deprotected using standard reaction conditions: dichloromethane (3 ml), TFA (3 eq.) and concentration in vacuo] and DIPEA (2 eq.) in dichloromethane (3 ml) was added dropwise at ice-cold reaction conditions. The reaction mixture was stirred at room temperature overnight. The mixture was diluted with dichloromethane, washed with saturated ammonium chloride, brine, saturated sodium bicarbonate solution and again brine. The organic layer was dried over anhydrous sodium sulfate and concentrated in vacuo. The crude product was purified by column chromatography (silica, methanol/dichloromethane). The free base of the desired compound was dissolved in dioxane (3 ml), stirred in dioxane saturated with HCl for 1 h and then concentrated under reduced pressure to give the desired product.

Yield: 43%

MS, $R_t$=2.7 min, m/z=613.4 [MH]$^+$

Example 81

2-[[(2S)-1-[(4-Methoxy-2,6-dimethyl-phenyl)sulfonyl]-piperidin-2-yl]-methoxy]-1-[4-pyridin-3-yl-4-(3-pyrrolidin-1-yl-propyl)-piperidin-1-yl]-ethanone hydrochloride

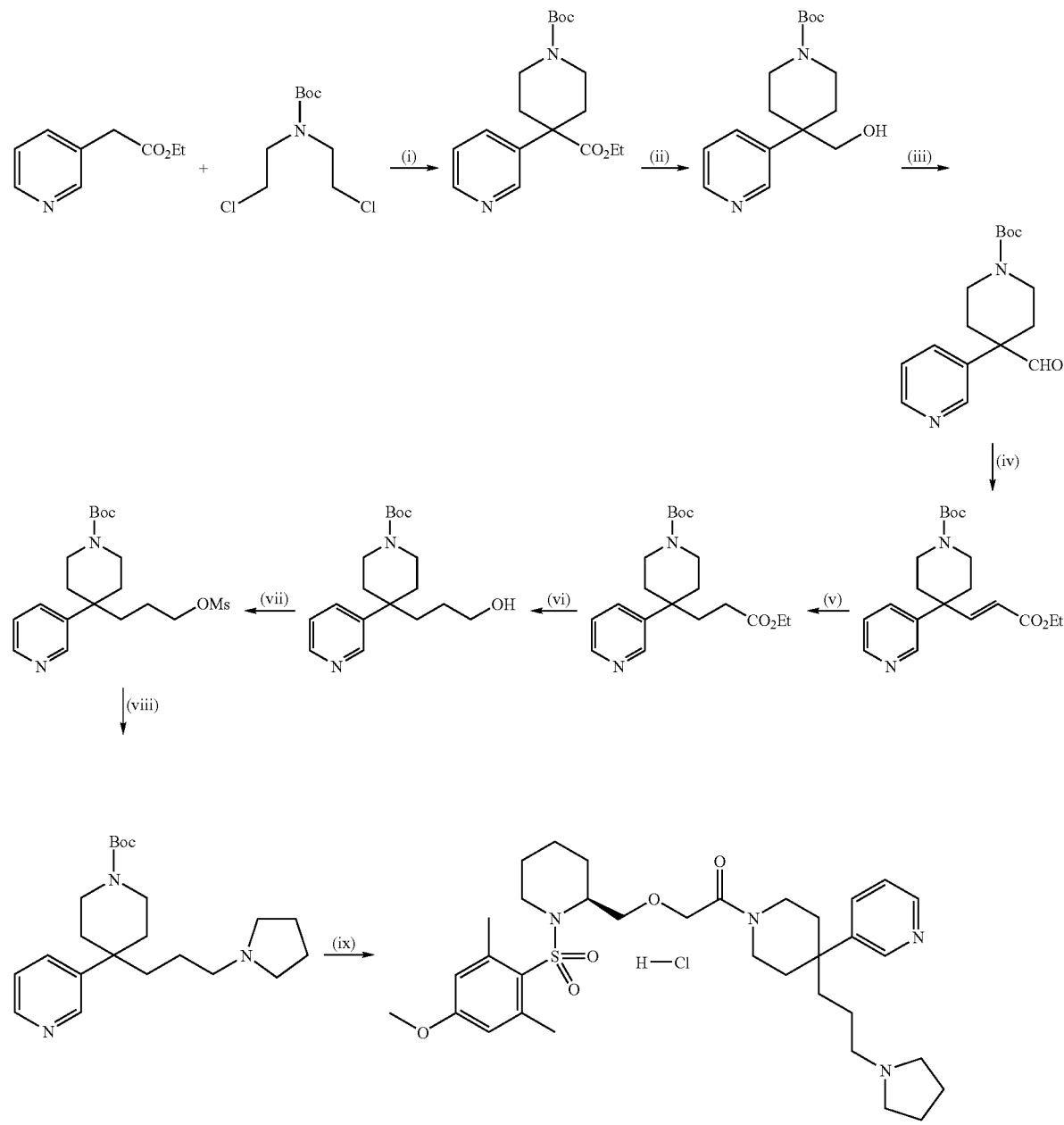

(i) To a tetrahydrofuran (36 ml) solution of ethyl 2-(pyridin-3-yl)acetate (2 g) was added bis-(2-chloro-ethyl)-carbamic acid tert-butyl ester (1.5 eq.), NaH (3 eq.), 18-crown-6 (0.2 eq.) and DMF (2 ml) at 25° C. and the resulting reaction mixture was allowed to stir at same temperature for 4 h (monitored by TLC). The reaction mixture was cooled to 0° C., quenched with crushed ice and diluted with ethyl acetate. The organic layer was washed successively with water and brine and finally dried over sodium sulfate. Evaporation of the organic layer under reduced pressure gave the crude product which was purified by column chromatography. Yield: 25%

(ii) To a cold (0° C.) suspension of LAH (1.2 eq.) in tetrahydrofuran (3 ml/mmol) under argon atmosphere was added dropwise a solution of 1-tert-butyl 4-ethyl 4-(pyridin-3-yl)piperidine-1,4-dicarboxylate (1 eq.) in tetrahydrofuran (2 ml/mmol). The reaction mixture was allowed to stir at this temperature for 2 h by which time the starting material had been consumed (monitored by TLC). The mixture was carefully quenched with a saturated aqueous sodium sulfate solution and filtered through a bed of celite. The residue was washed with ethyl acetate and the combined organic layers were dried over sodium sulfate. The organics were evaporated under reduced pressure to give the crude product which was used directly in the next step without further purification. Yield: 90%

(iii) To a dichloromethane (3 ml/mmol) solution of oxalyl chloride (1.1 eq.) was added DMSO (2 eq.) at −78° C. under an argon atmosphere and the resulting mixture was stirred at this temperature for 15 min. To this cold mixture was added tert-butyl 4-(hydroxymethyl)-4-(pyridin-3-yl)piperidine-1-carboxylate (1 eq.) in dichloromethane (3 ml/mmol) in a dropwise fashion. The resulting mixture was allowed to stir at this temperature for 1 h. Triethylamine (5 eq.) was added to the reaction and it was allowed to slowly warm to ambient temperature and stir at this temperature for 1 h. The reaction mixture was diluted with dichloromethane and the organic layer was washed with saturated aqueous ammonium chloride, water and brine and finally dried over sodium sulfate. Evaporation of the organic layer under reduced pressure gave the crude product which was used directly in the next step without further purification. Yield: 90%

(iv) To a cold (0° C.) suspension of 60% NaH (1.1 eq.) in dry tetrahydrofuran (5 ml/mmol) was added slowly a solution of ethyl 2-(diethoxyphosphoryl)acetate (1.1 eq.) in tetrahydrofuran (5 ml/mmol) and the resulting reaction mixture was allowed to stir at 25° C. for 30 min. It was then cooled to 0° C. and tert-butyl 4-formyl-4-(pyridin-3-yl)piperidine-1-carboxylate (1 eq.) in dry tetrahydrofuran (5 ml/mmol) was added dropwise maintaining the same temperature. The reaction mixture was allowed to stir at 25° C. for 16 h by which time the starting material was consumed. It was quenched with ice and brine solution and the aqueous layer was extracted with ethyl acetate. The organic layer was washed with water and brine. It was dried over sodium sulfate and evaporated under reduced pressure to yield the crude product which was purified by column chromatography (50% ethyl acetate in hexane). Yield: 50%

(v) A solution of (E)-tert-butyl 4-(3-ethoxy-3-oxoprop-1-enyl)-4-(pyridin-3-yl)piperidine-1-carboxylate (1 eq.) in methanol (5 ml/mmol) was deoxygenated with argon for 15 min followed by the addition of 10% Pd/C (50% by weight). The resulting reaction mixture was hydrogenated under atmospheric pressure for 1 h (monitored by LCMS). It was filtered through a bed of celite and the residue was washed with methanol. The combined organic layers were evaporated to give the crude product which was used in the next step without further purification. Yield: 95%

(vi) To a cold (0° C.) suspension of LAH (1.2 eq.) in tetrahydrofuran (3 ml/mmol) under an argon atmosphere was added dropwise a solution of tert-butyl 4-(3-ethoxy-3-oxopropyl)-4-(pyridin-3-yl)piperidine-1-carboxylate (1 eqv) in tetrahydrofuran (2 ml/mmol). The reaction mixture was allowed to stir at this temperature for 2 h by which time starting material was completely consumed (monitored by TLC). The reaction was carefully quenched with a saturated aqueous sodium sulfate solution and filtered through a bed of celite. The residue was washed with ethyl acetate and the combined organic layers were dried over sodium sulfate and evaporated under reduced pressure to give the crude product which was used directly in the next step without further purification. Yield: 90%

(vii) To a dichloromethane solution (22 ml) of tert-butyl 4-(3-hydroxypropyl)-4-(pyridin-3-yl)piperidine-1-carboxylate (5.3 mmol) was added triethylamine (21.2 mmol) and MsCl (7.95 mmol) at 0° C. and the resulting reaction mixture was allowed to stir at the same temperature for 2 h (monitored by TLC). The reaction mixture was diluted with dichloromethane, washed with water and brine and the organic layer was finally dried over sodium sulfate. Evaporation of the organic layer under reduced pressure gave the crude product which was used directly in the next step. Yield: quantitative (viii) To a toluene solution (30 ml) of tert-butyl 4-(3-(methylsulfonyloxy)propyl)-4-(pyridin-3-yl)piperidine-1-carboxylate (5.3 mmol) was added potassium carbonate (26.5 mmol) and pyrrolidine (6.36 mmol) and the resulting reaction mixture was refluxed for 16 h. It was then cooled to 25° C. and diluted with ethyl acetate. The organic layer was successively washed with water and brine. After drying over sodium sulfate, the organic layer was evaporated under reduced pressure to give the crude product which was purified by column chromatography (5% methanol in dichloromethane). Yield: 50%

(ix) After removing the Boc protecting group of tert-butyl 4-(pyridin-3-yl)-4-(3-(pyrrolidin-1-yl)propyl)piperidine-1-carboxylate by using standard TFA/dichloromethane reaction conditions (see step (vi)/example 25; TFA (3-13 eq.)) it was reacted with 2-(2-(4-methoxy-2,6-dimethylphenylsulfonyl)benzyloxy)-acetic acid [carboxylic acid 1] by using the standard EDCI/HOBt amidation procedure (see for example step (x)/Example 77). The crude product was purified by chromatography (alumina) and then treated with HCl/dioxane solution to yield the hydrochloride salt od the desired product. Yield: 34%

MS, $R_t$=2.6 min, m/z=627.5 [MH]$^+$

Synthesis of Carboxylic Acid 1 (Acid Structural Unit)

(S)-2-((1-(4-Methoxy-2,6-dimethylphenylsulfonyl)piperidin-2-yl)methoxy)acetic acid Used in the Synthesis of Examples 25, 80 and 81

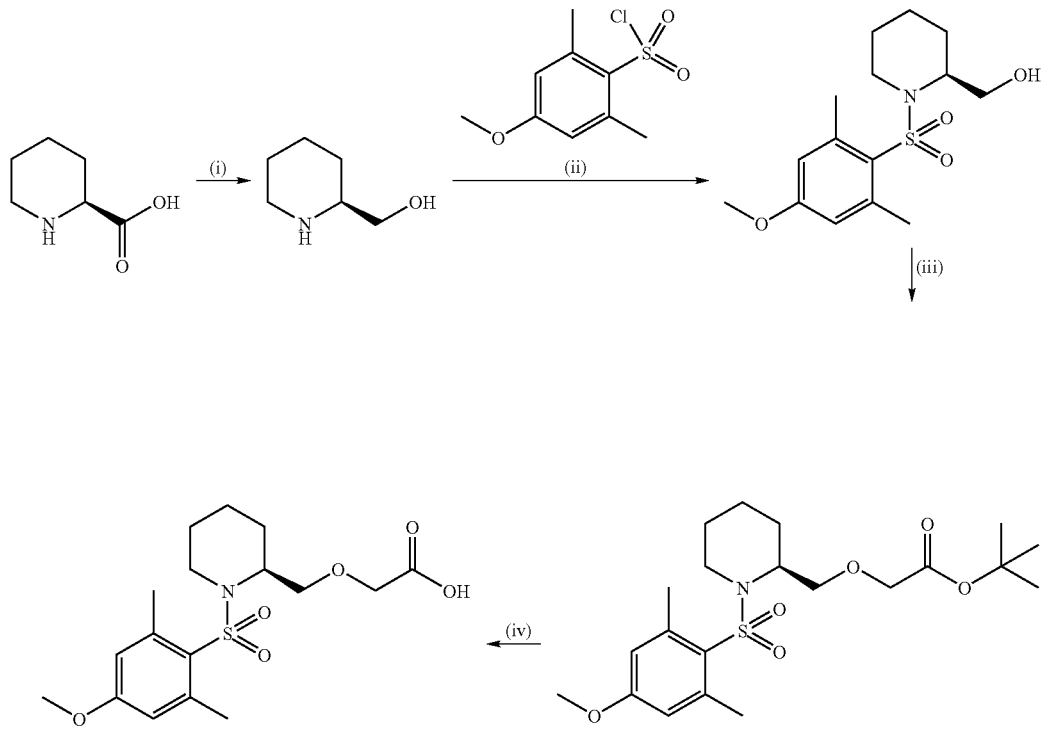

(i): (S)-Piperidine-2-carboxylic acid (2 g, 15.5 mmol) was placed in tetrahydrofuran (20 ml); boron trifluoride etherate (2.1 ml, 117.1 mmol) was added, followed by boron dimethylsulfide in tetrahydrofuran (dropwise, 3 ml, 30.9 mmol). The reaction mixture was then refluxed for 16 h. Quenching was carried out with ice-cold methanol (10 ml); hydrogen chloride solution (conc. aq., 3 ml) was added dropwise, and refluxing was carried out for 30 min. After cooling, the mixture was rendered alkaline with dilute sodium hydroxide solution (4%) and extracted with dichloromethane (3×50 ml). The combined organic phases were dried over sodium sulfate and concentrated in vacuo. The crude product was used in the next stage without being purified further. Yield: 44%

(ii) (a) Chlorosulfonic acid (2 eq.) in dichloromethane (0.2 ml/mmol) was added dropwise at 0° C. to a solution, cooled to, of 3,5-dimethylanisole (1 eq.) in dichloromethane (1.3 ml/mmol). When the reaction was complete (TLC monitoring), ice-water was added and the organic phase was extracted with water and saturated sodium chloride solution. The organic phase was dried over sodium sulfate and concentrated in vacuo. The sulfonyl chloride so obtained was reacted further directly without being purified further. Yield: 70%; (b) (S)-Piperidin-2-ylmethanol (1.1 eq.) was dissolved in dichloromethane (4 ml/mmol) and cooled, and triethylamine (2.5 eq.) was added. A solution of 4-methoxy-2,6-dimethylbenzene-sulfonyl chloride (1 eq.) in dichloromethane (2 ml/mmol) was added dropwise at 0° C., and then stirring was carried out for 90 min at room temperature. Hydrogen chloride solution (eq., 0.5 mol/l, 2 ml/mmol) was added, stirring was carried out for 15 min, and the phases were separated. The organic phase was washed with water, dried over sodium sulfate and concentrated in vacuo. The crude product was used in the next stage without being purified further. Yield: 20%

(iii): Tetra-n-butylammonium chloride (0.33 eq.) and sodium hydroxide solution (5 ml/mmol, 35%) were added at 0° C. to a cooled solution of (S)-1-(4-methoxy-2,6-dimethylphenylsulfonyl)piperidin-2-yl)methanol (1 eq.) in toluene (5 ml/mmol). Tert-butyl bromoacetate (1.5 eq.) was then added slowly at 0° C. After stirring for 90 min at room temperature, the phases were separated, and the organic phase was washed with water until pH neutral, dried over sodium sulfate and concentrated in vacuo. The crude product was used in the next stage without being purified further. Yield: 64%

(iv): (S)-tert-butyl 2-((1-(4-methoxy-2,6-dimethylphenylsulfonyl)piperidin-2-yl)-methoxy)acetate (1 eq.) was dissolved in dichloromethane (10 ml/mmol) and cooled, and trifluoroacetic acid (13 eq.) was added slowly at 0° C. After stirring for 2 h at room temperature, the reaction mixture was concentrated in vacuo and dried. The crude product was used in the next stage without being purified further. [Alternatively, the amount of trifluoracetic acid may be reduced to 3 eq.]

Yield: quantitative

Synthesis of Carboxylic Acid 2 (Acid Structural Unit)

2-(2-(2-Chloro-N-cyclopropyl-6-methylphenylsulfonamido)ethoxy)acetic acid

Used in the Synthesis of Examples 77-79

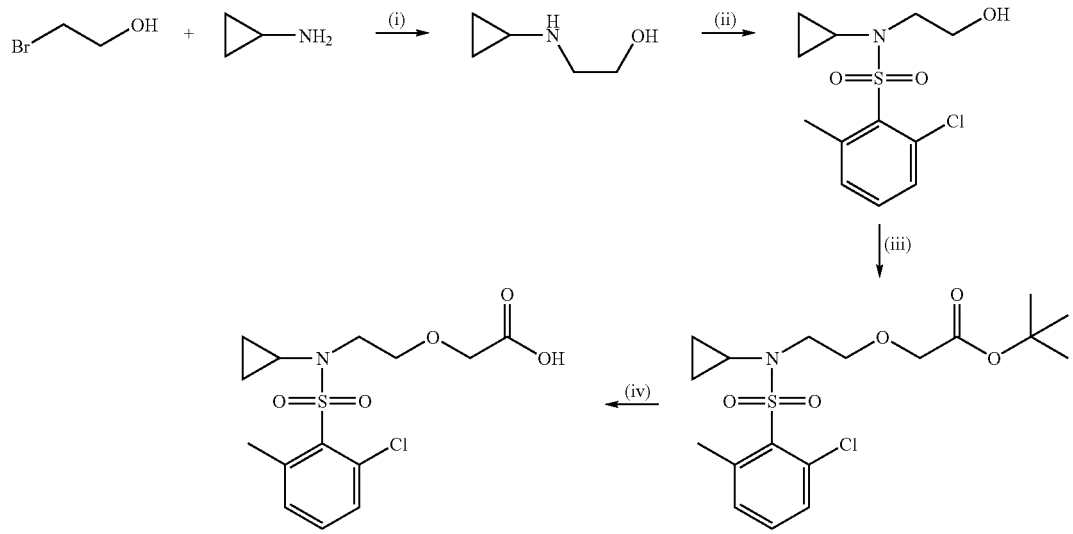

(i) Cyclopropylamine (5 g, 1 eq.) was dissolved in ethanol (60 ml) and 2-bromo ethanol (0.5 eq.) was added. The resulting reaction mixture was heated to 60° C. for 16 h. The reaction mixture was evaporated under reduced pressure and used directly in the next step without further purification. Yield: 70%

(ii) To 2-(cyclopropylamino)ethanol (2 eq.) was added triethylamine (2.5 eq.) and the mixture was cooled to 0° C. To this cold reaction mixture was added 2-chloro-6-methylbenzene sulfonyl chloride (1 eq.) and the mixture was allowed to stir at 25° C. for 2 h. It was diluted with dichloromethane and the organic layer was washed with water and brine and finally dried over sodium sulfate. Evaporation of the organic layer under reduced pressure gave the crude product which was purified by column chromatography (10% ethyl acetate in hexane). Yield: 50%

(iii) To a cold solution of 2-chloro-N-cyclopropyl-N-(2-hydroxyethyl)-6-methylbenzenesulfonamide (1 eq.) in DCM (15 ml) was added tetrabutylammonium chloride (0.1 eq.) and 35% sodium hydroxide solution (15 ml) at 0° C. tert-Butyl 2-omoacetate (1.2 eq.) was added dropwise to this cold reaction mixture maintaining the same temperature. After addition was complete, the reaction mixture was allowed to stir at room temperature for 16 h (monitored by TLC). It was diluted with dichloromethane and the organic layer was washed with water and brine and finally dried over sodium sulfate. Evaporation of the organic layer under reduced pressure gave the crude product which was purified by column chromatography (20% ethyl acetate in hexane). Yield: 70%

(iv) To a dichloromethane (10 ml/mmol) solution of tert-butyl 2-(2-(2-chloro-N-cyclopropyl-6-methylphenylsulfonamido)ethoxy)acetate (1 eq.) was added TFA (13 eq.) at 0° C. and the resulting reaction mixture was allowed to stir at ambient temperature for 2 h. The solvent was evaporated and the residue dried under vacuum to remove traces of TFA. The crude product was used in the next step without further purification. Yield: quantitative Functional Study on the Human Bradykinin Receptor 1 (B1R)

The agonistic or antagonistic action of substances can be determined on the bradykinin receptor 1 (B1R) of the species human and rat using the following assay. According to this assay, the $Ca^{2+}$ influx through the channel is quantified with the aid of a $Ca^{2+}$-sensitive dye (Fluo-4 type, Molecular Probes Europe BV, Leiden, Netherlands) using a Fluorescent Imaging Plate Reader (FLIPR, Molecular Devices, Sunnyvale, USA).

1 Method:

Chinese hamster ovary cells (CHO K1 cells) which have been stably transfected with the human B1R gene (hB1R cells) or with the B1R gene of the rat (rB1R cells) are used. For functional studies, the cells are plated out on black 96-well plates having a clear base (BD Biosciences, Heidelberg, Germany or Greiner, Frickenhausen, Germany) in a density of 20,000-35,000 cells/well. The cells are incubated overnight at 37° C. and with 5% $CO_2$ in culture medium (hB1R cells: Nutrient Mixture Ham's F12, Gibco Invitrogen GmbH, Karlsruhe, Germany or DMEM, Sigma-Aldrich, Taufkirchen, Germany; rB1R cells: D-MEM/F12, Gibco Invitrogen GmbH, Karlsruhe, Germany), with 10 vol. % FBS (fetal bovine serum, Gibco Invitrogen GmbH, Karlsruhe, Germany or PAN Biotech GmbH, Aidenbach, Germany).

On the following day, the cells are loaded for 60 minutes at 37° C. with 2.13 µM Fluo-4 (Molecular Probes Europe BV, Leiden, Netherlands) in HBSS buffer (Hank's buffered saline solution, Gibco Invitrogen GmbH, Karlsruhe, Germany) with 2.5 M probenecid (Sigma-Aldrich, Taufkirchen, Germany) and 10 mM HEPES (Sigma-Aldrich, Taufkirchen, Germany). The plates are then washed twice with HBSS buffer, and HBSS buffer additionally containing 0.1% BSA (bovine serum albumin; Sigma-Aldrich, Taufkirchen, Germany), 5.6 mM glucose and 0.05% gelatin (Merck KGaA, Darmstadt, Germany) is added to the plates. After incubation for a further 20 minutes at room temperature, the plates are inserted into the FLIPR for $Ca^{2+}$ measurement.

Alternatively, washing is carried out with buffer A (15 mM HEPES, 80 mM NaCl, 5 mM KCl, 1.2 mM $CaCl_2$, 0.7 mM $MgSO_4$, 2 g/l glucose, 2.5 mM probenecid) followed by loading with buffer A with added 2.5 µM Fluo-4 and 0.025% Pluronic F127 (Sigma-Aldrich, Taufkirchen, Germany). The cells are then washed twice with buffer A and incubated for 30 minutes at room temperature with buffer A additionally containing 0.05% BSA and 0.05% gelatin and are then inserted into the FLIPR for $Ca^{2+}$ measurement.

The $Ca^{2+}$-dependent fluorescence is measured before and after the addition of substances ($\lambda_{ex}$=488 nm, $\lambda_{em}$=540 nm). Quantification is carried out by measuring the highest fluorescence intensity (FC, fluorescence counts) over time.

2 FLIPR Assay:

The FLIPR protocol consists of two substance additions. Test substances (10 µM) are first pipetted onto the cells and the $Ca^{2+}$ influx is compared with the control (hB1R: Lys-Des-$Arg^9$-bradykinin >=50 nM; rB1R: Des-$Arg^9$-bradykinin 10 µM). This gives the activation in %, based on the $Ca^{2+}$ signal after addition of Lys-Des-$Arg^9$-bradykinin (>=50 nM) or Des-$Arg^9$-bradykinin (10 µM). After 10-20 minutes' incubation, Lys-Des-$Arg^9$-bradykinin (hB1R) or Des-$Arg^9$-bradykinin (rB1R) is applied in the concentration of the $EC_{80}$, and the influx of $Ca^{2+}$ is likewise determined. Antagonists lead to suppression of the $Ca^{2+}$ influx. The % inhibition compared with the maximum achievable inhibition is calculated. In order to determine the $IC_{50}$ value, the substances are added in various concentrations. Duplicate or triplicate determinations (n=2 or n=3) are carried out, and these are repeated in at least one further independent experiment (N>=2).

3 Results of the Pharmacological Studies

The agonistic or antagonistic action of the compounds according to the invention on the bradykinin receptor 1 (B1R) of the species human and rat was determined as described above. Antagonists lead to suppression of the $Ca^{2+}$ influx. The % inhibition compared with the maximum achievable inhibition was calculated.

| Example | B1R antagonism, human [10 µM] % inhibition | B1R antagonism, rat [10 µM] % inhibition |
|---|---|---|
| 1 | 104 | 63 |
| 2 | 103 | 102 |
| 3 | 103 | 101 |
| 4 | 103 | 102 |
| 5 | 101 | 61 |
| 6 | 100 | 85 |
| 7 | 89 | 37 |
| 8 | 104 | 102 |
| 9 | 104 | 102 |
| 10 | 103 | 65 |
| 11 | 102 | 101 |
| 12 | 103 | 90 |
| 13 | 97 | 101 |
| 14 | 35 | 64 |
| 15 | 84 | 76 |
| 16 | 97 | 102 |
| 17 | 94 | 81 |
| 18 | 62 | 102 |
| 19 | 82 | 98 |
| 20 | 57 | 94 |
| 21 | 56 | 98 |
| 22 | 98 | 102 |
| 23 | 100 | 101 |
| 24 | 38 | 60 |
| 25 | 97 | 63 |
| 26 | 100 | 103 |
| 27 | 100 | 102 |
| 28 |  | 97 |
| 29 | 100 | 101 |
| 30 |  | 100 |
| 31 | 100 | 101 |
| 32 |  | 100 |
| 37 | 100 | 103 |
| 38 | 100 | 101 |
| 39 |  | 99 |
| 40 |  | 100 |
| 41 | 100 | 104 |
| 42 | 100 | 102 |
| 43 |  | 101 |
| 44 |  | 100 |
| 45 |  | 100 |
| 46 |  | 101 |
| 47 |  | 53 |
| 48 | 100 | 103 |
| 49 | 100 | 103 |
| 50 |  | 100 |
| 51 |  | 80 |
| 52 |  | 83 |
| 53 | 100 | 102 |
| 54 | 100 | 102 |
| 55 |  | 98 |
| 56 |  | 97 |
| 57 |  | 70 |
| 58 |  | 99 |
| 59 |  | 101 |
| 60 | 100 | 104 |
| 61 | 100 | 103 |
| 62 |  | 100 |
| 63 |  | 102 |
| 64 |  | 46 |
| 65 |  | 63 |
| 66 |  | 99 |
| 67 | 100 | 102 |
| 68 | 100 | 101 |
| 69 |  | 99 |
| 70 |  | 100 |
| 71 | 100 | 103 |
| 72 | 100 | 103 |
| 73 |  | 84 |
| 74 | 100 | 93 |
| 75 |  | 68 |
| 76 |  | 101 |
| 77 | 100 | 92 |
| 78 | 97 | 92 |
| 79 | 100 | 103 |
| 80 | 100 | 104 |
| 81 | 100 | 102 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:
1. A substituted sulfonamide compound corresponding to formula (I):

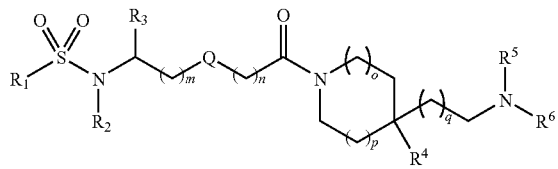

wherein
m represents 0, 1 or 2;
n represents 1 or 2;
o represents 0, 1 or 2;
p represents 0, 1 or 2;
q represents 0, 1, 2, 3 or 4;
Q represents a single bond, —O— or —CH$_2$—;
R$^1$ represents aryl or heteroaryl, or aryl or heteroaryl bonded via a C$_{1-3}$-alkylene group;
R$^2$ represents H, C$_{1-16}$-alkyl, C$_{3-8}$-cycloalkyl, bicyclic 8- to 12-membered carbocyclyl, CH(aryl)$_2$, aryl or heteroaryl; or C$_{3-8}$-cycloalkyl, bicyclic 8- to 12-membered carbocyclyl, CH(aryl)$_2$, aryl or heteroaryl bonded via a C$_{1-6}$-alkylene group, C$_{2-6}$-alkenylene group or C$_{2-6}$-alkynylene group; and
R$^3$ represents H, C$_{1-6}$-alkyl, aryl or heteroaryl; or aryl or heteroaryl bonded via a C$_{1-6}$-alkylene group, C$_{2-6}$-alkenylene group or C$_{2-6}$-alkynylene group; or
R$^2$ and R$^3$ together with the group —N—(CH—)— joining them, form a 4-, 5-, 6- or 7-membered heterocycle, which optionally may be fused to an aryl or heteroaryl group, wherein said heterocycle may be saturated or mono- or polyunsaturated but not aromatic, and optionally may contain, in addition to the N heteroatom to which R$^2$ is bonded, one or more further heteroatoms or heteroatom groups selected from the group consisting of N, NR$^7$, O, S, S═O and S(═O)$_2$; wherein
R$^7$ denotes H, C$_{1-6}$-alkyl, —C(═O)—R$^8$, C$_{3-8}$-cycloalkyl, aryl, heteroaryl, or C$_{3-8}$-cycloalkyl, aryl or heteroaryl bonded via a C$_{1-3}$-alkylene group, and
R$^8$ denotes C$_{1-6}$-alkyl, C$_{3-8}$-cycloalkyl, aryl, heteroaryl, or C$_{3-8}$-cycloalkyl, aryl or heteroaryl bonded via a C$_{1-3}$-alkylene group;
R$^4$ denotes aryl, heteroaryl, or aryl or heteroaryl bonded via a C$_{1-6}$-alkylene group;
R$^5$ and R$^6$ each independently denote H, C$_{1-6}$-alkyl, C$_{3-8}$-cycloalkyl, or C$_{3-8}$-cycloalkyl bonded via a C$_{1-3}$-alkylene group, wherein R$^5$ and R$^6$ do not simultaneously represent H; or
R$^5$ and R$^6$ together represent a substituted or unsubstituted 5- or 6-membered heteroaryl which optionally may contain, in addition to the N atom to which R$^5$ and R$^6$ are bonded, at least one further heteroatom selected from the group consisting of N, O and S, or
R$^5$ and R$^6$ together represent a group selected from —(CH$_2$)$_d$— and —(CH$_2$)$_e$—X—(CH$_2$)$_f$—, wherein
d denotes 2, 3, 4, 5 or 6,
e and f each independently denote 1, 2 or 3, with the proviso that e+f is not greater than 5;
X denotes NR$^{12}$, CF$_2$, O, S, S(═O) or S(═O)$_2$; wherein
R$^{12}$ denotes H, C$_{1-6}$-alkyl, C$_{3-8}$-cycloalkyl, aryl, heteroaryl, or C$_{3-8}$-cycloalkyl, aryl or heteroaryl bonded via a C$_{1-3}$-alkylene group; and wherein
said C$_{1-6}$-alkyl, C$_{1-6}$-alkylene, C$_{2-6}$-alkenylene, C$_{2-6}$-alkynylene, C$_{3-8}$-cycloalkyl, C$_{3-8}$-heterocycloalkyl, bicyclic 8- to 12-membered carbocyclyl, aryl and heteroaryl may each be unsubstituted or mono- or poly-substituted by identical or different substituents, and
said C$_{1-6}$-alkyl, C$_{1-6}$-alkylene, C$_{2-6}$-alkenylene and C$_{2-6}$-alkynylene may each be branched or unbranched;
or a physiologically acceptable salt thereof.

2. A compound as claimed in claim 1, wherein said compound is in the form of a mixture of stereoisomers in any mixing ratio.

3. A compound as claimed in claim 2, wherein said compound is in the form of a racemic mixture.

4. A compound as claimed in claim 1, wherein said compound is in the form of an individual stereoisomer.

5. A compound as claimed in claim 1, wherein
said C$_{1-6}$-alkyl, C$_{1-6}$-alkylene, C$_{2-6}$-alkenylene, C$_{2-6}$-alkynylene, C$_{3-8}$-cycloalkyl and C$_{3-8}$-heterocycloalkyl groups each may optionally be unsubstituted or mono- or polysubstituted by identical or different substituents independently selected from the group consisting of F, Cl, Br, I, CN, NH$_2$, NH—C$_{1-6}$-alkyl, NH—C$_{1-6}$-alkylene-OH, C$_{1-6}$-alkyl, N(C$_{1-6}$-alkyl)$_2$, N(C$_{1-6}$-alkylene-OH)$_2$, NO$_2$, SH, S—C$_{1-6}$-alkyl, S-benzyl, O—C$_{1-6}$-alkyl, OH, O—C$_{1-6}$-alkylene-OH, ═O,O-benzyl, C(═O)C$_{1-6}$-alkyl, CO$_2$H, CO$_2$—C$_{1-6}$-alkyl and benzyl;
said aryl and heteroaryl groups each may optionally be unsubstituted or mono- or poly-substituted by identical or different substituents independently selected from the group consisting of F, Cl, Br, I, CN, NH$_2$, NH—C$_{1-6}$-alkyl, NH—C$_{1-6}$-alkylene-OH, N(C$_{1-6}$-alkyl)$_2$, N(C$_{1-6}$-alkylene-OH)$_2$, NH-aryl$^1$, N(aryl$^1$)$_2$, N(C$_{1-6}$-alkyl)aryl$^1$, pyrrolinyl, piperazinyl, morpholinyl, NO$_2$, SH, S—C$_{1-6}$-alkyl, OH, O—C$_{1-6}$-alkyl, O—C$_{1-6}$-alkyl-OH, C(═O)C$_{1-6}$-alkyl, NHSO$_2$C$_{1-6}$-alkyl, NHCOC$_{1-6}$-alkyl, CO$_2$H, CH$_2$SO$_2$-phenyl, CO$_2$—C$_{1-6}$-alkyl, OCF$_3$, CF$_3$, —O—CH$_2$—O—, —O—CH$_2$—CH$_2$—O—, —O—C(CH$_3$)$_2$—CH$_2$—, unsubstituted C$_{1-6}$-alkyl, pyrrolidinyl, imidazolyl, piperidinyl, benzyloxy, phenoxy, phenyl, naphthyl, pyridinyl, —C$_{1-3}$-alkylene-aryl$^1$, benzyl, thienyl and furyl, wherein aryl$^1$ represents phenyl, furyl, thienyl or pyridinyl; and
said bicyclic 8- to 12-membered carbocyclyl groups each may optionally be unsubstituted or mono- or polysubstituted by identical or different substituents, wherein substituents bonded to a saturated or partially unsaturated ring system of said carbocyclyl groups are selected from the group of substituents defined above for cycloalkyl groups, and substituents bonded to an aromatic ring system of said carbocyclyl groups are selected from the group of substituents defined above for aryl and heteroaryl groups.

6. A compound as claimed in claim 1, wherein R$^1$ represents phenyl, naphthyl, indolyl, benzofuranyl, benzothiophenyl, benzooxazolyl, benzoxadiazolyl, pyrrolyl, furanyl, thienyl, pyridinyl, pyridazinyl, pyrimidinyl, pyrazinyl, imidazothiazolyl, carbazolyl, dibenzofuranyl or dibenzothiophenyl, benzyl or 2-phenylethyl.

7. A compound as claimed in claim 6, wherein R$^1$ represents phenyl, naphthyl, benzothiophenyl, benzoxadiazolyl, thiophenyl, pyridinyl, imidazothiazolyl or dibenzofuranyl.

8. A compound as claimed in claim 1, wherein
p and o each represent 1, or
p represents 1 and o represents 0.

9. A compound as claimed in claim 1, wherein
Q represents a single bond,
m represents 0 or 1, and n represents 1 or 2;
or
Q represents —O—,
m represents 1 or 2, and
n represents 1.

10. A compound as claimed in claim 1, wherein $R^4$ represents phenyl, phenyl bonded via a $C_{1-3}$-alkylene group, 2-, 3- or 4-pyridinyl, or 2-, 3- or 4-pyridinyl bonded via a $C_{1-3}$-alkylene group, wherein phenyl may optionally be mono- or polysubstituted by F, Cl or $CF_3$.

11. A compound as claimed in claim 1, wherein q represents 0, 1 or 2.

12. A compound as claimed in claim 1, wherein
$R^5$ and $R^6$ each independently represent unsubstituted or mono- or poly-substituted $C_{1-6}$-alkyl; or
$R^5$ and $R^6$ together represent a group selected from the group consisting of —N=CH—CH=CH—, —CH=CH—N=CH—, —CH$_2$—CH$_2$—CH$_2$—; —CH$_2$—CH$_2$—CH$_2$—CH$_2$—, —CH$_2$—CH$_2$—CH$_2$—CH$_2$—CH$_2$— and —CH$_2$—CH$_2$—NR$^9$—CH$_2$—CH$_2$—, wherein $R^9$ represents H or $C_{1-6}$-alkyl.

13. A compound as claimed in claim 1, wherein
$R^2$ represents H, $C_{1-6}$-alkyl, $C_{3-6}$-cycloalkyl, 8- to 10-membered benzo-fused cycloalkyl, —CH(phenyl)$_2$, aryl or heteroaryl; or
$R^2$ denotes $C_{3-6}$-cycloalkyl, aryl or heteroaryl bonded via a $C_{1-6}$-alkylene group, $C_{2-6}$-alkenylene group or $C_{2-6}$-alkynylene group;
wherein said $C_{1-6}$-alkyl, $C_{3-6}$-cycloalkyl, $C_{2-6}$-alkylene, $C_{2-6}$-alkenylene, $C_{2-6}$-alkynylene, 8- to 10-membered benzo-fused cycloalkyl, aryl and heteroaryl groups each may optionally be unsubstituted or mono- or polysubstituted by identical or different substituents selected from the group consisting of $C_{1-6}$-alkyl, $C_{1-6}$-alkyl-O—, F, Cl, Br, I, $CF_3$, $OCF_3$, OH and SH.

14. A compound as claimed in claim 1, wherein
$R^3$ represents H, $C_{1-6}$-alkyl or aryl; or aryl bonded via a $C_{1-6}$-alkylene group, $C_{2-6}$-alkenylene group or $C_{2-6}$-alkynylene group;
wherein said $C_{1-6}$-alkyl, $C_{3-6}$-cycloalkyl, $C_{2-6}$-alkylene, $C_{2-6}$-alkenylene, $C_{2-6}$-alkynylene or aryl groups each may optionally be unsubstituted or mono- or polysubstituted by identical or different substituents selected from the group consisting of $C_{1-6}$-alkyl, $C_{1-6}$-alkyl-O—, F, Cl, Br, I, $CF_3$, $OCF_3$, OH and SH.

15. A compound as claimed in claim 1, wherein $R^2$ and $R^3$, together with the group —N—(CH—)— joining them, form a heterocycle corresponding to formula (II)

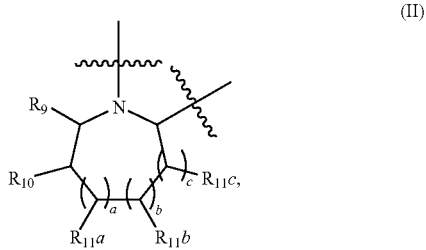

(II)

wherein
a, b and c each independently represent 0 or 1; and
$R^9$, $R^{10}$, $R^{11a}$, $R^{11b}$ and $R^{11c}$ each independently represent H, or two vicinal groups selected from $R^9$, $R^{10}$, $R^{11a}$, $R^{11b}$ and $R^{11c}$ together form a 5- or 6-membered fused aryl or heteroaryl group, which may be unsubstituted or mono- or polysubstituted by identical or different substituents.

16. A compound as claimed in claim 1, selected from the group consisting of:
(1) N-(3-Oxo-1-phenyl-3-(4-(pyridin-3-yl)-4-(2-(pyrrolidin-1-yl)ethyl)piperidin-1-yl)propyl)naphthalene-2-sulfonamide
(2) 2-((1-(4-Methoxy-2,6-dimethylphenylsulfonyl)piperidin-2-yl)methoxy)-1-(4-(pyridin-3-yl)-4-(2-(pyrrolidin-1-yl)ethyl)piperidin-1-yl)ethanone
(3) 4-Methoxy-N,2,6-trimethyl-N-(2-(2-oxo-2-(4-(pyridin-3-yl)-4-(2-(pyrrolidin-1-yl)ethyl)piperidin-1-yl)ethoxy)ethyl)benzenesulfonamide
(4) 1-(4-(Pyridin-3-yl)-4-(2-(pyrrolidin-1-yl)ethyl)piperidin-1-yl)-2-(1-(3-(trifluoromethyl)phenylsulfonyl)piperidin-2-yl)ethanone
(5) 3-(1-(4-Chloro-2,5-dimethylphenylsulfonyl)piperidin-2-yl)-1-(4-(pyridin-3-yl)-4-(2-(pyrrolidin-1-yl)ethyl)piperidin-1-yl)propan-1-one
(6) 2-((1-(3,4-Dichlorophenylsulfonyl)-1,2,3,4-tetrahydroquinolin-2-yl)methoxy)-1-(4-(pyridin-3-yl)-4-(2-(pyrrolidin-1-yl)ethyl)piperidin-1-yl)ethanone
(7) N-(3-(4-(2-(Dimethylamino)ethyl)-4-(pyridin-3-yl)piperidin-1-yl)-3-oxo-1-phenylpropyl)naphthalene-2-sulfonamide
(8) 1-(4-(2-(Dimethylamino)ethyl)-4-(pyridin-3-yl)piperidin-1-yl)-2-((1-(4-methoxy-2,6-dimethylphenylsulfonyl)piperidin-2-yl)methoxy)ethanone
(9) N-(2-(2-(4-(2-(Dimethylamino)ethyl)-4-(pyridin-3-yl)piperidin-1-yl)-2-oxoethoxy)ethyl)-4-methoxy-N,2,6-trimethylbenzenesulfonamide
(10) 1-(4-(2-(Dimethylamino)ethyl)-4-(pyridin-3-yl)piperidin-1-yl)-2-(1-(3-(trifluoromethyl)phenylsulfonyl)piperidin-2-yl)ethanone
(11) 3-(1-(4-Chloro-2,5-dimethylphenylsulfonyl)piperidin-2-yl)-1-(4-(2-(dimethylamino)ethyl)-4-(pyridin-3-yl)piperidin-1-yl)propan-1-one
(12) 2-((1-(3,4-Dichlorophenylsulfonyl)-1,2,3,4-tetrahydroquinolin-2-yl)methoxy)-1-(4-(2-(dimethylamino)ethyl)-4-(pyridin-3-yl)piperidin-1-yl)ethanone
(13) 4-Methoxy-N,2,6-trimethyl-N-(2-(2-oxo-2-(4-(pyridin-3-yl)-4-(3-(pyrrolidin-1-yl)propyl)piperidin-1-yl)ethoxy)ethyl)benzenesulfonamide
(14) 1-(4-(Pyridin-3-yl)-4-(3-(pyrrolidin-1-yl)propyl)piperidin-1-yl)-2-(1-(3-(trifluoromethyl)phenylsulfonyl)piperidin-2-yl)ethanone
(15) 3-(1-(4-Chloro-2,5-dimethylphenylsulfonyl)piperidin-2-yl)-1-(4-(pyridin-3-yl)-4-(3-(pyrrolidin-1-yl)propyl)piperidin-1-yl)propan-1-one
(16) 2-((1-(4-Methoxy-2,6-dimethylphenylsulfonyl)piperidin-2-yl)methoxy)-1-(4-(pyridin-3-yl)-4-(3-(pyrrolidin-1-yl)propyl)piperidin-1-yl)ethanone
(17) N-(3-Oxo-1-phenyl-3-(4-(pyridin-3-yl)-4-(3-(pyrrolidin-1-yl)propyl)piperidin-1-yl)propyl)naphthalene-2-sulfonamide
(18) 2-((1-(3,4-Dichlorophenylsulfonyl)-1,2,3,4-tetrahydroquinolin-2-yl)methoxy)-1-(4-(pyridin-3-yl)-4-(3-(pyrrolidin-1-yl)propyl)piperidin-1-yl)ethanone
(19) 3-(1-(4-Chloro-2,5-dimethylphenylsulfonyl)piperidin-2-yl)-1-(4-(3-(dimethylamino)propyl)-4-(pyridin-3-yl)piperidin-1-yl)propan-1-one
(20) N-(3-(4-(3-(Dimethylamino)propyl)-4-(pyridin-3-yl)piperidin-1-yl)-3-oxo-1-phenylpropyl)naphthalene-2-sulfonamide

(21) 2-((1-(3,4-Dichlorophenylsulfonyl)-1,2,3,4-tetrahydroquinolin-2-yl)methoxy)-1-(4-(3-(dimethylamino)propyl)-4-(pyridin-3-yl)piperidin-1-yl)ethanone
(22) 1-(4-(3-(Dimethylamino)propyl)-4-(pyridin-3-yl)piperidin-1-yl)-2-((1-(4-methoxy-2,6-dimethylphenylsulfonyl)piperidin-2-yl)methoxy)ethanone
(23) N-(2-(2-(4-(3-(Dimethylamino)propyl)-4-(pyridin-3-yl)piperidin-1-yl)-2-oxoethoxy)ethyl)-4-methoxy-N,2,6-trimethylbenzenesulfonamide
(24) 1-(4-(3-(Dimethylamino)propyl)-4-(pyridin-3-yl)piperidin-1-yl)-2-(1-(3-(trifluoromethyl)phenylsulfonyl)piperidin-2-yl)ethanone
(25) (S)-2-((1-(4-Methoxy-2,6-dimethylphenylsulfonyl)piperidin-2-yl)methoxy)-1-(4-(pyridin-3-yl)-4-(pyrrolidin-1-ylmethyl)piperidin-1-yl)ethanone
(26) 2-[[1-[(4-Methoxy-2,6-dimethyl-phenyl)sulfonyl]-piperidin-2-yl]-methoxy]-1-[4-pyridin-3-yl-4-(3-pyrrolidin-1-yl-propyl)-piperidin-1-yl]-ethanone
(27) 2-[[1-[(4-Methoxy-2,6-dimethyl-phenyl)sulfonyl]-piperidin-2-yl]-methoxy]-1-[4-pyridin-3-yl-4-(3-pyrrolidin-1-yl-propyl)-piperidin-1-yl]-ethanone
(28) 2-[[1-[(4-Methoxy-2,6-dimethyl-phenyl)sulfonyl]-piperidin-2-yl]-methoxy]-1-[4-pyridin-4-yl-4-(3-pyrrolidin-1-yl-propyl)-piperidin-1-yl]-ethanone
(29) 4-Methoxy-N,2,6-trimethyl-N-[2-[2-oxo-2-[4-pyridin-3-yl-4-(3-pyrrolidin-1-yl-propyl)-piperidin-1-yl]-ethoxy]-ethyl]-benzenesulfonic acid amide
(30) 4-Methoxy-N,2,6-trimethyl-N-[2-[2-oxo-2-[4-pyridin-4-yl-4-(3-pyrrolidin-1-yl-propyl)-piperidin-1-yl]-ethoxy]-ethyl]-benzenesulfonic acid amide
(31) 4-Methoxy-N,2,3,6-tetramethyl-N-[2-[2-oxo-2-[4-pyridin-3-yl-4-(3-pyrrolidin-1-yl-propyl)-piperidin-1-yl]-ethoxy]-ethyl]-benzenesulfonic acid amide
(32) 4-Methoxy-N,2,3,6-tetramethyl-N-[2-[2-oxo-2-[4-pyridin-4-yl-4-(3-pyrrolidin-1-yl-propyl)-piperidin-1-yl]-ethoxy]-ethyl]-benzenesulfonic acid amide
(37) N-Benzyl-4-Methoxy-2,6-dimethyl-N-[2-[2-oxo-2-[4-pyridin-3-yl-4-(3-pyrrolidin-1-yl-propyl)-piperidin-1-yl]-ethoxy]-ethyl]-benzenesulfonic acid amide
(38) N-benzyl-4-Methoxy-2,6-dimethyl-N-[2-[2-oxo-2-[4-pyridin-3-yl-4-(3-pyrrolidin-1-yl-propyl)-piperidin-1-yl]-ethoxy]-ethyl]-benzenesulfonic acid amide
(39) N-benzyl-4-Methoxy-2,6-dimethyl-N-[2-[2-oxo-2-[4-pyridin-4-yl-4-(3-pyrrolidin-1-yl-propyl)-piperidin-1-yl]-ethoxy]-ethyl]-benzenesulfonic acid amide
(40) N-benzyl-4-Methoxy-2,6-dimethyl-N-[2-[2-oxo-2-[4-pyridin-4-yl-4-(3-pyrrolidin-1-yl-propyl)-piperidin-1-yl]-ethoxy]-ethyl]-benzenesulfonic acid amide
(41) 1-[4-Pyridin-3-yl-4-(3-pyrrolidin-1-yl-propyl)-piperidin-1-yl]-2-[[1-[[2-(trifluoromethyl)-phenyl]sulfonyl]-piperidin-2-yl]-methoxy]-ethanone
(42) 1-[4-Pyridin-3-yl-4-(3-pyrrolidin-1-yl-propyl)-piperidin-1-yl]-2-[[1-[[2-(trifluoromethyl)-phenyl]sulfonyl]-piperidin-2-yl]-methoxy]-ethanone
(43) 1-[4-Pyridin-4-yl-4-(3-pyrrolidin-1-yl-propyl)-piperidin-1-yl]-2-[[1-[[2-(trifluoromethyl)-phenyl]sulfonyl]-piperidin-2-yl]-methoxy]-ethanone
(44) 1-[4-Pyridin-4-yl-4-(3-pyrrolidin-1-yl-propyl)-piperidin-1-yl]-2-[[1-[[2-(trifluoromethyl)-phenyl]sulfonyl]-piperidin-2-yl]-methoxy]-ethanone
(45) 2-[2-[1-[(4-Methoxy-2,6-dimethyl-phenyl)sulfonyl]-piperidin-2-yl]-ethoxy]-1-[4-pyridin-3-yl-4-(3-pyrrolidin-1-yl-propyl)-piperidin-1-yl]-ethanone
(46) 2-[2-[1-[(4-Methoxy-2,6-dimethyl-phenyl)sulfonyl]-piperidin-2-yl]-ethoxy]-1-[4-pyridin-3-yl-4-(3-pyrrolidin-1-yl-propyl)-piperidin-1-yl]-ethanone
(47) N-Methyl-N-[4-Oxo-4-[4-pyridin-3-yl-4-(3-pyrrolidin-1-yl-propyl)-piperidin-1-yl]-butyl]-3-(trifluoromethyl)-benzenesulfonic acid amide
(48) 4-Methoxy-2,6-Dimethyl-N-[2-[2-oxo-2-[4-pyridin-3-yl-4-(3-pyrrolidin-1-yl-propyl)-piperidin-1-yl]-ethoxy]-ethyl]-N-phenyl-benzenesulfonic acid amide
(49) 4-Methoxy-2,6-Dimethyl-N-[2-[2-oxo-2-[4-pyridin-3-yl-4-(3-pyrrolidin-1-yl-propyl)-piperidin-1-yl]-ethoxy]-ethyl]-N-phenyl-benzenesulfonic acid amide
(50) 4-Methoxy-2,6-Dimethyl-N-[2-[2-oxo-2-[4-pyridin-4-yl-4-(3-pyrrolidin-1-yl-propyl)-piperidin-1-yl]-ethoxy]-ethyl]-N-phenyl-benzenesulfonic acid amide
(51) 2-[[1-(Naphthalen-2-ylsulfonyl)-1,2,3,4-tetrahydroquinolin-2-yl]-methoxy]-1-[4-pyridin-3-yl-4-(3-pyrrolidin-1-yl-propyl)-piperidin-1-yl]-ethanone
(52) 2-[[1-(Naphthalen-2-ylsulfonyl)-1,2,3,4-tetrahydroquinolin-2-yl]-methoxy]-1-[4-pyridin-3-yl-4-(3-pyrrolidin-1-yl-propyl)-piperidin-1-yl]-ethanone
(53) 2-[[1-[(4-methoxy-2,6-dimethyl-phenyl)sulfonyl]-1,2,3,4-tetrahydro-quinolin-2-yl]-methoxy]-1-[4-pyridin-3-yl-4-(3-pyrrolidin-1-yl-propyl)-piperidin-1-yl]-ethanone
(54) 2-[[1-[(4-Methoxy-2,6-dimethyl-phenyl)sulfonyl]-1,2,3,4-tetrahydro-quinolin-2-yl]-methoxy]-1-[4-pyridin-3-yl-4-(3-pyrrolidin-1-yl-propyl)-piperidin-1-yl]-ethanone
(55) 2-[[1-[(4-Methoxy-2,6-dimethyl-phenyl)sulfonyl]-1,2,3,4-tetrahydro-quinolin-2-yl]-methoxy]-1-[4-pyridin-4-yl-4-(3-pyrrolidin-1-yl-propyl)-piperidin-1-yl]-ethanone
(56) 4-[1-[(2-Chloro-6-methyl-phenyl)sulfonyl]-piperidin-2-yl]-1-[4-pyridin-4-yl-4-(3-pyrrolidin-1-yl-propyl)-piperidin-1-yl]-butan-1-one
(57) 1-[4-Pyridin-3-yl-4-(3-pyrrolidin-1-yl-propyl)-piperidin-1-yl]-4-[1-[[2-(trifluoromethyl)-phenyl]sulfonyl]-piperidin-2-yl]-butan-1-one
(58) 1-[4-Pyridin-4-yl-4-(3-pyrrolidin-1-yl-propyl)-piperidin-1-yl]-4-[1-[[2-(trifluoromethyl)-phenyl]sulfonyl]-piperidin-2-yl]-butan-1-one
(59) 1-[4-Pyridin-4-yl-4-(3-pyrrolidin-1-yl-propyl)-piperidin-1-yl]-4-[1-[[2-(trifluoromethyl)-phenyl]sulfonyl]-piperidin-2-yl]-butan-1-one
(60) 4-[1-[(4-Methoxy-2,6-dimethyl-phenyl)sulfonyl]-piperidin-2-yl]-1-[4-pyridin-3-yl-4-(3-pyrrolidin-1-yl-propyl)-piperidin-1-yl]-butan-1-one
(61) 4-[1-[(4-Methoxy-2,6-dimethyl-phenyl)sulfonyl]-piperidin-2-yl]-1-[4-pyridin-3-yl-4-(3-pyrrolidin-1-yl-propyl)-piperidin-1-yl]-butan-1-one
(62) 4-[1-[(4-Methoxy-2,6-dimethyl-phenyl)sulfonyl]-piperidin-2-yl]-1-[4-pyridin-4-yl-4-(3-pyrrolidin-1-yl-propyl)-piperidin-1-yl]-butan-1-one
(63) 4-[1-[(4-Methoxy-2,6-dimethyl-phenyl)sulfonyl]-piperidin-2-yl]-1-[4-pyridin-4-yl-4-(3-pyrrolidin-1-yl-propyl)-piperidin-1-yl]-butan-1-one
(64) 4-[1-(Naphthalen-1-ylsulfonyl)-piperidin-2-yl]-1-[4-pyridin-4-yl-4-(3-pyrrolidin-1-yl-propyl)-piperidin-1-yl]-butan-1-one
(65) N-Benzhydryl-N-[2-[2-oxo-2-[4-pyridin-4-yl-4-(3-pyrrolidin-1-yl-propyl)-piperidin-1-yl]-ethoxy]-ethyl]-methanesulfonic acid amide
(66) N-Benzhydryl-N-[2-[2-oxo-2-[4-pyridin-4-yl-4-(3-pyrrolidin-1-yl-propyl)-piperidin-1-yl]-ethoxy]-ethyl]-methanesulfonic acid amide
(67) 2-[[4-[(4-Methoxy-2,6-dimethyl-phenyl)sulfonyl]-3,4-dihydro-2H-[1,4]benzoxazin-3-yl]-methoxy]-1-[4-pyridin-3-yl-4-(3-pyrrolidin-1-yl-propyl)-piperidin-1-yl]-ethanone

(68) 2-[[4-[(4-Methoxy-2,6-dimethyl-phenyl)sulfonyl]-3,4-dihydro-2H-[1,4]benzoxazin-3-yl]-methoxy]-1-[4-pyridin-3-yl-4-(3-pyrrolidin-1-yl-propyl)-piperidin-1-yl]-ethanone

(69) 2-[[4-[(4-Methoxy-2,6-dimethyl-phenyl)sulfonyl]-3,4-dihydro-2H-[1,4]benzoxazin-3-yl]-methoxy]-1-[4-pyridin-4-yl-4-(3-pyrrolidin-1-yl-propyl)-piperidin-1-yl]-ethanone

(70) 2-[[4-[(4-Methoxy-2,6-dimethyl-phenyl)sulfonyl]-3,4-dihydro-2H-[1,4]benzoxazin-3-yl]-methoxy]-1-[4-pyridin-4-yl-4-(3-pyrrolidin-1-yl-propyl)-piperidin-1-yl]-ethanone

(71) 4-Methoxy-2,6-Dimethyl-N-[2-[2-oxo-2-[4-pyridin-3-yl-4-(3-pyrrolidin-1-yl-propyl)-piperidin-1-yl]-ethoxy]-ethyl]-N-(quinolin-3-yl-methyl)-benzenesulfonic acid amide

(72) 2-[[4-[(2-Chloro-6-methyl-phenyl)sulfonyl]-3,4-dihydro-2H-[1,4]benzoxazin-3-yl]-methoxy]-1-[4-pyridin-3-yl-4-(3-pyrrolidin-1-yl-propyl)-piperidin-1-yl]-ethanone

(73) 1-[4-Pyridin-3-yl-4-(3-pyrrolidin-1-yl-propyl)-piperidin-1-yl]-2-[[4-[[2-(trifluoromethyl)-phenyl]sulfonyl]-3,4-dihydro-2H-[1,4]benzoxazin-3-yl]-methoxy]-ethanone

(74) 1-[4-Pyridin-3-yl-4-(3-pyrrolidin-1-yl-propyl)-piperidin-1-yl]-2-[[4-[[2-(trifluoromethyl)-phenyl]sulfonyl]-3,4-dihydro-2H-[1,4]benzoxazin-3-yl]-methoxy]-ethanone

(75) 1-[4-Pyridin-4-yl-4-(3-pyrrolidin-1-yl-propyl)-piperidin-1-yl]-2-[[4-[[2-(trifluoromethyl)-phenyl]sulfonyl]-3,4-dihydro-2H-[1,4]benzoxazin-3-yl]-methoxy]-ethanone

(76) N-(4H-[1,3]Benzodioxin-7-yl-methyl)-4-methoxy-2,6-dimethyl-N-[2-[2-oxo-2-[4-pyridin-4-yl-4-(3-pyrrolidin-1-yl-propyl)-piperidin-1-yl]-ethoxy]-ethyl]-benzenesulfonic acid amide

(77) 2-Chloro-N-[2-[2-[4-(3-chlorophenyl)-4-(3-pyrrolidin-1-yl-propyl)-piperidin-1-yl]-2-oxo-ethoxy]-ethyl]-N-cyclopropyl-6-methyl-benzenesulfonic acid amide

(78) 2-Chloro-N-cyclopropyl-6-methyl-N-[2-[2-oxo-2-[4-(3-pyrrolidin-1-yl-propyl)-4-[3-(trifluoromethyl)phenyl]-piperidin-1-yl]-ethoxy]-ethyl]-benzenesulfonic acid amide

(79) 2-Chloro-N-cyclopropyl-N-[2-[2-[4-(3-fluorophenyl)-4-(3-pyrrolidin-1-yl-propyl)-piperidin-1-yl]-2-oxo-ethoxy]-ethyl]-6-methyl-benzenesulfonic acid amide

(80) 2-[[(2S)-1-[(4-Methoxy-2,6-dimethyl-phenyl)sulfonyl]-piperidin-2-yl]-methoxy]-1-[4-pyridin-3-yl-4-(2-pyrrolidin-1-yl-ethyl)-piperidin-1-yl]-ethanone hydrochloride

(81) 2-[[(2S)-1-[(4-Methoxy-2,6-dimethyl-phenyl)sulfonyl]-piperidin-2-yl]-methoxy]-1-[4-pyridin-3-yl-4-(3-pyrrolidin-1-yl-propyl)-piperidin-1-yl]-ethanone hydrochloride or a physiologically acceptable salt thereof.

17. A pharmaceutical composition comprising a compound as claimed in claim 1 and at least one pharmaceutically acceptable carrier or auxiliary substance.

18. A process for preparing a compound as claimed in claim 1, said process comprising reacting a carboxylic acid corresponding to formula (S) with a free amine corresponding to formula (A) according to the following reaction scheme:

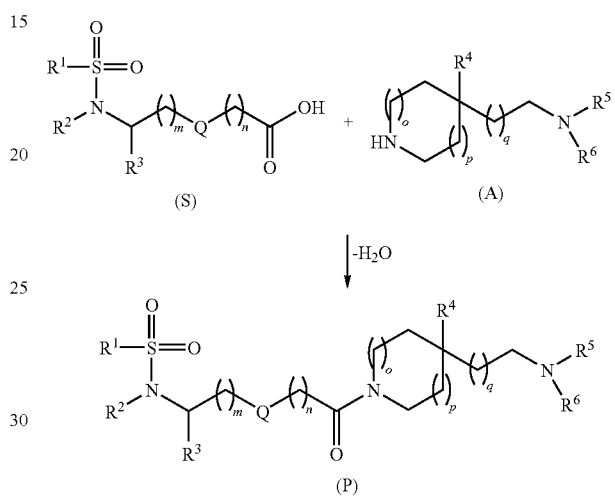

in an organic solvent in the presence of a water-removing agent and of an organic base to form an amide corresponding to formula (P).

19. A method of treating or inhibiting a condition selected from the group consisting of pain, migraine, diabetes, Asthma bronchiale, allergies, COPD, cystic fibrosis, ulcerative colitis, Crohn's disease, multiple sclerosis, neurodegeneration, skin inflammation, rheumatoid arthritis, osteoarthritis, septic shock, reperfusion syndrome, and obesity, or of inhibiting angiogenesis in a subject in need thereof, said method comprising administering to said subject a pharmaceutically effective amount of a compound as claimed in claim 1.

20. A method as claimed in claim 19, wherein said condition is pain selected from the group consisting of acute pain, visceral pain, neuropathic pain, chronic pain, and inflammatory pain.

* * * * *